(12) United States Patent
Johnson et al.

(10) Patent No.: US 6,593,337 B1
(45) Date of Patent: Jul. 15, 2003

(54) TRICYCLIC COMPOUNDS USEFUL AS HIV REVERSE TRANSCRIPTASE INHIBITORS

(75) Inventors: Barry L. Johnson, Wilmington, DE (US); Mona Patel, Bridgewater, NJ (US); James D. Rodgers, Landenberg, PA (US); Christine M. Tarby, Hockessin, DE (US); Rajagopal Bakthavatchalam, Wilmington, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 09/691,249

(22) Filed: Oct. 18, 2000

Related U.S. Application Data

(60) Provisional application No. 60/160,329, filed on Oct. 19, 1999, and provisional application No. 60/226,171, filed on Aug. 17, 2000.

(51) Int. Cl.$^7$ .................. C07D 471/04; C07D 471/14; A61K 31/4375; A61P 31/18
(52) U.S. Cl. .......................... 514/293; 546/81
(58) Field of Search .................. 546/81; 514/293

(56) References Cited

U.S. PATENT DOCUMENTS

| | | |
|---|---|---|
| 4,503,066 A | 3/1985 | Brittain et al. |
| 5,087,625 A | 2/1992 | Hargrave et al. ........... 514/220 |
| 5,171,745 A | 12/1992 | De Noble et al. |
| 5,519,021 A | 5/1996 | Young et al. |
| 5,561,117 A | 10/1996 | Wong et al. |
| 5,594,001 A | 1/1997 | Teleha et al. |
| 5,750,528 A | 5/1998 | Brown et al. |
| 5,874,430 A | 2/1999 | Christ et al. |
| 6,124,302 A | 9/2000 | Corbett et al. |

FOREIGN PATENT DOCUMENTS

| | | |
|---|---|---|
| DD | 204480 | 11/1983 |
| DE | 43 20 347 | 12/1994 |
| DE | 4344452 | 6/1995 |
| EP | 0393530 | 10/1990 |
| EP | 0393604 | 10/1990 |
| EP | 0 530 994 | 3/1993 |
| WO | WO 93/04047 | 3/1993 |
| WO | WO 94/07910 | 4/1994 |
| WO | WO 95/12583 | 5/1995 |
| WO | WO 96/31469 | 10/1996 |

OTHER PUBLICATIONS

Meisel et al. Pharmazie (1984), 39 (10), 671–2.*
Houpis et al, Tetr. Lett., 1994, 35 (37) 6811–6814.
Tucker et al, J. Med. Chem., 1994, 37, 2437–2444.
Huffman et al, J. Org. Chem., 1995, 60, 1590–1594.
Meisel et al, Synthese von 10–Substituierten 5,5–Dimethyl–5, 10–Dihydrobenzo'b!–1, 8!Naphthyridinen, Pharmazie, 1984, pp. 671–672, vol. 39, No. 10.
Kurfurst et al, On Reactivity of 2,6–Dichloro–3,5–Diformyl–1,4–Trimethyl–1,4–Dihydropyridine, Collect. Czech Chem. Commun., 1989, pp. 1705–1715, vol. 54, No. 7.

* cited by examiner

*Primary Examiner*—Mark L. Berch
*Assistant Examiner*—Kahsay Habte
(74) *Attorney, Agent, or Firm*—Mary K. VanAtten

(57) ABSTRACT

The present invention relates to tricyclic compounds of formula (I):

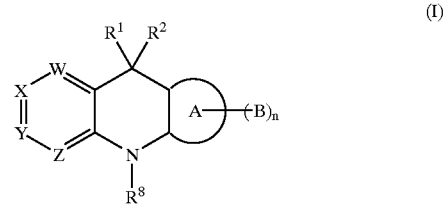

or stereoisomeric forms, stereoisomeric mixtures, or pharmaceutically acceptable salt forms thereof, which are useful as inhibitors of HIV reverse transcriptase, and to pharmaceutical compositions and diagnostic kits comprising the same, and methods of using the same for treating viral infection or as an assay standard or reagent.

53 Claims, No Drawings

TRICYCLIC COMPOUNDS USEFUL AS HIV REVERSE TRANSCRIPTASE INHIBITORS

This application claims the benefit of U. S. Provisional Application No. 60/160,329, filed Oct. 19, 1999 and a U.S. Provisional Appln. not yet assigned a serial number filed on Aug. 17, 2000.

FIELD OF THE INVENTION

This intention relates generally to tricyclic compounds and also tricyclic compounds which are useful as inhibitors of HIV reverse transcriptase, pharmaceutical compositions and diagnostic kits comprising the same, methods of using the same for treating viral infection or as assay standards or reagents, and intermediates and processes for making such tricyclic compounds.

BACKGROUND OF THE INVENTION

Two distinct retroviruses, human immunodeficiency virus (HIV) type-1 (HIV-1) or type-2 (HIV-2), have been etiologically linked to the immunosuppressive disease, acquired immunodeficiency syndrome (AIDS). HIV seropositive individuals are initially asymptomatic but typically develop AIDS related complex (ARC) followed by AIDS. Affected individuals exhibit severe immunosuppression which predisposes them to debilitating and ultimately fatal opportunistic infections.

The disease AIDS is the consequence of HIV-1 or HIV-2 virus following its complex viral life cycle. The virion life cycle involves the virion attaching itself to the host human T-4 lymphocyte immune cell through the binding of a glycoprotein on the surface of the virion's protective coat with the CD4 glycoprotein on the lymphocyte cell. Once attached, the virion sheds its glycoprotein coat, penetrates into the membrane of the host cell, and uncoats its RNA. The virion enzyme, reverse transcriptase, directs the process of transcribing the RNA into single-stranded DNA. The viral RNA is degraded and a second DNA strand is created. The now double-stranded DNA is integrated into the human cell's genes and those genes are used for virus reproduction.

RNA polymerase transcribes the integrated viral DNA into viral mRNA. The viral RNA is translated into the precursor gag-pol fusion polyprotein. The polyprotein is then cleaved by the HIV protease enzyme to yield the mature viral proteins. Thus, HIV protease is responsible for regulating a cascade of cleavage events that lead to the virus particle's maturing into a virus that is capable of full infectivity.

The typical human immune system response, killing the invading virion, is taxed because the virus infects and kills the immune system's T cells. In addition, viral reverse transcriptase, the enzyme used in making a new virion particle, is not very specific, and causes transcription mistakes that result in continually changed glycoproteins on the surface of the viral protective coat. This lack of specificity decreases the immune system's effectiveness because antibodies specifically produced against one glycoprotein may be useless against another, hence reducing the number of antibodies available to fight the virus. The virus continues to reproduce while the immune response system continues to weaken. In most cases, without therapeutic intervention, HIV causes the host's immune system to be debilitated, allowing opportunistic infections to set in. Without the administration of antiviral agents, immunomodulators, or both, death may result.

There are at least three critical points in the HIV life cycle which have been identified as possible targets for antiviral drugs: (1) the initial attachment of the virion to the T-4 lymphocyte or macrophage site, (2) the transcription of viral RNA to viral DNA (reverse transcriptase, RT), and (3) the processing of gag-pol protein by HIV protease.

Inhibition of the virus at the second critical point, the viral RNA to viral DNA transcription process, has provided a number of the current therapies used in treating AIDS. This transcription must occur for the virion to reproduce because the virion's genes are encoded in RNA and the host cell transcribes only DNA. By introducing drugs that block the reverse transcriptase from completing the formation of viral DNA, HIV-1 replication can be stopped.

A number of compounds that interfere with viral replication have been developed to treat AIDS. For example, nucleoside analogs, such as 3'-azido-3'-deoxythymidine (AZT), 2',3'-dideoxycytidine (ddC), 2',3'-dideoxythymidinene (d4T), 2',3'-dideoxyinosine (ddI), and 2',3'-dideoxy-3'-thia-cytidine (3TC) have been shown to be relatively effective in certain cases in halting HIV replication at the reverse transcriptase (RT) stage.

An active area of research is in the discovery of non-nucleoside HIV reverse transcriptase inhibitors (NNRTIs). As an example, it has been found that certain benzoxazinones and quinazolinones are active in the inhibition of HIV reverse transcriptase, the prevention or treatment of infection by HIV and the treatment of AIDS.

U.S. Pat. No. 5,874,430 describes benzoxazinone non-nucleoside reverse transcriptase inhibitors for the treatment of HIV. U.S. Pat. No. 5,519,021 describe non-nucleoside reverse transcriptase inhibitors which are benzoxazinones of the formula:

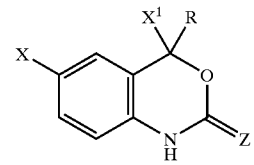

wherein X is a halogen, Z may be O.

EP 0,530,994 and WO 93/04047 describe HIV reverse transcriptase inhibitors which are quinazolinones of the formula (A):

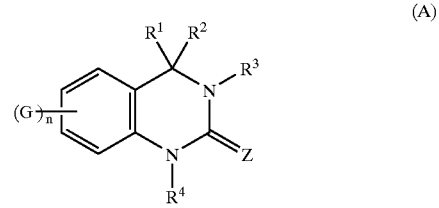

(A)

wherein G is a variety of groups, $R^3$ and $R^4$ may be H, Z may be O, $R^2$ may be unsubstituted alkyl, unsubstituted alkenyl, unsubstituted alkynyl, unsubstituted cycloalkyl, unsubstituted heterocycle, and optionally substituted aryl, and $R^1$ may be a variety of groups including substituted alkyl.

WO 95/12583 also describes HIV reverse transcriptase inhibitors of formula A. In this publication, G is a variety of groups, $R^3$ and $R^4$ may be H, Z may be O, $R^2$ is substituted alkenyl or substituted alkynyl, and $R^1$ is cycloalkyl, alkynyl, alkenyl, or cyano. WO 95/13273 illustrates the asymmetric synthesis of one of the compounds of WO 95/12583, (S)-(−)-6-chloro-4-cyclopropyl-3,4-dihydro-4((2-pyridy)ethynyl)-2(1H)-quinazolinone.

Synthetic procedures for making quinazolinones like those described above are detailed in the following references: Houpis et al., *Tetr. Lett.* 1994, 35(37), 6811–6814; Tucker et al., *J. Med. Chem.* 1994, 37, 2437–2444; and, Huffman et al., *J. Org. Chem.* 1995, 60, 1590–1594.

DE 4,320,347 illustrates quinazolinones of the formula:

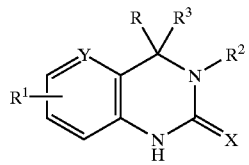

wherein R is a phenyl, carbocyclic ring, or a heterocyclic ring. Compounds of this sort are not considered to be part of the present invention.

Even with the current success of reverse transcriptase inhibitors, it has been found that HIV patients can become resistant to a given inhibitor. Thus, there is an important need to develop additional inhibitors to further combat HIV infection.

SUMMARY OF THE INVENTION

Accordingly, one object of the present invention is to provide novel reverse transcriptase inhibitors.

It is another object of the present invention to provide a novel method for treating HIV infection which comprises administering to a host in need of such treatment a therapeutically effective amount of at least one of the compounds of the present invention, including a pharmaceutically acceptable salt form thereof.

It is another object of the present invention to provide a novel method for treating HIV infection which comprises administering to a host in need thereof a therapeutically effective combination of (a) one of the compounds of the present invention and (b) one or more compounds selected from the group consisting of HIV reverse transcriptase inhibitors and HIV protease inhibitors.

It is another object of the present invention to provide pharmaceutical compositions with reverse transcriptase inhibiting activity comprising a pharmaceutically acceptable carrier and a therapeutically effective amount of at least one of the compounds of the present invention or a pharmaceutically acceptable salt form thereof.

It is another object of the present invention to provide novel tricyclic compounds for use in therapy.

It is another object of the present invention to provide the use of novel tricyclic compounds for the manufacture of a medicament for the treatment of HIV infection.

These and other objects, which will become apparent during the following detailed description, have been achieved by the inventors' discovery that compounds of formula (I):

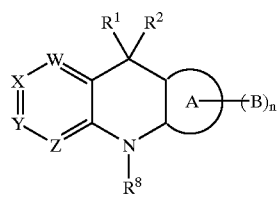

wherein $R^1$, $R^2$, $R^8$, n, A, B, W, X, Y, and Z are defined below, including any stereoisomeric form, mixtures of stereoisomeric forms, complexes, prodrug forms or pharmaceutically acceptable salt forms thereof, are effective reverse transcriptase inhibitors.

DETAILED DESCRIPTION OF PREFERRED EMBODIMENTS

[1] Thus, in a first embodiment, the present invention provides a novel compound of formula (I):

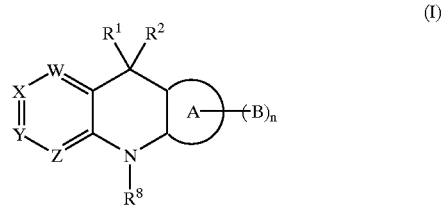

or a stereoisomeric form, mixtures of stereoisomeric forms, complexes, prodrug forms or pharmaceutically acceptable salt form thereof, wherein:

n is selected from 0, 1, 2 and 3;

A is a ring selected from the group:

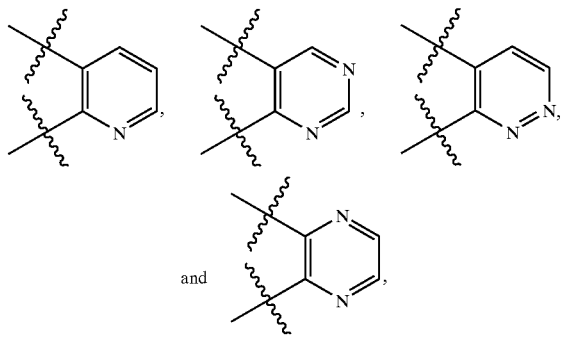

wherein a ring nitrogen in ring A may optionally be in an N-oxide form;

said ring A being substituted with 0–3 B, said substituent B being independently selected from the group $C_{1-4}$ alkyl, —OH, $C_{1-4}$ alkoxy, —S—$C_{1-4}$alkyl, $OCF_3$, $CF_3$, F, Cl, Br, I, —$NO_2$, —CN, and —$NR^5R^{5a}$;

W is N or $CR^3$;

X is N or $CR^{3a}$;

Y is N or $CR^{3b}$;

Z is N or $CR^{3c}$;

provided that if two of W, X, Y, and Z are N, then the remaining are other than N;

$R^1$ is selected from the group $C_{1-3}$ alkyl substituted with 0–7 halogen, and cyclopropyl substituted with 0–5 halogen;

$R^2$ is selected from the group —$R^{2c}$, —OH, —CN, —$OR^{2c}$, —$OCHR^{2a}R^{2b}$, —$OCH_2CHR^{2a}R^{2b}$, —$O(CH_2)_2CHR^{2a}R^{2b}$, —$OCHR^{2a}C(R^{2a})=C(R^{2b})_2$, —$OCHR^{2a}C(R^{2a})=C(R^{2b})_2$, —$OCHR^{2a}C\equiv C-R^{2b}$, —$SR^{2c}$, —$SCHR^{2a}R^{2b}$, —$SCH_2CHR^{2a}R^{2b}$, —$S(CH_2)_2CHR^{2a}R^{2b}$, —$SCHR^{2a}C(R^{2a})=C(R^{2b})_2$, —$SCHR^{2a}C(R^{2a})=(R^{2b})_2$, —$SCHR^{2a}C\equiv C-R^{2b}$, —$NR^{2a}R^{2c}$, —$NHCHR^{2a}R^{2b}$, —$NHCH_2CHR^{2a}R^{2b}$, —$NH(CH_2)_2CHR^{2a}R^{2b}$, —$NHCHR^{2a}C(R^{2a})=C(R^{2b})_2$, —$NHCHR^{2a}C(R^{2a})=(R^{2b})_2$, and —$NHCHR^{2a}C\equiv C-R^{2b}$;

$R^{2a}$ is selected from the group H, $CH_3$, $CH_2CH_3$, $CH(CH_3)_2$, and $CH_2CH_2CH_3$;

$R^{2b}$ is H or $R^{2c}$;

$R^{2c}$ is selected from the group methyl substituted with 0–3 $R^{3f}$, $C_{1-6}$ alkyl substituted with 0–3 $R^4$, $C_{2-5}$ alkenyl substituted with 0–2 $R^4$, $C_{2-5}$ alkynyl substituted with 0–1 $R^4$, $C_{3-6}$ cycloalkyl substituted with 0–2 $R^{3d}$, phenyl substituted with 0–2 $R^{3d}$, and 3–6 membered heterocyclic system containing 1–3 heteroatoms selected from the group O, N, and S, substituted with 0–2 $R^{3d}$;

alternatively, the group —$NR^{2a}R^{2c}$ represents a 4–7 membered cyclic amine, wherein 0–1 carbon atoms are replaced by O or $NR^5$;

$R^3$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, —$SO_2NR^5R^{5a}$, and a 5–6 membered heteroaromatic ring containing 1–4 heteroatoms selected from the group O, N, and S;

$R^{3a}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, —$SO_2NR^5R^{5a}$, and a 5–6 membered heteroaromatic ring containing 1–4 heteroatoms selected from the group O, N, and S;

alternatively, $R^3$ and $R^{3a}$ together form —$OCH_2O$—;

$R^{3b}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

alternatively, $R^{3a}$ and $R^{3b}$ together form —$OCH_2O$—;

$R^{3c}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

alternatively, $R^{3b}$ and $R^{3c}$ together form —$OCH_2O$—;

$R^{3d}$, at each occurrence, is independently selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

$R^{3e}$, at each occurrence, is independently selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

$R^{3f}$, is selected from the group group H, F, Cl, Br, I, —OH, —O—$R^{11}$, —O—$C_{3-10}$ carbocycle substituted with 0–2 $R^{3e}$, —O (CO) —$R^{13}$, —OS $(O)_2C_{1-4}$alkyl, —$NR^{12}R^{12a}$, —$C(O)R^{13}$, —$NHC(O)R^{13}$, —$NHSO_2R^{10}$, and —$SO_2NR^{12}R^{12a}$;

$R^4$ is selected from the group H, F, Cl, Br, I, —OH, —O—$R^{11}$, —O—$C_{3-10}$ carbocycle substituted with 0–2 $R^{3e}$, —$OS(O)_2C_{1-4}$alkyl, —$NR^{12}R^{12a}$, $C_{1-6}$ alkyl substituted with 0–2 $R^{3e}$, $C_{3-10}$ carbocycle substituted with 0–2 $R^{3e}$, phenyl substituted with 0–5 $R^{3e}$, and a 5–10 membered heterocyclic system containing 1–3 heteroatoms selected from the group O, N, and S, substituted with 0–2 $R^{3e}$;

$R^5$ and $R^{5a}$ are independently selected from the group H and $C_{1-4}$ alkyl;

alternatively, $R^5$ and $R^{5a}$, together with the nitrogen to which they are attached, combine to form a 5–6 membered ring containing 0–1 O or N atoms;

$R^6$ is selected from the group H, OH, $C_{1-4}$ alkyl, $C_{1-4}$ alkoxy, and $NR^5R^{5a}$;

$R^7$ is selected from the group H, $C_{1-3}$ alkyl and $C_{1-3}$ alkoxy;

$R^8$ is selected from the group H, ($C_{1-6}$ alkyl)carbonyl, $C_{1-6}$ alkoxyalkyl, ($C_{1-4}$ alkoxy)carbonyl, $C_{6-10}$ aryloxyalkyl, ($C_{6-10}$ aryl)oxycarbonyl, ($C_{6-10}$ aryl)methylcarbonyl, ($C_{1-4}$ alkyl)carbonyloxy($C_{1-4}$ alkoxy)carbonyl, $C_{6-10}$ arylcarbonyloxy($C_{1-4}$ alkoxy)carbonyl, $C_{1-6}$ alkylaminocarbonyl, phenylaminocarbonyl, phenyl($C_{1-4}$ alkoxy)carbonyl, and ($C_{1-6}$ alkyl substitued with $NR^5R^{5a}$)carbonyl; and $R^{10}$ is selected from the group $C_{1-4}$ alkyl and phenyl $R^{11}$ is selected from $C_{1-6}$ alkyl, $C_{1-6}$ haloalkyl, $C_{1-6}$ alkyl substituted with $C_{3-6}$cycloalkyl, $C_{2-6}$ alkenyl, $C_{2-6}$ alkynyl, $C_{3-6}$ cycloalkyl;

$R^{12}$ and $R^{12a}$ are independently selected from H, $C_{1-6}$ alkyl, and $C_{3-6}$ cycloalkyl;

alternatively, $R^{12}$ and $R^{12a}$ can join to form 4–7 membered ring; and $R^{13}$ is selected from the group H, $C_{1-6}$ alkyl, $C_{1-6}$ haloalkyl, $C_{1-6}$ alkoxy, $C_{2-6}$ alkenyl, $C_{2-6}$ alkynyl, —O—$C_{2-6}$ alkenyl, —O—$C_{2-6}$ alkynyl, $NR^{12}R^{12a}$, $C_{3-6}$carbocycle, and —O—$C_{3-6}$carbocycle.

[2] In another embodiment, the present invention provides compounds of formula (I) as set forth above, wherein:

$R^1$ is selected from the group $C_{1-3}$ alkyl substituted with 1–7 halogen, and cyclopropyl;

$R^2$ is selected from the group —$R^{2c}$, —OH, —CN, —$OR^{2c}$, —$OCHR^{2a}R^{2b}$, —$OCH_2CHR^{2a}R^{2b}$, —$O(CH_2)_2CHR^{2a}R^{2b}$, —$OCHR^{2a}CH$=$CHR^{2b}$, —$OCHR^{2a}CH$=$CHR^{2c}$, —$OCHR^{2a}C$≡$CR^{2b}$, —$NR^{2a}R^{2c}$, —$SR^{2c}$, —$SCHR^{2a}R^{2b}$, —$SCH_2CHR^{2a}R^{2b}$, —$SCHR^{2a}CH$=$CHR^{2b}$, —$SCHR^{2a}CH$=$CHR^{2c}$, and —$SCHR^{2a}C$≡$CR^{2b}$;

$R^{2a}$ is selected from the group H, $CH_3$, $CH_2CH_3$, $CH(CH_3)_2$, and $CH_2CH_2CH_3$;

$R^{2b}$ is H or $R^{2c}$;

$R^{2c}$ is selected from the group methyl substituted with 0–3 $R^{3f}$, $C_{1-5}$ alkyl substituted with 0–3 $R^4$, $C_{2-5}$ alkenyl substituted with 0–2 $R^4$, $C_{2-5}$ alkynyl substituted with 0–1 $R^4$, $C_{3-6}$ cycloalkyl substituted with 0–2 $R^{3d}$, and phenyl substituted with 0–2 $R^{3d}$;

$R^3$ and $R^{3a}$, at each occurrence, are independently selected from the group H, $C_{1-4}$ alkyl, OH, $C_{1-4}$ alkoxy, F, Cl, Br, I, $NR^5R^{5a}$, $NO_2$, —CN, $C(O)R^6$, $NHC(O)R^7$, $NHC(O)NR^5R^{5a}$, and a 5–6 membered heteroaromatic ring containing 1–4 heteroatoms selected from the group O, N, and S;

alternatively, $R^3$ and $R^{3a}$ together form —$OCH_2O$—;

$R^{3b}$ and $R^{3c}$, at each occurrence, are independently selected from the group H, $C_{1-4}$ alkyl, OH, $C_{1-4}$ alkoxy, F, Cl, Br, I, $NR^5R^{5a}$, $NO_2$, —CN, $C(O)R^6$, $NHC(O)R^7$, and $NHC(O)NR^5R^{5a}$;

alternatively, $R^{3a}$ and $R^{3b}$ together form —$OCH_2O$—;

$R^4$ is selected from the group H, Cl, F, —OH, —O—$C^{1-6}$alkyl, —O—$C_{3-5}$ carbocycle substituted with 0–2 $R^{3e}$, —$OS(O)_2C_{1-4}$alkyl, —$NR^{12}R^{12a}$, $C_{1-4}$ alkyl substituted with 0–2 $R^{3e}$, $C_{3-5}$ carbocycle substituted with 0–2 $R^{3e}$, phenyl substituted with 0–5 $R^{3e}$, and a 5–6 membered heterocyclic system containing 1–3 heteroatoms selected from the group O, N, and S, substituted with 0–2 $R^{3e}$;

$R^5$ and $R^{5a}$ are independently selected from the group H, $CH_3$ and $C_2H_5$;

$R^6$ is selected from the group H, OH, $CH_3$, $C_2H_5$, $OCH_3$, $OC_2H_5$, and $NR^5R^{5a}$; and $R^7$ is selected from the group $CH_3$, $C_2H_5$, $CH(CH_3)_2$, $OCH_3$, $OC_2H_5$, and $OCH(CH_3)_2$.

[3] In an alternative embodiment the present invention also provides compounds of formula (I) as described above, wherein:

ring A is selected from

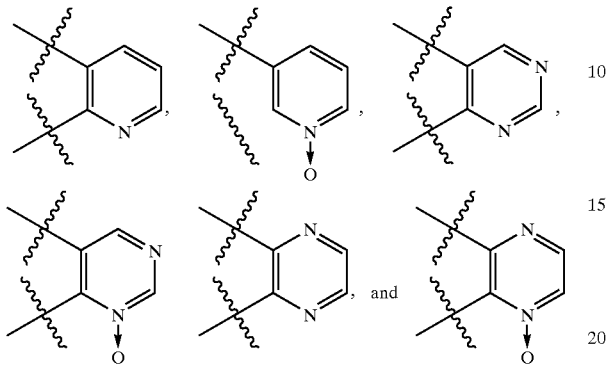

$R^1$ is selected from the group $CF_3$, $C_2F_5$, $CHF_2$, $CF_2CH_3$ and cyclopropyl;

$R^2$ is selected from the group $-R^{2c}$, $-OH$, $-CN$, $-OR^{2c}$, $-OCHR^{2a}R^{2b}$, $-OCH_2CHR^{2a}R^{2b}$, $-OCHR^{2a}CH=CHR^{2b}$, $-OCHR^{2a}CH=CHR^{2c}$, $-OCHR^{2a}C\equiv CR^{2b}$, and $-NR^{2a}R^{2c}$;

$R^{2a}$ is selected from the group H, $CH_3$, $CH_2CH_3$, $CH(CH_3)_2$, and $CH_2CH_2CH_3$;

$R^{2b}$ is H or $R^{2c}$;

$R^{2c}$ is selected from the group methyl substituted with 0–3 $R^{3f}$, $C_{1-3}$ alkyl substituted with 0–3 $R^4$, $C_{2-3}$ alkenyl substituted with 0–2 $R^4$, $C_{2-3}$ alkynyl substituted with 0–1 $R^4$, and $C_{3-6}$ cycloalkyl substituted with 0–2 $R^{3d}$;

$R^3$, $R^{3a}$, $R^{3b}$, and $R^{3c}$, at each occurrence, are independently selected from the group H, $C_{1-3}$ alkyl, OH, $C_{1-3}$ alkoxy, F, Cl, Br, I, $NR^5R^{5a}$, $NO_2$, $-CN$, $C(O)R^6$, $NHC(O)R^7$, and $NHC(O)NR^5R^{5a}$;

alternatively, $R^3$ and $R^{3a}$ together form $-OCH_2O-$;

$R^{3e}$, at each occurrence, is independently selected from the group H, $C_{1-4}$ alkyl, $-OH$, $C_{1-4}$ alkoxy, $OCF_3$, F, Cl, $-NR^5R^{5a}$, $-C(O)R^6$, and $-SO_2NR^5R^{5a}$;

$R^{3f}$ is selected from the group group H, F, Cl, Br, $-OH$, $-O-R^{11}$, $-O$-cyclopropyl substituted with 0–2 $R^{3e}$, $-O$-cyclobutyl substituted with 0–2 $R^{3e}$, $-O$-phenyl substituted with 0–2 $R^{3e}$, $-O(CO)-R^{13}$, $-OS(O)_2C_{1-4}$alkyl $-NR^{12}R^{12a}$, $-C(O)R^{13}$, $-NHC(O)R^{13}$, $-NHSO_2R^{10}$, and $-SO_2NR^{12}R^{12a}$;

$R^4$ is selected from the group H, Cl, F, $-OH$, $-O-C_{1-6}$alkyl, $-O-C_{3-10}$ carbocycle substituted with 0–2 $R^{3e}$, $-OS(O)_2C_{1-4}$alkyl, $-NR^{12}R^{12a}$ $C_{1-4}$ alkyl substituted with 0–1 $R^{3e}$, $C_{3-5}$ carbocycle substituted with 0–2 $R^{3e}$, phenyl substituted with 0–2 $R^{3e}$, and a 5–6 membered heterocyclic system containing 1–3 heteroatoms selected from the group O, N, and S, substituted with 0–1 $R^{3e}$;

$R^5$ and $R^{5a}$ are independently selected from the group H, $CH_3$ and $C_2H_5$;

$R^6$ is selected from the group H, OH, $CH_3$, $C_2H_5$, $OCH_3$, $OC_2H_5$, and $NR^5R^{5a}$; and $R^7$ is selected from the group $CH_3$, $C_2H_5$, $OCH_3$, and $OC_2H_5$;

$R^{11}$ is selected from methyl, ethyl, propyl, i-propyl, butyl, pentyl, hexyl, $CF_3$, $CH_2CF_3$, $CH_2CH_2CF_3$, $-CH_2$-cyclopropyl, and cyclopropyl;

$R^{12}$ and $R^{12a}$ are independently selected from H, methyl, ethyl, propyl, i-propyl, butyl, pentyl, and cyclopropyl;

$R^{13}$ is selected from the group H, methyl, ethyl, propyl, i-propyl, butyl, pentyl, hexyl, $C_{1-6}$ haloalkyl, methoxy, ethoxy, propoxy, i-propoxy, butoxy, $NR^{12}R^{12a}$, cyclopropyl, cyclobutyl, cyclopropoxy, and cyclobutoxy.

[4] Another embodiment of the present invention include compounds of formula (I) as described above, wherein:

$R^1$ is $CF_3$, $CF_2CH_3$, or $CHF_2$;

$R^2$ is selected from the group $-R^{2c}$, $-OH$, $-CN$, $-OCH_2R^{2b}$, $-OCH_2CH_2R^{2b}$, $-OCH_2CH=CHR^{2b}$, $-OCH_2C\equiv CR^{2b}$, and $-NR^{2a}R^{2c}$;

$R^{2b}$ is H or $R^{2c}$;

$R^{2c}$ is selected from the group methyl substituted with 0–3 $R^{3f}$, $C_{1-3}$ alkyl substituted with 0–3 $R^4$, $C_{2-3}$ alkenyl substituted with 1 $R^4$, and $C_{2-3}$ alkynyl substituted with 1 $R^4$;

$R^3$, $R^{3a}$, $R^{3b}$, and $R^{3c}$, at each occurrence, are independently selected from the group H, $C_{1-3}$ alkyl, OH, $C_{1-3}$ alkoxy, F, Cl, $NR^5R^{5a}$, $NO_2$, $-CN$, $C(O)R^6$, $NHC(O)R^7$, and $NHC(O)NR^5R^{5a}$;

alternatively, $R^3$ and $R^{3a}$ together form $-OCH_2O-$;

$R^{3e}$, at each occurrence, is independently selected from the group $CH_3$, $-OH$, $OCH_3$, $OCF_3$, F, Cl, and $-NR^5R^{5a}$;

$R^{3f}$, is selected from the group group H, F, Cl, $-OH$, $-O-R^{11}$, $-O(CO)-R^{13}$, $-OS(O)_2C_{1-4}$alkyl, $-NR^{12}R^{12a}$, and $-NHC(O)NR^{12}R^{12a}$;

$R^4$ is selected from the group H, Cl, F, $CH_3$, $CH_2CH_3$, cyclopropyl substituted with 0–1 $R^{3e}$, 1-methylcyclopropyl substituted with 0–1 $R^{3e}$, cyclobutyl substituted with 0–1 $R^{3e}$, phenyl substituted with 0–2 $R^{3e}$, and a 5–6 membered heterocyclic system containing 1–3 heteroatoms selected from the group O, N, and S, substituted with 0–1 $R^{3e}$, wherein the heterocyclic system is selected from the group 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, 2-imidazolyl, morpholinyl, piperidinyl, pyrrolidinyl, and piperazinyl;

$R^5$ and $R^{5a}$ are independently selected from the group H, $CH_3$ and $C_2H_5$;

$R^6$ is selected from the group H, OH, $CH_3$, $C_2H_5$, $OCH_3$, $OC_2H_5$, and $NR^5R^{5a}$; and $R^7$ is selected from the group $CH_3$, $C_2H_5$, $OCH_3$, and $OC_2H_5$.

[5] Another embodiment of the present invention include compounds of formula (I) as described above, wherein:

n is 0 or 1;

ring A is optionally in an N-oxide form;

$R^1$ is $CF_3$, $CHF_2$, or $CF_2CH_3$;

$R^2$ is selected from the group $-R^{2c}$, $-OR^{2c}$, $-OH$, $-CN$, $-OCH_2R^{2b}$, $-OCH_2CH_2R^{2b}$, $-OCH_2C=C-R^{2b}$, $-OCH_2C\equiv C-R^{2b}$, $-NR^{2a}R^{2c}$, $-SR^{2c}$, $-SCH_2R^{2b}$, $-SCH_2CH_2R^{2b}$, $-SCH_2CH=CHR^{2b}$, and $-SCH_2C\equiv CR^{2b}$;

$R^{2b}$ is H or $R^{2c}$;

$R^{2c}$ is selected from the group methyl substituted with 0–2 $R^{3f}$, ethyl substituted with 0–3 $R^4$, propyl substituted with 0–2 $R^4$, ethenyl substituted with 0–2 $R^4$, 1-propenyl substituted with 0–2 $R^4$, 2-propenyl substituted with 0–2 $R^4$ ethynyl substituted with 0–2 $R^4$, 1-propynyl substituted with 0–2 $R^4$, 2-propynyl substituted with 0–2 $R^4$, and cyclopropyl substituted with 0–1 $R^{3d}$;

$R^{3e}$, at each occurrence, is independently selected from the group $CH_3$, —OH, $OCH_3$, $OCF_3$, F, Cl, and —$NR^5R^{5a}$;

$R^{3f}$, is selected from the group group H, F, Cl, —OH, —O—$R^{11}$, —O(CO) —$R^{13}$, —OS(O)$_2C_{1-4}$alkyl, —$NR^{12}R^{12a}$, and —NHC (O)$NR^{12}R^{12a}$;

$R^4$ is selected from the group H, Cl, F, $CH_3$, $CH_2CH_3$, cyclopropyl substituted with 0–1 $R^{3e}$, 1-methyl-cyclopropyl substituted with 0–1 $R^{3e}$, cyclobutyl substituted with 0–1 $R^{3e}$, phenyl substituted with 0–2 $R^{3e}$, and a 5–6 membered heterocyclic system containing 1–3 heteroatoms selected from the group O, N, and S, substituted with 0–1 $R^{3e}$, wherein the heterocyclic system is selected from the group 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, 2-imidazolyl, morpholinyl, piperidinyl, pyrrolidinyl, and piperazinyl;

$R^5$ and $R^{5a}$ are independently selected from the group H, $CH_3$ and $C_2H_5$;

$R^6$ is selected from the group H, OH, $CH_3$, $C_2H_5$, $OCH_3$, $OC_2H_5$, and $NR^5R^{5a}$;

$R^7$ is selected from the group $CH_3$, $C_2H_5$, $OCH_3$, and $OC_2H_5$; $R^8$ is H.

[6] Another embodiment of the present invention include compounds of formula (I) as described above, wherein:

n is selected from 0 or 1;

A is selected from

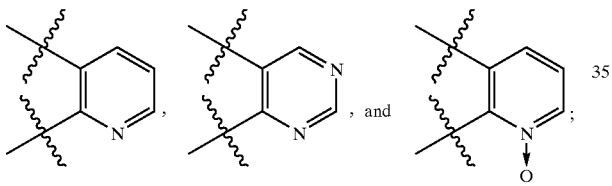

B is selected from methyl, ethyl, propyl, —OH, Cl, Br, —S—$CH_3$,

W is $CR^3$;

X is $CR^{3a}$;

Y is $CR^{3a}$;

Z is N or $CR^{3a}$;

$R^1$ is selected from $CF_3$, $CHF_2$, and $CF_2CH_3$;

$R^2$ is selected from —$R^{2c}$, —OH, —CN, —$OR^{2c}$, —$OCH_2C$=$C$—$R^{2b}$, —$OCH_2C$≡$C$—$R^{2b}$, and —$NR^{2a}R^{2c}$;

$R^{2a}$ is H;

$R^{2b}$ is H;

$R^{2c}$ is selected from the group methyl substituted with 0–3 $R^{3f}$, ethyl substituted with 0–3 $R^4$, propyl substituted with 0–3 $R^4$, i-propyl substituted with 0–3 $R^4$, butyl substituted with 0–3 $R^4$, 1-propenyl substituted with 0–2 $R^4$, 2-propenyl substituted with 0–2 $R^4$, 1-propynyl substituted with 0–2 $R^4$, 2-propynyl substituted with 0–2 $R^4$;

$R^3$ is H;

$R^{3a}$ is H, F, Cl, or Br;

$R^{3b}$ is H;

$R^{3c}$ is H;

$R^{3e}$, at each occurrence, is independently selected from the group H, methyl, and ethyl, —OH, $C_{1-4}$ alkoxy, $OCF_3$, F, Cl, Br, I, —$NR^5R^{5a}$, —$NO_2$, —CN, —C(O)$R^6$, —NHC(O)$R^7$, —NHC(O)$NR^5R^{5a}$, —$NHSO_2R^{10}$, and —$SO_2NR^5R^{5a}$;

$R^{3f}$ is selected from H, F, Cl, OH, —$OR^{11}$, —$OSO_2$methyl, —$NR^{12}R^{12a}$, and —NHC(O)$NR^5R^{5a}$;

$R^4$ is selected from H, F, —OH, —O—i-propyl, —OS(O)$_2CH_3$, cyclopropyl substituted with 0–1 $R^{3e}$, cyclobutyl substituted with 0–1 $R^{3e}$, phenyl, N-morpholinyl, 2-pyridyl, 3-pyridyl, 4-pyridiyl, N2-methyl-N1-piperidinyl, N-piperidinyl, N-pyrrolidinyl, and N-piperazinyl;

$R^8$ is H;

$R^{11}$ is selected from H, methyl, ethyl, propyl, i-propyl, $CH_2$cyclopropyl, and cyclopropyl; and $R^{12}$ and $R^{12a}$ are independently selected from H, methyl, ethyl, propyl, i-propyl, and cyclopropyl.

[7] Another embodiment of the present invention includes those compounds wherein the compound is of formula (Ic):

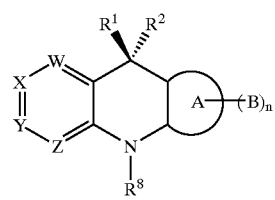

(Ic)

[8] Another embodiment of the present invention includes those compounds wherein the compound is of formula (Id):

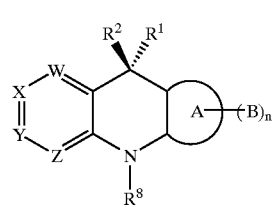

(Id)

Another embodiment of the present invention include compounds of formula (I) wherein:

ring A is selected from:

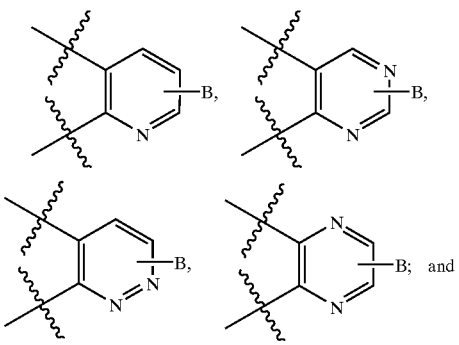

ring A is optionally in an N-oxide form.

Another embodiment of the present invention include compounds of formula (I) wherein:
ring A is selected from:

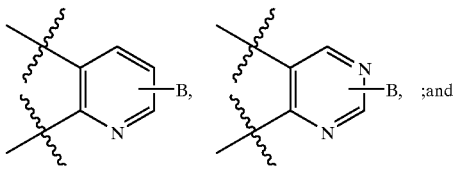

ring A is optionally in an N-oxide form.

In another embodiment, the present invention provides ring A is

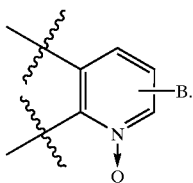

In another embodiment, the present invention provides ring A is

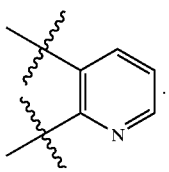

In another embodiment, the present invention provides ring A is

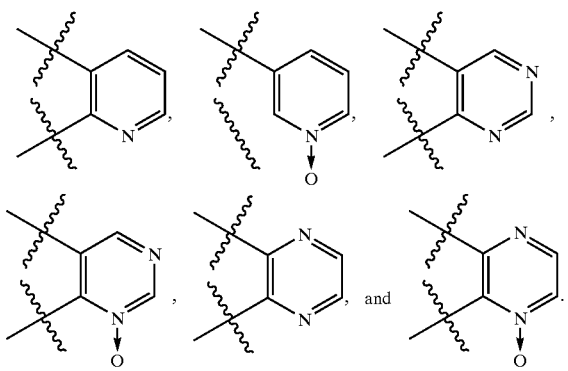

In another embodiment, the present invention provides the N on ring A is in the N-oxide form.

In another embodiment, the present invention provides the N on ring A is not in the N-oxide form.

Another embodiment of the present invention include compounds of formula (I) wherein:
W is $CR^3$;
X is $CR^{3a}$;
Y is $CR^{3b}$; and
Z is $CR^{3c}$.

Another embodiment of the present invention include compounds of formula (I) wherein:
W is $CR^3$;
X is $CR^{3a}$;
Y is $CR^{3b}$; and
Z is selected from N and $CR^{3c}$.

Another embodiment of the present invention include compounds of formula (I) wherein:
$R^2$ is selected from the group $-R^{2c}$, $-OH$, $-CN$, $OR^{2c}$, $-OCHR^{2a}R^{2b}$, $-OCH_2CHR^{2a}R^{2b}$, $-O(CH_2)_2CHR^{2a}R^{2b}$, $-OCHR^{2a}CH=CHR^{2b}$, $-OCHR^{2a}CH=CHR^{2c}$, $-OCHR^{2a}C\equiv CR^{2b}$, $-NR^{2a}R^{2c}$, $-SR^{2c}$, $-SCHR^{2a}R^{2b}$, $-SCH_2CHR^{2a}R^{2b}$, $-SCHR^{2a}CH=CHR^{2b}$, $-SCHR^{2a}CH=CHR^{2c}$, and $-SCHR^{2a}C\equiv CR^{2b}$.

Another embodiment of the present invention include compounds of formula (I) wherein:
$R^2$ is selected from the group $-R^{2c}$, $-OH$, $-CN$, $-OR^{2c}$, $-OCHR^{2a}R^{2b}$, $-OCH_2CHR^{2a}R^{2b}$, $-OCHR^{2a}CH=CHR^{2b}$, $-OCHR^{2a}CH=CHR^{2c}$, $-OCHR^{2a}C\equiv CR^{2b}$, and $-NR^{2a}R^{2c}$.

Another embodiment of the present invention include compounds of formula (I) wherein:
$R^2$ is selected from the group $-R^{2c}$, $-OR^{2c}$, $-OCHR^{2a}R^{2b}$, $OCH_2CHR^{2a}R^{2b}$, $-OCHR^{2a}CH=CHR^{2b}$, $-OCHR^{2a}CH=CHR^{2c}$, $-OCHR^{2a}C\equiv CR^{2b}$, and $-NR^{2a}R^{2c}$.

Another embodiment of the present invention include compounds of formula (I) wherein:
$R^{2c}$ is selected from the group methyl substituted with 0–3 $R^{3f}$, $C_{1-5}$ alkyl substituted with 0–3 $R^4$, $C_{2-5}$ alkenyl substituted with 0–2 $R^4$, $C_{2-5}$ alkynyl substituted with 0–1 $R^4$, $C_{3-6}$ cycloalkyl substituted with 0–2 $R^{3d}$, and phenyl substituted with 0–2 $R^{3d}$.

Another embodiment of the present invention include compounds of formula (I) wherein:
$R^{2c}$ is selected from the group methyl substituted with 0–3 $R^{3f}$, $C_{1-3}$ alkyl substituted with 0–3 $R^4$, $C_{2-3}$ alkenyl substituted with 1 $R^4$, and $C_{2-3}$ alkynyl substituted with 1 $R^4$.

Another embodiment of the present invention include compounds of formula (I) wherein:
$R^{2c}$ is selected from the group methyl substituted with 0–2 $R^{3f}$, ethyl substituted with 0–3 $R^4$, propyl substituted with 0–2 $R^4$, ethenyl substituted with 0–2 $R^4$, 1-propenyl substituted with 0–2 $R^4$, 2-propenyl substituted with 0–2 $R^4$, ethynyl substituted with 0–2 $R^4$, 1-propynyl substituted with 0–2 $R^4$, 2-propynyl substituted with 0–2 $R^4$, and cyclopropyl substituted with 0–1 $R^{3d}$.

Another embodiment of the present invention include compounds of formula (I) wherein:
$R^4$ is selected from the group H, Cl, F, $CH_3$, $CH_2CH_3$, cyclopropyl substituted with 0–1 $R^{3e}$, 1-methylcyclopropyl substituted with 0–1 $R^{3e}$, cyclobutyl substituted with 0–1 $R^{3e}$, phenyl substituted with 0–2 $R^{3e}$, and a 5–6 membered heterocyclic system containing 1–3 heteroatoms selected from the group O, N, and S, substituted with 0–1 $R^{3e}$, wherein the heterocyclic system is selected from the group 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, 2-imidazolyl, morpholinyl, piperidinyl, pyrrolidinyl, and piperazinyl.

Another embodiment of the present invention include compounds of formula (I) wherein:
$R^8$ is H.

Another embodiment of the present invention include compounds of formula (I) wherein:
$R^4$ is selected from H, F, $-OH$, $-O-i$-propyl, $-OS(O)_2CH_3$, cyclopropyl substituted with 0–1 $R^{3e}$, cyclobutyl substituted with 0–1 $R^{3e}$, phenyl, N-morpholinyl, 2-pyridyl, 3-pyridyl, 4-pyridiyl, N2-methyl-N1-piperidinyl, N-piperidinyl, N-pyrrolidinyl, and N-piperazinyl; and

[7] Compounds of the present invention include compounds of formula (I), or a stereoisomeric form, mixtures of stereoisomeric forms, complexes, prodrug forms or pharmaceutically acceptable salt form thereof, or N-oxide forms thereof, wherein the compound of formula (I) is selected from:

the compounds of the Examples, Table 1, Table 2, Table 3, Table 4, and

7-Chloro-5-(cyclopropylmethoxy)-5,10-dihydro-5-(trifluoromethyl)benzo[b][1,8]naphthyridine, 7-Chloro-5-(benzyloxy)-5,10-dihydro-5-(trifluoromethyl)benzo[b][1,8]naphthyridine, 7-Chloro-5-(cyclobutylmethoxy)-5,10-dihydro-5-(trifluoromethyl)benzo[b][1,8]naphthyridine, 7-Chloro-5-(ethoxy)-5,10-dihydro-5-(trifluoromethyl)benzo[b][1,8] naphthyridine, 7-Chloro-5-(hydroxy)-5,10-dihydro-5-(trifluoromethyl)benzo[b][1,8]naphthyridine, 7-Chloro-5-(n-propoxy)-5,10-dihydro-5-(trifluoromethyl)benzo[b][1,8]naphthyridine, 7-Chloro-5-(i-propoxy)-5,10-dihydro-5-(trifluoromethyl)benzo[b][1,8]naphthyridine, 7-Chloro-5-(butyl)-5,10-dihydro-5-(trifluoromethyl)benzo[b][1,8]naphthyridine, 7-Chloro-5-(methoxy)-5,10-dihydro-5-(trifluoromethyl)benzo[b][1,8]naphthyridine, 7-Chloro-5(S)-(cyclopropylmethoxy)-5,10-dihydro-5-(trifluoromethyl)benzo[b][1,8]naphthyridine, 7-Chloro-5(R)-(cyclopropylmethoxy)-5,10-dihydro-5-(trifluoromethyl)benzo[b][1,8]naphthyridine, 7-Chloro-5-(2-cyclopropylethyl)-5,10-dihydro-5-(trifluoromethyl)benzo[b][1,8]naphthyridine, 7-Chloro-5-(2,2,2-trifluoroethoxy)-5,10-dihydro-5-(trifluoromethyl)benzo[b][1,8]naphthyridine, 7-Chloro-5-(propargoxy)-5,10-dihydro-5-(trifluoromethyl)benzo[b][1,8]naphthyridine, 7-Chloro-5-(ethyl)-5,10-dihydro-5-(trifluoromethyl)benzo[b][1,8]naphthyridine, 7-Chloro-5-(cyclopropylmethoxy)-2-methyl-5,10-dihydro-5-(trifluoromethyl)benzo[b][1,8]naphthyridine, 7-Chloro-5-(n-butyl)-2-methyl-5,10-dihydro-5-(trifluoromethyl)benzo[b][1,8]naphthyridine, 7-Chloro-5-(2-cyclopropylethyl)-2-methyl-5,10-dihydro-5-(trifluoromethyl)benzo[b][1,8]naphthyridine, 7-Chloro-5-(cyclopropylmethoxy)-5,10-dihydro-2-(methylthio)-5-(trifluoromethyl)pyrimido[4,5-b]quinoline, 7-Chloro-5-(i-butoxy)-5,10-dihydro-2-(methylthio)-5-(trifluoromethyl)pyrimido[4,5-b]quinoline, 7-Chloro-5-(benzyloxy)-5,10-dihydro-2-(methylthio)-5-(trifluoromethyl)pyrimido[4,5-b]quinoline, 7-Chloro-5-(2-pyridylmethoxy)-5,10-dihydro-2-(methylthio)-5-(trifluoromethyl)pyrimido[4,5-b]quinoline, 7-Chloro-5-(cyclopropylmethoxy)-5,10-dihydro-5-(trifluoromethyl)pyrimido[4,5-b]quinoline, 7-Chloro-5-(cyclopropylamino)-5,10-dihydro-5-(trifluoromethyl)benzo[b][1,8]naphthyridine, 7-Chloro-5-(i-propylamino)-5,10-dihydro-5-(trifluoromethyl)benzo[b][1,8]naphthyridine, 7-Chloro-5-(N,N-dimethylaminoethoxy)-5,10-dihydro-5-(trifluoromethyl)benzo[b][1,8]naphthyridine, 7-Chloro-5-(N-morpholinylethylamino)-5,10-dihydro-5-(trifluoromethyl)benzo[b][1,8]naphthyridine, 7-Chloro-5-((1-methylcyclopropyl)methoxy)-5,10-dihydro-5-(trifluoromethyl)benzo[b][1,8]naphthyridine, 7-Chloro-5-(3,3,3-trifluoroprop-1-oxy)-5,10-dihydro-5-(trifluoromethyl)benzo[b][1,8]naphthyridine, 7-Chloro-5-(cyclopropylmethylamino)-5,10-dihydro-5-(trifluoromethyl)benzo[b][1,8]naphthyridine, 7-Chloro-5-(methylamino)-5,10-dihydro-5-(trifluoromethyl)benzo[b][1,8]naphthyridine, 7-Chloro-5-(ethylamino)-5,10-dihydro-5-(trifluoromethyl)benzo[b][1,8]naphthyridine, (S)-7-Chloro-5-(cyclopropylethyl)-5,10-dihydro-5-(trifluoromethyl)benzo[b][1,8]naphthyridine, (R)-7-Chloro-5-(cyclopropylethyl)-5,10-dihydro-5-(trifluoromethyl)benzo[b][1,8]naphthyridine, 7-Fluoro-5-(cyclopropylmethoxy)-5,10-dihydro-5-(trifluoromethyl)benzo[b][1,8]naphthyridine, 7-Fluoro-5-(cyclopropylethoxy)-5,10-dihydro-5-(trifluoromethyl)benzo[b][1,8]naphthyridine, 7-Fluoro-5-(allyloxy)-5,10-dihydro-5-(trifluoromethyl)benzo[b][1,8]naphthyridine, 7-Chloro-5-(phenylamino)-5,10-dihydro-5-(trifluoromethyl)benzo[b][1,8]naphthyridine, 7-Chloro-5-(cyclopropylmethoxy)-2-methyl-5,10-dihydro-5-(trifluoromethyl)benzo[b][1,8]naphthyridine, 7-Chloro-5-(n-butyl)-2-methyl-5,10-dihydro-5-(trifluoromethyl)benzo[b][1,8]naphthyridine, 7-Chloro-5-(cyclopropylethyl)-2-methyl-5,10-dihydro-5-(trifluoromethyl)benzo[b][1,8]naphthyridine, 7-Chloro-5-(cyclobutylmethoxy)-5,10-dihydro-5-(trifluoromethyl)pyrimido[4,5-b]quinoline, 7-Chloro-5-(methoxy)-5,10-dihydro-5-(trifluoromethyl)pyrimido[4,5-b]quinoline, (S)-7-Chloro-5-(cyclopropylmethoxy)-5,10-dihydro-5-(trifluoromethyl)pyrimido[4,5-b]quinoline, (R)-7-Chloro-5-(cyclopropylmethoxy)-5,10-dihydro-5-(trifluoromethyl)pyrimido[4,5-b]quinoline, 7-Chloro-5-(N-piperidinylethoxy)-5,10-dihydro-5-(trifluoromethyl)pyrimido[4,5-b]quinoline, 7-Chloro-5-(N-pyrrolidinylethoxy)-5,10-dihydro-5-(trifluoromethyl)pyrimido[4,5-b]quinoline, 7-Chloro-5-((4-methylpiperazin-1-yl)prop-1-oxy)-5,10-dihydro-5-(trifluoromethyl)pyrimido[4,5-b]quinoline, 7-Chloro-5-(prop-1-oxy)-5,10-dihydro-5-(trifluoromethyl)pyrimido[4,5-b]quinoline, 7-Chloro-5-(N,N-dimethylaminoprop-1-yl)-5,10-dihydro-5-(trifluoromethyl)pyrimido[4,5-b]quinoline, 7-Chloro-5-(benzyloxy)-5,10-dihydro-5-(trifluoromethyl)pyrimido[4,5-b]quinoline, 7-Chloro-5-(3-pyridinylmethyl)-5,10-dihydro-5-(trifluoromethyl)pyrimido[4,5-b]quinoline, 7-Chloro-5-(allyloxy)-5,10-dihydro-5-(trifluoromethyl)pyrimido[4,5-b]quinoline, 7-Chloro-5-(propargoxy)-5,10-dihydro-5-(trifluoromethyl)pyrimido[4,5-b]quinoline, and 7-Chloro-5-(N,N-dimethylaminoethyl)-5,10-dihydro-5-(trifluoromethyl)pyrimido[4,5-b]quinoline;

7-Chloro-5-cyclopropylmethoxy-5-trifluoromethyl-5,10-dihydro-benzo[b][1,8]naphthyridine 1-oxide;

5-Allyloxy-7-fluoro-5-trifluoromethyl-5,10-dihydro-benzo[b][1,8]naphthyridine;

7-Fluoro-5-trifluoromethyl-5,10-dihydro-benzo[b][1,8]naphthyridine-5-carbonitrile;

7-Fluoro-5-trifluoromethyl-5,10-dihydro-benzo[b][1,8]naphthyridin-5-ol;

5-Cyclopropylmethoxy-7-fluoro-5-trifluoromethyl-5,10-dihydro-benzo[b][1,8]naphthyridine 1-oxide;

7-Chloro-5-prop-2-ynyloxy-5-trifluoromethyl-5,10-dihydro-benzo[b][1,8]naphthyridine 1-oxide;

7-Chloro-5-(1-methyl-cyclopropylmethoxy)-5-trifluoromethyl-5,10-dihydro-benzo[b][1,8]naphthyridine 1-oxide;

7-Chloro-5-(2-cyclopropyl-ethoxy)-5-trifluoromethyl-5,10-dihydro-benzo[b][1,8]naphthyridine 1-oxide;

(7-Chloro-5-trifluoromethyl-5,10-dihydro-benzo[b][1,8]naphthyridin-5-yl)-isopropyl-amine;

(7-Chloro-5-trifluoromethyl-5,10-dihydro-benzo[b][1,8]naphthyridin-5-yl)-cyclobutylmethyl-amine;

7-Chloro-5-(2-cyclopropyl-ethyl)-5-trifluoromethyl-5,10-dihydro-benzo[b][1,8]naphthyridine 1-oxide;

5-Cyclobutylmethoxy-7-fluoro-5-trifluoromethyl-5,10-dihydro-benzo[b][1,8]naphthyridine 1-oxide;

(7-Fluoro-1-oxy-5-trifluoromethyl-5,10-dihydro-benzo[b][1,8]naphthyridin-5-yl)-isopropyl-amine;

5-Cyclobutylmethoxy-7-fluoro-5-trifluoromethyl-5,10-dihydro-benzo[b][1,8]naphthyridin-2-ol;

7-Chloro-5-(pyridin-2-ylmethoxy)-5-trifluoromethyl-5,10-dihydro-benzo[b][1,8]naphthyridine;

5-Butyl-7-fluoro-5-trifluoromethyl-5,10-dihydro-benzo[b][1,8]naphthyridine;

7-Chloro-1-oxy-5-trifluoromethyl-5,10-dihydro-benzo[b][1,8]naphthyridin-5-ol;

7-Chloro-5-cyclopropylmethoxy-5-trifluoromethyl-5,10-dihydro-benzo[b][1,8]naphthyridine 1-oxide;

7-Chloro-5-pyridin-2-ylmethyl-5-trifluoromethyl-5,10-dihydro-benzo[b][1,8]naphthyridine 1-oxide;

7-Fluoro-5-pyridin-2-ylmethyl-5-trifluoromethyl-5,10-dihydro-benzo[b][1,8]naphthyridine;

5-Cyclopropylmethoxy-7-fluoro-5-trifluoromethyl-5,10-dihydro-benzo[b][1,8]naphthyridine 1-oxide;

7-Chloro-5-pyridin-2-ylmethyl-5-trifluoromethyl-5,10-dihydro-benzo[b][1,8]naphthyridine;

3,7-Dichloro-5-cyclopropylmethoxy-5-trifluoromethyl-5,10-dihydro-benzo[b][1,8]naphthyridine;

3,7-Dichloro-5-cyclopropylmethoxy-5-trifluoromethyl-5,10-dihydro-benzo[b][1,8]naphthyridine 1-oxide;

3,7-Dichloro-5-pentyl-5-trifluoromethyl-5,10-dihydro-benzo[b][1,8]naphthyridine 1-oxide;

5-(2-Cyclopropyl-ethyl)-7-fluoro-5-trifluoromethyl-5,10-dihydro-benzo[b][1,8]naphthyridine;

5-(2-Cyclopropyl-ethyl)-7-fluoro-5-trifluoromethyl-5,10-dihydro-benzo[b][1,8]naphthyridine 1-oxide;

3,7-Dichloro-5-cyclopropylmethoxy-5-trifluoromethyl-5,10-dihydro-benzo[b][1,8]naphthyridine 1-oxide;

5-(2-Cyclopropyl-ethyl)-7-fluoro-5-trifluoromethyl-5,10-dihydro-benzo[b][1,8]naphthyridine 1-oxide;

3-Chloro-5-cyclopropylmethoxy-7-fluoro-5-trifluoromethyl-5,10-dihydro-benzo[b][1,8]naphthyridine;

3-Chloro-5-cyclopropylmethoxy-7-fluoro-5-trifluoromethyl-5,10-dihydro-benzo[b][1,8]naphthyridine 1-oxide;

7-Chloro-5-isobutoxy-5-trifluoromethyl-5,10-dihydro-benzo[b][1,8]naphthyridine 1-oxide;

5-Butyl-7-chloro-5-trifluoromethyl-5,10-dihydro-benzo[b][1,8]naphthyridine 1-oxide;

(S) 3-Chloro-5-cyclopropylmethoxy-7-fluoro-5-trifluoromethyl-5,10-dihydro-benzo[b][1,8]naphthyridine 1-oxide;

(7-Chloro-5-trifluoromethyl-5,10-dihydro-benzo[b][1,8]naphthyridin-5-yl)-methanol;

7-Fluoro-5-isobutoxy-5-trifluoromethyl-5,10-dihydro-benzo[b][1,8]naphthyridine 1-oxide;

7-Fluoro-5-isopropoxy-5-trifluoromethyl-5,10-dihydro-benzo[b][1,8]naphthyridine 1-oxide;

Methanesulfonic acid 7-chloro-5-trifluoromethyl-5,10-dihydro-benzo[b][1,8]naphthyridin-5-ylmethyl ester;

7-Chloro-5-isopropoxy-5-trifluoromethyl-5,10-dihydro-benzo[b][1,8]naphthyridine 1-oxide;

(7-Fluoro-5-trifluoromethyl-5,10-dihydro-benzo[b][1,8]naphthyridin-5-yl)-acetonitrile;

7-Fluoro-5-trifluoromethyl-5,10-dihydro-benzo[b][1,8]naphthyridine-5-carbaldehyde;

3-Bromo-5-cyclopropylmethoxy-7-fluoro-5-trifluoromethyl-5,10-dihydro-benzo[b][1,8]naphthyridine 1-oxide;

5-Butyl-7-fluoro-5-trifluoromethyl-5,10-dihydro-benzo[b][1,8]naphthyridine 1-oxide;

5-Diisopropoxymethyl-7-fluoro-5-trifluoromethyl-5,10-dihydro-benzo[b][1,8]naphthyridine;

7-Fluoro-5-isopropoxymethyl-5-trifluoromethyl-5,10-dihydro-benzo[b][1,8]naphthyridine 1-oxide;

7-Chloro-5-isobutyl-5-trifluoromethyl-5,10-dihydro-benzo[b][1,8]naphthyridine 1-oxide;

7-Chloro-5-propoxy-5-trifluoromethyl-5,10-dihydro-benzo[b][1,8]naphthyridine 1-oxide;

(S) 7-Fluoro-5-isobutoxy-5-trifluoromethyl-5,10-dihydro-benzo[b][1,8]naphthyridine 1-oxide;

(R) 7-Fluoro-5-isobutoxy-5-trifluoromethyl-5,10-dihydro-benzo[b][1,8]naphthyridine 1-oxide;

(7-Chloro-5-trifluoromethyl-5,10-dihydro-benzo[b][1,8]naphthyridin-5-yl)-acetaldehyde;

7-Chloro-5-(2,2-diisopropoxy-ethyl)-5-trifluoromethyl-5,10-dihydro-benzo[b][1,8]naphthyridine;

7-Chloro-5-(2-isopropoxy-ethyl)-5-trifluoromethyl-5,10-dihydro-benzo[b][1,8]naphthyridine;

2-(7-Chloro-5-trifluoromethyl-5,10-dihydro-benzo[b][1,8]naphthyridin-5-yl)-ethanol;

7-Chloro-5-(2-isopropoxy-ethyl)-5-trifluoromethyl-5,10-dihydro-benzo[b][1,8]naphthyridine 1-oxide;

(R) 7-Fluoro-5-(2-isopropoxy-ethyl)-5-trifluoromethyl-5,10-dihydro-benzo[b][1,8]naphthyridine 1-oxide;

(7-Fluoro-5-trifluoromethyl-5,10-dihydro-benzo[b][1,8]naphthyridin-5-yl)-acetic acid tert-butyl ester;

(7-Fluoro-1-oxy-5-trifluoromethyl-5,10-dihydro-benzo[b][1,8]naphthyridin-5-yl)-acetic acid tert-butyl ester;

(7-Fluoro-5-trifluoromethyl-5,10-dihydro-benzo[b][1,8]naphthyridin-5-yl)-acetic acid;

7-Chloro-5-cyclopropylmethoxy-2-methylsulfanyl-5-trifluoromethyl-5,10-dihydro-pyrimido[4,5-b]quinoline;

7-Chloro-5-isobutoxy-2-methylsulfanyl-5-trifluoromethyl-5,10-dihydro-pyrimido[4,5-b]quinoline;

5-Benzyloxy-7-chloro-2-methylsulfanyl-5-trifluoromethyl-5,10-dihydro-pyrimido[4,5-b]quinoline;

7-Chloro-2-methylsulfanyl-5-(pyridin-2-ylmethoxy)-5-trifluoromethyl-5,10-dihydro-pyrimido[4,5-b]quinoline;

7-Chloro-5-cyclopropylmethoxy-5-trifluoromethyl-5,10-dihydro-pyrimido[4,5-b]quinoline 1-oxide;

7-Chloro-5-cyclopropylmethoxy-5-(1,1-difluoro-ethyl)-5,10-dihydro-benzo[b][1,8]naphthyridine 1-oxide;

5-Cyclopropylmethoxy-5-(1,1-difluoro-ethyl)-7-fluoro-5,10-dihydro-benzo[b][1,8]naphthyridine;

5-Cyclopropylmethoxy-5-(1,1-difluoro-ethyl)-7-fluoro-5,10-dihydro-benzo[b][1,8]naphthyridine 1-oxide;

7-Chloro-5-(1,1-difluoro-ethyl)-5-isobutoxy-5,10-dihydro-benzo[b][1,8]naphthyridine;

7-Chloro-5-(1,1-difluoro-ethyl)-5-isobutoxy-5,10-dihydro-benzo[b][1,8]naphthyridine 1-oxide;

(R) 7-Chloro-5-cyclopropylmethoxy-5-(1,1-difluoro-ethyl)-5,10-dihydro-benzo[b][1,8]naphthyridine 1-oxide;

(S) 7-Chloro-5-cyclopropylmethoxy-5-(1,1-difluoro-ethyl)-5,10-dihydro-benzo[b][1,8]naphthyridine 1-oxide;

3-Chloro-10-cyclopropylmethoxy-10-trifluoromethyl-9,10-dihydro-1,8,9-triaza-anthracene;

3-Chloro-10-cyclopropylmethoxy-10-trifluoromethyl-9,10-dihydro-1,8,9-triaza-anthracene 8-oxide;

3,6-Dichloro-10-cyclopropylmethoxy-10-trifluoromethyl-9,10-dihydro-1,8,9-triaza-anthracene;

3-Chloro-10-isobutoxy-10-trifluoromethyl-9,10-dihydro-1,8,9-triaza-anthracene;

3-Chloro-10-isobutoxy-10-trifluoromethyl-9,10-dihydro-1,8,9-triaza-anthracene 8-oxide;

7-Chloro-5-difluoromethyl-5-isopropoxymethyl-5,10-dihydro-benzo[b][1,8]naphthyridine;

7-Chloro-5-difluoromethyl-5-isopropoxymethyl-5,10-dihydro-benzo[b][1,8]naphthyridine 1-oxide;

7-chloro-1,5-dihydro-5-(N-ethylaminomethyl)-5-(trifluoromethyl)benzo[b][1,8]napthyridine;

7-chloro-5,10-dihydro-5-(N-isopropylaminomethyl)-5-(trifluoromethyl)benzo[b][1,8]napthyridine;

7-chloro-5,10-dihydro-5-(N-isopropyl-N-ethylaminomethyl)-5-(trifluoromethyl)benzo[b][1,8]napthyridine;

7-chloro-5-(N,N-diethylaminomethyl)-5,10-dihydro-5-(trifluoromethyl)benzo[b][1,8]napthyridine;

5-(acetamidomethyl)-7-chloro-5,10-dihydro-5-(trifluoromethyl)benzo[b][1,8]napthyridine;

5,10-dihydro-7-fluoro-5-(N-methylsulfonylmethyl)-5-(trifluoromethyl)benzo[b][1,8]napthyridine;

5,10-dihydro-7-fluoro-5-(isopropylamidomethyl)-5-(trifluoromethyl)benzo[b][1,8]napthyridine;

5,10-dihydro-7-fluoro-5-(isopropylguanadinomethyl)-5-(trifluormethyl)benzo[b][1,8]napthyridine;

1,5-dihydro-7-fluoro-5-(N-isopropylmethyl)-5-(trifluoromethyl)benzo[b][1,8]napthyridine-1-(N-oxide);

5-(N,N-diethylaminomethyl)-5,10-dihydro-7-fluoro-5-(trifluoromethyl)benzo[b][1,8]napthyridine-1-(N-oxide);

5,10-dihydro-5-(N,N-dimethylaminomethyl)-7-fluoro-5-(trifluoromethyl)benzo[b][1,8]napthyridine-1-(N-oxide);

7-chloro-5,10-dihydro-5-(N-isopropylaminomethyl)-5-(trifluoromethyl)benzo[b][1,8]napthyridine-1-(N-oxide);

7-chloro-5-(N,N-diethylaminomethyl)-5,10-dihydro-5-(trifluoromethyl)benzo[b][1,8]napthyridine-1-(N-oxide); and 7-chloro-5,10-dihydro-5-(N,N-dimethylaminomethyl)-5-(trifluoromethyl)benzo[b][1,8]napthyridine-1-(N-oxide.

Another embodiment of the present invention are those compounds wherein the heterocyclic ring A is in an N-oxide form.

The present invention also provides a novel pharmaceutical composition comprising a pharmaceutically acceptable carrier and a therapeutically effective amount of a compound of formula (I) or a pharmaceutically acceptable salt form thereof The compositions and methods of use comprising the compounds of the present invention include compositions and methods of use comprising the compounds of the present invention and stereoisomeric forms thereof, mixtures of stereoisomeric forms thereof, complexes thereof, crystalline forms thereof, prodrug forms thereof and pharmaceutically acceptable salt forms thereof In another embodiment, the present invention provides a novel method for treating HIV infection which comprises administering to a host in need of such treatment a therapeutically effective amount of a compound of formula (I) or a pharmaceutically acceptable salt form thereof In another embodiment, the present invention provides a novel method of treating HIV infection which comprises administering, in combination, to a host in need thereof a therapeutically effective amount of:

(a) a compound of formula (I); and (b) at least one compound selected from the group consisting of HIV reverse transcriptase inhibitors and HIV protease inhibitors.

Preferred reverse transcriptase inhibitors useful in the above method of treating HIV infection are selected from the group AZT, ddC, ddI, d4T, 3TC, delavirdine, efavirenz, nevirapine, Ro 18,893, trovirdine, MKC-442, HBY 097, HBY1293, GW867, ACT, UC-781, UC-782, RD4-2025, MEN 10979, and AG1549 (S1153). Preferred protease inhibitors useful in the above method of treating HIV infection are selected from the group saquinavir, ritonavir, indinavir, amprenavir, nelfinavir, palinavir, BMS-232623, GS3333, KNI-413, KNI-272, LG-71350, CGP-61755, PD 173606, PD 177298, PD 178390, PD 178392, U-140690, and ABT-378.

In another embodiment, the reverse transcriptase inhibitor is selected from the group AZT, efavirenz, and 3TC and the protease inhibitor is selected from the group saquinavir, ritonavir, nelfinavir, and indinavir.

In another embodiment, the reverse transcriptase inhibitor is AZT.

In another embodiment, the protease inhibitor is indinavir.

In another embodiment, the present invention provides a pharmaceutical kit useful for the treatment of HIV infection, which comprises a therapeutically effective amount of:

(a) a compound of formula (I); and, (b) at least one compound selected from the group consisting of HIV reverse transcriptase inhibitors and HIV protease inhibitors, in one or more sterile containers.

In another embodiment, the present invention provides novel tricyclic compounds for use in therapy.

In another embodiment, the present invention provides the use of novel tricyclic compounds for the manufacture of a medicament for the treatment of HIV infection.

The invention may be embodied in other specific forms without departing from the spirit or essential attributes thereof. This invention also encompasses all combinations of preferred aspects of the invention noted herein. It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments.

DEFINITIONS

It will be appreciated that the compounds of the present invention contain an asymmetrically substituted carbon atom, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

The present invention is intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

As used herein, the following terms and expressions have the indicated meanings.

As used herein, "alkyl" is intended to include both branched and straight-chain saturated aliphatic hydrocarbon groups having the specified number of carbon atoms. By way of illustration, the term "$C_{1-10}$ alkyl" or "$C_1-C_{10}$ alkyl" is intended to include $C_1$, $C_2$, $C_3$, $C_4$, $C_5$, $C_6$, $C_7$, $C_8$, $C_9$, and $C_{10}$ alkyl groups. "$C_{1-4}$ alkyl" is intended to include $C_1$, $C_2$, $C_3$, and $C_4$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, 2,2,2-trifluoroethyl, 3,3,3-trifluoropropyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. "Alkenyl" is intended to include hydrocarbon chains of either a straight or branched configuration and one or more unsaturated carbon-carbon bonds which may occur in any stable point along the chain, such as ethenyl, propenyl and the like. $C_{2-10}$ alkenyl, is intended to include $C_2$, $C_3$, $C_4$, $C_5$, $C_6$, $C_7$, $C_8$, $C_9$, and $C_{10}$ alkenyl groups. "Alkynyl" is intended to include hydrocarbon chains of either a straight or branched configuration and one or more triple carbon-carbon bonds which may occur in any stable point along the chain, such as ethynyl, propynyl and the like. $C_{2-10}$ alkynyl, is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo and iodo. "Counterion" is used to represent a small, negatively charged species such as chloride, bromide, hydroxide, acetate, sulfate and the like.

As used herein, "aryl" or "aromatic residue" is intended to mean an aromatic moiety containing the specified number of carbon atoms, such as phenyl or naphthyl. As used herein, "carbocycle" or "carbocyclic residue" is intended to mean any stable 3, 4, 5, 6, or 7-membered monocyclic or bicyclic or 7, 8, 9, 10, 11, 12 or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, or tetrahydronaphthyl.

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated partially unsaturated or unsaturated (aromatic), and which consists of carbon atoms and 1, 2, 3, or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. An oxo group may be a substituent on a nitrogen heteroatom to form an N-oxide. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, O and S. It is preferred that the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, 5,10-dihydro-benzo[b][1,8] naphthyridinyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4- oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrimido[4,5-b]quinolinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

As used herein, "HIV reverse transcriptase inhibitor" is intended to refer to both nucleoside and non-nucleoside inhibitors of HIV reverse transcriptase (RT). Examples of nucleoside RT inhibitors include, but are not limited to, AZT, ddC, ddI, d4T, and 3TC. Examples of non-nucleoside RT inhibitors include, but are no limited to, delavirdine (Pharmacia and Upjohn U90152S), efavirenz (DuPont), nevirapine (Boehringer Ingelheim), Ro 18,893 (Roche), trovirdine (Lilly), MKC-442 (Triangle), HBY 097 (Hoechst), HBY1293 (Hoechst), GW867 (Glaxo Wellcome), ACT (Korean Research Institute), UC-781 (Rega Institute), UC-782 (Rega Institute), RD4-2025 (Tosoh Co. Ltd.), MEN 10979 (Menarini Farmaceutici) and AG1549 (S1153; Agouron).

As used herein, "HIV protease inhibitor" is intended to refer to compounds which inhibit HIV protease. Examples include, but are not limited, saquinavir (Roche, Ro31-8959), ritonavir (Abbott, ABT-538), indinavir (Merck, MK-639), amprenavir (Vertex/Glaxo Wellcome), nelfinavir (Agouron, AG-1343), palinavir (Boehringer Ingelheim), BMS-232623 (Bristol-Myers Squibb), GS3333 (Gilead Sciences), KNI-413 (Japan Energy), KNI-272 (Japan Energy), LG-71350 (LG Chemical), CGP-61755 (Ciba-Geigy), PD 173606 (Parke Davis), PD 177298 (Parke Davis), PD 178390 (Parke Davis), PD 178392 (Parke Davis), U-140690 (Pharmacia and Upjohn), and ABT-378. Additional examples include the cyclic protease inhibitors disclosed in WO93/07128, WO 94/19329, WO 94/22840, and PCT Application Number US96/03426.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention. Examples of prodrugs at $R^8$ are $C_{1-6}$ alkylcarbonyl, $C_{1-6}$ alkoxy, $C_{1-4}$ alkoxycarbonyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl.

"Stable compound" and "stable structure" are meant to indicate a compound that is sufficiently robust to survive isolation to a useful degree of purity from a reaction mixture, and formulation into an efficacious therapeutic agent. Only stable compounds are contemplated by the present invention.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

"Therapeutically effective amount" is intended to include an amount of a compound of the present invention alone or in combination with other active ingredients or an amount of the combination of compounds claimed effective to inhibit HIV infection or treat the symptoms of HIV infection in a host. The combination of compounds is preferably a synergistic combination. Synergy, as described for example by Chou and Talalay, Adv. Enzyme Regul. 22:27–55 (1984), occurs when the effect (in this case, inhibition of HIV replication) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include but are not limited to those described below. Each of the references cited below are hereby incorporated herein by reference. In the Schemes which follow, $R^1$ is shown as a $CF_3$ group, but could be any one of the presently described $R^1$ groups.

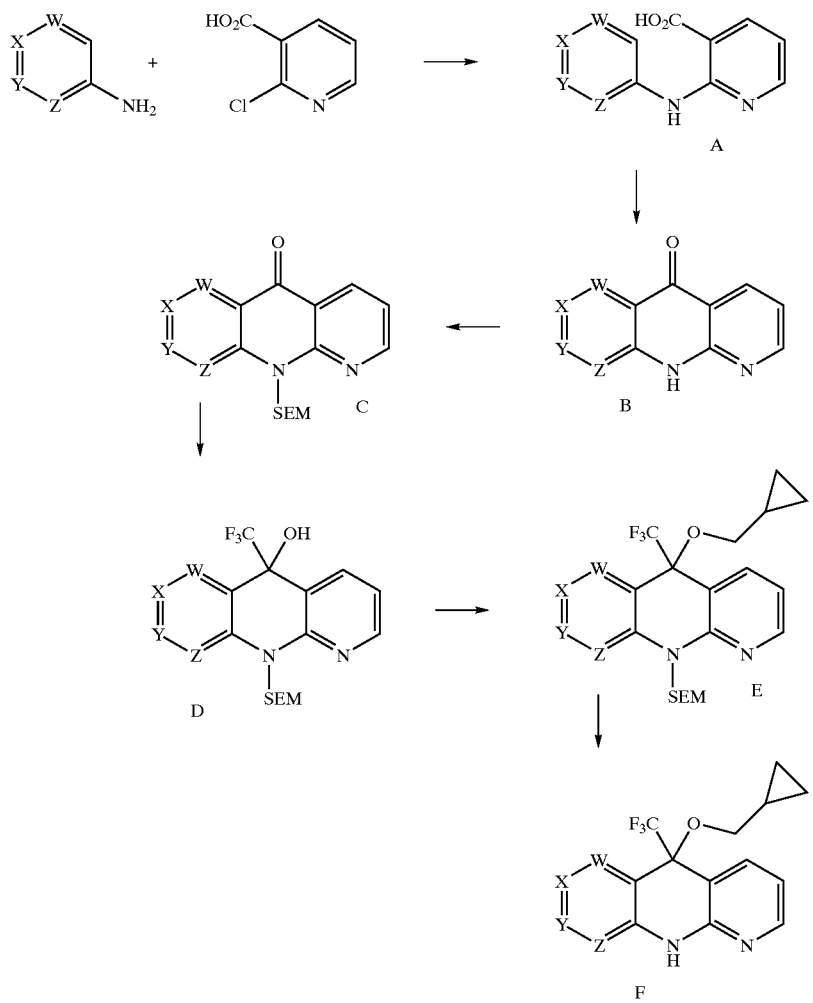

Scheme 1 illustrates the reaction between an aryl/heterocyclic amine with 2-chloronicotinic acid to obtain the di-substituted amine A which can be cyclized using PPA to give B. Protection of the amine, followed by reaction with $TMSCF_3$ in the presence of TBAF gives D, which can be alkylated using a base and an alkylhalide and then deprotected to give F.

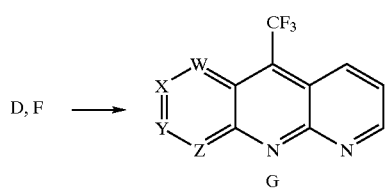

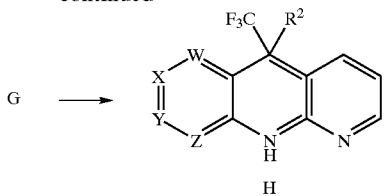

Scheme 2 illustrates the aromatization of either D or F to give the compound G. The compound G can then be alkylated either through reaction with a Grignard reagent, or alternatively, by reaction with an organometalic reagent to give H.

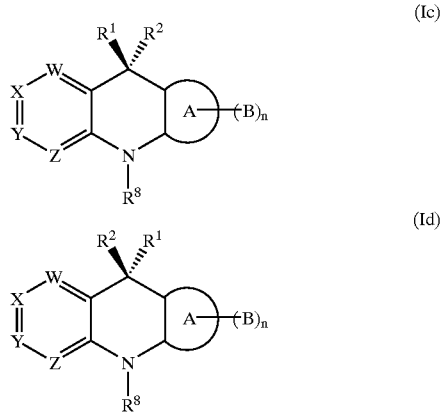

When required, separation of the diasteriomeric material can be achieved by HPLC using a chiral column or by a resolution using a resolving agent such as camphonic chloride as in Thomas J. Tucker, et al, *J. Med. Chem.* 1994, 37, 2437–2444. A chiral compound of formula (I) may also be directly synthesized using a chiral catalyst or a chiral ligand, e.g. Mark A. Huffman, et al, *J. Org. Chem.* 1995, 60, 1590–1594.

Other features of the invention will become apparent in the course of the following descriptions of exemplary embodiments which are given for illustration of the invention and are not intended to be limiting thereof.

EXAMPLES

Abbreviations used in the Examples are defined as follows: "°C" for degrees Celsius, "d" for doublet, "dd" for doublet of doublets, "eq" or "equiv" for equivalent or equivalents, "g" for gram or grams, "mg" for milligram or milligrams, "mL" for milliliter or milliliters, "H" for hydrogen or hydrogens, "hr" for hour or hours, "m" for multiplet, "M" for molar, "min" for minute or minutes, "MHz" for megahertz, "mp" for melting point, "MS" for mass spectroscopy, "nmr" or "NMR" for nuclear magnetic resonance spectroscopy, "t" for triplet, "TLC" for thin layer chromatography, "CDI" for carbonyl diimidazole, "DIEA" for diisopropylethylamine, "DIPEA" for diisopropylethylamine, "DMAP" for dimethylaminopyridine, "DME" for dimethoxyethane, "EDAC" for 1-(3-dimethylaminopropyl)-3-ethylcarbodiimide hydrochloride, "LAH" for lithium aluminium hydride, "MCPBA" is meta-chloroperbenzoic acid, "TBAF" for tetrabutylammonium fluoride, "TBS-Cl" for t-butyldimethylsilyl chloride, "TEA" for triethylamine, "PPA" for polyphosphoric acid, "SEM-Cl" for 2-(trimethylsilyl)ethoxymethyl chloride, "TMS-CF$_3$" for trifluoromethyltrimethylsilane, "THF" for tetrahydrofuran, "DMF" for dimethylformamide, "TFA" for trifluoroactic acid, "NCS" for N-chlorosuccinimide, "EtOAc" for ethyl acetate, and "LDA" for lithium diisopropylamide.

All reactions were run under a nitrogen atmosphere at room temperature and most w ere not optimized. The reactions were followed by TLC. Reactions run overnight were done so for adequate time. Reagents were used as received. Dimethylformamide, tetrahydrofuran and acetonitrile were dried over molecular sieves. All other solvents were reagent grade. Ethanol and methanol were absolute and water was deionized. Melting points were determined in open capillary tubes on a Mel-Temp apparatus and are uncorrected. Column chromatographies were done on flash silica gel. Exceptions to any of the conditions above are noted in the text. Chiral HPLC separations were done using chiral columns which gave the enantiomers in >99% EE.

The following methods are illustrated in the synthetic schemes which follow the methods. While the examples are described for specific compounds, the same methods were employed to synthesize the other compounds which are listed in the table of examples.

Example 1

Synthesis of 7-Chloro-5-(cyclopropyymethoxy)-5,10-dihydro-5-(trifluoromethyl)benzo[b][1,8]naphthyridine Method A. A mixture of the 4-chloroaniline (18.3 g, 144 mmol) and 2-chloronicotinic acid (24.6 g, 144 mmol) in toluene (250 mL) was refluxed for 3 hours. The reaction was poured into a mixture of hexane and saturated NaHCO$_3$ (200 mL and 500 mL) and it was stirred vigorously for 30 minutes. Filtration gave 1 as a light creamy white powder that was used without further purification, 32 g (85%).

Method B. A mixture of 1 (30 g, 114 mmol) in PPA (35 mL) was stirred at 170 degrees C. for 1.5 hours. The reaction was diluted with 1 N NaOH (400 mL) and the pH was adjusted to 2 with 50% NaOH then filtered. The solid cake was re-suspended in water (400 mL) and the pH adjusted to 8 with 1N NaOH. Filtration gave 2 as a light tan powder that was used without further purification, 22.8 g (82%).

Method C. To a mixture of 2 (8.31 g, 36.1 mmol) and SEM-Cl (9.55 mL, 54.2 mmol) in DMF (100 mL) was added NaH (60%, 2.89 g, 72.3 mmol). After stirring overnight, the reaction was diluted with ethyl acetate (200 mL), washed with saturated NaHCO$_3$ (3×200 mL) and saturated NaCl (50 mL), dried (MgSO$_4$) and evaporated at reduced pressure. Chromatography of the residue (hexane/ethyl acetate, 5–10%) gave a creamy foam on evaporation. It was crystallized from hexane giving 3 as creamy white needles, 9.02 g (69%).

Method D. To a solution of 3 (7.84 g, 21.8 mmol) and TMS-CF$_3$ (4.82 mL, 32.7 mmol) in chilled THF (0 degrees C., 150 mL) was added TBAF (1N in THF, 16.3 mL). After stirring for 10 minutes, the reaction was diluted with ethyl acetate (100 mL), washed with saturated NaHCO$_3$ (3×150 mL) and saturated NaCl (50 mL), dried (MgSO$_4$) and evaporated at reduced pressure giving a reddish brown powder. It was crystallized from hexane giving 4 as a light tan powder, 8.09 g (86%).

Method E. To a solution of 4 (4.00 g, 9.30 mmol) and cyclopropylmethylbromide (1.08 mL, 11.2 mmol) in DMF (50 mL) was added NaH (0.63 g, 15.7 mmol). After stirring overnight, the reaction was diluted with ethyl acetate (100 mL), washed with saturated NaHCO$_3$ (3×70 mL) and saturated NaCl (20 mL), dried (MgSO$_4$) and evaporated at reduced pressure which gave 5 as a thick light brown oil that was used without further purification.

Method F. A solution of 5 (~9.30 mmol) and TFA (5 mL) in dichloromethane (40 mL) was stirred under a glass stopper for one hour. The reaction was diluted with ethyl acetate (100 mL), washed with saturated NaHCO$_3$ (3×70 mL) and saturated NaCl (20 mL), dried (MgSO$_4$) and evaporated at reduced pressure giving a brown foam. Chromatography (hexane/ethyl acetate, 20%) gave a light yellow foam on evaporation. It was crystallized from hexane giving 6 as creamy white micro-needles, 2.06 g (63% for steps E and F).

Example 2

Synthesis of 7-Chloro-5-trifluoromethyl-benzo[b][1,8]naphthyridine

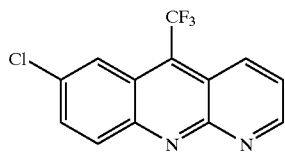

Method G. A solution of 6 (1.41 g, 3.98 mmol) in TFA (14 mL) was stirred overnight. The reaction was evaporated at reduced pressure and the residue was dissolved in dichloromethane (35 mL), washed with saturated NaHCO$_3$ (3×20 mL) and saturated NaCl (5 mL), dried (MgSO$_4$) and evaporated at reduced pressure giving a tan crystalline powder. It was triturated in hexane giving 7 as a light tan powder, 1.01 g (90%).

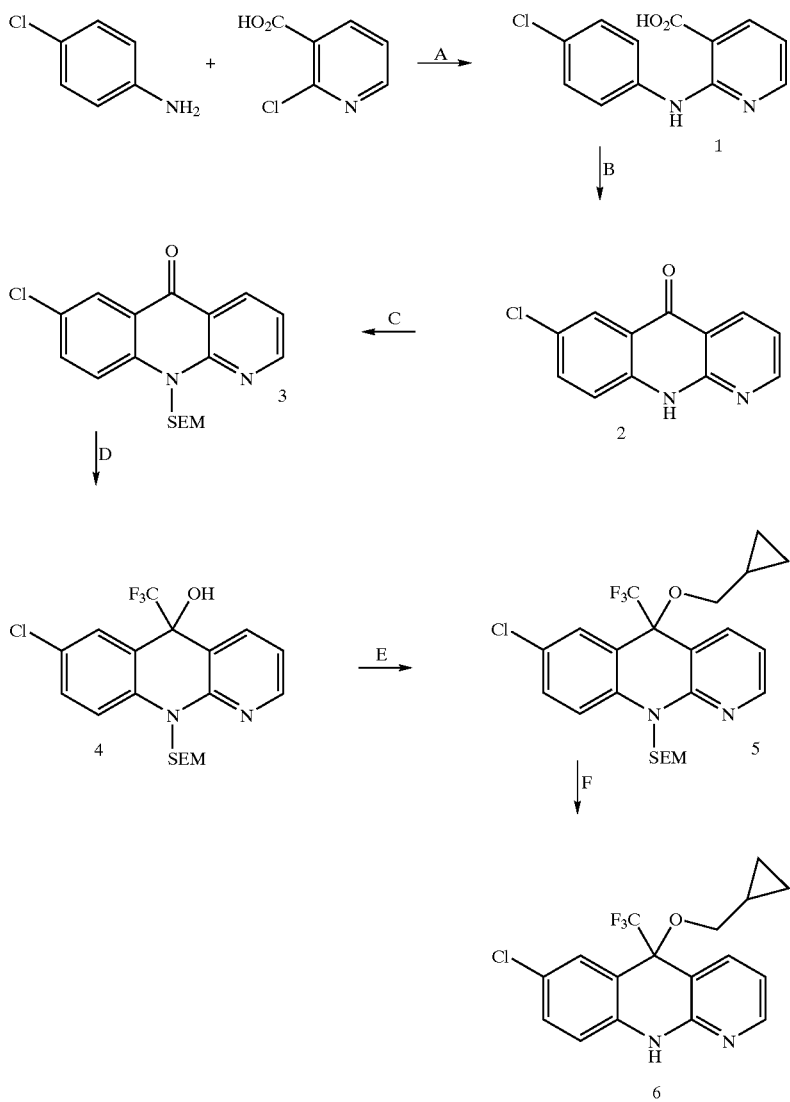

Example 3

Synthesis of 7-Chloro-5-(ethoxy)-5,10-dihydro-5-(trifluoromethyl)benzo[b][1,8]naphthyridine Method H. A solution of 6 (31 mg, 0.088 mmol) and THF (0.2 mL) in ethanol (3 mL) was refluxed for 4 hours. The reaction was diluted with ethyl acetate (30 mL), washed with saturated NaHCO$_3$ (3×25 mL) and saturated NaCl (5 mL), dried (MgSO$_4$) and evaporated at reduced pressure giving a white powder. Chromatography (ether/hexane, 20%) gave a white powder, which was crystallized from dichloromethane and hexane giving 8 as a white crystalline powder, 18 mg (63%).

Example 4

Synthesis of 7-Chloro-5-(n-butyl)-5,10-dihydro-5-(trifluoromethyl)benzo[b][1,8]naphthyridine Method I. To a chilled (0 degree C.) solution of 7 (86 mg, 0.304 mmol) in THF (3 mL) was added butylmagnesium chloride (0.460 mL, 0.915 mmol). After stirring for 10 minutes, the reaction was diluted with ethyl acetate (30 mL), washed with saturated NaHCO$_3$ (3×25 mL) and saturated NaCl (5 mL), dried (MgSO$_4$) and evaporated at reduced pressure giving clear brown film. Chromatography (hexane/ethyl acetate, 20%) gave a white powder, which was crystallized from hexane giving 9 as a white crystalline powder, 24 mg (23%).

Example 5

Synthesis of 7-Chloro-5-(ethyl)-5,10-dihydro-5-(trifluoromethyl)benzo[b][1,8]naphthyridine Method J. To a chilled (15 degree C.) solution of 7 (30.0 g, 0.106 mmol) in benzene (3 mL) was added diethyl zinc (1N in hexane, 0.530 mL). After stirring overnight, the reaction was diluted with ethyl acetate (20 mL), washed with saturated NaHCO$_3$ (3×15 mL) and saturated NaCl (5 mL), dried (MgSO$_4$) and evaporated at reduced pressure giving a light brown film. Chromatography (hexane/ethyl acetate, 20%) gave a white powder, which was crystallized from hexane giving 10 as a white microcrystalline powder, 12 mg (34%).

Method K. A mixture of 3' (1.96 g, 4.80 mmol, synthesized by route A, B & C starting with ethyl 4-chloro-2-methylthio-5-pyrimidine carboxylate instead of 2-chloronicotinic acid) and Raney Nickel (excess) was refluxed in ethanol (15 mL) for 30 minutes. The reaction was filtered through celite and evaporated at reduced pressure giving a yellow solid. Chromatography (hexane/ethyl acetate, 20%) gave 3" as a yellow powder on evaporation, 580 mg (33%).

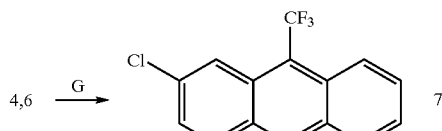

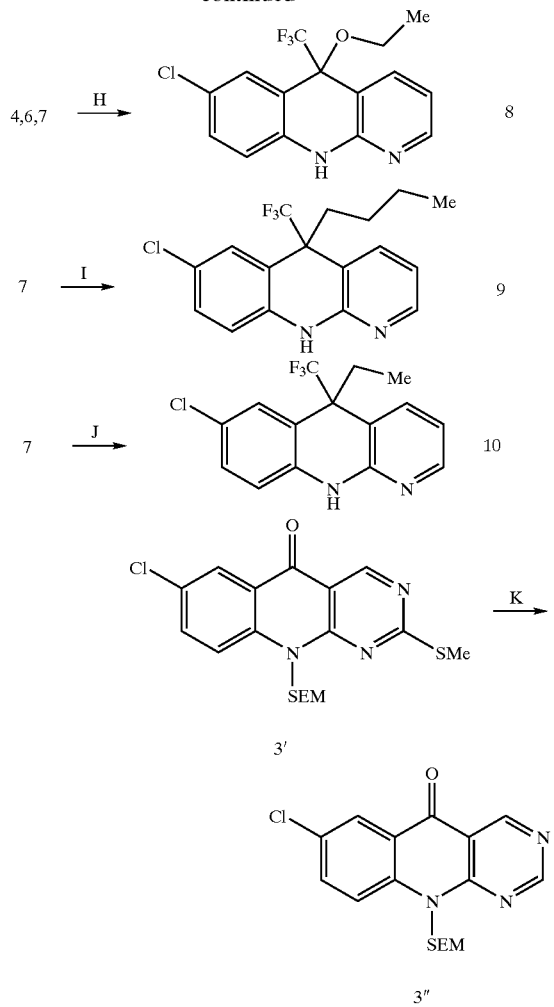

Example 6

Synthesis of Cyclopropylethyl Magnesium Bromide

Method L. To a chilled (0 degree C.) solution of cyclopropylacetic acid (5.0 g, 50 mmol) in THF (50 mL) was added BH$_3$.THF (iN in THF, 70 mL). After stirring overnight at room temperature, the reaction was quenched with water. It was then diluted with ethyl acetate (50 mL), washed with 1N HCl (3×30 mL) and saturated NaCl (10 mL), dried (MgSO$_4$) and evaporated at reduced pressure giving 11 as a colorless oil that was used without further purification, 4.3 g.

Method M. A mixture of 11 (4.3 g, 50 mmol), I$_2$ (12.7 g, 50 mmol), Ph$_3$P (13.1 g, 50 mmol) and imidazole (3.41 g, 50 mmol) in dichloromethane (140 mL) was stirred for two hours. The reaction was evaporated at reduced pressure and chromatography (hexane) gave 12 as a brown oil on evaporation, 6.3 g (64%).

Method N. To a chilled (−78 degree C.) solution of 12 (0.245 mL, 1.06 mmol) in THF (5 mL) was added t-butyl lithium (1.25 mL, 2.13 mmol). After warming to room temperature and stirring for one hour, the solution was re-chilled (to −78 degree C.) and MgBr$_2$ was added (1N in ether/benzene, 1.06 mL). The reaction was then allowed to warm to room temperature and then it was stirred for one hour affording a solution of 13.

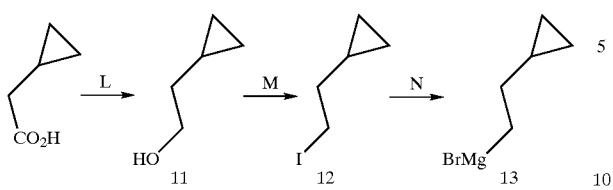

Example 7

Synthesis of 7-Chloro-5-(cyclopropylmethylamino)-5,10-dihydro-5-(trifluoromethyl)benzo[b][1,8]naphthyridine Method O. A solution of 7 (50 mg, 0.177 mmol) cyclopropylmethylamine (0.031 mL, 0.355 mmol) in DMF (2 mL) was stirred for 1 hour. The reaction was diluted with ethyl acetate (20 mL), washed with saturated NaHCO₃ (3×15 mL) and saturated NaCl (5 mL), dried (MgSO₄) and evaporated at reduced pressure giving a yellow film. Chromatography (hexane/ethyl acetate, 30%) gave a white powder, which was crystallized from hexane giving 14 as a white crystalline powder, 26 mg (42%).

Example 8

Synthesis of 7-Chloro-5-(phenylamino)-5,10-dihydro-5-(trifluoromethyl)benzo[b][1,8]naphthyridine Method P. To a solution of 7 (50 mg, 0.177 mmol) and aniline (0.024 mL, 0.266 mmol) in DMF (3 mL) was added NaH (excess). After stirring 15 minutes, the reaction was diluted with ethyl acetate (20 mL), washed with saturated NaHCO3 (3×15 mL) and saturated NaCl (5 mL), dried (MgSO₄) and evaporated at reduced pressure which gave a brown film. Chromatography (hexane/ethyl acetate, 30%) gave a yellow film, which was crystallized from hexane and dichloromethane giving 15 as a creamy white crystalline powder, 27 mg (41%).

Example 9

Synthesis of 7-Chloro-5-(3,3,3-trifluoroprop-1-oxy)-5,10-dihydro-5-(trifluoromethyl)benzo[b][1,8]naphthyridine Method O. To a solution of 7 (50 mg, 0.177 mmol) and 3,3,3-trifluoropropanol (0.040 mL, 0.355 mmol) in DMF (3 mL) was added NaH (excess). After stirring 15 minutes, the reaction was quenched with saturated NH₄Cl, diluted with ethyl acetate (20 mL), washed with saturated NaHCO₃ (3×15 mL) and saturated NaCl (5 mL), dried (MgSO₄) and evaporated at reduced pressure which gave a yellow film. It was crystallized from hexane giving 16 as a tan crystalline powder, 54 mg (77%).

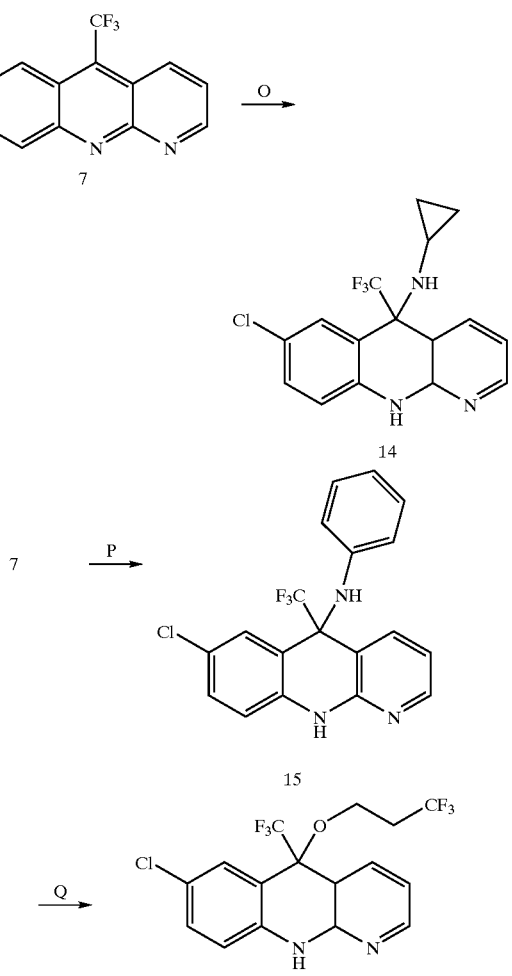

Example 9a

Synthesis of 7-Chloro-5-pyridin-2-ylmethyl-5-trifluoromethyl-5,10-dihydro-benzo[b][1,8]naphthyridine Method R; A solution of 2-picoline (5.0 mL, 51 mmol) and LDA (50 mmol) in THF (50 mL) was stirred for 3 hours under nitrogen at −78° C. The azaacridine 7 was added and the reaction was stirred at −78° C. for 30 minutes then it was allowed to warm to room temperature over 30 minutes. The reaction was quenched with saturated NH₄Cl then diluted with ethyl acetate (50 mL), washed with saturated NaHCO₃ (3×30 mL) and saturated NaCl (5 mL), dried (MgSO₄) and evaporated at reduced pressure giving a brown syrup. Chromatography (ethyl acetate/hexane, 40%) gave a creamy film, which was crystallized from dichloromethane and hexane giving 19 as a creamy white crystalline powder, 645 mg (20%).

Example 9b

Synthesis of 3,7-Dichloro-5-trifluoromethyl-5,10-dihydro-benzo[b][1,8]naphthyridin-5-ol Method S; A solution of the azaacridine hydrate 20 (100 mg, 0.33 mmol) and NCS (49 mg, 0.37 mmol) in isopropanol (5 mL) was refluxed for 15 minutes under nitrogen. The reaction was diluted with ethyl acetate (20 mL), washed with 1N HCl (3×10 mL) and saturated NaCl (5 mL), dried (MgSO₄) and evaporated at reduced pressure giving a yellow powder. Trituration from dichloromethane and gave the 3-chloroazaacridine 21 as a creamy white crystalline powder, 102 mg (92%).

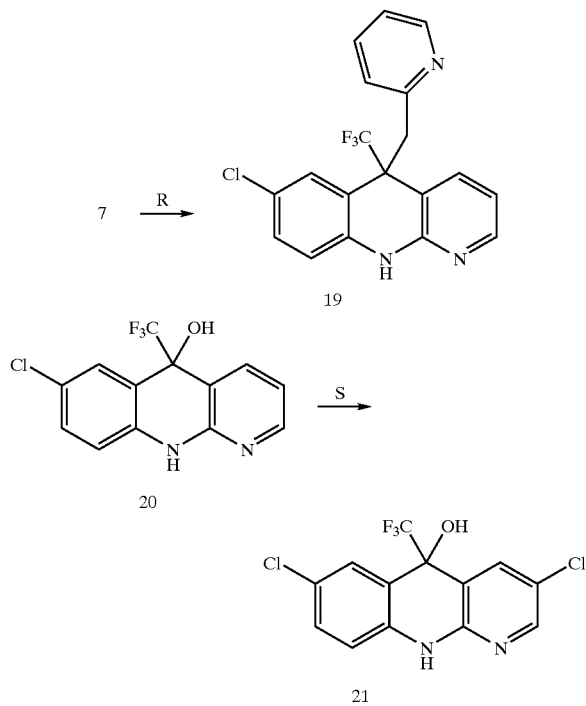

Example 10

Synthesis of 7-Chloro-5-(cyclopropylmethoxy)-5, 10-dihydro-1N-oxo-5-(trifluoromethyl)benzo[b][1,8] naphthyridine Method U. A solution of 17 (150 mg, 0.424 mmol) mCPBA (3-chloroperbenzoic acid) (91 mg, 0.424 mmol) in dichloromethane (3 mL) was stirred for 2 hours. The reaction was diluted with ethyl acetate (10 mL), washed with 1N NaOH (3×10 mL) and saturated NaCl (5 mL), dried (MgSO₄) and evaporated at reduced pressure giving a brown film. Chromatography (ethyl acetate) gave a colorless film, which was crystallized from dichloromethane and hexane giving 18 as a creamy white crystalline powder, 56 mg (36%).

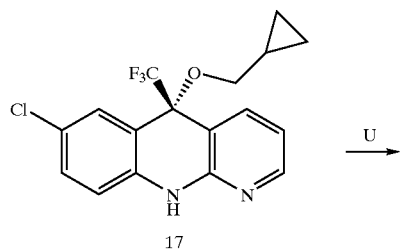

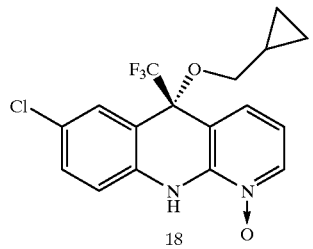

Method Z. Chiral HPLC separation was performed using chiral columns which gave the (R) and (S) enantiomers in >99% EE.

Example 11

Synthesis of 7-Chloro-5-cyclopropylmethoxy-5-difluoromethyl-5,10-dihydro-benzo[b][1,8] naphthyridine (X=Cl in Scheme 5, below)

Method AA. Preparation of 2-Chloro-3-difluoroacetylpyridine. To a 1000 mL 3-necked round bottom flask equipped with a magnetic stirrer, cooling bath, thermometer, addition funnel, septum and a nitrogen inlet was added diisopropylamine (20.2 g, 30 mL, d=0.722, 0.21 moles) and THF (200.0 mL). The solution was cooled to −20° C. n-Butyl lithium in hexane (2.5 M, 86 mL, 0.20 mole) was added over 30 min. The reaction mixture was stirred at −20° C. for 30 min and then cooled to −78° C. 2-Chloropyridine (11.3 g, 9.4 mL, 0.1 moles) was added dropwise over 5 min and the reaction mixture was stirred at −78° C. for 4 h. Ethyl difluoroacetate (24.8 g, 0.01 moles) was added dropwise over 15 min and the reaction mixture was stirred at −78° C. After 2 h, the reaction mixture was quenched with sat. ammonium chloride solution (100 mL) and extracted with EtOAc (2×200 mL). The combined organics were washed with brine, dried (MgSO₄) and concentrated to afford a brown yellow oil. Column chromatography (SiO₂, 15–30% EtOAc-hexane, gradient elution) afforded the desired material 23 (11.6 g, 61% as brown yellow oil.

Method BB Preparation of 2-amino-N-(4-chlorophenyl)-3-difluoroacetylpyridine: In a 100.0 mL round bottom flask equipped with a magnetic stirrer, oil bath, thermometer, reflux condenser and a nitrogen inlet, 2-chloro-3-difluoroacetylpyridine 23 (2.75 g, 14.4 mmol) and 4-chloroaniline were dissolved in 3% H₂O-AcOH and were heated to reflux for 14 h. The reaction mixture was cooled and concentrated by rotary evaporation. The resulting brown residue was diluted with water, neutralized with NaHCO₃, and extracted with EtOAc (3×150 mL). The combined organic layers were washed with brine and dried. Column chromatography (SiO₂, 10% EtOAc-hexane) provided the desired material 24 (2.15 g, mp 73–74° C., 53% yield) as yellow solid.

Method CC: Preparation of 4-aza-7-chloro-9-difluoromethylacridine. To a 50.0 mL round bottom flask equipped with a magnetic stirrer and nitrogen inlet was added conc. H₂SO₄ followed by 2-amino-N-(4-chlorophenyl)-3-difluoroacetylpyridine (2.5 g, 8.8 mmol) in portions over 15 min. The reaction mixture became an orange yellow homogeneous solution and was stirred at 23° C. for 48 h. The reaction was quenched with ice (250 g) and neutralized carefully with NaHCO₃ (30–32 g). The cream precipitate was filtered, washed with water and dried in vacuum to afford 2.3 g (98%) of the desired product 25 which was used without further purification (mp 232–233° C.).

Method DD: Preparation of 7-Chloro-9-Cyclopropylmethoxy-9-difluoromethyl-4-azaacridine. To a 250.0 mL round bottom equipped with a magnetic stirrer, a cooling bath, and nitrogen inlet was added 4-aza-7-chloro-9-difluoromethylacridine (2.0 g, 7.56 mmol), cyclopropyl carbinol (0.82 g, 11.4 mmol, 1.5 equiv) and anhydrous DMF (50 mL). The cream colored suspension was cooled to −10° C. under N₂ and then NaH (60% oil dispersion) was added in portions over 10 min. The reaction mixture was stirred for 3 h at 0–5° C. before quenching with ice. The resulting mixture was extracted with EtOAc (3×200 mL), washed with brine, dried and concentrated. Column chromatography (SiO₂, 25% EtOAc-hexane-1% Et₃N) afforded 1.4 g of the desired product 26 as a cream colored solid (mp 83–84° C., 55%).

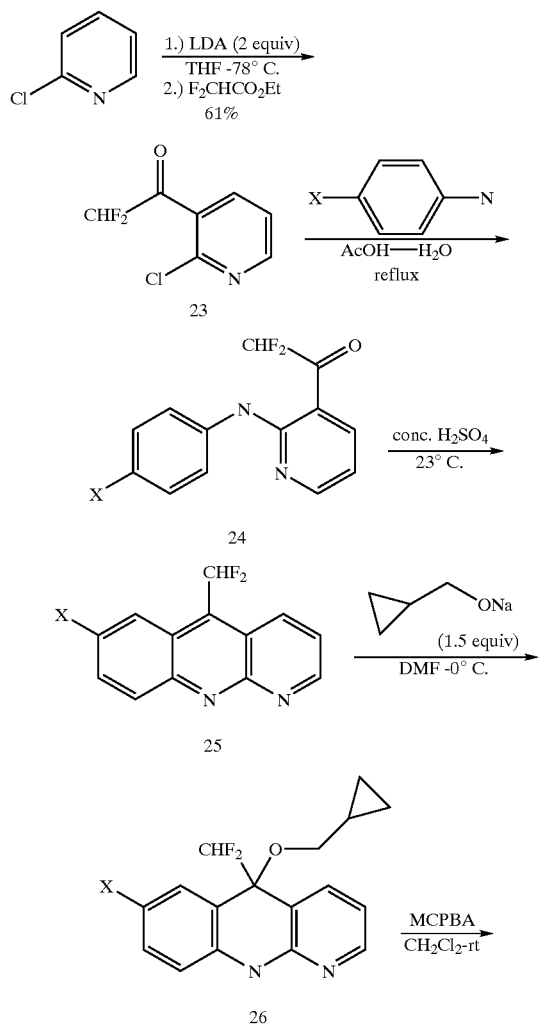

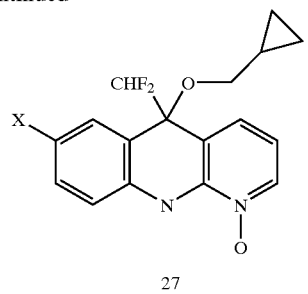

Examples 12–14 were prepared according to the procedure described in Example 11:

Example 12

7-Fluoro-5-cyclopropylmethoxy-5-difluoromethyl-5,10-dihydro-benzo[b][1,8]naphthyridine, 900 mg, mp 137–138° C.

Example 13

7-Chloro-5-(2-cyclopropyl-ethoxy)-5-difluoromethyl-5,10-dihydro-benzo[b][1,8]naphthyridine, 274 mg, mp 148–149° C.

Example 14

7-Chloro-5-pyridin-2-ylmethyl-5-difluoromethyl-5,10-dihydro-benzo[b][1,8]naphthyridine, 17 mg, mp 204–205° C.

Example 15

Synthesis of 3-chloro-7-fluoro-5-cyclopropylmethoxy-5-difluoromethyl-5,10-dihydro-benzo[b][1,8]naphthyridine Method EE: A solution of 28 (800 mg, 2.38 mmol) in isopropanol (16 mL) was treated with N-chlorosuccinimide (316 mg, 2.38 mmol). The resulting suspension was heated to 90° C. resulting in a homogeneous solution. A new precipitate formed after heating for 10 minutes. The reaction was cooled to 23° C. and concentrated. The residue was partitioned between EtOAc and H₂O and the aqueous phase was extracted with EtOAc (4×25 mL). The combined organics were dried (Na₂SO₄) and concentrated to provide a yellowish solid. Column chromatography (SiO₂, 65% EtOAc-hexane to 100% EtOAc, gradient elution) afforded the desired material 29 (372 mg, 55%).

Treatment with cyclopropylcarbinol as shown in example 11, method DD, afforded 7-Fluoro-2-chloro-9-cyclopropylmethoxy-9-difluoromethyl-4-azaacridine (141 mg, mp 169–170° C.).

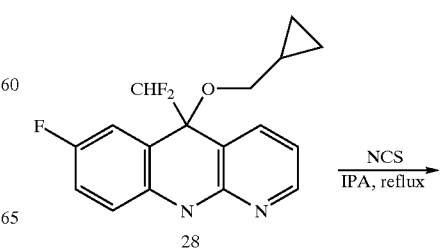

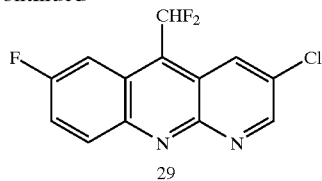

Example 16

Synthesis of 7-Chloro-5-cyclopropylmethoxy-5-difluoromethyl-5,10-dihydro-benzo[b][1,8]naphthyridine 1-oxide Method FF: To a 10.0 mL round bottom equipped with a magnetic stirrer, and nitrogen inlet was added 7-fluoro-9-cyclopropylmethoxy-9-difluoromethyl-4-azaacridine (1.4 g, 4.15 mmol) and anhydrous $CH_2Cl_2$ (50 mL). MCPBA (1.23 g, 4.64 mmol) was added in portions and stirred at 23° C. for 4 h. The reaction mixture was diluted with $CH_2Cl_2$, washed with sat. $NaHCO_3$ solution (3×100 mL), brine and dried ($MgSO_4$). Concentration afforded a yellow residue which was purified by column chromatography ($SiO_2$, 1% $Et_3N$-EtOAc) to afford 1.03 g of 7-Chloro-5-cyclopropylmethoxy-5-difluoromethyl-5,10-dihydro-benzo[b][1,8]naphthyridine 1-oxide as a light green solid (mp 185–186° C., 70% yield).

Examples 17–20 were prepared according to the procedure described in Example 16:

Example 17

7-Fluoro-5-cyclopropylmethoxy-5-difluoromethyl-5,10-dihydro-benzo[b][1,8]naphthyridine 1-oxide, 102 mg, mp 166–167° C.

Example 18

7—Chloro-5-(2-cyclopropyl-ethoxy)-5-difluoromethyl-5,10-dihydro-benzo[b][1,8]naphthyridine 1-oxide, 164 mg, mp 175–176° C.

Example 19

7—Chloro-5-pyridin-2-ylmethyl-5-difluoromethyl-5,10-dihydro-benzo[b][1,8]naphthyridine 1-oxide, 9.2 mg, mp 210–211° C.

Example 20

3,7-Dichloro-5-cyclopropylmethoxy-5-difluoromethyl-5,10-dihydro-benzo[b][1,8]naphthyridine 1-oxide, 84 mg, mp 163–164° C.

Example 21

Synthesis of 5-Butyl-7-chloro-5-difluoromethyl-5,10-dihydro-benzo[b][1,8]naphthyridine Method GG: A solution of 7-chloro-9-difluoromethyl-4-azaacridine (396 mg 1.5 mmol) in THF (10 mL) was cooled under $N_2$ to −78° C. n-Butyl lithium was added dropwise over 15 min and the reaction mixture was stirred at −78° C. for 5 h. The reaction was quenched with sat. $NH_4Cl$ solution and extracted with EtOAc (3×20 mL). The combined organic layers were washed with brine, dried and concentrated. Column chromatography ($SiO_2$, 10% EtOAc-hexane-1% $Et_3N$) afforded the desired material 5-Butyl-7-chloro-5-difluoromethyl-5,10-dihydro-benzo[b][1,8]naphthyridine as a viscous yellow oil (10 mg, 2.1%).

Example 22 was prepared according to the procedure described in Example 21:

Example 22

5-(2-cyclopropylethyl)-7-chloro-5-difluoromethyl-5,10-dihydro-benzo[b][1,8]naphthyridine, 29 mg, viscous oil, MS m/z 335.1122 ($M^+$+H) $C_{18}H_{18}ClF_2N_2$.

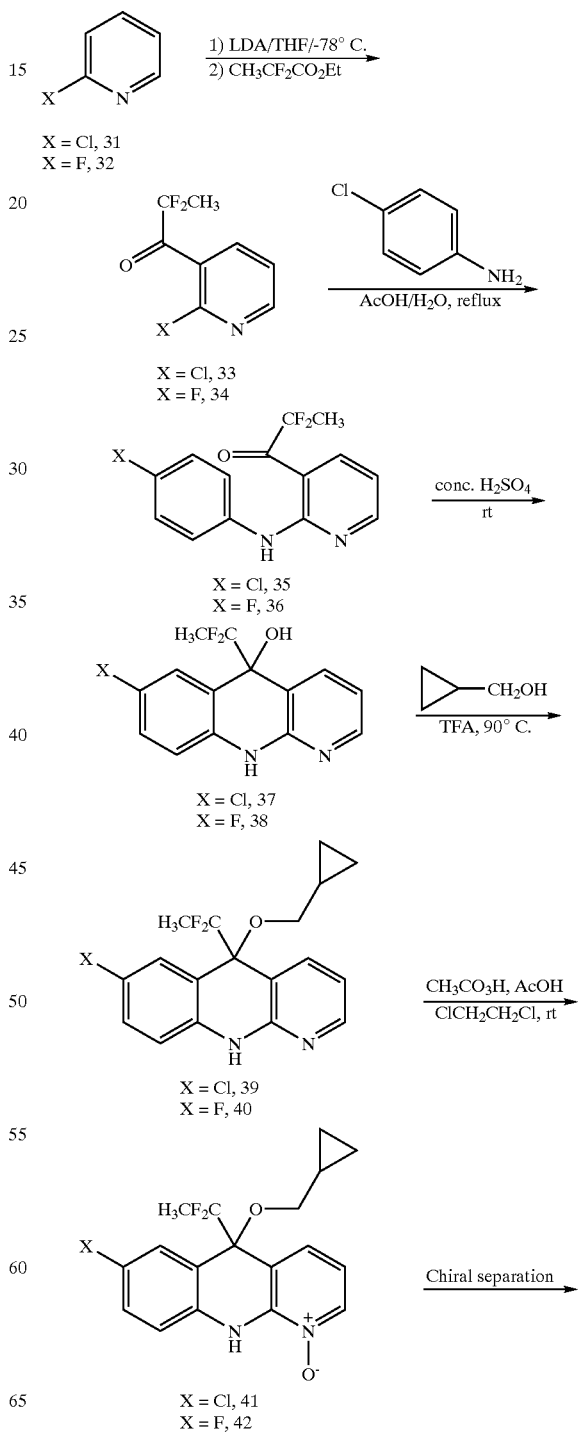

Scheme 6

-continued

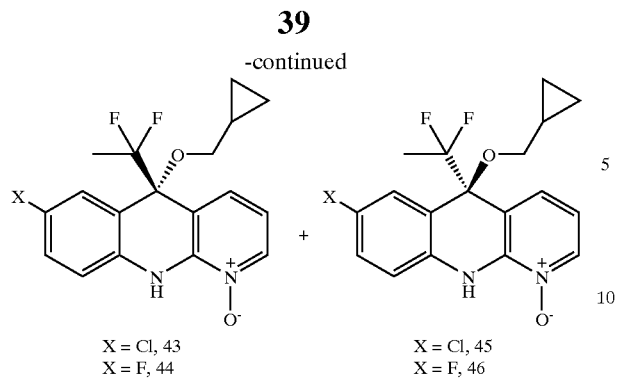

X = Cl, 43
X = F, 44

X = Cl, 45
X = F, 46

Example 23 and 24

Synthesis of 7-chloro-5-hydroxy-5-(1,1-difluoroethyl)-5,10-dihydrobenzo[b][1,8]naphthyridine (37) and 7-Fluoro-5-hydroxy-5-(1,1-difluoroethyl)-5,10-dihydrobenzo [b][1,8]naphthyridine (38)

Method HH Preparation of 2-chloro-3-(2,2-difluoropropionyl)pyridine (33): To a stirred solution of diisopropylamine (11.8 mL, 84.00 mmol) in anhydrous THF (80 mL) at −20° C. was added n-BuLi (2.5 M in Hexanes, 32.0 mL, 80.00 mmol) dropwise. The reaction mixture was stirred at −20° C. for 30 min and then cooled to −78° C. 2-Chloropyridine (3.82 mL, 40.00 mmol) was then added dropwise. The resulting yellow solution was stirred at −78° C. for 3 h 20 min. Ethyl 2,2-difluoropropanoate was then added dropwise. After 3 h 40 min at −78°, the reaction was quenched with saturated aqueous ammonium chloride (40 mL) and extracted with EtOAc (2×). The combined organic layers were washed with brine, dried over MgSO$_4$, filtered and concentrated in vacuo. Flash chromatography (15% EtOAc-hexane) gave 33 (3.544 g, 86% yield) as a yellow oil.

2-Fluoro-3-(2,2-difluoropropionyl)pyridine (34) was Prepared According to the Procedure Described in Method HH Preparation of 2-Amino-N-(4-chlorophenyl)-3-(2,2-difluoropropionyl)pyridine (35)

Method II: To a cloudy solution of 2-chloro-3-(2,2-difluoropropionyl)pyridine (33) (3.190 g, 15.52 mmol) in 10:1 AcOH-H$_2$O (38.5 mL) at room temperature was added 4-chloroaniline (3.000 g, 23.28 mmol). The reaction mixture was heated to gently reflux for 21 h. The reaction mixture was then concentrated in vacuo. The resulting brown residue was diluted with EtOAc, neutralized with saturated aqueous NaHCO$_3$ (40 mL), and extracted with EtOAc (2×). The combined organic layers were washed with brine, dried over MgSO$_4$, filtered and concentrated in vacuo. Flash chromatography (10% EtOAc-hexane) afforded 35 (3.740 g, 81% yield) as a yellow solid (m.p. 85–86° C.).

2-Amino-N-(4-fluorophenyl)-3-(2,2-difluoropropionyl)pyridine (36) was Prepared According to the Procedure Described in the Method II Preparation of 7-Chloro-5-hydroxy-5-(1,1-difluoroethyl)-5,10-dihydrobenzo[b][1,8]naphthyridine (37)

Method JJ: 2-Amino-N-(4-chlorophenyl)-3-(2,2-difluoropropionyl)pyridine (35) (190 mg, 0.640 mmol) was treated with conc. sulfuric acid (1 mL). The resulting red homogeneous solution was stirred at room temperature for 47.5 h. The reaction was quenched with saturated aqueous Na$_2$CO$_3$ (15 mL), and extracted with EtOAc (3×). The combined organic layers were washed with brine, dried over MgSO$_4$, filtered and concentrated in vacuo. Flash chromatography (50% EtOAc-hexane) provided 37 (173 mg, 91% yield) as an off-white solid (m.p. 188–190° C.).

7-Fluoro-5-hydroxy-5-(1,1-difluoroethyl)-5,10-dihydrobenzo[b][1,8]naphthyridine (38) was Prepared According to the Procedure Described in Method JJ Example 25

Preparation of 7-Chloro-5-(cyclopropylmethoxy)-5-(1,1-difluoroethyl)-5,10-dihydrobenzo[b][1,8]naphthyridine (39)

Method KK: To a stirred suspension of 7-chloro-5-hydroxy-5-(1,1-difluoroethyl)-5,10-dihydrobenzo[b] [1,8]naphthyridine (37) (173 mg, 0.583 mmol) in cyclopropyl methanol (1.2 mL, 14.58 mmol) was added trifluoroacetic acid (446 µL, 5.83 mmol). The resulting solution was heated at reflux for 3 h 15 min. The reaction mixture was concentrated in vacuo, the residue was purified by flash chromatography (40% EtOAc-hexane) afforded 39 (176 mg, 86% yield) as an off-white solid.

Example 26

7-Fluoro-5-(cyclopropylmethoxy)-5-(1,1-difluoroethyl)-5,10-dihydrobenzo[b][1,8]naphthyridine (40) was Prepared According to the Procedure Described in Method KK Example 27

Preparation of 7-Chloro-5-(cyclopropylmethoxy)-5-(1,1-difluoroethyl)-5,10-dihydrobenzo[b][1,8]naphthyridine-1-N-oxide (41)

Method LL: To a stirred solution of 7-chloro-5-(cyclopropylmethoxy)-5-(1,1-difluoroethyl)-5,10-dihydrobenzo[b][1,8]naphthyridine (39) (156 mg, 0.445 mmol) in anhydrous 1,2-dichloroethane (2 mL) at rt was added peracetic acid (32 wt. % in ACOH, 122 µL, 0.579 mmol). After 15 h at room temperature, the reaction was quenched with 1:1 aqueous 10% Na$_2$S$_2$O$_3$/saturated aqueous NaHCO$_3$ (10 mL), and extracted with EtOAc (2×). The combined organic layers were washed with brine, dried over MgSO$_4$, filtered and concentrated in vacuo. Flash chromatography (10% MeOH—CH$_2$Cl$_2$) furnished 41 (160 mg, 98% yield) as a pale yellow solid (m.p. 65–66° C.).

Example 28

7-Fluoro-5-(cyclopropylmethoxy)-5-(1,1-difluoroethyl)-5,10-dihydrobenzo[b][1,8]naphthyridine-1-N-oxide (42) was Prepared According to the Procedure Described in Method LL Scheme 7

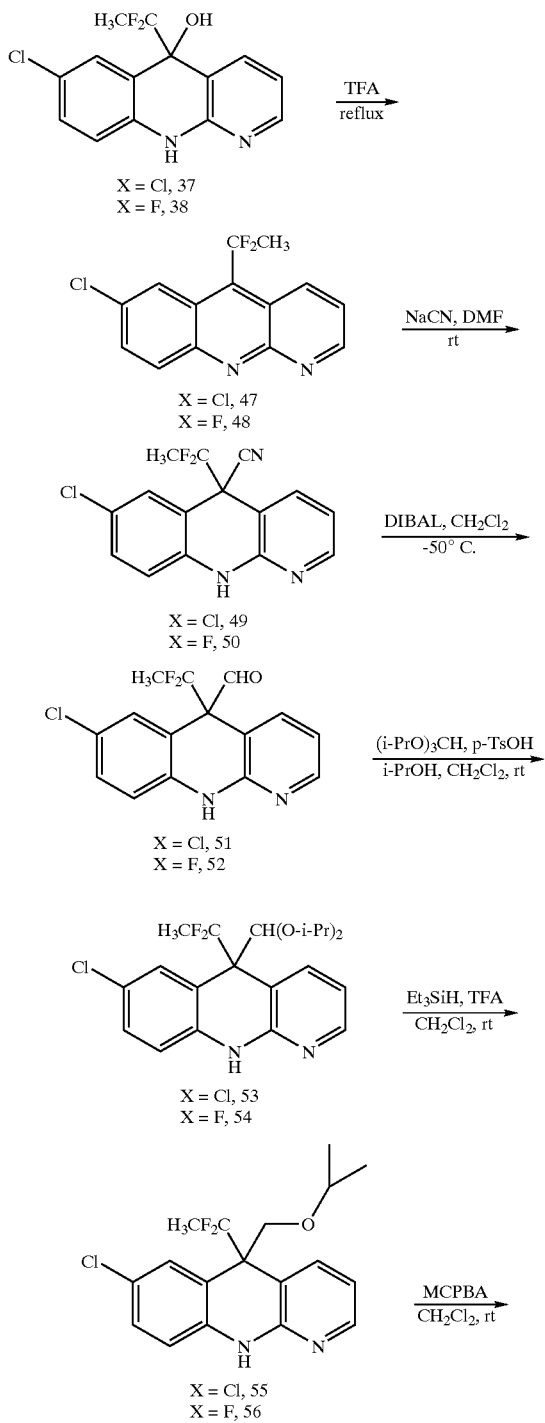

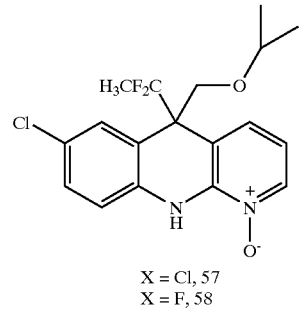

X = Cl, 57
X = F, 58

Example 29

Preparation of 7-Chloro-5-cyano-5-(1,1-difluoroethyl)-5,10-dihydrobenzo[b][1,8]naphthyridine (49)

Method MM: A stirred solution of 7-chloro-5-10 hydroxy-5-(1,1-difluoroethyl)-5,10-dihydrobenzo[b][1,8]naphthyridine (37) (1.620 g, 5.393 mmol) in trifluoroacetic acid (11 mL) was heated at reflux for 16 h. The reaction mixture was concentrated in vacuo, the residue was purified by flash chromatography (90%–95% EtOAc-hexane, gradient elution) afforded 47 (1.460 g, 97% yield) as a yellow solid (m.p. 151–153° C.).

7-Fluoro-5-(1,1-difluoroethyl)benzo[b][1,8]naphthyridine (48) was Prepared According to the Procedure Described in Method MM Preparation of 7-Chloro-5-cyano-5-(1,1-difluoroethyl)-5,10-dihydrobenzo[b][1,8]naphthyridine (49)

Method NN: To a stirred solution of 7-chloro-9-(1,1-difluoroethyl)-4-azaacridine (47) (1.440 g, 5.167 mmol) in anhydrous DMF (25 mL) at room temperature was added NaCN (533 mg, 10.334 mmol). After 15 h at room temperature, the reaction was quenched with 1:1 saturated aqueous $NaHCO_3/H_2O$ (50 mL), and extracted with EtOAc (3×). The combined organic layers were washed with brine, dried over $MgSO_4$, filtered and concentrated in vacuo. Flash chromatography (20%–40% EtOAc-hexane, gradient elution) furnished 49 (1.106 g, 70% yield) as a yellow solid.

Example 30

7-Fluoro-5-cyano-5-(1,1-difluoroethyl)-5,10-dihydrobenzo[b][1,8]naphthyridine (50) was Prepared According to the Procedure Described in Method NN Preparation of 7-Chloro-5-formyl-5-(1,1-difluoroethyl)-5,10-dihydrobenzo[b][1,8]naphthyridine (51)

Method OO: To a stirred solution of 7-chloro-5-cyano-5-(1,1-difluoroethyl)-5,10-dihydrobenzo[b][1,8]naphthyridine (49) (862 mg, 2.820 mmol) in anhydrous methylene chloride (35 mL) at −78° C. was added DIBAL (1.0 M in $CH_2Cl_2$, 8.46 mL) dropwise. After 3 h 40 min at −50° C., the reaction was quenched with 1 N HCl (35 mL), and extracted with EtOAc (3×). The combined organic layers were washed with brine, dried over $MgSO_4$, filtered and concentrated in vacuo. Flash chromatography (30%–50% EtOAc-hexane, gradient elution) furnished 51 (706 mg, 81% yield) as a yellow solid.

Example 32

7-Fluoro-5-formyl-5-(1,1-difluoroethyl)-5,10-dihydrobenzo[b][1,8]naphthyridine (52) was Prepared According to the Procedure Described in Method OO

Example 33

Preparation of 7-Chloro-5-diisopropoxymethyl-5-(1,1-difluoroethyl)-5,10-dihydrobenzo[b][1,8]naphthyridine (53)

Method PP: To a stirred solution of 7-chloro-5-formyl-5-(1,1-difluoroethyl)-5,10-dihydrobenzo[b][1,8]naphthyridine (51) (619 mg, 2.005 mmol) in anhydrous triisopropyl orthoformate (30.0 mL, 134 mmol), anhydrous isopropanol (10 mL) and anhydrous methylene chloride (10 mL) at room temperature was added p-TsOH.H$_2$O (763 mg, 4.010 mmol). After 18 h at room temperature, the reaction was quenched with saturated aqueous NaHCO$_3$ (25 mL), and extracted with EtOAc (2×). The combined organic layers were washed with brine, dried over MgSO$_4$, filtered and concentrated in vacuo. Flash chromatography (30%–40% EtOAc-hexane, gradient elution) afforded 53 (400 mg, 49% yield) as a yellow solid as well as 45% recovery of starting material 51 (280 mg).

Example 34

7-Fluoro-5-diisopropoxymethyl-5-(1,1-difluoroethyl)-5,10-dihydrobenzo[b][1,8]naphthyridine (54) was Prepared According to the Procedure Described in Method PP

Example 35

Preparation of 7-Chloro-5-isopropoxymethyl-5-(1,1-difluoroethyl)-5,10-dihydrobenzo[b][1,8]naphthyridine (55)

Method QQ: To a stirred solution of 7-chloro-5-diisopropoxymethyl-5-(1,1-difluoroethyl)-5,10-dihydrobenzo[b][1,8]naphthyridine (53) (360 mg, 0.876 mmol) in anhydrous methylene chloride (4 mL) at room temperature was added trifluoroacetic acid (8 mL) and triethylsilane (6.0 mL, 36.44 mmol). After 14 h at room temperature, the reaction mixture was concentrated in vacuo, the residue was purified by flash chromatography (30%–40% EtOAc-hexane, gradient elution) afforded 55 (248 mg, 80% yield) as a yellow solid (m.p. 148–149° C.).

Example 36

7-Fluoro-5-isopropoxymethyl-5-(1,1-difluoroethyl)-5,10-dihydrobenzo[b][1,8]naphthyridine (56) was Prepared According to the Procedure Described in Method QQ

Example 37

Preparation of 7-chloro-5-isopropoxymethyl-5-(1,1-difluoroethyl)-5,10-dihydrobenzo[b][1,8]naphthyridine-1-N-oxide (57)

Method RR: To a stirred solution of 7-chloro-5-isopropoxymethyl-5-(1,1-difluoroethyl)-5,10-dihydrobenzo[b][1,8]naphthyridine (55) (108 mg, 0.306 mmol) in methylene chloride (3 mL) at room temperature was added MCPBA (77% max, 103 mg, 0.459 mmol). After 2 h 15 min at room temperature, the reaction was quenched with 1:1 aqueous 10% Na$_2$S$_2$O$_3$/saturated aqueous NaHCO$_3$ (10 mL), and extracted with EtOAc (2×). The combined organic layers were washed with brine, dried over MgSO$_4$, filtered and concentrated in vacuo. Flash chromatography (5% MeOH-CH$_2$Cl$_2$) furnished 57 (102 mg, 90% yield) as a pale yellow solid (m.p. 56–57° C.).

Example 38

7-Fluoro-5-isopropoxymethyl-5-(1,1-difluoroethyl)-5,10-dihydrobenzo[b][1,8]naphthyridine-1-N-oxide (58) was Prepared According to the Procedure Described in Method RR

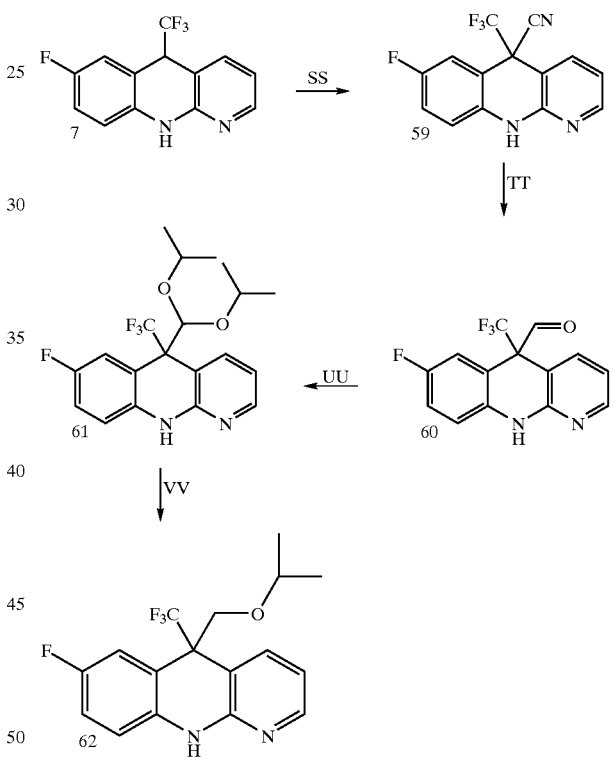

Scheme 8

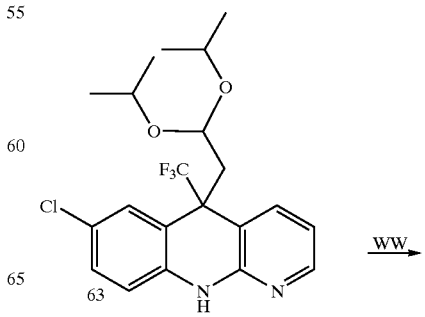

Scheme 9

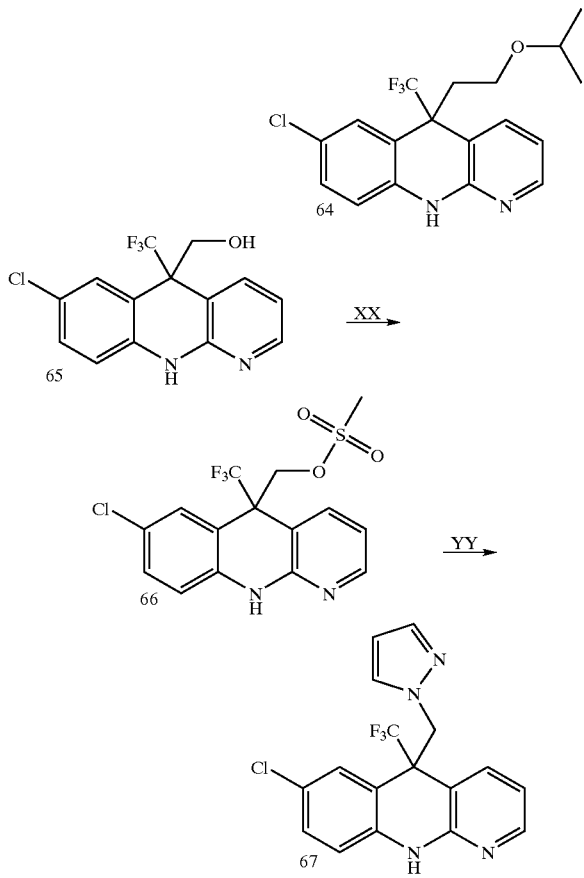

Example 38

Preparation of 7-Fluoro-5-trifluoromethyl-5,10-dihydro-benzo[b][1,8]naphthyridine-5-carbonitrile Method SS; To a solution of 7 (5.01 g, 18.8 mmol) in DMF (80 mL) was added KCN (1.47 g, 22.6 mmol) and the reaction was stirred for 30 minutes. It was diluted with ethyl acetate (100 mL), washed with saturated NaHCO$_3$ (3×60 mL) and saturated NaCl (10 mL), dried (MgSO$_4$) and evaporated at reduced pressure. The residue was triturated in hexane and ethyl acetate giving 59 as a tan powder, 5.06 g (92%).

Example 39

Preparation of 7-Fluoro-5-trifluoromethyl-5,10-dihydro-benzo[b][1,8]naphthyridine-5-carbaldehyde Method TT; To a chilled solution (−50° C.) of 59 (4.81 g, 16.4 mmol) in dichloromethane (100 mL) was added DIBAL-H (1N in dichloromethane, 49.2 mL, 49.2 mmol) and the rxn was stirred for 1 hour. It was carefully quenched and then hydrolyzed at −50° C. with 1N HCl. The reaction was diluted with ethyl acetate (80 mL), washed with saturated NaHCO$_3$ (3×60 mL) and saturated NaCl (10 mL), dried (MgSO$_4$) and evaporated at reduced pressure. The residue was triturated in hexane and ethyl acetate giving 60 as a tan powder, 3.15 g (65%).

Example 40

Preparation of 5-Diisopropoxymethyl-7-fluoro-5-trifluoromethyl-5,10-dihydro-benzo[b][1,8]naphthyridine Method UU; Concentrated H$_2$SO$_4$ (54 mL, 1.02 mmol) was added to a solution of 60 (302 mg, 1.02 mmol) and triethoxy orthoformate (0.85 mL, 5.1 mmol) in ethanol (3 ml) and the reaction was stirred overnight. It was diluted with ethyl acetate (30 mL), washed with saturated NaHCO$_3$ (3×20 mL) and saturated NaCl (5 mL), dried (MgSO$_4$) and evaporated at reduced pressure giving 61 as a yellow film. The residue was used without further purification.

Example 41

Preparation of 7-Fluoro-5-isopropoxymethyl-5-trifluoromethyl-5,10-dihydro-benzo[b][1,8]naphthyridine Method VV; To a solution of 61 (310 mg, 0.779 mmol) in TFA (3 mL) was added BH$_3$.Me$_2$S (0.219 ml, 2.34 mmol) drop wise and the reaction was stirred overnight. It was diluted with ethyl acetate (30 mL), washed with iN NaOH (3×20 mL) and saturated NaCl (5 mL), dried (MgSO$_4$) and evaporated at reduced pressure giving a honey colored syrup. The residue was stirred in methanol (5 mL) with HCl (4N in dioxane, 1 mL) for one hour. The reaction was diluted with ethyl acetate (30 mL), washed with saturated NaHCO$_3$ (3×20 mL) and saturated NaCl (5 mL), dried (MgSO$_4$) and evaporated giving 62 as a yellow foam. The residue was used without further purification.

Example 42

Method WW; To a solution of the ketal 63 (85 mg, 0.198 mmol) and triethylsilane (0.320 mL, 1.98 mmol) in dichloromethane (0.3 mL) was added TFA (0.6 mL) and the reaction was stirred overnight. It was diluted with ethyl acetate (30 mL), washed with saturated NaHCO$_3$ (3×20 mL) and saturated NaCl (5 mL), dried (MgSO$_4$) and evaporated at reduced pressure. Chromatography of the residue (hexane/ethyl acetate, 20%) gave 64 (after triturating in hexane) as a creamy white powder, 58 mg (79%) and 65 (after triturating in hexane) as a white powder, 15 mg (23%).

Example 43

Preparation of 7-Chloro-5-pyrazol-1-ylmethyl-5-trifluoromethyl-5,10-dihydro-benzo[b][1,8]naphthyridine Method XX; To a solution of 65 (682 mg, 2.17 mmol) and diisopropylethylamine (1.13 mL, 6.52 mmol) in DMF (10 mL) was added methanesulfonyl chloride (0.336 mL, 4.34 mmol) and the reaction was stirred for 2 hours. It was diluted with ethyl acetate (30 mL), washed with 1N HCl (3×20 mL) and saturated NaCl (5 mL), dried (MgSO$_4$), clarified with activated charcoal and evaporated at reduced pressure. Chromatography of the residue (hexane/ethyl acetate, 20%) gave a colorless film. It was triturated in dicholromethane and hexane giving 66 as a white powder, 688 mg (81%).

Method YY; A mixture of 66 (26 mg, 0.066 mmol), pyrizole (22 mg, 0.33 mmol) and excess K$_2$CO$_3$ in DMF (3 mL) was stirred at 100° C. for 6 hours. It was diluted with ethyl acetate (30 mL), washed with saturated NaHCO$_3$ (3×20 mL) and saturated NaCl (5 mL), dried (MgSO$_4$) and evaporated at reduced pressure. Chromatography of the residue (hexane/ethyl acetate, 30%) gave a colorless film. It was triturated in hexane giving 67 as a white powder, 12 mg (50%).

Scheme 10

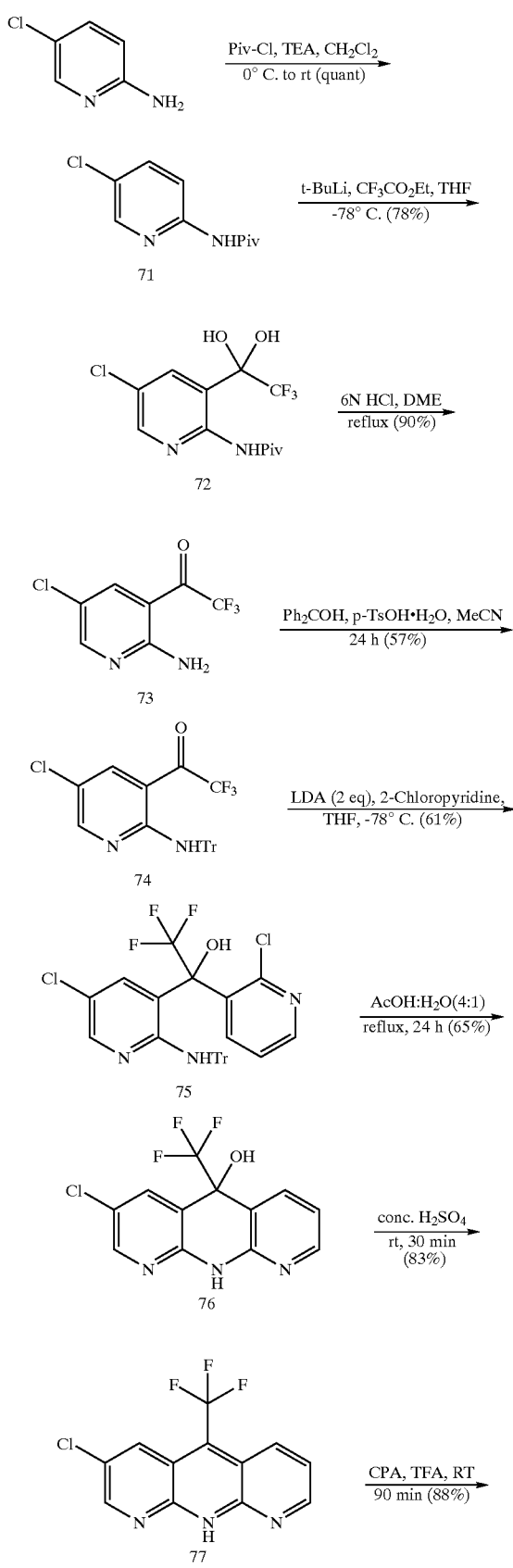

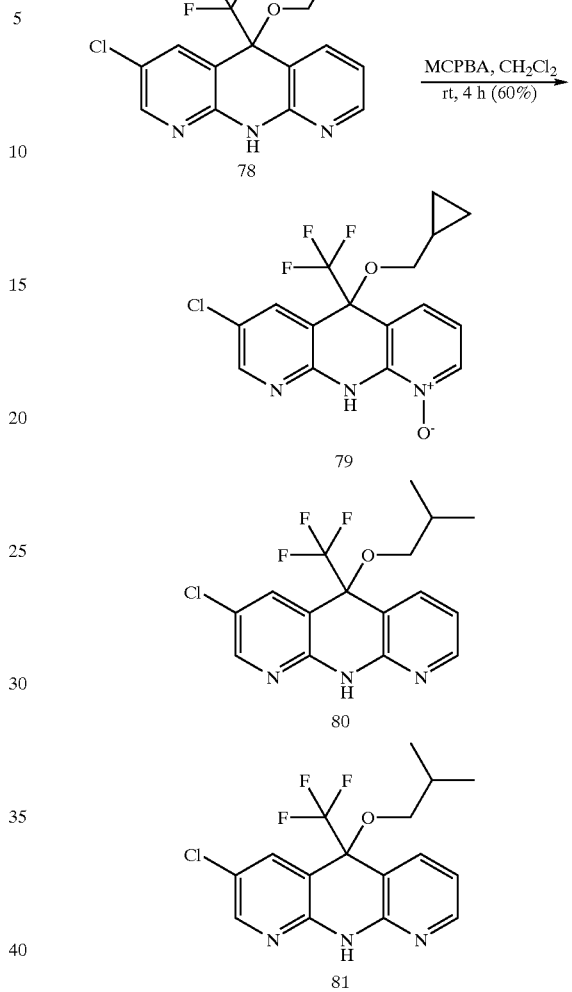

Example 44

Synthesis of 3-Chloro-10-trifluoromethyl-9,10-dihydro-1,8,9-triaza-anthracen-10-ol Method ZZ; To a suspension of 2-amino-5-chloropyridine (5 g, 38.89 mmol) in dichloromethane (75 mL) cooled to 0° C. was added triethylamine (9.7 mL, 70 mmol) in a stream followed by the dropwise addition of pivaloyl chloride (7.2 mL, 58.33 mmol) over 10 minutes. The reaction was stirred and allowed to warm to room temperature over 1 hour. The reaction was quenched with saturated ammonium chloride (100 mL) and extracted with 50% diethyl ether-hexane mixture (2×200 mL). The combined organic layers were washed with brine (2×100 mL) and dried over MgSO$_4$. Filtration and concentration yielded a pale yellow oil which was dissolved in a 50% mixture of diethyl ether in hexane (100 mL) and filtered through a plug of silica gel. Evaporation afforded 8.6 g (quant.) of 71 as an off-white solid which was used without further purification.

Synthesis of N-[5-Chloro-3-(2,2,2-trifluoro-1,1-dihydroxyethyl)-2-pyridyl]-2,2-dimethylpropanamide Method AAA; To a solution of N-(5-Chloro-2-pyridyl)-2,2-dimethylpropanamide (2.5 g, 11.75 mmol) in THF (50 mL) at −78° C. was added t-Butyllithium (1.7 M in pentane, 15.2 mL, 25.85 mmol) dropwise over 10 minutes. The reaction was stirred at −78° C. for 3 hours and ethyl trifluoroactetate (4.2 mL, 35.25 mmol) was added dropwise. The mixture was stirred for 15 minutes at −78° C. and allowed to warm to room temperature over 45 minutes. After stirring at room temperature for an additional 30 minutes, the reaction was quenched with a dropwise addition of saturated ammonium chloride (100 mL) and partitioned between diethyl ether (150 mL) and water (150 mL). The organic layer was washed with brine (100 mL) and diluted with hexane (150 ml). After standing overnight, the off-white crystals 72 were collected and dried in vacuo, 2.85 g (78.5%) and used without further purification.

Synthesis of 1-(2-Amino-5-chloro-3-pyridinyl)-2,2,2-trifluoroethanone

Method BBB; N-[5-Chloro-3-(2,2,2-trifluoro-1,1-dihydroxyethyl)-2-pyridyl]-2,2-dimethylpropanamide 72 (1 g, 3.23 mmol) was dissolved in a mixture of 6 N HCl (12 mL) and dimethoxyethane (3 mL) and heated to 110° C. for 2 h. After cooling to room temperature, the reaction mixture was poured onto ice and made basic by portionwise addition of $NaHCO_3$. The mixture was extracted with a 50% mixture of diethyl ether in ethyl acetate (2×50 mL) and the combined organic layers were washed with brine (50 mL) and dried ($MgSO_4$). Concentration yielded 73 as a bright yellow solid, 0.66 g (90%) which was used without further purification.

Synthesis of 1-[5-Chloro-2-(tritylamino)-3-pyridinyl]-2,2,2-trifluoroethanone Method CCC; 1-(2-Amino-5-chloro-3-pyridinyl)-2,2,2-trifluoroethanone (4.86 g, 21.69 mmol), triphenylmethylcarbinol (6.78 g, 26.02 mmol) and p-toluenesulfonic acid monohydrate (0.41 g, 2.16 mmol) were dissolved in acetonitrile (75 mL) in a 200 mL round bottom flask fitted with a Dean—Stark trap and a reflux condenser. After heating to reflux for 16 hours, the reaction mixture was cooled and diluted with ethyl acetate (100 mL). The organic layer was washed with saturated $NaHCO_3$ (2×100 mL), brine (1×100 mL) and concentrated. Chromatography ($SiO_2$, 20% diethyl ether-hexane) afforded the product 74 as a yellow solid, 5.76 g (57%).

Synthesis of 1-(2-Chloro-3-pyridinyl)-1-[5-chloro-2-(tritylamino)-3-pyridinyl]-2,2,2-trifluoroethanol Method DDD; A solution of diisopropylamine (1.08 mL, 7.71 mmol) in THF at −78° C. was treated with n-BuLi (2.5 M in hexane, 3.2 mL, 7.9 mmol) dropwise such that the temperature remained below −65° C. After stirring at −78° C. for 1 hour, 2-chloropyridine (0.435 mL, 4.62 mmol) was added to the reaction at a rate to keep the temperature below −70° C. After stirring at −78° C. for 3 hours, a solution of 1-[5-Chloro-2-(tritylamino)-3-pyridinyl]-2,2,2-trifluoroethanone (1.8 g, 3.82 mmol in 20 mL THF) was added to the reaction dropwise such that the temperature did not rise above −70° C. The reaction was stirred at −78° C. for 1 hour then warmed to room temperature over 90 minutes. After stirring for an additional 30 minutes, the reaction was quenched by dropwise addition of saturated ammonium chloride (50 mL) and partitioned between ethyl acetate (150 mL) and water (100 mL). The organic layer was washed with brine (100 mL), dried with $MgSO_4$ and concentrated. Trituration of the resulting solid with diethyl ether (100 mL) yielded the desired product 75 as a brown solid, 1.37 g (61%) which was used without further purification.

Synthesis of 3-Chloro-5-hydroxy-5-trifluoromethyl-5,10-dihydropyrido[2,3-b][1,8]naphthyridine Method EEE; 1-(2-Chloro-3-pyridinyl)-1-[5-chloro-2-(tritylamino)-3-pyridinyl]-2,2,2-trifluoroethanol (3.6 g, 6.2 mmol) was dissolved in a mixture of acetic acid (36 mL) and water (9 mL) and heated to reflux. After 24 hours, the reaction was cooled to room temperature and poured onto ice. The mixture was made basic by portionwise addition of $NaHCO_3$ and extracted with ethyl acetate (2×75 mL). The combined organic layers were washed with brine (100 mL), dried with $MgSO_4$, and concentrated. Chromatography ($SiO_2$, 40% ethyl acetate-hexane) provided the desired material 76 as an off white solid, 1.22 g (65.2%).

Example 45

Synthesis of 3-Chloro-10-cyclopropylmethoxy-10-trifluoromethyl-9,10-dihydro-1,8,9-triaza-anthracene Method FFF; A solution of 3-chloro-5-(hydroxy)-5-(trifluoromethyl)-5,10-dihydropyrido[2,3-b][1,8]naphthyridine (50 mg, 0.166 mmol) in concentrated $H_2SO_4$ (1.5 mL) was stirred at room temperature. After 30 minutes, the reaction mixture was added dropwise to a vigorously stirring solution of saturated $NaHCO_3$ and extracted with ethyl acetate (25 mL). The organic phase was washed with brine (25 mL), dried with $MgSO_4$, and concentrated to yield 77 as a light brown solid, 38.7 mg (82.5%) which was used without further purification.

Synthesis of 3-Chloro-5-(cyclopropylmethoxy)-5-(trifluoromethyl)-5,10-dihydropyrido[2,3-b][1,8]naphthyridine Method GGG; A solution of 5-trifluoromethyl-3-chloropyrido[2,3-b][1,8]naphthyridine (20 mg 0.056 mmol) in cyclopropyl methyl alcohol (1.5 mL) was treated with trifluoroacetic acid (14 μL, 0.18 mmol) and stirred for 90 minutes. After concentration, the residue was dissolved in ethyl acetate (25 mL), washed with saturated $NaHCO_3$ (25 mL), brine (25 mL), and dried over $MgSO_4$. Concentration followed by chromatography ($SiO_2$, 20% ethyl acetate-hexane) yielded 78 as a white solid, 22 mg (87.7%, mp 188° C.).

Example 46

Synthesis of 3-Chloro-5-(cyclopropylmethoxy)-5-(trifluoromethyl)-5,10-dihydropyrido[2,3-b][1,8]naphthyridine-9-N-oxide Method HHH; A solution of 3-chloro-5-(cyclopropylmethoxy)-5-(trifluoromethyl)-5,10-dihydropyrido[2,3-b][1,8]naphthyridine (0.02 g, 0.056 mmol) in dichloromethane (4 mL) was treated with m-chloroperbenzoic acid in one portion and stirred at room temperature for 4 hours. The reaction was quenched with saturated $NaHCO_3$ and was partitioned between dichloromethane (20 mL) and water (20 mL). The organic layer was washed with brine and dried over $MgSO_4$. Concentration and chromatography ($SiO_2$, 60% ethyl acetate-hexane to 100% ethyl acetate to 5% methanol-dichloromethane, gradient elution) afforded 12.5 mg of a white solid 79 (60%).

Example 47

Synthesis of 3-Chloro-5-(isopropylmethoxy)-5-(trifluoromethyl)-5,10-dihydropyrido[2,3-b][1,8]naphthyridine (10) was According to the Procedure Described in Method GGG (55 mg, 15%)

Example 48

Synthesis of 3-Chloro-5-(isopropylmethoxy)-5-(trifluoromethyl)-5,10-dihydropyrido[2,3-b][1,8]naphthyridine-9-N-oxide (11) was According to the Procedure Described in Method HHH (35 mg, 82%)

Scheme 11

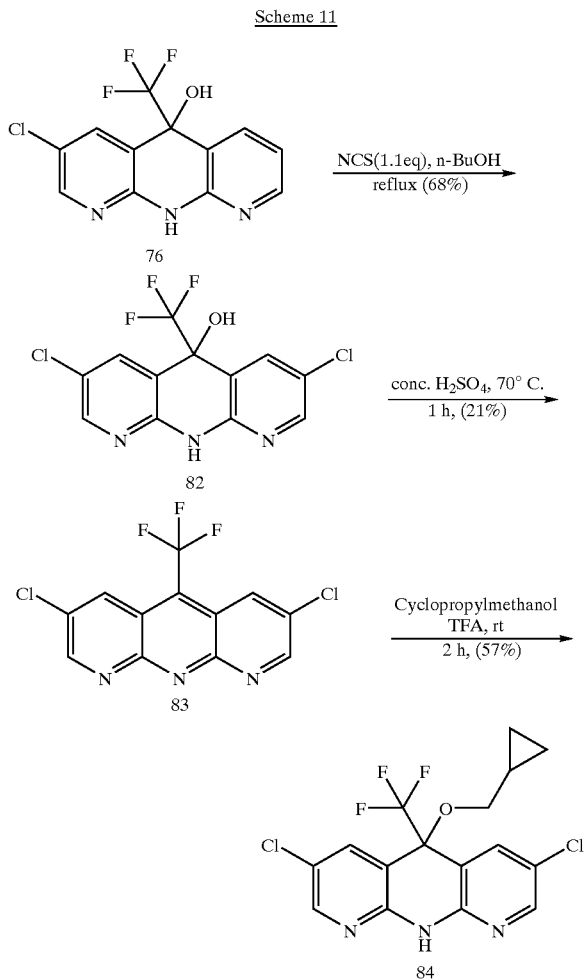

Example 49

Synthesis of 3,7-Dichloro-5-hydroxy-5-trifluoromethyl-5,10-dihydropyrido[2,3-b][1,8]naphthyridine Method III; To a solution of 3-chloro-5-hydroxy-5-trifluoromethyl-5,10-dihydropyrido[2,3-b][1,8]naphthyridine (0.23 g, 0.76 mmol) in n-BuOH (5 mL) was added N-chlorosuccinamide (0.11 g, 0.84 mmol) and the reaction was stirred at 120° C. for 1 hour. The reaction was cooled to room temperature and poured into saturated NaHCO$_3$. The resulting mixture was extracted with ethyl acetate (20 mL) and the organic layer was washed with brine (20 mL) and dried over MgSO$_4$. Concentration and trituration with diethyl ether yielded 82 as a white colored solid, 0.175 g (68.1%).

Example 50

Synthesis of 5-Trifluoromethyl-3,7-dichloropyrido[2,3-b][1,8]naphthyridine

Method JJJ; A solution of 3,7-dichloro-5-hydroxy-5-trifluoromethyl-5,10-dihydropyrido[2,3-b][1,8]naphthyridine (75 mg, 0.223 mmol) in concentrated H$_2$SO$_4$ (2.0 mL) was stirred at 70° C. for 1 h. After the reaction was complete, the mixture was added dropwise to a vigorously stirring solution of saturated NaHCO$_3$ and was extracted with ethyl acetate (25 mL). The organic layer was washed with brine (25 mL), dried with MgSO$_4$, and concentrated to yield 83 as a light brown solid, 85 mg (21%) which was used without further purification.

Example 50a

Synthesis of 3,7-Dichloro-5-(cyclopropylmethoxy)-5-trifluoromethyl-5,10-dihydropyrido[2,3-b][1,8]naphthyridine (84)was Prepared According to the Procedure Described in Method GGG (10.5 mg, 57%)

Scheme 12

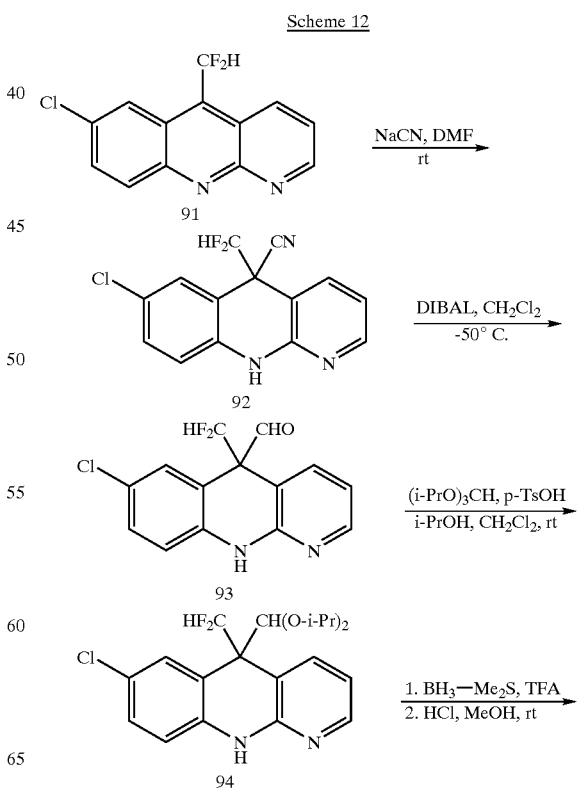

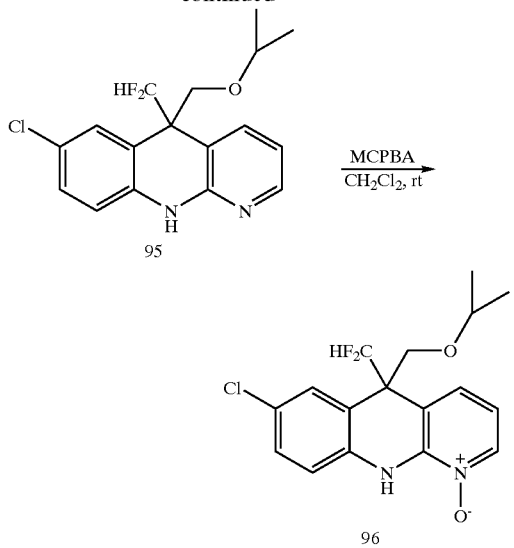

Example 51

Preparation of 7-Chloro-5-cyano-5-(difluoromethyl)-5,10-dihydrobenzo[b][1,8]naphthyridine (92)

Method KKK To a stirred solution of 7-chloro-9-(difluoromethyl)-4-azaacridine (91) (1.28 g, 4.84 mmol) in anhydrous DMF (30 mL) at room temperature was added NaCN (711 mg, 14.51 mmol). After 15 h at room temperature, the reaction was quenched with $H_2O$ (150 mL), and extracted with EtOAc (3×). The combined organic layers were washed with brine, dried over $Na_2SO_4$, filtered and concentrated in vacuo. Flash chromatography ($SiO_2$, 30% EtOAc-hexane) furnished 92 (747 mg, 53% yield) as a brown solid.

Example 52

Preparation of 7-Chloro-5-(difluoromethyl)-5-formyl-5,10-dihydrobenzo[b][1,8]naphthyridine (93)

Method LLL To a stirred solution of 7-chloro-5-cyano-5-(difluoromethyl)-5,10-dihydrobenzo[b][1,8]naphthyridine (92) (747 mg, 2.55 mmol) in anhydrous methylene chloride (40 mL) at −78° C. was added DIBAL (1.0 M in $CH_2Cl_2$, 7.67 mL) dropwise. After 3 h at −50° C., the reaction was quenched with 1.0 N HCl (40 mL), and extracted with EtOAc (3×). The combined organic layers were washed with brine, dried over $Na_2SO_4$, filtered and concentrated in vacuo. Flash chromatography ($SiO_2$, 30% EtOAc-hexane) furnished 93 (299 mg, 39% yield) as a yellow solid.

Example 53

Preparation of 7-chloro-5-(difluoromethyl)-5-diisopropoxymethyl-5,10-dihydrobenzo[b][1,8]naphthyridine (94)

Method MMM To a stirred solution of 7-chloro-5-(difluoromethyl)-5-formyl-5,10-dihydrobenzo[b][1,8]naphthyridine (93) (294 mg, 1.0 mmol) in anhydrous triisopropyl orthoformate (8.24 mL, 36.98 mmol) and anhydrous isopropanol (5 mL) at room temperature was added p-TsOH.$H_2O$ (380 mg, 2.0 mmol). After 1.5 h at room temperature, the reaction was concentrated in vacuo. Flash chromatography ($SiO_2$, 30% EtOAc-hexane) afforded 94 (132 mg, 34% yield) as a yellow solid.

Example 54

Preparation of 7-Chloro-5-(difluoromethyl)-5-isopropoxymethyl-5,10-dihydrobenzo[b][1,8]naphthyridine (95)

Method NNN To a stirred solution 7-chloro-5-(difluoromethyl)-5-diisopropoxymethyl-5,10-dihydrobenzo[b][1,8]naphthyridine (94) (50 mg, 0.13 mmol) in trifluoroacetic acid (2 mL) at room temperature was added borane-methyl sulfide complex (36 μL, 0.38 mmol). After 14 h at room temperature, the reaction mixture was quenched with 1.0 N NaOH and extracted with EtOAc (3×). The combined layers were dried over $MgSO_4$, filtered and concentrated in vacuo. The resulting yellow residue was taken up in MeOH (3 mL), acidified with 4 N HCl in dioxane (100 μL), and stirred at room temperature for 3 hours. The solution was quenched with saturated aqueous $NaHCO_3$ (50 mL) and extracted with EtOAc (3×). The combined organic layers were dried over $MgSO_4$, filtered and concentrated in vacuo. The residue afforded 95 in quantitative yield.

Example 55

Preparation of 7-chloro-5-(difluoromethyl)-5-isopropoxymethyl-5,10-dihydrobenzo[b][1,8]naphthyridine-1-N-oxide (96)

Method OOO To a stirred solution of 7-chloro-5-(difluoromethyl)-5-isopropoxymethyl-5,10-dihydrobenzo[b][1,8]naphthyridine (95) (44 mg, 0.13 mmol) in methylene chloride (3 mL) at room temperature was added MCPBA (77% max, 44 mg, 0.19 mmol). After 16 h at room temperature, the reaction was quenched with 1:1 aqueous 10% $Na_2S_2O_3$/saturated aqueous $NaHCO_3$ (10 mL), and extracted with EtOAc (2×). The combined organic layers were washed with brine, dried over $MgSO_4$, filtered and concentrated in vacuo. Flash chromatography ($SiO_2$, 5% MeOH—$CH_2Cl_2$) furnished 96 (6 mg, 13% yield) as a red oil.

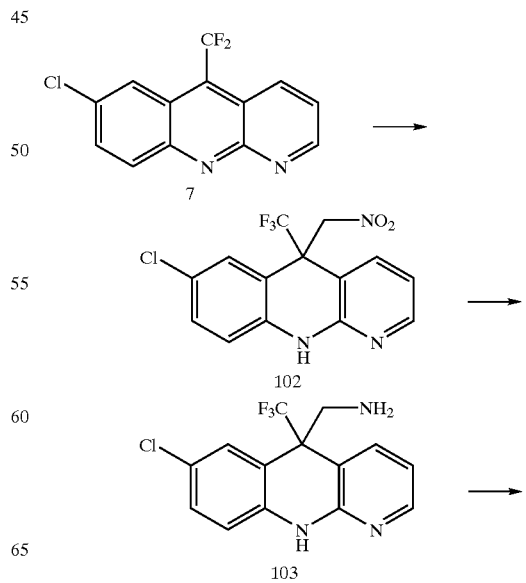

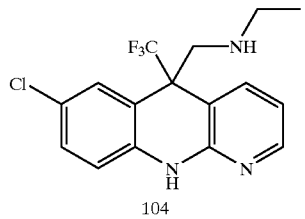

104

Example 56

Preparation of 7-Chloro-1,5-dihydro-5-(N-ethylaminomethyl)-5-(trifluoromethyl)benzo[b][1,8]napthyridine To a solution of 7 (1.77 g, 6.26 mmol) in dry acetonitrile (20 mL) was added nitromethane (6 mL) followed by DBU (1.9 mL, 12.52 mmol). The solution was stirred at room temperature for 2 h and was then warmed to 70° C. for 1 h. The reaction was cooled to room temperature, poured into saturated $NH_4Cl$ and extracted with EtOAc. The organic phase was dried over $MgSO_4$, filtered, and concentrated. The crude product was purified via column chromatography (20% EtOAc/hex) to provide 102 (1.74 g, 81%) in the form of a yellow foam.

A mixture of 102 (1.74 g, 5.06 mmol) and stannous chloride dihydrate (5.70 g, 25.26 mmol) in EtOH (6 mL) was warmed to 60° C. Concentrated HCl (6 mL) was then added and the resulting solution was stirred at 60° C. for 30 min. The volatiles were removed in vacuo and the remaining residue was adjusted to pH 12 with 1N NaOH. This aqueous phase was extracted with EtOAc. The organic phase was dried over $MgSO_4$, filtered and concentrated to provide 1.38 g (87%) of 103 which was isolated as a pale pink solid.

A mixture of primary amine 103 (100 mg, 0.32 mmol), iodoethane (0.118 mL, 0.48 mmol), and $K_2CO_3$ (133 mg, 0.96 mmol) in acetonitrile (2.5 mL) was heated at 70° C. for 2 h. The reaction mixture was poured into $H_2O$ and was extracted with $CH_2Cl_2$. The organic phase was dried over $MgSO_4$, filtered, and concentrated. The crude product was purified using column chromatography (50% EtOAc/hexane→5% MeOH/$CH_2Cl_2$) to provide 46 mg (42%, mp 142.3–144.2° C.) of 104, which crystallized upon slow evaporation from a solution in $Et_2O$.

Example 57

Preparation of 7-Chloro-5,10-dihydro-5-(N-isopropylaminomethyl)-5-(trifluoromethyl)benzo[b][1,8]napthyridine

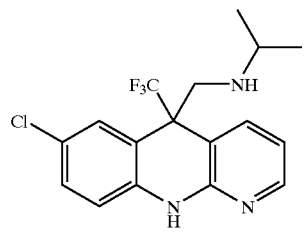

105

A mixture of amine 103 (100 mg, 0.32 mmol) and acetone (0.026 mL, 0.35 mmol) in MeOH (1.6 mL) was cooled to 0° C. The reaction mixture was brought to pH 4 by adding several drops of glacial acetic acid, upon addition of which, solution occurred. The solution was stirred for 15 min before adding $NaCNBH_4$ (22 mg, 0.34 mmol). The reaction was stirred for 3 h while allowing it to warm to room temperature and was then slowly poured into saturated $NaHCO_3$. Extraction with EtOAc followed by drying over $MgSO_4$, filtration and concentration provided 116 mg (100%, mp 182.2–184.8° C.) of 105 in the form of a white foam which crystallized upon slow evaporation from a solution in hexane.

Example 58

Preparation of 7-Chloro-5,10-dihydro-5-(N-isopropyl-N-ethylaminomethyl)-5-(trifluoromethyl)benzo[b][1,8]napthyridine

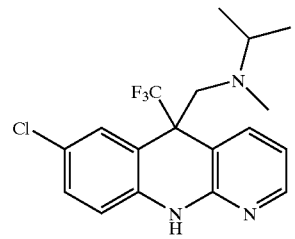

A mixture of 104 (76 mg, 0.21 mmol) and formaldehyde (37% aqueous, 0.040 mL) in MeOH (2.5 mL) at 0° C. was adjusted to pH 4 by adding several drops of glacial acetic acid. After 15 min, $NaCNBH_4$ (21 mg, 0.32 mmol) was added and the reaction mixture was stirred for 3 h while allowing it to gradually warm to room temperature. The solution was then poured into saturated $NaHCO_3$, the MeOH was removed in vacuo and the remaining aqueous phase was extracted with $CH_2Cl_2$. The organic phase was dried ove $MgSO_4$, filtered and concentrated to provide 76 mg (99%, mp 139.6–141.2° C.) of the title compound which crystallized upon slow evaporation from a solution in hexane.

Example 59

Preparation of 7-Chloro-5-(N,N-diethylaminomethyl)-5,10-dihydro-5-(trifluoromethyl)benzo[b][1,8]napthyridine

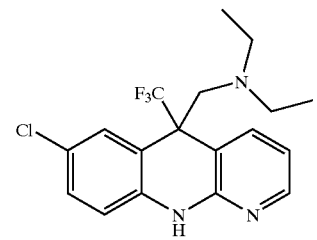

A solution of 104 (110 mg, 0.32 mmol) and excess acetaldehyde in MeOH (3 mL) at 0° C. was adjusted to pH 4 by adding several drops of glacial acetic acid. After 15 min, $NaCNBH_4$ (44 mg, 0.66 mmol) was added and the reaction mixture was allowed to warm to room temperature. After 2 h, the reaction mixture was poured into saturated $NaHCO_3$ and was extracted with $CH_2Cl_2$. The organic phase was dried over $MgSO_4$, filtered, and concentrated to provide 48 mg (40%, mp 115–117° C.) of the title compound which crystallized upon slow evaporation from a solution in hexane.

Example 60

Preparation of 5-(Acetamidomethyl)-7-chloro-5,10-dihydro-5-(trifluoromethyl)[b][1,8]napthyridine

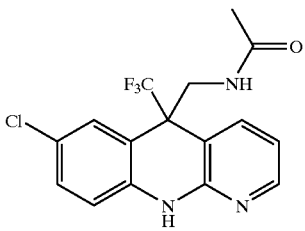

To a solution of 103 (60 mg, 0.19 mmol) in pyridine (1 mL) at room temperature was added acetic anhydride (0.180 mL, 1.9 mmol). After stirring the resulting solution for 2 h, it was poured into water and was extracted with EtOAc. The organic phase was dried over $MgSO_4$, filtered and concentrated, then co-concentrated with heptane. The crude solid was washed with $CH_2Cl_2$ to provide 45 mg (67%, mp 271.6–273.2° C.) of the title compound in the form of colorless crystals.

Example 61

Preparation of 5,10-Dihydro-7-fluoro-5-(N-methylsulfonylmethyl)-5-(trifluoromethyl)[b][1,8]napthyridine

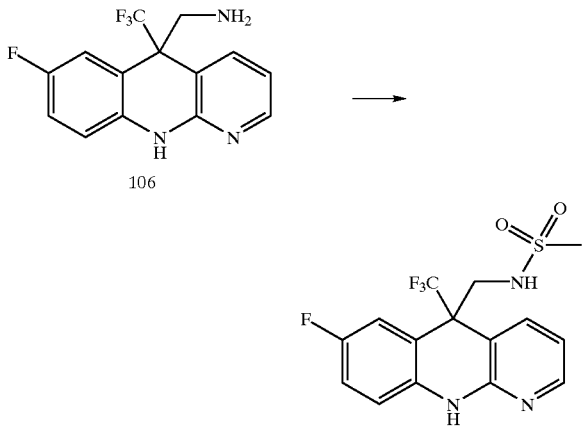

Methanesulfonic anhydride (79 mg, 0.45 mmol) was added to a solution of amine 106 (prepared according to the method of Example 1 using 7-fluoro-5-)trifluoromethyl)-1-azaacridine as the starting material) and triethylamine (0.146 mL, 1.05 mmol) in $CH_2Cl_2$ (2 mL) at room temperature. After 1 h, the reaction mixture was poured into water and was extracted with $CH_2Cl_2$. The organic phase was dried over $MgSO_4$, filtered and concentrated to a residue that crystallized upon slow evaporation from a $CH_2CH_2$ solution. The title compound (47mg, 33%, mp 234.9–237.4° C.(d)) was obtained in the form of pale yellow crystals.

Example 62

Preparation of 5,10-Dihydro-7-fluoro-5-(isopropylamidomethyl)-5-(trifluoromethyl)[b][1,8]napthyridine

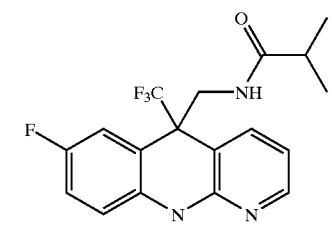

The title compound (mp 228.6–229.4° C.) was prepared according to the method of Example 61 by substituting methanesulfonic anhydride with isobutyryl chloride.

Example 63

Preparation of 5,10-Dihydro-7-fluoro-5-(isopropylguanadinomethyl)-5-(trifluormethyl)[b][1,8]napthyridine

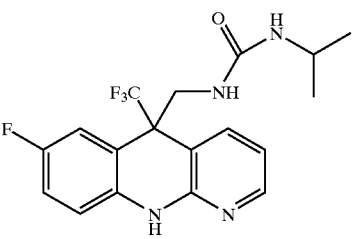

To a solution of amine 106 (50 mg, 0.17 mmol) and triethylamine (0.24 mL, 0.17 mmol) in DMF (1 mL) at room temperature was added isopropyl isocyanate (0.017 mL, 0.17 mmol). After stirring for 1 h, the reaction mixture was poured into $H_2O$ and was extracted with $CH_2Cl_2$. Several drops of MeOH were added to the organic phase in order to achieve solution. This solution was then dried over $MgSO_4$, filtered and concentrated. The remaining solid residue was washed with $CH_2CH_2$ to afford 25 mg (38%, mp 273.2–275.0° C.) of pure title compound in the form of a white solid.

Example 64

Preparation of 1,5-dihydro-7-fluoro-5-(isopropylmethyl)-5-(trifluoromethyl)[b][1,8]napthyridine-1-(N-oxide)

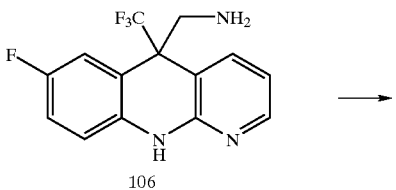

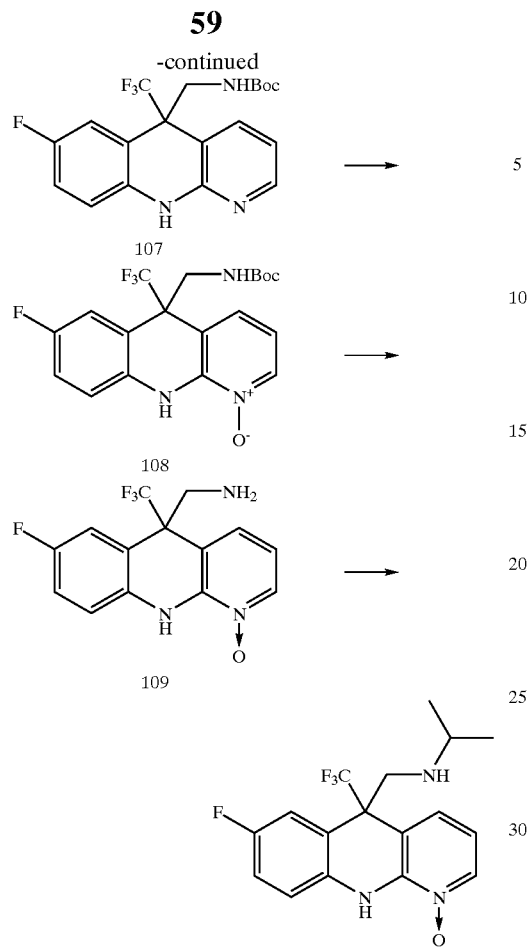

To a suspension of amine 106 (1.0 g, 3.5 mmol) in acetonitrile (32 mL) at room temperature was added NEt₃ (0.975 mL, 7.0 mmol), then Boc₂O (0.885 mL, 3.9 mmol). The reaction mixture was stirred for 1.5 h and was poured into saturated NH₄Cl. The aqueous phase was extracted with EtOAc. The organic phase was then dried over MgSO₄, filtered and concentrated. The crude product was purified via column chromatography (50% EtOAc/hexane) to provide 1.0 g (75%) of 107 in the form of a white solid.

A solution of 107 (1.1 g, 2.3 mmol) and MCPBA (1.1 g, 3.4 mmol) in CH₂Cl₂ (15 mL) was stirred at room temperature for 2 h. The reaction mixture was then poured into saturated NaHCO₃ and was extracted with CH₂Cl₂. The organic phase was dried over MgSO₄, filtered and concentrated. The crude product was purified via column chromatography (5% MeOH/CH₂Cl₂) to afford 906 mg (79%) of 108 in the form of a brown foam.

A solution of 108 (413 mg, 0.73 mmol) in TFA (3 mL) was stirred at room temperature for 1 h. The TFA was removed in vacuo and the remaining residue was adjusted to pH 11 with 1N NaOH. The aqueous phase was extracted with EtOAc. The organic phase was dried over MgSO₄, filtered and concentrated to provide 218 mg (95%) of 109 in the form of a pale brown solid.

A solution of amine 109 (218 mg, 0.70 mmol) and acetone (0.56 mL, 0.76 mmol) in MeOH (3.5 mL) at 0° C. was adjusted to pH 4 by adding several drops of glacial acetic acid. After 15 minutes, NaCNBH₄ (48 mg, 0.73 mmol) was added. The reaction mixture was allowed to warm to room temperature and was stirred for 1.5 h after which time the mixture was poured into saturated NaHCO₃. The MeOH was removed in vacuo and the remaining aqueous phase was extracted with EtOAc. The organic layer was dried over MgSO₄, filtered and concentrated to afford 213 mg (86%, mp 172.1–173.6° C.) of the title compound in the form of a foam which crystallized upon slow evaporation from a solution in Et₂O.

Example 65

Preparation of 5-(N,N-Diethylaminomethyl)-5,10-dihydro-7-fluoro-5-(trifluoromethyl)[b][1,8]napthyridine-1-(N-oxide)

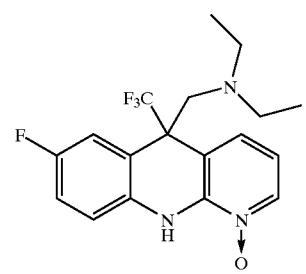

A solution of amine 109 (60 mg, 0.19 mmol) and excess acetaldehyde in MeOH (1.0 mL) at 0° C. was adjusted to pH 4 by adding several drops of glacial acetic acid. After 15 minutes, NaCNBH₄ (26 mg, 0.42 mmol) was added. The reaction mixture was allowed to warm to room temperature and was stirred for 1.5 h after which time the mixture was poured into saturated NaHCO₃. The MeOH was removed in vacuo and the remaining aqueous phase was extracted with EtOAc. The organic layer was dried over MgSO₄, filtered and concentrated. The crude product was purified via column chromatography (10% MeOH/Et₂O) to afford 60 mg (86%, mp 166.9–168.6° C.) of the title compound which crystallized upon slow evaporation from a solution in Et₂O.

Example 66

Preparation of 5,10-Dihydro-5-(N,N-dimethylaminomethyl)-7-fluoro-5-(trifluoromethyl)[b][1,8]napthyridine-1-(N-oxide)

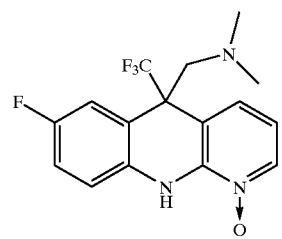

The title compound (mp 180.5–182.2° C.) was prepared by the method of Example 65 substituting acetaldehyde with a 37% solution of formaldehyde.

Example 67

Preparation of 7-Chloro-5,10-dihydro-5-(N-isopropylaminomethyl)-5-(trifluoromethyl)[b][1,8]napthyridine-1-(N-oxide)

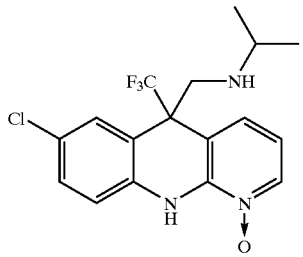

The title compound (mp 169.9–172.1° C.) was prepared according to the method of Example 64 by substituting amine 106 with amine 103.

Example 68

Preparation of 7-Chloro-5-(N,N-diethylaminomethyl)-5,10-dihydro-5-(trifluoromethyl)[b][1,8]napthyridine-1-(N-oxide)

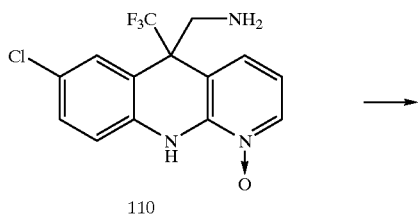

110

⟶

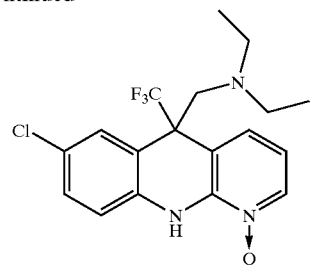

The title compound (mp 153.7–155.4° C.) was prepared from amine 110 (prepared according to the method of Example 64 using amine 103 as the starting material) by the method described in Example 65.

Example 69

Preparation of 7-Chloro-5,10-dihydro-5-(N,N-dimethylaminomethyl)-5-(trifluoromethyl)[b][1,8]napthyridine-1-(N-oxide)

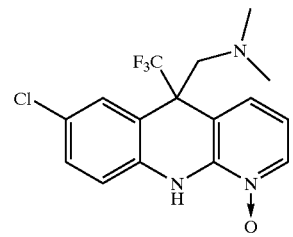

The title compound (mp 151.3–153.5° C.) was Prepared from 110 using the method of Example 66.

The following compounds may be synthesized using the methods described above.

TABLE 1*

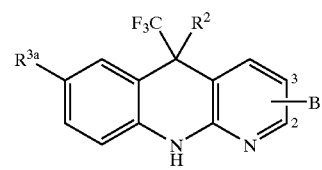

| No. | R² | B | R³ᵃ | MP (C.) | MS (M + H) | Synthesis Method |
|---|---|---|---|---|---|---|
| 21 | O-cyclopropylmethyl | H | Cl | 166–167 | 355 | A, B, C, D, E, F |
| 22 | O-benzyl | H | Cl | 126–127 | 391 | E, F |
| 23 | O-cyclobutylmethyl | H | Cl | 183–184 | 369 | E, F |
| 24 | O-ethyl | H | Cl | 221–222 | 329 | H |
| 25 | OH | H | Cl | 206–207 | 301 | D, F |
| 26 | O-n-propyl | H | Cl | 155–156 | 343 | H |
| 27 | O-i-propyl | H | Cl | 147–148 | 343 | H |
| 28 | n-butyl | H | Cl | 133–134 | 341 | G, I |
| 29 | O-methyl | H | Cl | 207–208 | 315 | H |
| 30 | O-cyclopropylmethyl (S) | H | Cl | 146–147 | 355 | Z |
| 31 | O-cyclopropylmethyl (R) | H | Cl | 146–147 | 355 | Z |
| 32 | cyclopropylethyl | H | Cl | 150–151 | 353 | L, M, N, I |
| 33 | O-2,2,2-trifluoroethyl | H | Cl | 153–154 | 383 | H |
| 34 | O-propargyl | H | Cl | 174–175 | 339 | E, F |
| 35 | ethyl | H | Cl | 148–149 | 312 | G, J |
| 36 | NH-cyclopropyl | H | Cl | 132–133 | 340 | G, O |
| 37 | NH-i-propyl | H | Cl | 126–127 | 342 | G, O |
| 38 | O-N,N-dimethylaminoethyl | H | Cl | 223–224 | 372 | G, Q |
| 39 | NH-(N-morpholinyl)ethyl | H | Cl | 174–175 | 413 | G, O |

TABLE 1*-continued

| No. | R² | B | R³ᵃ | MP (C.) | MS (M + H) | Synthesis Method |
|---|---|---|---|---|---|---|
| 40 | O-(1-methylcyclopropyl)methyl | H | Cl | 172–173 | 369 | G, Q |
| 41 | O-3,3,3-trifluoropropyl | H | Cl | 166–167 | 397 | G, Q |
| 42 | NH-cyclopropylmethyl | H | Cl | 163–164 | 354 | G, O |
| 43 | NH-methyl | H | Cl | 186–187 | 314 | G, O |
| 44 | NH-ethyl | H | Cl | 149–150 | 328 | G, O |
| 45 | cyclopropylethyl (S) | H | Cl | 68–69 | 353 | L, M, N, I |
| 46 | cylopropylethyl (R) | H | Cl | 68–69 | 353 | L, M, N, I |
| 47 | O-cylopropylmethyl | H | F | 166–167 | 339 | G, Q |
| 48 | O-cyclopropylethyl | H | F | 154–155 | 353 | G, Q |
| 49 | O-allyl | H | F | 161–162 | 325 | G, Q |
| 50 | NH-phenyl | H | Cl | 236–237 | 376 | G, P |
| 51 | O-cyclopropylmethyl | 2-methyl | Cl | 185–190 | 369 | A, B, C, D, E, F |
| 52 | n-butyl | 2-methyl | Cl | 115–118 | 469 | H, I |
| 53 | cyclopropylethyl | 2-methyl | Cl |  | 368 | L, M, N, I |
| 54 | allyl | H | F | 173–174 | 309 | L, M, N, I |
| 55 | nitrile | H | F | 218–219 | 294 | L, M, N, I |
| 56 | OH | H | F | 186–187 | 285 | D, F |
| 57 | NH-i-propyl | H | Cl | 131–132 | 340 | Q |
| 58 | O-cyclobutylmethyl | H | Cl | 157–158 | 353 | H |
| 59 | O-cyclobutylmethyl | 2-OH | F | 110–111 | 369 | H |
| 60 | 2-pyridylmethyl | H | Cl | 193–195 | 376 | R |
| 61 | butyl | H | F | 93–94 | 325 | I |
| 62 | 2-pyridylmethyl | H | F | 210–211 | 360 | R |
| 63 | 2-pyridylmethyl (R) | H | Cl | 89–90 | 376 | R |
| 64 | O-cyclopropylmethyl | 3-Cl | Cl | 166–167 | 390 | H |
| 65 | cyclopropylethyl | H | F | 143–144 | 337 | I |
| 66 | O-cyclopropylmethyl | 3-Cl | F | 156–157 | 373 | H, U |
| 67 | hydroxymethyl | H | Cl | 210–211 | 315 | D, F |
| 68 | (methanesulfonicether)methyl | H | Cl | 187–188 | 393 | T |
| 69 | O-cyclopropylmethyl | 2-methyl | Cl | 185–190 | 369 | A, B, C, D, E, F |
| 70 | n-butyl | 2-methyl | Cl | 115–118 | 469 | H, I |
| 71 | cyclopropylethyl | 2-methyl | Cl | 140–143 | 368 | L, M, N, I |
| 72 | O-cyclopropylmethyl | 2-S-methyl | Cl | NA | 402 | A, B, C, D, E, F |
| 73 | O-i-butyl | 2-S-methyl | Cl | NA | 404 | E, F |
| 74 | O-benzyl | 2-S-methyl | Cl | NA | 438 | E, F |
| 75 | O-2-pyridylmethyl | 2-S-methyl | Cl | NA | 439 | E, F |
| 76 | O-cyclopropylmethyl | H | Cl | none | 356 | E, K, F |
| 77 | O-cyclobutylinethyl | H | Cl | none | 370 | E, K, F |
| 78 | O-methyl | H | Cl | none | 316 | E, K, F |
| 79 | O-cyclopropylmethyl (S) | H | Cl | none | 356 | E, K, F |
| 80 | O-cyclopropylmethyl (R) | H | Cl | none | 356 | E, K, F |
| 81 | O-N-piperidinylethyl | H | Cl | none | 413 | E, K, F |
| 82 | O-N-pyrrolidinylethyl | H | Cl | none | 415 | E, K, F |
| 83 | O-(N2-methyl)-N1-piperazinepropyl | H | Cl | none | 399 | E, K, F |
| 84 | O-propyl | H | Cl | none | 442 | E, K, F |
| 85 | O-N,N-dimethylaminopropyl | H | Cl | none | 344 | E, K, F |
| 86 | O-benzyl | H | Cl | none | 387 | E, K, F |
| 87 | O-3-pyridinylmethyl | H | Cl | none | 392 | E, K, F |
| 88 | O-allyl | H | Cl | none | 393 | E, K, F |
| 89 | O-propargyl | H | Cl | none | 340 | E, K, F |
| 90 | O-N,N-dimethylaminoethyl | H | Cl | none | 373 | E, K, F |
| 91 | N-ethylaminomethyl | H | Cl | 142.3–144.2 |  |  |
| 92 | N-isopropylaminomethyl | H | Cl | 182.2–184.8 |  |  |
| 93 | N-isopropyl-N-ethylaminomethyl | H | Cl | 139.6–141.2 |  |  |
| 94 | N,N-diethylaminomethyl | H | Cl | 115–117 |  |  |
| 95 | acetamidomethyl | H | Cl | 271.6–273.2 |  |  |
| 96 | N-methylsulfonyl methyl | H | F | 234.9–237.4(d) |  |  |
| 97 | isopropylamidomethyl | H | F | 228.6–229.4° C. |  |  |
| 98 | isopropylguanadinomethyl | H | F | 273.2–275.0 |  |  |

TABLE 2*

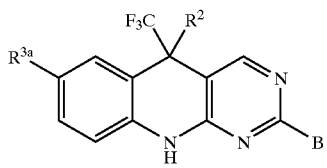

| No. | R² | B | R³ᵃ | MS (M + H) | Synthesis Method |
|---|---|---|---|---|---|
| 99 | O-cyclopropyl-methyl | S-methyl | Cl | 402 | A, B, C, D, E, F |
| 100 | O-i-butyl | S-methyl | Cl | 404 | E, F |
| 101 | O-benzyl | S-methyl | Cl | 438 | E, F |
| 102 | O-2-pyridylmethyl | S-methyl | Cl | 439 | E, F |
| 103 | O-cyclopropyl-methyl | H | Cl | 356 | E, K, F |
| 104 | O-cyclobutylmethyl | H | Cl | 370 | E, K, F |
| 105 | O-methyl | H | Cl | 316 | E, K, F |
| 106 | O-cyclopropyl-methyl (S) | H | Cl | 356 | E, K, F |
| 107 | O-cyclopropyl-methyl (R) | H | Cl | 356 | E, K, F |
| 108 | O-(N-piperidinyl)ethyl | H | Cl | 413 | E, K, F |

TABLE 2*-continued

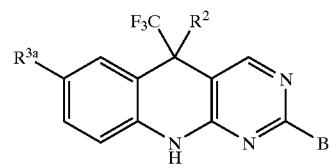

| No. | R² | B | R³ᵃ | MS (M + H) | Synthesis Method |
|---|---|---|---|---|---|
| 109 | O-(N-pyrrolidinyl)ethyl | H | Cl | 415 | E, K, F |
| 110 | O-(N2-methyl)-N1-piperazinepropyl | H | Cl | 399 | E, K, F |
| 111 | O-propyl | H | Cl | 442 | E, K, F |
| 112 | O-N,N-dimethyl-aminopropyl | H | Cl | 344 | E, K, F |
| 113 | O-benzyl | H | Cl | 387 | E, K, F |
| 114 | O-3-pyridinylmethyl | H | Cl | 392 | E, K, F |
| 115 | O-allyl | H | Cl | 393 | E, K, F |
| 116 | O-propargyl | H | Cl | 340 | E, K, F |
| 117 | O-N,N-dimethyl-aminoethyl | H | Cl | 373 | E, K, F |
| 118 | O-cyclopropyl-methyl | H | Cl | | |
| 119 | butyl | H | Cl | 347 | A, B, C, D, E, F |

TABLE 3*

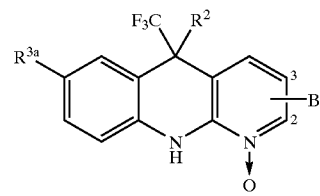

| No. | R² | B | R³ᵃ | MP (C.) | MS (M + H) | Synthesis Method |
|---|---|---|---|---|---|---|
| 120 | O-cyclopropylmethyl | H | Cl | 165–166 | 371 | H, U |
| 121 | O-benzyl | H | Cl | | | |
| 122 | O-cyclobutylmethyl | H | Cl | | | |
| 123 | O-ethyl | H | Cl | | | |
| 124 | OH | H | Cl | 274–275 | 317 | U |
| 125 | O-n-propyl | H | Cl | | | |
| 126 | O-i-propyl | H | Cl | | | |
| 127 | n-butyl | H | Cl | | | |
| 128 | O-methyl | H | Cl | | | |
| 129 | O-cyclopropylmethyl (S) | H | Cl | 114–116 | 371 | U |
| 130 | O-cyclopropylmethyl (R) | H | Cl | | | |
| 131 | cyclopropylethyl | H | Cl | | | |
| 132 | O-2,2,2-trifluoroethyl | H | Cl | | | |
| 133 | O-propargyl | H | Cl | 172–173 | 355 | U |
| 134 | ethyl | H | Cl | | | |
| 135 | NH-cyclopropyl | H | Cl | | | |
| 136 | NH-i-propyl | H | Cl | | | |
| 137 | O-N,N-dimethylaminoethyl | H | Cl | | | |
| 138 | NH-N-morpholinylethyl | H | Cl | | | |
| 139 | O-(1-methylcyclopropyl)methyl | H | Cl | 167–168 | 385 | U |
| 140 | O-3,3,3-trifluoropropyl | H | Cl | | | |

TABLE 3*-continued

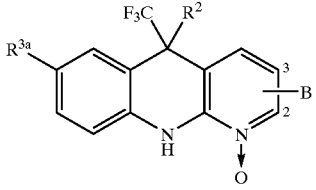

| No. | R² | B | R³ᵃ | MP (C.) | MS (M + H) | Synthesis Method |
|---|---|---|---|---|---|---|
| 141 | NH-cyclopropylmethyl | H | Cl | | | |
| 142 | NH-methyl | H | Cl | | | |
| 143 | NH-ethyl | H | Cl | | | |
| 144 | cyclopropylethyl (S) | H | Cl | 120–121 | 369 | U |
| 145 | cylopropylethyl (R) | H | Cl | | | |
| 146 | O-cylopropylmethyl | H | F | 193–194 | 355 | U |
| 147 | O-cyclopropylethyl | H | Cl | 97–98 | 369 | U |
| 148 | O-allyl | H | F | | | |
| 149 | NH-phenyl | H | Cl | | | |
| 150 | O-cyclopropylmethyl | 2-methyl | Cl | 225–227 | 385 | U |
| 151 | n-butyl | 2-methyl | Cl | | | |
| 152 | cyclopropylethyl | 2-methyl | Cl | 205–207 | 384 | |
| 153 | allyl | H | F | | | |
| 154 | nitrile | H | F | | | |
| 155 | OH | H | F | | | |
| 156 | O-cyclobutylmethyl | H | F | 171–172 | 369 | H, U |
| 157 | NH-i-propyl | H | F | 206–207 | 356 | O, U |
| 158 | 2-pyridylmethyl | H | Cl | 251–252 | 392 | R, U |
| 159 | 2-pyridylmethyl | H | Cl | 303–304 | 408 | R, U |
| 160 | O-cyclopropylmethyl (S) | H | F | 115–116 | 354 | H, U |
| 161 | O-cyclopropylmethyl | 3-Cl | Cl | 244–245 | 406 | S, H, U |
| 162 | pentyl | 3-Cl | Cl | 214–215 | 406 | S, I, U |
| 163 | cyclopropylethyl | H | F | 196–197 | 354 | I, U |
| 164 | O-cyclopropylmethyl (S) | 3-Cl | F | 223–224 | 406 | H, U |
| 165 | cyclopropylethyl (R) | H | F | 153–154 | 354 | I, U |
| 166 | O-cyclopropylmethyl | 3-Cl | F | 191–192 | 389 | H, U |
| 167 | O-i-butyl | H | Cl | 165–166 | 373 | H, U |
| 168 | butyl | H | Cl | 161–162 | 357 | I, U |
| 169 | O-cyclopropylmethyl (S) | 3-Cl | F | 173–174 | 389 | H, U |
| 170 | O-i-butyl | H | F | 142–143 | 357 | H, U |
| 171 | O-i-propyl | H | F | 156–157 | 343 | H, U |
| 172 | O-i-propyl | H | Cl | 115–116 | 358 | H, U |
| 173 | N-isopropylmethyl | H | F | 172.1–173.6 | | |
| 174 | N,N-diethylaminomethyl | H | F | 166.9–168.6 | | |
| 175 | N,N-dimethylaminomethyl | H | F | 180.5–182.2 | | |
| 176 | N-isopropylaminomethyl | H | Cl | 169.9–172.1 | | |
| 177 | N,N-diethylaminomethyl | H | Cl | 153.7–155.4 | | |
| 178 | N,N-dimethylaminomethyl | H | Cl | 151.3–153.5 | | |

TABLE 4*

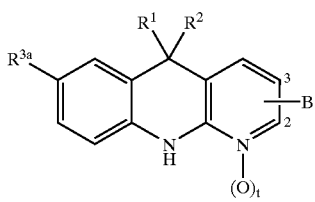

| No. | R² | R¹ | B | R³ᵃ | t | Mp °C. |
|---|---|---|---|---|---|---|
| 179 | O-cyclopropylmethyl | CHF₂ | H | Cl | 0 | 83–84 |
| 180 | O-cyclopropylmethyl | CHF₂ | H | F | 0 | 137–138 |
| 181 | O-cycloproylethyl | CHF₂ | H | Cl | 0 | 148–149 |
| 182 | 2-pyridylmethyl | CHF₂ | H | Cl | 0 | 204–205 |
| 183 | O-cyclopropylethyl | CHF₂ | 3-Cl | F | 0 | 169–170 |
| 184 | O-cyclopropylmethyl | CHF₂ | H | Cl | 1 | 185–186 |
| 185 | O-cyclopropylmethyl | CHF₂ | H | F | 1 | 166–167 |
| 186 | O-cyclopropylethyl | CHF₂ | H | Cl | 1 | 175–176 |
| 187 | 2-pyridylmethyl | CHF₂ | H | Cl | 1 | 210–211 |

TABLE 4*-continued

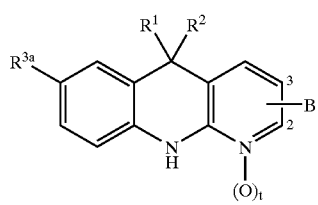

| No. | R² | R¹ | B | R³ᵃ | t | Mp °C. |
|---|---|---|---|---|---|---|
| 188 | O-cyclopropylmethyl | CHF₂ | 3-Cl | F | 1 | 163–164 |
| 189 | n-butyl | CHF₂ | H | Cl | 0 | oil |
| 190 | (2-cyclopropyl)ethyl | CHF₂ | H | Cl | 0 | oil |
| 191 | O-cyclopropylmethyl | CF₂CH₃ | H | Cl | 0 | 65–66 |
| 192 | O-cyclopropylmethyl | CF₂CH₃ | H | F | 0 | 132–135 |
| 193 | O-cyclopropylmethyl | CF₂CH₃ | H | F | 1 | 199–202 |
| 194 | O-i-propyl | CF₂CH₃ | H | Cl | 0 | 148–149 |
| 195 | O-i-propyl | CF₂CH₃ | H | Cl | 1 | 56–57 |

TABLE 4*-continued

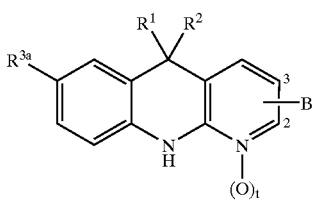

| No. | R² | R¹ | B | R³ᵃ | t | Mp °C. |
|---|---|---|---|---|---|---|
| 196 | (S) O-cyclopropylmethyl | CF₂CH₃ | H | Cl | 1 | |
| 197 | (R) O-cyclopropylmethyl | CF₂CH₃ | H | Cl | 1 | |
| 198 | i-propoxymethyl | CHF₂ | H | Cl | 0 | |
| 199 | i-propoxymethyl | CHF₂ | H | Cl | 1 | |

TABLE 5*

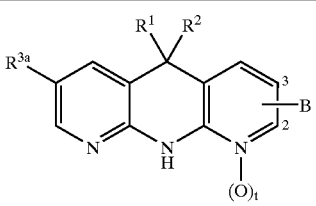

| No. | R² | R¹ | B | R³ᵃ | t | Mp °C. |
|---|---|---|---|---|---|---|
| 200 | O-cyclopropylmethyl | CF₃ | H | Cl | 0 | |
| 201 | O-cyclopropylmethyl | CF₃ | H | Cl | 1 | |
| 202 | O-cyclopropylmethyl | CF₃ | 3-Cl | Cl | 0 | |
| 203 | O-i-butyl | CF₃ | H | Cl | 0 | |
| 204 | O-i-butyl | CF₃ | H | Cl | 1 | |

*Unless otherwise noted, stereochemistry is racemic (+/−).

The following compounds shown in Table 6 can be made using the procedure described above or by those known to one skilled in the art. Each of the cores at the beginning of the table (a-ff) are meant to be paired with each entry in the table. For example, core e can be combined with entry 10 to provide one example. The number for R³* is indicated in core a and is the same throughout the different core structures.

TABLE 6

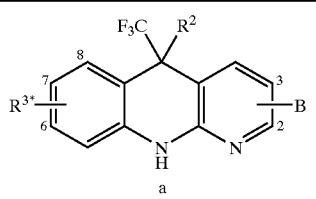

a

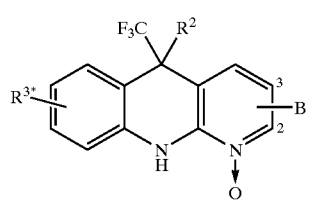

b

TABLE 6-continued

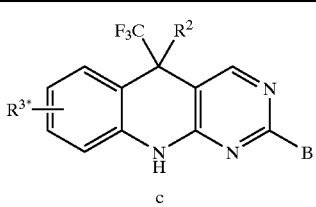

c

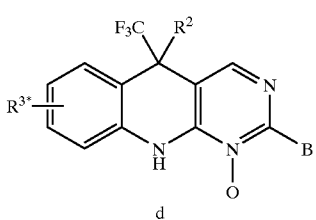

d

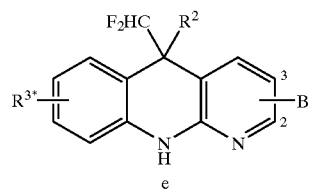

e

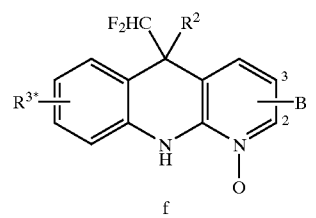

f

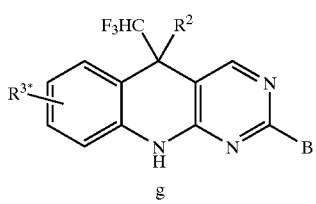

g

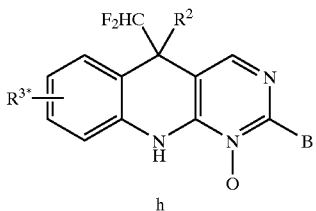

h

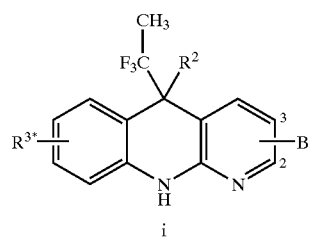

i

TABLE 6-continued
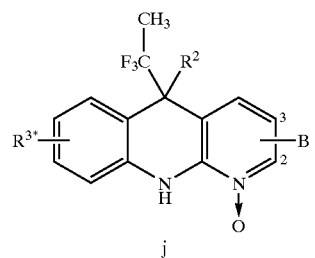
j
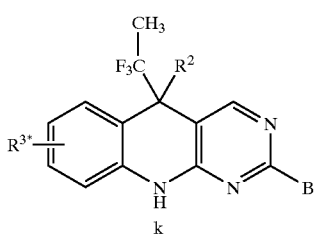
k
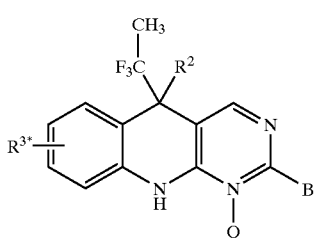
l
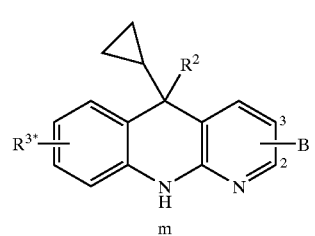
m
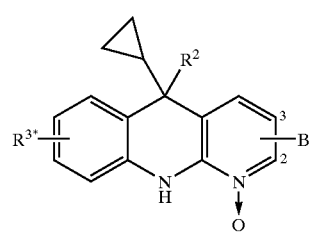
n
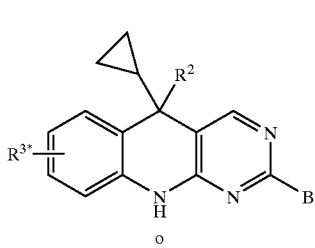
o
TABLE 6-continued
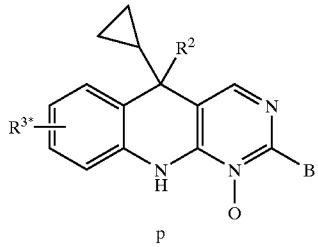
p
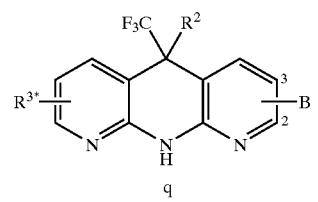
q
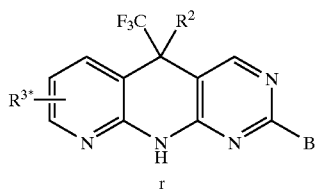
r
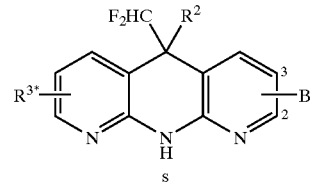
s
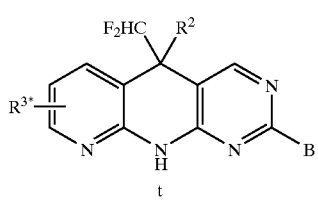
t
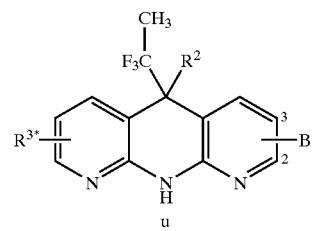
u
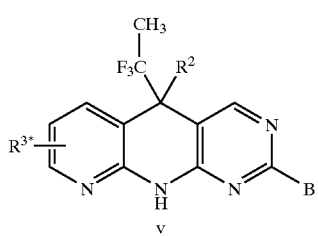
v TABLE 6-continued

| Entry # | B | R³ᵃ | R² |
|---|---|---|---|
| 205 | H | 7-Cl | —OH |
| 206 | H | 7-Cl | —O-methyl |
| 207 | H | 7-Cl | —O-ethyl |
| 208 | H | 7-Cl | —O-n-propyl |
| 209 | H | 7-Cl | —O-i-propyl |
| 210 | H | 7-Cl | —O-butyl |
| 211 | H | 7-Cl | —O—CH₂-cyclopropyl |
| 212 | H | 7-Cl | —O—CH₂-(1-methylcyclopropyl) |
| 213 | H | 7-Cl | —O—CH₂CH₂-cyclopropyl |
| 214 | H | 7-Cl | —O—CH₂-cyclobutyl |
| 215 | H | 7-Cl | —O—CH₂CH₂-cyclobutyl |
| 216 | H | 7-Cl | —O-benzyl |
| 217 | H | 7-Cl | —O-2,2,2-trifluoroethyl |
| 218 | H | 7-Cl | —O-trifluoromethyl |
| 219 | H | 7-Cl | —O-3,3,3-trifluoropropyl |
| 220 | H | 7-Cl | —O-allyl |
| 221 | H | 7-Cl | —O-propargyl |
| 222 | H | 7-Cl | —O—CH₂CH₂—N(CH₃)₂ |
| 223 | H | 7-Cl | —O—CH₂CH₂—(N-morpholinyl) |
| 224 | H | 7-Cl | —O—CH₂-3-Pyridyl |
| 225 | H | 7-Cl | —O—CH₂-4-Pyridyl |
| 226 | H | 7-Cl | —O—CH₂-2-furanyl |
| 227 | H | 7-Cl | —O—CH₂-3-furanyl |
| 228 | H | 7-Cl | —O—CH₂-2-thienyl |
| 229 | H | 7-Cl | —O—CH₂-3-thienyl |
| 230 | H | 7-Cl | —O—CH₂-2-oxazolyl |
| 231 | H | 7-Cl | —O—CH₂-2-thiazolyl |
| 232 | H | 7-Cl | —O—CH₂-4-isoxazolyl |
| 233 | H | 7-Cl | —O—CH₂-2-imidazolyl |
| 234 | H | 7-Cl | —NH-methyl |
| 235 | H | 7-Cl | —NH-ethyl |
| 236 | H | 7-Cl | —NH-n-propyl |
| 237 | H | 7-Cl | —NH-i-propyl |
| 238 | H | 7-Cl | —NH-butyl |
| 239 | H | 7-Cl | —NH—CH₂-cyclopropyl |
| 240 | H | 7-Cl | —NH—CH₂-(1-methylcyclopropyl) |
| 241 | H | 7-Cl | —NH—CH₂CH₂-cyclopropyl |
| 242 | H | 7-Cl | —NH—CH₂-cyclobutyl |
| 243 | H | 7-Cl | —NH—CH₂CH₂-cyclobutyl |
| 244 | H | 7-Cl | —NH-benzyl |
| 245 | H | 7-Cl | —NH-2,2,2-trifluoroethyl |
| 246 | H | 7-Cl | —NH-trifluoromethyl |
| 247 | H | 7-Cl | —NH-3,3,3-trifluoropropyl |
| 248 | H | 7-Cl | —NH-allyl |
| 249 | H | 7-Cl | —NH-propargyl |
| 250 | H | 7-Cl | —NH—CH₂CH₂—N(CH₃)₂ |
| 251 | H | 7-Cl | —NH—CH₂CH₂—(N-morpholinyl) |
| 252 | H | 7-Cl | —NH—CH₂-3-Pyridyl |
| 253 | H | 7-Cl | —NH—CH₂-4-Pyridyl |
| 254 | H | 7-Cl | —NH—CH₂-2-furanyl |
| 255 | H | 7-Cl | —NH—CH₂-3-furanyl |
| 256 | H | 7-Cl | —NH—CH₂-2-thienyl |
| 257 | H | 7-Cl | —NH—CH₂-3-thienyl |
| 258 | H | 7-Cl | —NH—CH₂-2-oxazolyl |
| 259 | H | 7-Cl | —NH—CH₂-2-thiazolyl |
| 260 | H | 7-Cl | —NH—CH₂-4-isoxazolyl |
| 261 | H | 7-Cl | —NH—CH₂-2-imidazolyl |
| 262 | H | 7-Cl | -benzyl |
| 263 | H | 7-Cl | -2,2,2-trifluoroethyl |
| 264 | H | 7-Cl | -trifluoromethyl |
| 265 | H | 7-Cl | -methyl |
| 266 | H | 7-Cl | -ethyl |
| 267 | H | 7-Cl | -propyl |
| 268 | H | 7-Cl | -i-propyl |
| 269 | H | 7-Cl | -butyl |
| 270 | H | 7-Cl | -i-butyl |
| 271 | H | 7-Cl | -t-butyl |
| 272 | H | 7-Cl | -pentyl |
| 273 | H | 7-Cl | —CH₂—CH₂-cyclopropyl |
| 274 | H | 7-Cl | —CH₂—CH₂-(1-methylcyclopropyl) |
| 275 | H | 7-Cl | —CH2—CH₂CH₂-cyclopropyl |
| 276 | H | 7-Cl | —CH2—CH₂-cyclobutyl |
| 277 | H | 7-Cl | —CH2—CH₂CH₂-cyclobutyl |
| 278 | H | 7-Cl | —CH2-benzyl |
| 279 | H | 7-Cl | —CH2-2,2,2-trifluoroethyl |
| 280 | H | 7-Cl | —CH2-trifluoromethyl |
| 281 | H | 7-Cl | —CH2-3,3,3-trifluoropropyl |
| 282 | H | 7-Cl | —CH2-allyl |
| 283 | H | 7-Cl | —CH2-propargyl |
| 284 | H | 7-Cl | —CH2—CH₂CH₂—N(CH₃)₂ |
| 285 | H | 7-Cl | —CH2—CH₂CH₂—(N-morpholinyl) |
| 286 | H | 7-Cl | —CH2—CH₂-3-Pyridyl |
| 287 | H | 7-Cl | —CH2—CH₂-4-Pyridyl |
| 288 | H | 7-Cl | —CH2—CH₂-2-furanyl |
| 289 | H | 7-Cl | —CH2—CH₂-3-furanyl |
| 290 | H | 7-Cl | —CH2—CH₂-2-thienyl |
| 291 | H | 7-Cl | —CH2—CH₂-3-thienyl |
| 292 | H | 7-Cl | —CH2—CH₂-2-oxazolyl |
| 293 | H | 7-Cl | —CH2—CH₂-2-thiazolyl |
| 294 | H | 7-Cl | —CH2—CH₂-4-isoxazolyl |
| 295 | H | 7-Cl | —CH2—CH₂-2-imidazolyl |
| 296 | H | 7-Cl | —C≡C-(2-OH)Ph |
| 297 | H | 7-Cl | —C≡C-(3-OH)Ph |
| 298 | H | 7-Cl | —C≡C-(4-OH)Ph |
| 299 | H | 7-Cl | —C≡C-(2-OMe)Ph |
| 300 | H | 7-Cl | —C≡C-(3-OMe)Ph |
| 301 | H | 7-Cl | —C≡C-(4-OMe)Ph |
| 302 | H | 7-Cl | —C≡C-(2-CN)Ph |
| 303 | H | 7-Cl | —C≡C-(3-CN)Ph |
| 304 | H | 7-Cl | —C≡C-(4-CN)Ph |
| 305 | H | 7-Cl | —C≡C-(2-NO₂)Ph |
| 306 | H | 7-Cl | —C≡C-(3-NO₂)Ph |
| 307 | H | 7-Cl | —C≡C-(4-NO₂)Ph |
| 308 | H | 7-Cl | —C≡C-(2-NH₂)Ph |
| 309 | H | 7-Cl | —C≡C-(3-NH₂)Ph |
| 310 | H | 7-Cl | —C≡C-(4-NH₂)Ph |
| 311 | H | 7-Cl | —C≡C-(2-NMe₂)Ph |
| 312 | H | 7-Cl | —C≡C-(3-NMe₂)Ph |
| 313 | H | 7-Cl | —C≡C-(4-NMe₂)Ph |
| 314 | H | 7-Cl | —C≡C-3-Pyridyl |
| 315 | H | 7-Cl | —C≡C-4-Pyridyl |
| 316 | H | 7-Cl | —C≡C-2-furanyl |
| 317 | H | 7-Cl | —C≡C-3-furanyl |
| 318 | H | 7-Cl | —C≡C-2-thienyl |
| 319 | H | 7-Cl | —C≡C-3-thienyl |
| 320 | H | 7-Cl | —C≡C-2-oxazolyl |
| 321 | H | 7-Cl | —C≡C-2-thiazolyl |
| 322 | H | 7-Cl | —C≡C-4-isoxazolyl |
| 323 | H | 7-Cl | —C≡C-2-imidazolyl |
| 324 | H | 7-Cl | —CH₂CH₂-cycPr |
| 325 | H | 7-Cl | —CH₂CH₂CH₂CH₂OH |
| 326 | H | 7-Cl | —CH₂CH₂—CH(OH)Me |
| 327 | H | 7-Cl | —CH₂CH₂-Ph |
| 328 | H | 7-Cl | —CH₂CH₂-(2-Cl)Ph |
| 329 | H | 7-Cl | —CH₂CH₂-(3-Cl)Ph |
| 330 | H | 7-Cl | —CH₂CH₂-(4-Cl)Ph |
| 331 | H | 7-Cl | —CH₂CH₂-(2-F)Ph |
| 332 | H | 7-Cl | —CH₂CH₂-(3-F)Ph |
| 333 | H | 7-Cl | —CH₂CH₂-(4-F)Ph |
| 334 | H | 7-Cl | —CH₂CH₂-(2-OH)Ph |
| 335 | H | 7-Cl | —CH₂CH₂-(3-OH)Ph |
| 336 | H | 7-Cl | —CH₂CH₂-(4-OH)Ph |
| 337 | H | 7-Cl | —CH₂CH₂-(2-OMe)Ph |
| 338 | H | 7-Cl | —CH₂CH₂-(3-OMe)Ph |
| 339 | H | 7-Cl | —CH₂CH₂-(4-OMe)Ph |
| 340 | H | 7-Cl | —CH₂CH₂-(2-CN)Ph |
| 341 | H | 7-Cl | —CH₂CH₂-(3-CN)Ph |
| 342 | H | 7-Cl | —CH₂CH₂-(4-CN)Ph |
| 343 | H | 7-Cl | —CH₂CH₂-(2-NO₂)Ph |
| 344 | H | 7-Cl | —CH₂CH₂-(3-NO₂)Ph |
| 345 | H | 7-Cl | —CH₂CH₂-(4-NO₂)Ph |
| 346 | H | 7-Cl | —CH₂CH₂-(2-NH₂)Ph |
| 347 | H | 7-Cl | —CH₂CH₂-(3-NH₂)Ph |
| 348 | H | 7-Cl | —CH₂CH₂-(4-NH₂)Ph |
| 349 | H | 7-Cl | —CH₂CH₂-(2-NMe₂)Ph |
| 350 | H | 7-Cl | —CH₂CH₂-(3-NMe₂)Ph |
| 351 | H | 7-Cl | —CH₂CH₂-(4-NMe₂)Ph |
| 352 | H | 7-Cl | —CH₂CH₂-2-Pyridyl |
| 353 | H | 7-Cl | —CH₂CH₂-3-Pyridyl |
| 354 | H | 7-Cl | —CH₂CH₂-4-Pyridyl |
| 355 | H | 7-Cl | —CH₂CH₂-2-furanyl |
| 356 | H | 7-Cl | —CH₂CH₂-3-furanyl |
| 357 | H | 7-Cl | —CH₂CH₂-4-furanyl |
| 358 | H | 7-Cl | —CH₂CH₂-3-thienyl |

TABLE 6-continued

| | | | |
|---|---|---|---|
| 359 | H | 7-Cl | —CH₂CH₂-2-oxazolyl |
| 360 | H | 7-Cl | —CH₂CH₂-2-thiazolyl |
| 361 | H | 7-Cl | —CH₂CH₂-4-isoxazolyl |
| 362 | H | 7-Cl | —CH₂CH₂-2-imidazolyl |
| 363 | H | 7-Cl | —C≡C-cycPr |
| 364 | H | 7-Cl | —C≡C-Ph |
| 365 | H | 7-Cl | —C≡C-2-Pyridyl |
| 366 | H | 7-Cl | —C≡C-3-Pyridyl |
| 367 | H | 7-Cl | —C≡C-4-Pyridyl |
| 368 | H | 7-Cl | —C≡C-2-furanyl |
| 369 | H | 7-Cl | —C≡C-3-furanyl |
| 370 | H | 7-Cl | —C≡C-2-thienyl |
| 371 | H | 7-Cl | —C≡C-3-thienyl |
| 372 | H | 7-Cl | —C≡C-cycPr |
| 373 | H | 7-Cl | —C≡C-Ph |
| 374 | H | 7-Cl | —C≡C-2-Pyridyl |
| 375 | H | 7-Cl | —C≡C-3-Pyridyl |
| 376 | H | 7-Cl | —C≡C-4-Pyridyl |
| 377 | H | 7-Cl | —C≡C-2-furanyl |
| 378 | H | 7-Cl | —C≡C-3-furanyl |
| 379 | H | 7-Cl | —C≡C-2-thienyl |
| 380 | H | 7-Cl | —C≡C-3-thienyl |
| 381 | H | 7-Cl | —CH₂CH₂-cycPr |
| 382 | H | 7-Cl | —CH₂CH₂-Ph |
| 383 | H | 7-Cl | —CH₂CH₂-2-Pyridyl |
| 384 | H | 7-Cl | —CH₂CH₂-3-Pyridyl |
| 385 | H | 7-Cl | —CH₂CH₂-4-Pyridyl |
| 386 | H | 7-Cl | —CH₂CH₂-2-furanyl |
| 387 | H | 7-Cl | —CH₂CH₂-3-furanyl |
| 388 | H | 7-Cl | —CH₂CH₂-2-thienyl |
| 389 | H | 7-Cl | —CH₂CH₂-3-thienyl |
| 390 | H | 7-Cl | —C≡C-cycPr |
| 391 | H | 7-Cl | —C≡C-Ph |
| 392 | H | 7-Cl | —C≡C-2-Pyridyl |
| 393 | H | 7-Cl | —C≡C-3-Pyridyl |
| 394 | H | 7-Cl | —C≡C-4-Pyridyl |
| 395 | H | 7-Cl | —C≡C-2-furanyl |
| 396 | H | 7-Cl | —C≡C-3-furanyl |
| 397 | H | 7-Cl | —C≡C-2-thienyl |
| 398 | H | 7-Cl | —C≡C-3-thienyl |
| 399 | H | 7-Cl | —C≡C-cycPr |
| 400 | H | 7-Cl | —C≡C-Ph |
| 401 | H | 7-Cl | —C≡C-2-Pyridyl |
| 402 | H | 7-Cl | —C≡C-3-Pyridyl |
| 403 | H | 7-Cl | —C≡C-4-Pyridyl |
| 404 | H | 7-Cl | —C≡C-2-furanyl |
| 405 | H | 7-Cl | —C≡C-3-furanyl |
| 406 | H | 7-Cl | —C≡C-2-thienyl |
| 407 | H | 7-Cl | —C≡C-3-thienyl |
| 408 | H | 7-Cl | —CH₂CH₂-cycPr |
| 409 | H | 7-Cl | —CH₂CH₂-Ph |
| 410 | H | 7-Cl | —CH₂CH₂-2-Pyridyl |
| 411 | H | 7-Cl | —CH₂CH₂-3-Pyridyl |
| 412 | H | 7-Cl | —CH₂CH₂-4-Pyridyl |
| 413 | H | 7-Cl | —CH₂CH₂-2-furanyl |
| 414 | H | 7-Cl | —CH₂CH₂-3-furanyl |
| 415 | H | 7-Cl | —CH₂CH₂-2-thienyl |
| 416 | H | 7-Cl | —CH₂CH₂-3-thienyl |
| 417 | 3-Cl | 7-Cl | —OH |
| 418 | 3-Cl | 7-Cl | —O-methyl |
| 419 | 3-Cl | 7-Cl | —O-ethyl |
| 420 | 3-Cl | 7-Cl | —O-n-propyl |
| 421 | 3-Cl | 7-Cl | —O-i-propyl |
| 422 | 3-Cl | 7-Cl | —O-butyl |
| 423 | 3-Cl | 7-Cl | —O—CH₂-cyclopropyl |
| 424 | 3-Cl | 7-Cl | —O—CH₂-(1-methylcyclopropyl) |
| 425 | 3-Cl | 7-Cl | —O—CH₂CH₂-cyclopropyl |
| 426 | 3-Cl | 7-Cl | —O—CH₂-cyclobutyl |
| 427 | 3-Cl | 7-Cl | —O—CH₂CH₂-cyclobutyl |
| 428 | 3-Cl | 7-Cl | —O-benzyl |
| 429 | 3-Cl | 7-Cl | —O-2,2,2-trifluoroethyl |
| 430 | 3-Cl | 7-Cl | —O-trifluoromethyl |
| 431 | 3-Cl | 7-Cl | —O-3,3,3-trifluoropropyl |
| 432 | 3-Cl | 7-Cl | —O-allyl |
| 433 | 3-Cl | 7-Cl | —O-propargyl |
| 434 | 3-Cl | 7-Cl | —O—CH₂CH₂—N(CH₃)₂ |
| 435 | 3-Cl | 7-Cl | —O—CH₂CH₂—(N-morpholinyl) |
| 436 | 3-Cl | 7-Cl | —O—CH₂-3-Pyridyl |
| 437 | 3-Cl | 7-Cl | —O—CH₂-4-Pyridyl |
| 438 | 3-Cl | 7-Cl | —O—CH₂-2-furanyl |
| 439 | 3-Cl | 7-Cl | —O—CH₂-3-furanyl |
| 440 | 3-Cl | 7-Cl | —O—CH₂-2-thienyl |
| 441 | 3-Cl | 7-Cl | —O—CH₂-3-thienyl |
| 442 | 3-Cl | 7-Cl | —O—CH₂-2-oxazolyl |
| 443 | 3-Cl | 7-Cl | —O—CH₂-2-thiazolyl |
| 444 | 3-Cl | 7-Cl | —O—CH₂-4-isoxazolyl |
| 445 | 3-Cl | 7-Cl | —O—CH₂-2-imidazolyl |
| 446 | 3-Cl | 7-Cl | —NH-methyl |
| 447 | 3-Cl | 7-Cl | —NH-ethyl |
| 448 | 3-Cl | 7-Cl | —NH-n-propyl |
| 449 | 3-Cl | 7-Cl | —NH-i-propyl |
| 450 | 3-Cl | 7-Cl | —NH-butyl |
| 451 | 3-Cl | 7-Cl | —NH—CH₂-cyclopropyl |
| 452 | 3-Cl | 7-Cl | —NH—CH₂-(1-methylcyclopropyl) |
| 453 | 3-Cl | 7-Cl | —NH—CH₂CH₂-cyclopropyl |
| 454 | 3-Cl | 7-Cl | —NH—CH₂-cyclobutyl |
| 455 | 3-Cl | 7-Cl | —NH—CH₂CH₂-cyclobutyl |
| 456 | 3-Cl | 7-Cl | —NH-benzyl |
| 457 | 3-Cl | 7-Cl | —NH-2,2,2-trifluoroethyl |
| 458 | 3-Cl | 7-Cl | —NH-trifluoromethyl |
| 459 | 3-Cl | 7-Cl | —NH-3,3,3-trifluoropropyl |
| 460 | 3-Cl | 7-Cl | —NH-allyl |
| 461 | 3-Cl | 7-Cl | —NH-propargyl |
| 462 | 3-Cl | 7-Cl | —NH—CH₂CH₂—N(CH₃)₂ |
| 463 | 3-Cl | 7-Cl | —NH—CH₂CH₂—(N-morpholinyl) |
| 464 | 3-Cl | 7-Cl | —NH—CH₂-3-Pyridyl |
| 465 | 3-Cl | 7-Cl | —NH—CH₂-4-Pyridyl |
| 466 | 3-Cl | 7-Cl | —NH—CH₂-2-furanyl |
| 467 | 3-Cl | 7-Cl | —NH—CH₂-3-furanyl |
| 468 | 3-Cl | 7-Cl | —NH—CH₂-2-thienyl |
| 469 | 3-Cl | 7-Cl | —NH—CH₂-3-thienyl |
| 470 | 3-Cl | 7-Cl | —NH—CH₂-2-oxazolyl |
| 471 | 3-Cl | 7-Cl | —NH—CH₂-2-thiazolyl |
| 472 | 3-Cl | 7-Cl | —NH—CH₂-4-isoxazolyl |
| 473 | 3-Cl | 7-Cl | —NH—CH₂-2-imidazolyl |
| 474 | 3-Cl | 7-Cl | -benzyl |
| 475 | 3-Cl | 7-Cl | -2,2,2-trifluoroethyl |
| 476 | 3-Cl | 7-Cl | -trifluoromethyl |
| 477 | 3-Cl | 7-Cl | -methyl |
| 478 | 3-Cl | 7-Cl | -ethyl |
| 479 | 3-Cl | 7-Cl | -propyl |
| 480 | 3-Cl | 7-Cl | -i-propyl |
| 481 | 3-Cl | 7-Cl | -butyl |
| 482 | 3-Cl | 7-Cl | -i-butyl |
| 483 | 3-Cl | 7-Cl | -t-butyl |
| 484 | 3-Cl | 7-Cl | -pentyl |
| 485 | 3-Cl | 7-Cl | —CH₂—cyclopropyl |
| 486 | 3-Cl | 7-Cl | —CH₂—CH₂-(1-methylcyclopropyl) |
| 487 | 3-Cl | 7-Cl | —CH2—CH₂CH₂-cyclopropyl |
| 488 | 3-Cl | 7-Cl | —CH2—CH₂-cyclobutyl |
| 489 | 3-Cl | 7-Cl | —CH2—CH₂CH₂-cyclobutyl |
| 490 | 3-Cl | 7-Cl | —CH2-benzyl |
| 491 | 3-Cl | 7-Cl | —CH2-2,2,2-trifluoroethyl |
| 492 | 3-Cl | 7-Cl | —CH2-trifluoromethyl |
| 493 | 3-Cl | 7-Cl | —CH2-3,3,3-trifluoropropyl |
| 494 | 3-Cl | 7-Cl | —CH2-allyl |
| 495 | 3-Cl | 7-Cl | —CH2-propargyl |
| 496 | 3-Cl | 7-Cl | —CH2—CH₂CH₂—N(CH₃)₂ |
| 497 | 3-Cl | 7-Cl | —CH2—CH₂CH₂-(N-morpholinyl) |
| 498 | 3-Cl | 7-Cl | —CH2—CH₂-3-Pyridyl |
| 499 | 3-Cl | 7-Cl | —CH2—CH₂-4-Pyridyl |
| 500 | 3-Cl | 7-Cl | —CH2—CH₂-2-furanyl |
| 501 | 3-Cl | 7-Cl | —CH2—CH₂-3-furanyl |
| 502 | 3-Cl | 7-Cl | —CH2—CH₂-2-thienyl |
| 503 | 3-Cl | 7-Cl | —CH2—CH₂-3-thienyl |
| 504 | 3-Cl | 7-Cl | —CH2—CH₂-2-oxazolyl |
| 505 | 3-Cl | 7-Cl | —CH2—CH₂-2-thiazolyl |
| 506 | 3-Cl | 7-Cl | —CH2—CH₂-4-isoxazolyl |
| 507 | 3-Cl | 7-Cl | —CH2—CH₂-2-imidazolyl |
| 508 | 3-Cl | 7-Cl | —C≡C-(2-OH)Ph |
| 509 | 3-Cl | 7-Cl | —C≡C-(3-OH)Ph |
| 510 | 3-Cl | 7-Cl | —C≡C-(4-OH)Ph |
| 511 | 3-Cl | 7-Cl | —C≡C-(2-OMe)Ph |
| 512 | 3-Cl | 7-Cl | —C≡C-(3-OMe)Ph |
| 513 | 3-Cl | 7-Cl | —C≡C-(4-OMe)Ph |
| 514 | 3-Cl | 7-Cl | —C≡C-(2-CN)Ph |
| 515 | 3-Cl | 7-Cl | —C≡C-(3-CN)Ph |
| 516 | 3-Cl | 7-Cl | —C≡C-(4-CN)Ph |

TABLE 6-continued

| | | | |
|---|---|---|---|
| 517 | 3-Cl | 7-Cl | —C≡C-(2-NO₂)Ph |
| 518 | 3-Cl | 7-Cl | —C≡C-(3-NO₂)Ph |
| 519 | 3-Cl | 7-Cl | —C≡C-(4-NO₂)Ph |
| 520 | 3-Cl | 7-Cl | —C≡C-(2-NH₂)Ph |
| 521 | 3-Cl | 7-Cl | —C≡C-(3-NH₂)Ph |
| 522 | 3-Cl | 7-Cl | —C≡C-(4-NH₂)Ph |
| 523 | 3-Cl | 7-Cl | —C≡C-(2-NMe₂)Ph |
| 524 | 3-Cl | 7-Cl | —C≡C-(3-NMe₂)Ph |
| 525 | 3-Cl | 7-Cl | —C≡C-(4-NMe₂)Ph |
| 526 | 3-Cl | 7-Cl | —C≡C-3-Pyridyl |
| 527 | 3-Cl | 7-Cl | —C≡C-4-Pyridyl |
| 528 | 3-Cl | 7-Cl | —C≡C-2-furanyl |
| 529 | 3-Cl | 7-Cl | —C≡C-3-furanyl |
| 530 | 3-Cl | 7-Cl | —C≡C-2-thienyl |
| 531 | 3-Cl | 7-Cl | —C≡C-3-thienyl |
| 532 | 3-Cl | 7-Cl | —C≡C-2-oxazolyl |
| 533 | 3-Cl | 7-Cl | —C≡C-2-thiazolyl |
| 534 | 3-Cl | 7-Cl | —C≡C-4-isoxazolyl |
| 535 | 3-Cl | 7-Cl | —C≡C-2-imidazolyl |
| 536 | 3-Cl | 7-Cl | —CH₂CH₂-cycPr |
| 537 | 3-Cl | 7-Cl | —CH₂CH₂CH₂CH₂OH |
| 538 | 3-Cl | 7-Cl | —CH₂CH₂—CH(OH)Me |
| 539 | 3-Cl | 7-Cl | —CH₂CH₂-Ph |
| 540 | 3-Cl | 7-Cl | —CH₂CH₂-(2-Cl)Ph |
| 541 | 3-Cl | 7-Cl | —CH₂CH₂-(3-Cl)Ph |
| 542 | 3-Cl | 7-Cl | —CH₂CH₂-(4-Cl)Ph |
| 543 | 3-Cl | 7-Cl | —CH₂CH₂-(2-F)Ph |
| 544 | 3-Cl | 7-Cl | —CH₂CH₂-(3-F)Ph |
| 545 | 3-Cl | 7-Cl | —CH₂CH₂-(4-F)Ph |
| 546 | 3-Cl | 7-Cl | —CH₂CH₂-(2-OH)Ph |
| 547 | 3-Cl | 7-Cl | —CH₂CH₂-(3-OH)Ph |
| 548 | 3-Cl | 7-Cl | —CH₂CH₂-(4-OH)Ph |
| 549 | 3-Cl | 7-Cl | —CH₂CH₂-(2-OMe)Ph |
| 550 | 3-Cl | 7-Cl | —CH₂CH₂-(3-OMe)Ph |
| 551 | 3-Cl | 7-Cl | —CH₂CH₂-(4-OMe)Ph |
| 552 | 3-Cl | 7-Cl | —CH₂CH₂-(2-CN)Ph |
| 553 | 3-Cl | 7-Cl | —CH₂CH₂-(3-CN)Ph |
| 554 | 3-Cl | 7-Cl | —CH₂CH₂-(4-CN)Ph |
| 555 | 3-Cl | 7-Cl | —CH₂CH₂-(2-NO₂)Ph |
| 556 | 3-Cl | 7-Cl | —CH₂CH₂-(3-NO₂)Ph |
| 557 | 3-Cl | 7-Cl | —CH₂CH₂-(4-NO₂)Ph |
| 558 | 3-Cl | 7-Cl | —CH₂CH₂-(2-NH₂)Ph |
| 559 | 3-Cl | 7-Cl | —CH₂CH₂-(3-NH₂)Ph |
| 560 | 3-Cl | 7-Cl | —CH₂CH₂-(4-NH₂)Ph |
| 561 | 3-Cl | 7-Cl | —CH₂CH₂-(2-NMe₂)Ph |
| 562 | 3-Cl | 7-Cl | —CH₂CH₂-(3-NMe₂)Ph |
| 563 | 3-Cl | 7-Cl | —CH₂CH₂-(4-NMe₂)Ph |
| 564 | 3-Cl | 7-Cl | —CH₂CH₂-2-Pyridyl |
| 565 | 3-Cl | 7-Cl | —CH₂CH₂-3-Pyridyl |
| 566 | 3-Cl | 7-Cl | —CH₂CH₂-4-Pyridyl |
| 567 | 3-Cl | 7-Cl | —CH₂CH₂-2-furanyl |
| 568 | 3-Cl | 7-Cl | —CH₂CH₂-3-furanyl |
| 569 | 3-Cl | 7-Cl | —CH₂CH₂-4-furanyl |
| 570 | 3-Cl | 7-Cl | —CH₂CH₂-3-thienyl |
| 571 | 3-Cl | 7-Cl | —CH₂CH₂-2-oxazolyl |
| 572 | 3-Cl | 7-Cl | —CH₂CH₂-2-thiazolyl |
| 573 | 3-Cl | 7-Cl | —CH₂CH₂-4-isoxazolyl |
| 574 | 3-Cl | 7-Cl | —CH₂CH₂-2-imidazolyl |
| 575 | 3-Cl | 7-Cl | —C≡C-cycPr |
| 576 | 3-Cl | 7-Cl | —C≡C-Ph |
| 577 | 3-Cl | 7-Cl | —C≡C-2-Pyridyl |
| 578 | 3-Cl | 7-Cl | —C≡C-3-Pyridyl |
| 579 | 3-Cl | 7-Cl | —C≡C-4-Pyridyl |
| 580 | 3-Cl | 7-Cl | —C≡C-2-furanyl |
| 581 | 3-Cl | 7-Cl | —C≡C-3-furanyl |
| 582 | 3-Cl | 7-Cl | —C≡C-2-thienyl |
| 583 | 3-Cl | 7-Cl | —C≡C-3-thienyl |
| 584 | 3-Cl | 7-Cl | —C≡C-cycPr |
| 585 | 3-Cl | 7-Cl | —C≡C-Ph |
| 586 | 3-Cl | 7-Cl | —C≡C-2-Pyridyl |
| 587 | 3-Cl | 7-Cl | —C≡C-3-Pyridyl |
| 588 | 3-Cl | 7-Cl | —C≡C-4-Pyridyl |
| 589 | 3-Cl | 7-Cl | —C≡C-2-furanyl |
| 590 | 3-Cl | 7-Cl | —C≡C-3-furanyl |
| 591 | 3-Cl | 7-Cl | —C≡C-2-thienyl |
| 592 | 3-Cl | 7-Cl | —C≡C-3-thienyl |
| 593 | 3-Cl | 7-Cl | —CH₂CH₂-cycPr |
| 594 | 3-Cl | 7-Cl | —CH₂CH₂-Ph |
| 595 | 3-Cl | 7-Cl | —CH₂CH₂-2-Pyridyl |
| 596 | 3-Cl | 7-Cl | —CH₂CH₂-3-Pyridyl |
| 597 | 3-Cl | 7-Cl | —CH₂CH₂-4-Pyridyl |
| 598 | 3-Cl | 7-Cl | —CH₂CH₂-2-furanyl |
| 599 | 3-Cl | 7-Cl | —CH₂CH₂-3-furanyl |
| 600 | 3-Cl | 7-Cl | —CH₂CH₂-2-thienyl |
| 601 | 3-Cl | 7-Cl | —CH₂CH₂-3-thienyl |
| 602 | 3-Cl | 7-Cl | —C≡C-cycPr |
| 603 | 3-Cl | 7-Cl | —C≡C-Ph |
| 604 | 3-Cl | 7-Cl | —C≡C-2-Pyridyl |
| 605 | 3-Cl | 7-Cl | —C≡C-3-Pyridyl |
| 606 | 3-Cl | 7-Cl | —C≡C-4-Pyridyl |
| 607 | 3-Cl | 7-Cl | —C≡C-2-furanyl |
| 608 | 3-Cl | 7-Cl | —C≡C-3-furanyl |
| 609 | 3-Cl | 7-Cl | —C≡C-2-thienyl |
| 610 | 3-Cl | 7-Cl | —C≡C-3-thienyl |
| 611 | 3-Cl | 7-Cl | —C≡C-cycPr |
| 612 | 3-Cl | 7-Cl | —C≡C-Ph |
| 613 | 3-Cl | 7-Cl | —C≡C-2-Pyridyl |
| 614 | 3-Cl | 7-Cl | —C≡C-3-Pyridyl |
| 615 | 3-Cl | 7-Cl | —C≡C-4-Pyridyl |
| 616 | 3-Cl | 7-Cl | —C≡C-2-furanyl |
| 617 | 3-Cl | 7-Cl | —C≡C-3-furanyl |
| 618 | 3-Cl | 7-Cl | —C≡C-2-thienyl |
| 619 | 3-Cl | 7-Cl | —C≡C-3-thienyl |
| 620 | 3-Cl | 7-Cl | —CH₂CH₂-cycPr |
| 621 | 3-Cl | 7-Cl | —CH₂CH₂-Ph |
| 622 | 3-Cl | 7-Cl | —CH₂CH₂-2-Pyridyl |
| 623 | 3-Cl | 7-Cl | —CH₂CH₂-3-Pyridyl |
| 624 | 3-Cl | 7-Cl | —CH₂CH₂-4-Pyridyl |
| 625 | 3-Cl | 7-Cl | —CH₂CH₂-2-furanyl |
| 626 | 3-Cl | 7-Cl | —CH₂CH₂-3-furanyl |
| 627 | 3-Cl | 7-Cl | —CH₂CH₂-2-thienyl |
| 628 | 3-Cl | 7-Cl | —CH₂CH₂-3-thienyl |
| 629 | 2-Me | 7-Cl | —OH |
| 630 | 2-Me | 7-Cl | —O-methyl |
| 631 | 2-Me | 7-Cl | —O-ethyl |
| 632 | 2-Me | 7-Cl | —O-n-propyl |
| 633 | 2-Me | 7-Cl | —O-i-propyl |
| 634 | 2-Me | 7-Cl | —O-butyl |
| 635 | 2-Me | 7-Cl | —O—CH₂-cyclopropyl |
| 636 | 2-Me | 7-Cl | —O—CH₂-(1-methylcyclopropyl) |
| 637 | 2-Me | 7-Cl | —O—CH₂CH₂-cyclopropyl |
| 638 | 2-Me | 7-Cl | —O—CH₂-cyclobutyl |
| 639 | 2-Me | 7-Cl | —O—CH₂CH₂-cyclobutyl |
| 640 | 2-Me | 7-Cl | —O-benzyl |
| 641 | 2-Me | 7-Cl | —O-2,2,2-trifluoroethyl |
| 642 | 2-Me | 7-Cl | —O-trifluoromethyl |
| 643 | 2-Me | 7-Cl | —O-3,3,3-trifluoropropyl |
| 644 | 2-Me | 7-Cl | —O-allyl |
| 645 | 2-Me | 7-Cl | —O-propargyl |
| 646 | 2-Me | 7-Cl | —O—CH₂CH₂—N(CH₃)₂ |
| 647 | 2-Me | 7-Cl | —O—CH₂CH₂—(N-morpholinyl) |
| 648 | 2-Me | 7-Cl | —O—CH₂-3-Pyridyl |
| 649 | 2-Me | 7-Cl | —O—CH₂-4-Pyridyl |
| 650 | 2-Me | 7-Cl | —O—CH₂-2-furanyl |
| 651 | 2-Me | 7-Cl | —O—CH₂-3-furanyl |
| 652 | 2-Me | 7-Cl | —O—CH₂-2-thienyl |
| 653 | 2-Me | 7-Cl | —O—CH₂-3-thienyl |
| 654 | 2-Me | 7-Cl | —O—CH₂-2-oxazolyl |
| 655 | 2-Me | 7-Cl | —O—CH₂-2-thiazolyl |
| 656 | 2-Me | 7-Cl | —O—CH₂-4-isoxazolyl |
| 657 | 2-Me | 7-Cl | —O—CH₂-2-imidazolyl |
| 658 | 2-Me | 7-Cl | —NH-methyl |
| 659 | 2-Me | 7-Cl | —NH-ethyl |
| 660 | 2-Me | 7-Cl | —NH-n-propyl |
| 661 | 2-Me | 7-Cl | —NH-i-propyl |
| 662 | 2-Me | 7-Cl | —NH-butyl |
| 663 | 2-Me | 7-Cl | —NH—CH₂-cyclopropyl |
| 664 | 2-Me | 7-Cl | —NH—CH₂-(1-methylcyclopropyl) |
| 665 | 2-Me | 7-Cl | —NH—CH₂CH₂-cyclopropyl |
| 666 | 2-Me | 7-Cl | —NH—CH₂-cyclobutyl |
| 667 | 2-Me | 7-Cl | —NH—CH₂CH₂-cyclobutyl |
| 668 | 2-Me | 7-Cl | —NH-benzyl |
| 669 | 2-Me | 7-Cl | —NH-2,2,2-trifluoroethyl |
| 670 | 2-Me | 7-Cl | —NH-trifluoromethyl |
| 671 | 2-Me | 7-Cl | —NH-3,3,3-trifluoropropyl |
| 672 | 2-Me | 7-Cl | —NH-allyl |
| 673 | 2-Me | 7-Cl | —NH-propargyl |
| 674 | 2-Me | 7-Cl | —NH—CH₂CH₂—N(CH₃)₂ |

TABLE 6-continued

| | | | |
|---|---|---|---|
| 675 | 2-Me | 7-Cl | —NH—CH₂CH₂—(N-morpholinyl) |
| 676 | 2-Me | 7-Cl | —NH—CH₂-3-Pyridyl |
| 677 | 2-Me | 7-Cl | —NH—CH₂-4-Pyridyl |
| 678 | 2-Me | 7-Cl | —NH—CH₂-2-furanyl |
| 679 | 2-Me | 7-Cl | —NH—CH₂-3-furanyl |
| 680 | 2-Me | 7-Cl | —NH—CH₂-2-thienyl |
| 681 | 2-Me | 7-Cl | —NH—CH₂-3-thienyl |
| 682 | 2-Me | 7-Cl | —NH—CH₂-2-oxazolyl |
| 683 | 2-Me | 7-Cl | —NH—CH₂-2-thiazolyl |
| 684 | 2-Me | 7-Cl | —NH—CH₂-4-isoxazolyl |
| 685 | 2-Me | 7-Cl | —NH—CH₂-2-imidazolyl |
| 686 | 2-Me | 7-Cl | -benzyl |
| 687 | 2-Me | 7-Cl | -2,2,2-trifluoroethyl |
| 688 | 2-Me | 7-Cl | -trifluoromethyl |
| 689 | 2-Me | 7-Cl | -methyl |
| 690 | 2-Me | 7-Cl | -ethyl |
| 691 | 2-Me | 7-Cl | -propyl |
| 692 | 2-Me | 7-Cl | -i-propyl |
| 693 | 2-Me | 7-Cl | -butyl |
| 694 | 2-Me | 7-Cl | -i-butyl |
| 695 | 2-Me | 7-Cl | -t-butyl |
| 696 | 2-Me | 7-Cl | -pentyl |
| 697 | 2-Me | 7-Cl | —CH₂—CH₂-cyclopropyl |
| 698 | 2-Me | 7-Cl | —CH₂—CH₂-(1-methylcyclopropyl) |
| 699 | 2-Me | 7-Cl | —CH2—CH₂CH₂-cyclopropyl |
| 700 | 2-Me | 7-Cl | —CH2—CH₂-cyclobutyl |
| 701 | 2-Me | 7-Cl | —CH2—CH₂CH₂-cyclobutyl |
| 702 | 2-Me | 7-Cl | —CH2-benzyl |
| 703 | 2-Me | 7-Cl | —CH2-2,2,2-trifluoroethyl |
| 704 | 2-Me | 7-Cl | —CH2-trifluoromethyl |
| 705 | 2-Me | 7-Cl | —CH2-3,3,3-trifluoropropyl |
| 706 | 2-Me | 7-Cl | —CH2-allyl |
| 707 | 2-Me | 7-Cl | —CH2-propargyl |
| 708 | 2-Me | 7-Cl | —CH2—CH₂—N(CH₃)₂ |
| 709 | 2-Me | 7-Cl | —CH2—CH₂CH₂-(N-morpholinyl) |
| 710 | 2-Me | 7-Cl | —CH2—CH₂-3-Pyridyl |
| 711 | 2-Me | 7-Cl | —CH2—CH₂-4-Pyridyl |
| 712 | 2-Me | 7-Cl | —CH2—CH₂-2-furanyl |
| 713 | 2-Me | 7-Cl | —CH2—CH₂-3-furanyl |
| 714 | 2-Me | 7-Cl | —CH2—CH₂-2-thienyl |
| 715 | 2-Me | 7-Cl | —CH2—CH₂-3-thienyl |
| 716 | 2-Me | 7-Cl | —CH2—CH₂-2-oxazolyl |
| 717 | 2-Me | 7-Cl | —CH2—CH₂-2-thiazolyl |
| 718 | 2-Me | 7-Cl | —CH2—CH₂-4-isoxazolyl |
| 719 | 2-Me | 7-Cl | —CH2—CH₂-2-imidazolyl |
| 720 | 2-Me | 7-Cl | —C≡C-(2-OH)Ph |
| 721 | 2-Me | 7-Cl | —C≡C-(3-OH)Ph |
| 722 | 2-Me | 7-Cl | —C≡C-(4-OH)Ph |
| 723 | 2-Me | 7-Cl | —C≡C-(2-OMe)Ph |
| 724 | 2-Me | 7-Cl | —C≡C-(3-OMe)Ph |
| 725 | 2-Me | 7-Cl | —C≡C-(4-OMe)Ph |
| 726 | 2-Me | 7-Cl | —C≡C-(2-CN)Ph |
| 727 | 2-Me | 7-Cl | —C≡C-(3-CN)Ph |
| 728 | 2-Me | 7-Cl | —C≡C-(4-CN)Ph |
| 729 | 2-Me | 7-Cl | —C≡C-(2-NO₂)Ph |
| 730 | 2-Me | 7-Cl | —C≡C-(3-NO₂)Ph |
| 731 | 2-Me | 7-Cl | —C≡C-(4-NO₂)Ph |
| 732 | 2-Me | 7-Cl | —C≡C-(2-NH₂)Ph |
| 733 | 2-Me | 7-Cl | —C≡C-(3-NH₂)Ph |
| 734 | 2-Me | 7-Cl | —C≡C-(4-NH₂)Ph |
| 735 | 2-Me | 7-Cl | —C≡C-(2-NMe₂)Ph |
| 736 | 2-Me | 7-Cl | —C≡C-(3-NMe₂)Ph |
| 737 | 2-Me | 7-Cl | —C≡C-(4-NMe₂)Ph |
| 738 | 2-Me | 7-Cl | —C≡C-3-Pyridyl |
| 739 | 2-Me | 7-Cl | —C≡C-4-Pyridyl |
| 740 | 2-Me | 7-Cl | —C≡C-2-furanyl |
| 741 | 2-Me | 7-Cl | —C≡C-3-furanyl |
| 742 | 2-Me | 7-Cl | —C≡C-2-thienyl |
| 743 | 2-Me | 7-Cl | —C≡C-3-thienyl |
| 744 | 2-Me | 7-Cl | —C≡C-2-oxazolyl |
| 745 | 2-Me | 7-Cl | —C≡C-2-thiazolyl |
| 746 | 2-Me | 7-Cl | —C≡C-4-isoxazolyl |
| 747 | 2-Me | 7-Cl | —C≡C-2-imidazolyl |
| 748 | 2-Me | 7-Cl | —CH₂CH₂-cycPr |
| 749 | 2-Me | 7-Cl | —CH₂CH₂CH₂CH₂OH |
| 750 | 2-Me | 7-Cl | —CH₂CH₂—CH(OH)Me |
| 751 | 2-Me | 7-Cl | —CH₂CH₂-Ph |
| 752 | 2-Me | 7-Cl | —CH₂CH₂-(2-Cl)Ph |
| 753 | 2-Me | 7-Cl | —CH₂CH₂-(3-Cl)Ph |
| 754 | 2-Me | 7-Cl | —CH₂CH₂-(4-Cl)Ph |
| 755 | 2-Me | 7-Cl | —CH₂CH₂-(2-F)Ph |
| 756 | 2-Me | 7-Cl | —CH₂CH₂-(3-F)Ph |
| 757 | 2-Me | 7-Cl | —CH₂CH₂-(4-F)Ph |
| 758 | 2-Me | 7-Cl | —CH₂CH₂-(2-OH)Ph |
| 759 | 2-Me | 7-Cl | —CH₂CH₂-(3-OH)Ph |
| 760 | 2-Me | 7-Cl | —CH₂CH₂-(4-OH)Ph |
| 761 | 2-Me | 7-Cl | —CH₂CH₂-(2-OMe)Ph |
| 762 | 2-Me | 7-Cl | —CH₂CH₂-(3-OMe)Ph |
| 763 | 2-Me | 7-Cl | —CH₂CH₂-(4-OMe)Ph |
| 764 | 2-Me | 7-Cl | —CH₂CH₂-(2-CN)Ph |
| 765 | 2-Me | 7-Cl | —CH₂CH₂-(3-CN)Ph |
| 766 | 2-Me | 7-Cl | —CH₂CH₂-(4-CN)Ph |
| 767 | 2-Me | 7-Cl | —CH₂CH₂-(2-NO₂)Ph |
| 768 | 2-Me | 7-Cl | —CH₂CH₂-(3-NO₂)Ph |
| 769 | 2-Me | 7-Cl | —CH₂CH₂-(4-NO₂)Ph |
| 770 | 2-Me | 7-Cl | —CH₂CH₂-(2-NH₂)Ph |
| 771 | 2-Me | 7-Cl | —CH₂CH₂-(3-NH₂)Ph |
| 772 | 2-Me | 7-Cl | —CH₂CH₂-(4-NH₂)Ph |
| 773 | 2-Me | 7-Cl | —CH₂CH₂-(2-NMe₂)Ph |
| 774 | 2-Me | 7-Cl | —CH₂CH₂-(3-NMe₂)Ph |
| 775 | 2-Me | 7-Cl | —CH₂CH₂-(4-NMe₂)Ph |
| 776 | 2-Me | 7-Cl | —CH₂CH₂-2-Pyridyl |
| 777 | 2-Me | 7-Cl | —CH₂CH₂-3-Pyridyl |
| 778 | 2-Me | 7-Cl | —CH₂CH₂-4-Pyridyl |
| 779 | 2-Me | 7-Cl | —CH₂CH₂-2-furanyl |
| 780 | 2-Me | 7-Cl | —CH₂CH₂-3-furanyl |
| 781 | 2-Me | 7-Cl | —CH₂CH₂-4-furanyl |
| 782 | 2-Me | 7-Cl | —CH₂CH₂-3-thienyl |
| 783 | 2-Me | 7-Cl | —CH₂CH₂-2-oxazolyl |
| 784 | 2-Me | 7-Cl | —CH₂CH₂-2-thiazolyl |
| 785 | 2-Me | 7-Cl | —CH₂CH₂-4-isoxazolyl |
| 786 | 2-Me | 7-Cl | —CH₂CH₂-2-imidazolyl |
| 787 | 2-Me | 7-Cl | —C≡C-cycPr |
| 788 | 2-Me | 7-Cl | —C≡C-Ph |
| 789 | 2-Me | 7-Cl | —C≡C-2-Pyridyl |
| 790 | 2-Me | 7-Cl | —C≡C-3-Pyridyl |
| 791 | 2-Me | 7-Cl | —C≡C-4-Pyridyl |
| 792 | 2-Me | 7-Cl | —C≡C-2-furanyl |
| 793 | 2-Me | 7-Cl | —C≡C-3-furanyl |
| 794 | 2-Me | 7-Cl | —C≡C-2-thienyl |
| 795 | 2-Me | 7-Cl | —C≡C-3-thienyl |
| 796 | 2-Me | 7-Cl | —C≡C-cycPr |
| 797 | 2-Me | 7-Cl | —C≡C-Ph |
| 798 | 2-Me | 7-Cl | —C≡C-2-Pyridyl |
| 799 | 2-Me | 7-Cl | —C≡C-3-Pyridyl |
| 800 | 2-Me | 7-Cl | —C≡C-4-Pyridyl |
| 801 | 2-Me | 7-Cl | —C≡C-2-furanyl |
| 802 | 2-Me | 7-Cl | —C≡C-3-furanyl |
| 803 | 2-Me | 7-Cl | —C≡C-2-thienyl |
| 804 | 2-Me | 7-Cl | —C≡C-3-thienyl |
| 805 | 2-Me | 7-Cl | —CH₂CH₂-cycPr |
| 806 | 2-Me | 7-Cl | —CH₂CH₂-Ph |
| 807 | 2-Me | 7-Cl | —CH₂CH₂-2-Pyridyl |
| 808 | 2-Me | 7-Cl | —CH₂CH₂-3-Pyridyl |
| 809 | 2-Me | 7-Cl | —CH₂CH₂-4-Pyridyl |
| 810 | 2-Me | 7-Cl | —CH₂CH₂-2-furanyl |
| 811 | 2-Me | 7-Cl | —CH₂CH₂-3-furanyl |
| 812 | 2-Me | 7-Cl | —CH₂CH₂-2-thienyl |
| 813 | 2-Me | 7-Cl | —CH₂CH₂-3-thienyl |
| 814 | 2-Me | 7-Cl | —C≡C-cycPr |
| 815 | 2-Me | 7-Cl | —C≡C-Ph |
| 816 | 2-Me | 7-Cl | —C≡C-2-Pyridyl |
| 817 | 2-Me | 7-Cl | —C≡C-3-Pyridyl |
| 818 | 2-Me | 7-Cl | —C≡C-4-Pyridyl |
| 819 | 2-Me | 7-Cl | —C≡C-2-furanyl |
| 820 | 2-Me | 7-Cl | —C≡C-3-furanyl |
| 821 | 2-Me | 7-Cl | —C≡C-2-thienyl |
| 822 | 2-Me | 7-Cl | —C≡C-3-thienyl |
| 823 | 2-Me | 7-Cl | —C≡C-cycPr |
| 824 | 2-Me | 7-Cl | —C≡C-Ph |
| 825 | 2-Me | 7-Cl | —C≡C-2-Pyridyl |
| 826 | 2-Me | 7-Cl | —C≡C-3-Pyridyl |
| 827 | 2-Me | 7-Cl | —C≡C-4-Pyridyl |
| 828 | 2-Me | 7-Cl | —C≡C-2-furanyl |
| 829 | 2-Me | 7-Cl | —C≡C-3-furanyl |
| 830 | 2-Me | 7-Cl | —C≡C-2-thienyl |
| 831 | 2-Me | 7-Cl | —C≡C-3-thienyl |
| 832 | 2-Me | 7-Cl | —CH₂CH₂-cycPr |

TABLE 6-continued

| | | | |
|---|---|---|---|
| 833 | 2-Me | 7-Cl | —CH$_2$CH$_2$-Ph |
| 834 | 2-Me | 7-Cl | —CH$_2$CH$_2$-2-Pyridyl |
| 835 | 2-Me | 7-Cl | —CH$_2$CH$_2$-3-Pyridyl |
| 836 | 2-Me | 7-Cl | —CH$_2$CH$_2$-4-Pyridyl |
| 837 | 2-Me | 7-Cl | —CH$_2$CH$_2$-2-furanyl |
| 838 | 2-Me | 7-Cl | —CH$_2$CH$_2$-3-furanyl |
| 839 | 2-Me | 7-Cl | —CH$_2$CH$_2$-2-thienyl |
| 840 | 2-Me | 7-Cl | —CH$_2$CH$_2$-3-thienyl |
| 841 | 2-OH | 7-Cl | —OH |
| 842 | 2-OH | 7-Cl | —O-methyl |
| 843 | 2-OH | 7-Cl | —O-ethyl |
| 844 | 2-OH | 7-Cl | —O-n-propyl |
| 845 | 2-OH | 7-Cl | —O-i-propyl |
| 846 | 2-OH | 7-Cl | —O-butyl |
| 847 | 2-OH | 7-Cl | —O—CH$_2$-cyclopropyl |
| 848 | 2-OH | 7-Cl | —O—CH$_2$-(1-methylcyclopropyl) |
| 849 | 2-OH | 7-Cl | —O—CH$_2$CH$_2$-cyclopropyl |
| 850 | 2-OH | 7-Cl | —O—CH$_2$-cyclobutyl |
| 851 | 2-OH | 7-Cl | —O—CH$_2$CH$_2$-cyclobutyl |
| 852 | 2-OH | 7-Cl | —O-benzyl |
| 853 | 2-OH | 7-Cl | —O-2,2,2-trifluoroethyl |
| 854 | 2-OH | 7-Cl | —O-trifluoromethyl |
| 855 | 2-OH | 7-Cl | —O-3,3,3-trifluoropropyl |
| 856 | 2-OH | 7-Cl | —O-allyl |
| 857 | 2-OH | 7-Cl | —O-propargyl |
| 858 | 2-OH | 7-Cl | —O—CH$_2$CH$_2$—N(CH$_3$)$_2$ |
| 859 | 2-OH | 7-Cl | —O—CH$_2$CH$_2$—(N-morpholinyl) |
| 860 | 2-OH | 7-Cl | —O—CH$_2$-3-Pyridyl |
| 861 | 2-OH | 7-Cl | —O—CH$_2$-4-Pyridyl |
| 862 | 2-OH | 7-Cl | —O—CH$_2$-2-furanyl |
| 863 | 2-OH | 7-Cl | —O—CH$_2$-3-furanyl |
| 864 | 2-OH | 7-Cl | —O—CH$_2$-2-thienyl |
| 865 | 2-OH | 7-Cl | —O—CH$_2$-3-thienyl |
| 866 | 2-OH | 7-Cl | —O—CH$_2$-2-oxazolyl |
| 867 | 2-OH | 7-Cl | —O—CH$_2$-2-thiazolyl |
| 868 | 2-OH | 7-Cl | —O—CH$_2$-4-isoxazolyl |
| 869 | 2-OH | 7-Cl | —O—CH$_2$-2-imidazolyl |
| 870 | 2-OH | 7-Cl | —NH-methyl |
| 871 | 2-OH | 7-Cl | —NH-ethyl |
| 872 | 2-OH | 7-Cl | —NH-n-propyl |
| 873 | 2-OH | 7-Cl | —NH-i-propyl |
| 874 | 2-OH | 7-Cl | —NH-butyl |
| 875 | 2-OH | 7-Cl | —NH—CH$_2$-cyclopropyl |
| 876 | 2-OH | 7-Cl | —NH—CH$_2$-(1-methylcyclopropyl) |
| 877 | 2-OH | 7-Cl | —NH—CH$_2$CH$_2$-cyclopropyl |
| 878 | 2-OH | 7-Cl | —NH—CH$_2$-cyclobutyl |
| 879 | 2-OH | 7-Cl | —NH—CH$_2$CH$_2$-cyclobutyl |
| 880 | 2-OH | 7-Cl | —NH-benzyl |
| 881 | 2-OH | 7-Cl | —NH-2,2,2-trifluoroethyl |
| 882 | 2-OH | 7-Cl | —NH-trifluoromethyl |
| 883 | 2-OH | 7-Cl | —NH-3,3,3-trifluoropropyl |
| 884 | 2-OH | 7-Cl | —NH-allyl |
| 885 | 2-OH | 7-Cl | —NH-propargyl |
| 886 | 2-OH | 7-Cl | —NH—CH$_2$CH$_2$—N(CH$_3$)$_2$ |
| 887 | 2-OH | 7-Cl | —NH—CH$_2$CH$_2$—(N-morpholinyl) |
| 888 | 2-OH | 7-Cl | —NH—CH$_2$-3-Pyridyl |
| 889 | 2-OH | 7-Cl | —NH—CH$_2$-4-Pyridyl |
| 890 | 2-OH | 7-Cl | —NH—CH$_2$-2-furanyl |
| 891 | 2-OH | 7-Cl | —NH—CH$_2$-3-furanyl |
| 892 | 2-OH | 7-Cl | —NH—CH$_2$-2-thienyl |
| 893 | 2-OH | 7-Cl | —NH—CH$_2$-3-thienyl |
| 894 | 2-OH | 7-Cl | —NH—CH$_2$-2-oxazolyl |
| 895 | 2-OH | 7-Cl | —NH—CH$_2$-2-thiazolyl |
| 896 | 2-OH | 7-Cl | —NH—CH$_2$-4-isoxazolyl |
| 897 | 2-OH | 7-Cl | —NH—CH$_2$-2-imidazolyl |
| 898 | 2-OH | 7-Cl | -benzyl |
| 899 | 2-OH | 7-Cl | -2,2,2-trifluoroethyl |
| 900 | 2-OH | 7-Cl | -trifluoromethyl |
| 901 | 2-OH | 7-Cl | -methyl |
| 902 | 2-OH | 7-Cl | -ethyl |
| 903 | 2-OH | 7-Cl | -propyl |
| 904 | 2-OH | 7-Cl | -i-propyl |
| 905 | 2-OH | 7-Cl | -butyl |
| 906 | 2-OH | 7-Cl | -i-butyl |
| 907 | 2-OH | 7-Cl | -t-butyl |
| 908 | 2-OH | 7-Cl | -pentyl |
| 909 | 2-OH | 7-Cl | —CH$_2$—CH$_2$-cyclopropyl |
| 910 | 2-OH | 7-Cl | —CH$_2$—CH$_2$-(1-methylcyclopropyl) |
| 911 | 2-OH | 7-Cl | —CH2—CH$_2$CH$_2$-cyclopropyl |
| 912 | 2-OH | 7-Cl | —CH2—CH$_2$-cyclobutyl |
| 913 | 2-OH | 7-Cl | —CH2—CH$_2$CH$_2$-cyclobutyl |
| 914 | 2-OH | 7-Cl | —CH2-benzyl |
| 915 | 2-OH | 7-Cl | —CH2-2,2,2-trifluoroethyl |
| 916 | 2-OH | 7-Cl | —CH2-trifluoromethyl |
| 917 | 2-OH | 7-Cl | —CH2-3,3,3-trifluoropropyl |
| 918 | 2-OH | 7-Cl | —CH2-allyl |
| 919 | 2-OH | 7-Cl | —CH2-propargyl |
| 920 | 2-OH | 7-Cl | —CH2—CH$_2$CH$_2$—N(CH$_3$)$_2$ |
| 921 | 2-OH | 7-Cl | —CH2—CH$_2$CH$_2$-(N-morpholinyl) |
| 922 | 2-OH | 7-Cl | —CH2—CH$_2$-3-Pyridyl |
| 923 | 2-OH | 7-Cl | —CH2—CH$_2$-4-Pyridyl |
| 924 | 2-OH | 7-Cl | —CH2—CH$_2$-2-furanyl |
| 925 | 2-OH | 7-Cl | —CH2—CH$_2$-3-furanyl |
| 926 | 2-OH | 7-Cl | —CH2—CH$_2$-2-thienyl |
| 927 | 2-OH | 7-Cl | —CH2—CH$_2$-3-thienyl |
| 928 | 2-OH | 7-Cl | —CH2—CH$_2$-2-oxazolyl |
| 929 | 2-OH | 7-Cl | —CH2—CH$_2$-2-thiazolyl |
| 930 | 2-OH | 7-Cl | —CH2—CH$_2$-4-isoxazolyl |
| 931 | 2-OH | 7-Cl | —CH2—CH$_2$-2-imidazolyl |
| 932 | 2-OH | 7-Cl | —C≡C-(2-OH)Ph |
| 933 | 2-OH | 7-Cl | —C≡C-(3-OH)Ph |
| 934 | 2-OH | 7-Cl | —C≡C-(4-OH)Ph |
| 935 | 2-OH | 7-Cl | —C≡C-(2-OMe)Ph |
| 936 | 2-OH | 7-Cl | —C≡C-(3-OMe)Ph |
| 937 | 2-OH | 7-Cl | —C≡C-(4-OMe)Ph |
| 938 | 2-OH | 7-Cl | —C≡C-(2-CN)Ph |
| 939 | 2-OH | 7-Cl | —C≡C-(3-CN)Ph |
| 940 | 2-OH | 7-Cl | —C≡C-(4-CN)Ph |
| 941 | 2-OH | 7-Cl | —C≡C-(2-NO$_2$)Ph |
| 942 | 2-OH | 7-Cl | —C≡C-(3-NO$_2$)Ph |
| 943 | 2-OH | 7-Cl | —C≡C-(4-NO$_2$)Ph |
| 944 | 2-OH | 7-Cl | —C≡C-(2-NH$_2$)Ph |
| 945 | 2-OH | 7-Cl | —C≡C-(3-NH$_2$)Ph |
| 946 | 2-OH | 7-Cl | —C≡C-(4-NH$_2$)Ph |
| 947 | 2-OH | 7-Cl | —C≡C-(2-NMe$_2$)Ph |
| 948 | 2-OH | 7-Cl | —C≡C-(3-NMe$_2$)Ph |
| 949 | 2-OH | 7-Cl | —C≡C-(4-NMe$_2$)Ph |
| 950 | 2-OH | 7-Cl | —C≡C-3-Pyridyl |
| 951 | 2-OH | 7-Cl | —C≡C-4-Pyridyl |
| 952 | 2-OH | 7-Cl | —C≡C-2-furanyl |
| 953 | 2-OH | 7-Cl | —C≡C-3-furanyl |
| 954 | 2-OH | 7-Cl | —C≡C-2-thienyl |
| 955 | 2-OH | 7-Cl | —C≡C-3-thienyl |
| 956 | 2-OH | 7-Cl | —C≡C-2-oxazolyl |
| 957 | 2-OH | 7-Cl | —C≡C-2-thiazolyl |
| 958 | 2-OH | 7-Cl | —C≡C-4-isoxazolyl |
| 959 | 2-OH | 7-Cl | —C≡C-2-imidazolyl |
| 960 | 2-OH | 7-Cl | —CH$_2$CH$_2$-cycPr |
| 961 | 2-OH | 7-Cl | —CH$_2$CH$_2$CH$_2$CH$_2$OH |
| 962 | 2-OH | 7-Cl | —CH$_2$CH$_2$—CH(OH)Me |
| 963 | 2-OH | 7-Cl | —CH$_2$CH$_2$-Ph |
| 964 | 2-OH | 7-Cl | —CH$_2$CH$_2$-(2-Cl)Ph |
| 965 | 2-OH | 7-Cl | —CH$_2$CH$_2$-(3-Cl)Ph |
| 966 | 2-OH | 7-Cl | —CH$_2$CH$_2$-(4-Cl)Ph |
| 967 | 2-OH | 7-Cl | —CH$_2$CH$_2$-(2-F)Ph |
| 968 | 2-OH | 7-Cl | —CH$_2$CH$_2$-(3-F)Ph |
| 969 | 2-OH | 7-Cl | —CH$_2$CH$_2$-(4-F)Ph |
| 970 | 2-OH | 7-Cl | —CH$_2$CH$_2$-(2-OH)Ph |
| 971 | 2-OH | 7-Cl | —CH$_2$CH$_2$-(3-OH)Ph |
| 972 | 2-OH | 7-Cl | —CH$_2$CH$_2$-(4-OH)Ph |
| 973 | 2-OH | 7-Cl | —CH$_2$CH$_2$-(2-OMe)Ph |
| 974 | 2-OH | 7-Cl | —CH$_2$CH$_2$-(3-OMe)Ph |
| 975 | 2-OH | 7-Cl | —CH$_2$CH$_2$-(4-OMe)Ph |
| 976 | 2-OH | 7-Cl | —CH$_2$CH$_2$-(2-CN)Ph |
| 977 | 2-OH | 7-Cl | —CH$_2$CH$_2$-(3-CN)Ph |
| 978 | 2-OH | 7-Cl | —CH$_2$CH$_2$-(4-CN)Ph |
| 979 | 2-OH | 7-Cl | —CH$_2$CH$_2$-(2-NO$_2$)Ph |
| 980 | 2-OH | 7-Cl | —CH$_2$CH$_2$-(3-NO$_2$)Ph |
| 981 | 2-OH | 7-Cl | —CH$_2$CH$_2$-(4-NO$_2$)Ph |
| 982 | 2-OH | 7-Cl | —CH$_2$CH$_2$-(2-NH$_2$)Ph |
| 983 | 2-OH | 7-Cl | —CH$_2$CH$_2$-(3-NH$_2$)Ph |
| 984 | 2-OH | 7-Cl | —CH$_2$CH$_2$-(4-NH$_2$)Ph |
| 985 | 2-OH | 7-Cl | —CH$_2$CH$_2$-(2-NMe$_2$)Ph |
| 986 | 2-OH | 7-Cl | —CH$_2$CH$_2$-(3-NMe$_2$)Ph |
| 987 | 2-OH | 7-Cl | —CH$_2$CH$_2$-(4-NMe$_2$)Ph |
| 988 | 2-OH | 7-Cl | —CH$_2$CH$_2$-2-Pyridyl |
| 989 | 2-OH | 7-Cl | —CH$_2$CH$_2$-3-Pyridyl |
| 990 | 2-OH | 7-Cl | —CH$_2$CH$_2$-4-Pyridyl |

TABLE 6-continued

| | | | |
|---|---|---|---|
| 991 | 2-OH | 7-Cl | —CH$_2$CH$_2$-2-furanyl |
| 992 | 2-OH | 7-Cl | —CH$_2$CH$_2$-3-furanyl |
| 993 | 2-OH | 7-Cl | —CH$_2$CH$_2$-4-furanyl |
| 994 | 2-OH | 7-Cl | —CH$_2$CH$_2$-3-thienyl |
| 995 | 2-OH | 7-Cl | —CH$_2$CH$_2$-2-oxazolyl |
| 996 | 2-OH | 7-Cl | —CH$_2$CH$_2$-2-thiazolyl |
| 997 | 2-OH | 7-Cl | —CH$_2$CH$_2$-4-isoxazolyl |
| 998 | 2-OH | 7-Cl | —CH$_2$CH$_2$-2-imidazolyl |
| 999 | 2-OH | 7-Cl | —C≡C-cycPr |
| 1000 | 2-OH | 7-Cl | —C≡C-Ph |
| 1001 | 2-OH | 7-Cl | —C≡C-2-Pyridyl |
| 1002 | 2-OH | 7-Cl | —C≡C-3-Pyridyl |
| 1003 | 2-OH | 7-Cl | —C≡C-4-Pyridyl |
| 1004 | 2-OH | 7-Cl | —C≡C-2-furanyl |
| 1005 | 2-OH | 7-Cl | —C≡C-3-furanyl |
| 1006 | 2-OH | 7-Cl | —C≡C-2-thienyl |
| 1007 | 2-OH | 7-Cl | —C≡C-3-thienyl |
| 1008 | 2-OH | 7-Cl | —C≡C-cycPr |
| 1009 | 2-OH | 7-Cl | —C≡C-Ph |
| 1010 | 2-OH | 7-Cl | —C≡C-2-Pyridyl |
| 1011 | 2-OH | 7-Cl | —C≡C-3-Pyridyl |
| 1012 | 2-OH | 7-Cl | —C≡C-4-Pyridyl |
| 1013 | 2-OH | 7-Cl | —C≡C-2-furanyl |
| 1014 | 2-OH | 7-Cl | —C≡C-3-furanyl |
| 1015 | 2-OH | 7-Cl | —C≡C-2-thienyl |
| 1016 | 2-OH | 7-Cl | —C≡C-3-thienyl |
| 1017 | 2-OH | 7-Cl | —CH$_2$CH$_2$-cycPr |
| 1018 | 2-OH | 7-Cl | —CH$_2$CH$_2$-Ph |
| 1019 | 2-OH | 7-Cl | —CH$_2$CH$_2$-2-Pyridyl |
| 1020 | 2-OH | 7-Cl | —CH$_2$CH$_2$-3-Pyridyl |
| 1021 | 2-OH | 7-Cl | —CH$_2$CH$_2$-4-Pyridyl |
| 1022 | 2-OH | 7-Cl | —CH$_2$CH$_2$-2-furanyl |
| 1023 | 2-OH | 7-Cl | —CH$_2$CH$_2$-3-furanyl |
| 1024 | 2-OH | 7-Cl | —CH$_2$CH$_2$-2-thienyl |
| 1025 | 2-CH | 7-Cl | —CH$_2$CH$_2$-3-thienyl |
| 1026 | 2-OH | 7-Cl | —C≡C-cycPr |
| 1027 | 2-OH | 7-Cl | —C≡C-Ph |
| 1028 | 2-OH | 7-Cl | —C≡C-2-Pyridyl |
| 1029 | 2-OH | 7-Cl | —C≡C-3-Pyridyl |
| 1030 | 2-OH | 7-Cl | —C≡C-4-Pyridyl |
| 1031 | 2-OH | 7-Cl | —C≡C-2-furanyl |
| 1032 | 2-OH | 7-Cl | —C≡C-3-furanyl |
| 1033 | 2-OH | 7-Cl | —C≡C-2-thienyl |
| 1034 | 2-OH | 7-Cl | —C≡C-3-thienyl |
| 1035 | 2-OH | 7-Cl | —C≡C-cycPr |
| 1036 | 2-OH | 7-Cl | —C≡C-Ph |
| 1037 | 2-OH | 7-Cl | —C≡C-2-Pyridyl |
| 1038 | 2-OH | 7-Cl | —C≡C-3-Pyridyl |
| 1039 | 2-OH | 7-Cl | —C≡C-4-Pyridyl |
| 1040 | 2-OH | 7-Cl | —C≡C-2-furanyl |
| 1041 | 2-OH | 7-Cl | —C≡C-3-furanyl |
| 1042 | 2-OH | 7-Cl | —C≡C-2-thienyl |
| 1043 | 2-OH | 7-Cl | —C≡C-3-thienyl |
| 1044 | 2-OH | 7-Cl | —CH$_2$CH$_2$-cycPr |
| 1045 | 2-OH | 7-Cl | —CH$_2$CH$_2$-Ph |
| 1046 | 2-OH | 7-Cl | —CH$_2$CH$_2$-2-Pyridyl |
| 1047 | 2-OH | 7-Cl | —CH$_2$CH$_2$-3-Pyridyl |
| 1048 | 2-OH | 7-Cl | —CH$_2$CH$_2$-4-Pyridyl |
| 1049 | 2-OH | 7-Cl | —CH$_2$CH$_2$-2-furanyl |
| 1050 | 2-OH | 7-Cl | —CH$_2$CH$_2$-3-furanyl |
| 1051 | 2-OH | 7-Cl | —CH$_2$CH$_2$-2-thienyl |
| 1052 | 2-OH | 7-Cl | —CH$_2$CH$_2$-3-thienyl |
| 1053 | H | 7-F | —OH |
| 1054 | H | 7-F | —O-methyl |
| 1055 | H | 7-F | —O-ethyl |
| 1056 | H | 7-F | —O-n-propyl |
| 1057 | H | 7-F | —O-i-propyl |
| 1058 | H | 7-F | —O-butyl |
| 1059 | H | 7-F | —O—CH$_2$-cyclopropyl |
| 1060 | H | 7-F | —O—CH$_2$-(1-methylcyclopropyl) |
| 1061 | H | 7-F | —O—CH$_2$CH$_2$-cyclopropyl |
| 1062 | H | 7-F | —O—CH$_2$-cyclobutyl |
| 1063 | H | 7-F | —O—CH$_2$CH$_2$-cyclobutyl |
| 1064 | H | 7-F | —O-benzyl |
| 1065 | H | 7-F | —O-2,2,2-trifluoroethyl |
| 1066 | H | 7-F | —O-trifluoromethyl |
| 1067 | H | 7-F | —O-3,3,3-trifluoropropyl |
| 1068 | H | 7-F | —O-allyl |
| 1069 | H | 7-F | —O-propargyl |
| 1070 | H | 7-F | —O—CH$_2$CH$_2$—N(CH$_3$)$_2$ |
| 1071 | H | 7-F | —O—CH$_2$CH$_2$—(N-morpholinyl) |
| 1072 | H | 7-F | —O—CH$_2$-3-Pyridyl |
| 1073 | H | 7-F | —O—CH$_2$-4-Pyridyl |
| 1074 | H | 7-F | —O—CH$_2$-2-furanyl |
| 1075 | H | 7-F | —O—CH$_2$-3-furanyl |
| 1076 | H | 7-F | —O—CH$_2$-2-thienyl |
| 1077 | H | 7-F | —O—CH$_2$-3-thienyl |
| 1078 | H | 7-F | —O—CH$_2$-2-oxazolyl |
| 1079 | H | 7-F | —O—CH$_2$-2-thiazolyl |
| 1080 | H | 7-F | —O—CH$_2$-4-isoxazolyl |
| 1081 | H | 7-F | —O—CH$_2$-2-imidazolyl |
| 1082 | H | 7-F | —NH-methyl |
| 1083 | H | 7-F | —NH-ethyl |
| 1084 | H | 7-F | —NH-n-propyl |
| 1085 | H | 7-F | —NH-i-propyl |
| 1086 | H | 7-F | —NH-butyl |
| 1087 | H | 7-F | —NH—CH$_2$-cyclopropyl |
| 1088 | H | 7-F | —NH—CH$_2$-(1-methylcyclopropyl) |
| 1089 | H | 7-F | —NH—CH$_2$CH$_2$-cyclopropyl |
| 1090 | H | 7-F | —NH—CH$_2$-cyclobutyl |
| 1091 | H | 7-F | —NH—CH$_2$CH$_2$-cyclobutyl |
| 1092 | H | 7-F | —NH-benzyl |
| 1093 | H | 7-F | —NH-2,2,2-trifluoroethyl |
| 1094 | H | 7-F | —NH-trifluoromethyl |
| 1095 | H | 7-F | —NH-3,3,3-trifluoropropyl |
| 1096 | H | 7-F | —NH-allyl |
| 1097 | H | 7-F | —NH-propargyl |
| 1098 | H | 7-F | —NH—CH$_2$CH$_2$—N(CH$_3$)$_2$ |
| 1099 | H | 7-F | —NH—CH$_2$CH$_2$—(N-morpholinyl) |
| 1100 | H | 7-F | —NH—CH$_2$-3-Pyridyl |
| 1101 | H | 7-F | —NH—CH$_2$-4-Pyridyl |
| 1102 | H | 7-F | —NH—CH$_2$-2-furanyl |
| 1103 | H | 7-F | —NH—CH$_2$-3-furanyl |
| 1104 | H | 7-F | —NH—CH$_2$-2-thienyl |
| 1105 | H | 7-F | —NH—CH$_2$-3-thienyl |
| 1106 | H | 7-F | —NH—CH$_2$-2-oxazolyl |
| 1107 | H | 7-F | —NH—CH$_2$-2-thiazolyl |
| 1108 | H | 7-F | —NH—CH$_2$-4-isoxazolyl |
| 1109 | H | 7-F | —NH—CH$_2$-2-imidazolyl |
| 1110 | H | 7-F | -benzyl |
| 1111 | H | 7-F | -2,2,2-trifluoroethyl |
| 1112 | H | 7-F | -trifluoromethyl |
| 1113 | H | 7-F | -methyl |
| 1114 | H | 7-F | -ethyl |
| 1115 | H | 7-F | -propyl |
| 1116 | H | 7-F | -i-propyl |
| 1117 | H | 7-F | -butyl |
| 1118 | H | 7-F | -i-butyl |
| 1119 | H | 7-F | -t-butyl |
| 1120 | H | 7-F | -pentyl |
| 1121 | H | 7-F | —CH$_2$—CH$_2$-cyclopropyl |
| 1122 | H | 7-F | —CH$_2$—CH$_2$-(1-methylcyclopropyl) |
| 1123 | H | 7-F | —CH2—CH$_2$CH$_2$-cyclopropyl |
| 1124 | H | 7-F | —CH2—CH$_2$-cyclobutyl |
| 1125 | H | 7-F | —CH2—CH$_2$CH$_2$-cyclobutyl |
| 1126 | H | 7-F | —CH2-benzyl |
| 1127 | H | 7-F | —CH2-2,2,2-trifluoroethyl |
| 1128 | H | 7-F | —CH2-trifluoromethyl |
| 1129 | H | 7-F | —CH2-3,3,3-trifluoropropyl |
| 1130 | H | 7-F | —CH2-allyl |
| 1131 | H | 7-F | —CH2-propargyl |
| 1132 | H | 7-F | —CH2—CH$_2$CH$_2$—N(CH$_3$)$_2$ |
| 1133 | H | 7-F | —CH2—CH$_2$CH$_2$—(N-morpholinyl) |
| 1134 | H | 7-F | —CH2—CH$_2$-3-Pyridyl |
| 1135 | H | 7-F | —CH2—CH$_2$-4-Pyridyl |
| 1136 | H | 7-F | —CH2—CH$_2$-2-furanyl |
| 1137 | H | 7-F | —CH2—CH$_2$-3-furanyl |
| 1138 | H | 7-F | —CH2—CH$_2$-2-thienyl |
| 1139 | H | 7-F | —CH2—CH$_2$-3-thienyl |
| 1140 | H | 7-F | —CH2—CH$_2$-2-oxazolyl |
| 1141 | H | 7-F | —CH2—CH$_2$-2-thiazolyl |
| 1142 | H | 7-F | —CH2—CH$_2$-4-isoxazolyl |
| 1143 | H | 7-F | —CH2—CH$_2$-2-imidazolyl |
| 1144 | H | 7-F | —C≡C-(2-OH)Ph |
| 1145 | H | 7-F | —C≡C-(3-OH)Ph |
| 1146 | H | 7-F | —C≡C-(4-OH)Ph |
| 1147 | H | 7-F | —C≡C-(2-OMe)Ph |
| 1148 | H | 7-F | —C≡C-(3-OMe)Ph |

TABLE 6-continued

| | | | |
|---|---|---|---|
| 1149 | H | 7-F | —C≡C-(4-OMe)Ph |
| 1150 | H | 7-F | —C≡C-(2-CN)Ph |
| 1151 | H | 7-F | —C≡C-(3-CN)Ph |
| 1152 | H | 7-F | —C≡C-(4-CN)Ph |
| 1153 | H | 7-F | —C≡C-(2-NO$_2$)Ph |
| 1154 | H | 7-F | —C≡C-(3-NO$_2$)Ph |
| 1155 | H | 7-F | —C≡C-(4-NO$_2$)Ph |
| 1156 | H | 7-F | —C≡C-(2-NH$_2$)Ph |
| 1157 | H | 7-F | —C≡C-(3-NH$_2$)Ph |
| 1158 | H | 7-F | —C≡C-(4-NH$_2$)Ph |
| 1159 | H | 7-F | —C≡C-(2-NMe$_2$)Ph |
| 1160 | H | 7-F | —C≡C-(3-NMe$_2$)Ph |
| 1161 | H | 7-F | —C≡C-(4-NMe$_2$)Ph |
| 1162 | H | 7-F | —C≡C-3-Pyridyl |
| 1163 | H | 7-F | —C≡C-4-Pyridyl |
| 1164 | H | 7-F | —C≡C-2-furanyl |
| 1165 | H | 7-F | —C≡C-3-furanyl |
| 1166 | H | 7-F | —C≡C-2-thienyl |
| 1167 | H | 7-F | —C≡C-3-thienyl |
| 1168 | H | 7-F | —C≡C-2-oxazolyl |
| 1169 | H | 7-F | —C≡C-2-thiazolyl |
| 1170 | H | 7-F | —C≡C-4-isoxazolyl |
| 1171 | H | 7-F | —C≡C-2-imidazolyl |
| 1172 | H | 7-F | —CH$_2$CH$_2$-cycPr |
| 1173 | H | 7-F | —CH$_2$CH$_2$CH$_2$CH$_2$OH |
| 1174 | H | 7-F | —CH$_2$CH$_2$—CH(OH)Me |
| 1175 | H | 7-F | —CH$_2$CH$_2$-Ph |
| 1176 | H | 7-F | —CH$_2$CH$_2$-(2-Cl)Ph |
| 1177 | H | 7-F | —CH$_2$CH$_2$-(3-Cl)Ph |
| 1178 | H | 7-F | —CH$_2$CH$_2$-(4-Cl)Ph |
| 1179 | H | 7-F | —CH$_2$CH$_2$-(2-F)Ph |
| 1180 | H | 7-F | —CH$_2$CH$_2$-(3-F)Ph |
| 1181 | H | 7-F | —CH$_2$CH$_2$-(4-F)Ph |
| 1182 | H | 7-F | —CH$_2$CH$_2$-(2-OH)Ph |
| 1183 | H | 7-F | —CH$_2$CH$_2$-(3-OH)Ph |
| 1184 | H | 7-F | —CH$_2$CH$_2$-(4-OH)Ph |
| 1185 | H | 7-F | —CH$_2$CH$_2$-(2-OMe)Ph |
| 1186 | H | 7-F | —CH$_2$CH$_2$-(3-OMe)Ph |
| 1187 | H | 7-F | —CH$_2$CH$_2$-(4-OMe)Ph |
| 1188 | H | 7-F | —CH$_2$CH$_2$-(2-CN)Ph |
| 1189 | H | 7-F | —CH$_2$CH$_2$-(3-CN)Ph |
| 1190 | H | 7-F | —CH$_2$CH$_2$-(4-CN)Ph |
| 1191 | H | 7-F | —CH$_2$CH$_2$-(2-NO$_2$)Ph |
| 1192 | H | 7-F | —CH$_2$CH$_2$-(3-NO$_2$)Ph |
| 1193 | H | 7-F | —CH$_2$CH$_2$-(4-NO$_2$)Ph |
| 1194 | H | 7-F | —CH$_2$CH$_2$-(2-NH$_2$)Ph |
| 1195 | H | 7-F | —CH$_2$CH$_2$-(3-NH$_2$)Ph |
| 1196 | H | 7-F | —CH$_2$CH$_2$-(4-NH$_2$)Ph |
| 1197 | H | 7-F | —CH$_2$CH$_2$-(2-NMe$_2$)Ph |
| 1198 | H | 7-F | —CH$_2$CH$_2$-(3-NMe$_2$)Ph |
| 1199 | H | 7-F | —CH$_2$CH$_2$-(4-NMe$_2$)Ph |
| 1200 | H | 7-F | —CH$_2$CH$_2$-2-Pyridyl |
| 1201 | H | 7-F | —CH$_2$CH$_2$-3-Pyridyl |
| 1202 | H | 7-F | —CH$_2$CH$_2$-4-Pyridyl |
| 1203 | H | 7-F | —CH$_2$CH$_2$-2-furanyl |
| 1204 | H | 7-F | —CH$_2$CH$_2$-3-furanyl |
| 1205 | H | 7-F | —CH$_2$CH$_2$-4-furanyl |
| 1206 | H | 7-F | —CH$_2$CH$_2$-3-thienyl |
| 1207 | H | 7-F | —CH$_2$CH$_2$-2-oxazolyl |
| 1208 | H | 7-F | —CH$_2$CH$_2$-2-thiazolyl |
| 1209 | H | 7-F | —CH$_2$CH$_2$-4-isoxazolyl |
| 1210 | H | 7-F | —CH$_2$CH$_2$-2-imidazolyl |
| 1211 | H | 7-F | —C≡C-cycPr |
| 1212 | H | 7-F | —C≡C-Ph |
| 1213 | H | 7-F | —C≡C-2-Pyridyl |
| 1214 | H | 7-F | —C≡C-3-Pyridyl |
| 1215 | H | 7-F | —C≡C-4-Pyridyl |
| 1216 | H | 7-F | —C≡C-2-furanyl |
| 1217 | H | 7-F | —C≡C-3-furanyl |
| 1218 | H | 7-F | —C≡C-2-thienyl |
| 1219 | H | 7-F | —C≡C-3-thienyl |
| 1220 | H | 7-F | —C≡C-cycPr |
| 1221 | H | 7-F | —C≡C-Ph |
| 1222 | H | 7-F | —C≡C-2-Pyridyl |
| 1223 | H | 7-F | —C≡C-3-Pyridyl |
| 1224 | H | 7-F | —C≡C-4-Pyridyl |
| 1225 | H | 7-F | —C≡C-2-furanyl |
| 1226 | H | 7-F | —C≡C-3-furanyl |
| 1227 | H | 7-F | —C≡C-2-thienyl |
| 1228 | H | 7-F | —C≡C-3-thienyl |
| 1229 | H | 7-F | —CH$_2$CH$_2$-cycPr |
| 1230 | H | 7-F | —CH$_2$CH$_2$-Ph |
| 1231 | H | 7-F | —CH$_2$CH$_2$-2-Pyridyl |
| 1232 | H | 7-F | —CH$_2$CH$_2$-3-Pyridyl |
| 1233 | H | 7-F | —CH$_2$CH$_2$-4-Pyridyl |
| 1234 | H | 7-F | —CH$_2$CH$_2$-2-furanyl |
| 1235 | H | 7-F | —CH$_2$CH$_2$-3-furanyl |
| 1236 | H | 7-F | —CH$_2$CH$_2$-2-thienyl |
| 1237 | H | 7-F | —CH$_2$CH$_2$-3-thienyl |
| 1238 | H | 7-F | —C≡C-cycPr |
| 1239 | H | 7-F | —C≡C-Ph |
| 1240 | H | 7-F | —C≡C-2-Pyridyl |
| 1241 | H | 7-F | —C≡C-3-Pyridyl |
| 1242 | H | 7-F | —C≡C-4-Pyridyl |
| 1243 | H | 7-F | —C≡C-2-furanyl |
| 1244 | H | 7-F | —C≡C-3-furanyl |
| 1245 | H | 7-F | —C≡C-2-thienyl |
| 1246 | H | 7-F | —C≡C-3-thienyl |
| 1247 | H | 7-F | —C≡C-cycPr |
| 1248 | H | 7-F | —C≡C-Ph |
| 1249 | H | 7-F | —C≡C-2-Pyridyl |
| 1250 | H | 7-F | —C≡C-3-Pyridyl |
| 1251 | H | 7-F | —C≡C-4-Pyridyl |
| 1252 | H | 7-F | —C≡C-2-furanyl |
| 1253 | H | 7-F | —C≡C-3-furanyl |
| 1254 | H | 7-F | —C≡C-2-thienyl |
| 1255 | H | 7-F | —C≡C-3-thienyl |
| 1256 | H | 7-F | —CH$_2$CH$_2$-cycPr |
| 1257 | H | 7-F | —CH$_2$CH$_2$-Ph |
| 1258 | H | 7-F | —CH$_2$CH$_2$-2-Pyridyl |
| 1259 | H | 7-F | —CH$_2$CH$_2$-3-Pyridyl |
| 1260 | H | 7-F | —CH$_2$CH$_2$-4-Pyridyl |
| 1261 | H | 7-F | —CH$_2$CH$_2$-2-furanyl |
| 1262 | H | 7-F | —CH$_2$CH$_2$-3-furanyl |
| 1263 | H | 7-F | —CH$_2$CH$_2$-2-thienyl |
| 1264 | H | 7-F | —CH$_2$CH$_2$-3-thienyl |
| 1265 | 3-Cl | 7-F | —OH |
| 1266 | 3-Cl | 7-F | —O-methyl |
| 1267 | 3-Cl | 7-F | —O-ethyl |
| 1268 | 3-Cl | 7-F | —O-n-propyl |
| 1269 | 3-Cl | 7-F | —O-i-propyl |
| 1270 | 3-Cl | 7-F | —O-butyl |
| 1271 | 3-Cl | 7-F | —O—CH$_2$-cyclopropyl |
| 1272 | 3-Cl | 7-F | —O—CH$_2$-(1-methylcyclopropyl) |
| 1273 | 3-Cl | 7-F | —O—CH$_2$CH$_2$-cyclopropyl |
| 1274 | 3-Cl | 7-F | —O—CH$_2$-cyclobutyl |
| 1275 | 3-Cl | 7-F | —O—CH$_2$CH$_2$-cyclobutyl |
| 1276 | 3-Cl | 7-F | —O-benzyl |
| 1277 | 3-Cl | 7-F | —O-2,2,2-trifluoroethyl |
| 1278 | 3-Cl | 7-F | —O-trifluoromethyl |
| 1279 | 3-Cl | 7-F | —O-3,3,3-trifluoropropyl |
| 1280 | 3-Cl | 7-F | —O-allyl |
| 1281 | 3-Cl | 7-F | —O-propargyl |
| 1282 | 3-Cl | 7-F | —O—CH$_2$CH$_2$—N(CH$_3$)$_2$ |
| 1283 | 3-Cl | 7-F | —O—CH$_2$CH$_2$—(N-morpholinyl) |
| 1284 | 3-Cl | 7-F | —O—CH$_2$-3-Pyridyl |
| 1285 | 3-Cl | 7-F | —O—CH$_2$-4-Pyridyl |
| 1286 | 3-Cl | 7-F | —O—CH$_2$-2-furanyl |
| 1287 | 3-Cl | 7-F | —O—CH$_2$-3-furanyl |
| 1288 | 3-Cl | 7-F | —O—CH$_2$-2-thienyl |
| 1289 | 3-Cl | 7-F | —O—CH$_2$-3-thienyl |
| 1290 | 3-Cl | 7-F | —O—CH$_2$-2-oxazolyl |
| 1291 | 3-Cl | 7-F | —O—CH$_2$-2-thiazolyl |
| 1292 | 3-Cl | 7-F | —O—CH$_2$-4-isoxazolyl |
| 1293 | 3-Cl | 7-F | —O—CH$_2$-2-imidazolyl |
| 1294 | 3-Cl | 7-F | —NH-methyl |
| 1295 | 3-Cl | 7-F | —NH-ethyl |
| 1296 | 3-Cl | 7-F | —NH-n-propyl |
| 1297 | 3-Cl | 7-F | —NH-i-propyl |
| 1298 | 3-Cl | 7-F | —NH-butyl |
| 1299 | 3-Cl | 7-F | —NH—CH$_2$-cyclopropyl |
| 1300 | 3-Cl | 7-F | —NH—CH$_2$-(1-methylcyclopropyl) |
| 1301 | 3-Cl | 7-F | —NH—CH$_2$CH$_2$-cyclopropyl |
| 1302 | 3-Cl | 7-F | —NH—CH$_2$-cyclobutyl |
| 1303 | 3-Cl | 7-F | —NH—CH$_2$CH$_2$-cyclobutyl |
| 1304 | 3-Cl | 7-F | —NH-benzyl |
| 1305 | 3-Cl | 7-F | —NH-2,2,2-trifluoroethyl |
| 1306 | 3-Cl | 7-F | —NH-trifluoromethyl |

TABLE 6-continued

| | | | |
|---|---|---|---|
| 1307 | 3-Cl | 7-F | —NH-3,3,3-trifluoropropyl |
| 1308 | 3-Cl | 7-F | —NH-allyl |
| 1309 | 3-Cl | 7-F | —NH-propargyl |
| 1310 | 3-Cl | 7-F | —NH—$CH_2CH_2$—$N(CH_3)_2$ |
| 1311 | 3-Cl | 7-F | —NH—$CH_2CH_2$—(N-morpholinyl) |
| 1312 | 3-Cl | 7-F | —NH—$CH_2$-3-Pyridyl |
| 1313 | 3-Cl | 7-F | —NH—$CH_2$-4-Pyridyl |
| 1314 | 3-Cl | 7-F | —NH—$CH_2$-2-furanyl |
| 1315 | 3-Cl | 7-F | —NH—$CH_2$-3-furanyl |
| 1316 | 3-Cl | 7-F | —NH—$CH_2$-2-thienyl |
| 1317 | 3-Cl | 7-F | —NH—$CH_2$-3-thienyl |
| 1318 | 3-Cl | 7-F | —NH—$CH_2$-2-oxazolyl |
| 1319 | 3-Cl | 7-F | —NH—$CH_2$-2-thiazolyl |
| 1320 | 3-Cl | 7-F | —NH—$CH_2$-4-isoxazolyl |
| 1321 | 3-Cl | 7-F | —NH—$CH_2$-2-imidazolyl |
| 1322 | 3-Cl | 7-F | -benzyl |
| 1323 | 3-Cl | 7-F | -2,2,2-trifluoroethyl |
| 1324 | 3-Cl | 7-F | -trifluoromethyl |
| 1325 | 3-Cl | 7-F | -methyl |
| 1326 | 3-Cl | 7-F | -ethyl |
| 1327 | 3-Cl | 7-F | -propyl |
| 1328 | 3-Cl | 7-F | -i-propyl |
| 1329 | 3-Cl | 7-F | -butyl |
| 1330 | 3-Cl | 7-F | -i-butyl |
| 1331 | 3-Cl | 7-F | -t-butyl |
| 1332 | 3-Cl | 7-F | -pentyl |
| 1333 | 3-Cl | 7-F | —$CH_2$—$CH_2$-cyclopropyl |
| 1334 | 3-Cl | 7-F | —$CH_2$—$CH_2$-(1-methylcyclopropyl) |
| 1335 | 3-Cl | 7-F | —CH2—$CH_2CH_2$-cyclopropyl |
| 1336 | 3-Cl | 7-F | —$CH_2$—$CH_2$-cyclobutyl |
| 1337 | 3-Cl | 7-F | —CH2—$CH_2CH_2$-cyclobutyl |
| 1338 | 3-Cl | 7-F | —CH2-benzyl |
| 1339 | 3-Cl | 7-F | —CH2-2,2,2-trifluoroethyl |
| 1340 | 3-Cl | 7-F | —CH2-trifluoromethyl |
| 1341 | 3-Cl | 7-F | —CH2-3,3,3-trifluoropropyl |
| 1342 | 3-Cl | 7-F | —CH2-allyl |
| 1343 | 3-Cl | 7-F | —CH2-propargyl |
| 1344 | 3-Cl | 7-F | —CH2—$CH_2CH_2$—$N(CH_3)_2$ |
| 1345 | 3-Cl | 7-F | —CH2—$CH_2CH_2$-(N-morpholinyl) |
| 1346 | 3-Cl | 7-F | —CH2—$CH_2$-3-Pyridyl |
| 1347 | 3-Cl | 7-F | —CH2—$CH_2$-4-Pyridyl |
| 1348 | 3-Cl | 7-F | —CH2—$CH_2$-2-furanyl |
| 1349 | 3-Cl | 7-F | —CH2—$CH_2$-3-furanyl |
| 1350 | 3-Cl | 7-F | —CH2—$CH_2$-2-thienyl |
| 1351 | 3-Cl | 7-F | —CH2—$CH_2$-3-thienyl |
| 1352 | 3-Cl | 7-F | —CH2—$CH_2$-2-oxazolyl |
| 1353 | 3-Cl | 7-F | —CH2—$CH_2$-2-thiazolyl |
| 1354 | 3-Cl | 7-F | —CH2—$CH_2$-4-isoxazolyl |
| 1355 | 3-Cl | 7-F | —CH2—$CH_2$-2-imidazolyl |
| 1356 | 3-Cl | 7-F | —C≡C-(2-OH)Ph |
| 1357 | 3-Cl | 7-F | —C≡C-(3-OH)Ph |
| 1358 | 3-Cl | 7-F | —C≡C-(4-OH)Ph |
| 1359 | 3-Cl | 7-F | —C≡C-(2-OMe)Ph |
| 1360 | 3-Cl | 7-F | —C≡C-(3-OMe)Ph |
| 1361 | 3-Cl | 7-F | —C≡C-(4-OMe)Ph |
| 1362 | 3-Cl | 7-F | —C≡C-(2-CN)Ph |
| 1363 | 3-Cl | 7-F | —C≡C-(3-CN)Ph |
| 1364 | 3-Cl | 7-F | —C≡C-(4-CN)Ph |
| 1365 | 3-Cl | 7-F | —C≡C-(2-$NO_2$)Ph |
| 1366 | 3-Cl | 7-F | —C≡C-(3-$NO_2$)Ph |
| 1367 | 3-Cl | 7-F | —C≡C-(4-$NO_2$)Ph |
| 1368 | 3-Cl | 7-F | —C≡C-(2-$NH_2$)Ph |
| 1369 | 3-Cl | 7-F | —C≡C-(3-$NH_2$)Ph |
| 1370 | 3-Cl | 7-F | —C≡C-(4-$NH_2$)Ph |
| 1371 | 3-Cl | 7-F | —C≡C-(2-$NMe_2$)Ph |
| 1372 | 3-Cl | 7-F | —C≡C-(3-$NMe_2$)Ph |
| 1373 | 3-Cl | 7-F | —C≡C-(4-$NMe_2$)Ph |
| 1374 | 3-Cl | 7-F | —C≡C-3-Pyridyl |
| 1375 | 3-Cl | 7-F | —C≡C-4-Pyridyl |
| 1376 | 3-Cl | 7-F | —C≡C-2-furanyl |
| 1377 | 3-Cl | 7-F | —C≡C-3-furanyl |
| 1378 | 3-Cl | 7-F | —C≡C-2-thienyl |
| 1379 | 3-Cl | 7-F | —C≡C-3-thienyl |
| 1380 | 3-Cl | 7-F | —C≡C-2-oxazolyl |
| 1381 | 3-Cl | 7-F | —C≡C-2-thiazolyl |
| 1382 | 3-Cl | 7-F | —C≡C-4-isoxazolyl |
| 1383 | 3-Cl | 7-F | —C≡C-2-imidazolyl |
| 1384 | 3-Cl | 7-F | —$CH_2CH_2$-cycPr |
| 1385 | 3-Cl | 7-F | —$CH_2CH_2CH_2CH_2OH$ |
| 1386 | 3-Cl | 7-F | —$CH_2CH_2$—CH(OH)Me |
| 1387 | 3-Cl | 7-F | —$CH_2CH_2$-Ph |
| 1388 | 3-Cl | 7-F | —$CH_2CH_2$-(2-Cl)Ph |
| 1389 | 3-Cl | 7-F | —$CH_2CH_2$-(3-Cl)Ph |
| 1390 | 3-Cl | 7-F | —$CH_2CH_2$-(4-Cl)Ph |
| 1391 | 3-Cl | 7-F | —$CH_2CH_2$-(2-F)Ph |
| 1392 | 3-Cl | 7-F | —$CH_2CH_2$-(3-F)Ph |
| 1393 | 3-Cl | 7-F | —$CH_2CH_2$-(4-F)Ph |
| 1394 | 3-Cl | 7-F | —$CH_2CH_2$-(2-OH)Ph |
| 1395 | 3-Cl | 7-F | —$CH_2CH_2$-(3-OH)Ph |
| 1396 | 3-Cl | 7-F | —$CH_2CH_2$-(4-OH)Ph |
| 1397 | 3-Cl | 7-F | —$CH_2CH_2$-(2-OMe)Ph |
| 1398 | 3-Cl | 7-F | —$CH_2CH_2$-(3-OMe)Ph |
| 1399 | 3-Cl | 7-F | —$CH_2CH_2$-(4-OMe)Ph |
| 1400 | 3-Cl | 7-F | —$CH_2CH_2$-(2-CN)Ph |
| 1401 | 3-Cl | 7-F | —$CH_2CH_2$-(3-CN)Ph |
| 1402 | 3-Cl | 7-F | —$CH_2CH_2$-(4-CN)Ph |
| 1403 | 3-Cl | 7-F | —$CH_2CH_2$-(2-$NO_2$)Ph |
| 1404 | 3-Cl | 7-F | —$CH_2CH_2$-(3-$NO_2$)Ph |
| 1405 | 3-Cl | 7-F | —$CH_2CH_2$-(4-$NO_2$)Ph |
| 1406 | 3-Cl | 7-F | —$CH_2CH_2$-(2-$NH_2$)Ph |
| 1407 | 3-Cl | 7-F | —$CH_2CH_2$-(3-$NH_2$)Ph |
| 1408 | 3-Cl | 7-F | —$CH_2CH_2$-(4-$NH_2$)Ph |
| 1409 | 3-Cl | 7-F | —$CH_2CH_2$-(2-$NMe_2$)Ph |
| 1410 | 3-Cl | 7-F | —$CH_2CH_2$-(3-$NMe_2$)Ph |
| 1411 | 3-Cl | 7-F | —$CH_2CH_2$-(4-$NMe_2$)Ph |
| 1412 | 3-Cl | 7-F | —$CH_2CH_2$-2-Pyridyl |
| 1413 | 3-Cl | 7-F | —$CH_2CH_2$-3-Pyridyl |
| 1414 | 3-Cl | 7-F | —$CH_2CH_2$-4-Pyridyl |
| 1415 | 3-Cl | 7-F | —$CH_2CH_2$-2-furanyl |
| 1416 | 3-Cl | 7-F | —$CH_2CH_2$-3-furanyl |
| 1417 | 3-Cl | 7-F | —$CH_2CH_2$-4-furanyl |
| 1418 | 3-Cl | 7-F | —$CH_2CH_2$-3-thienyl |
| 1419 | 3-Cl | 7-F | —$CH_2CH_2$-2-oxazolyl |
| 1420 | 3-Cl | 7-F | —$CH_2CH_2$-2-thiazolyl |
| 1421 | 3-Cl | 7-F | —$CH_2CH_2$-4-isoxazolyl |
| 1422 | 3-Cl | 7-F | —$CH_2CH_2$-2-imidazolyl |
| 1423 | 3-Cl | 7-F | —C≡C-cycPr |
| 1424 | 3-Cl | 7-F | —C≡C-Ph |
| 1425 | 3-Cl | 7-F | —C≡C-2-Pyridyl |
| 1426 | 3-Cl | 7-F | —C≡C-3-Pyridyl |
| 1427 | 3-Cl | 7-F | —C≡C-4-Pyridyl |
| 1428 | 3-Cl | 7-F | —C≡C-2-furanyl |
| 1429 | 3-Cl | 7-F | —C≡C-3-furanyl |
| 1430 | 3-Cl | 7-F | —C≡C-2-thienyl |
| 1431 | 3-Cl | 7-F | —C≡C-3-thienyl |
| 1432 | 3-Cl | 7-F | —C≡C-cycPr |
| 1433 | 3-Cl | 7-F | —C≡C-Ph |
| 1434 | 3-Cl | 7-F | —C≡C-2-Pyridyl |
| 1435 | 3-Cl | 7-F | —C≡C-3-Pyridyl |
| 1436 | 3-Cl | 7-F | —C≡C-4-Pyridyl |
| 1437 | 3-Cl | 7-F | —C≡C-2-furanyl |
| 1438 | 3-Cl | 7-F | —C≡C-3-furanyl |
| 1439 | 3-Cl | 7-F | —C≡C-2-thienyl |
| 1440 | 3-Cl | 7-F | —C≡C-3-thienyl |
| 1441 | 3-Cl | 7-F | —$CH_2CH_2$-cycPr |
| 1442 | 3-Cl | 7-F | —$CH_2CH_2$-Ph |
| 1443 | 3-Cl | 7-F | —$CH_2CH_2$-2-Pyridyl |
| 1444 | 3-Cl | 7-F | —$CH_2CH_2$-3-Pyridyl |
| 1445 | 3-Cl | 7-F | —$CH_2CH_2$-4-Pyridyl |
| 1446 | 3-Cl | 7-F | —$CH_2CH_2$-2-furanyl |
| 1447 | 3-Cl | 7-F | —$CH_2CH_2$-3-furanyl |
| 1448 | 3-Cl | 7-F | —$CH_2CH_2$-2-thienyl |
| 1449 | 3-Cl | 7-F | —$CH_2CH_2$-3-thienyl |
| 1450 | 3-Cl | 7-F | —C≡C-cycPr |
| 1451 | 3-Cl | 7-F | —C≡C-Ph |
| 1452 | 3-Cl | 7-F | —C≡C-2-Pyridyl |
| 1453 | 3-Cl | 7-F | —C≡C-3-Pyridyl |
| 1454 | 3-Cl | 7-F | —C≡C-4-Pyridyl |
| 1455 | 3-Cl | 7-F | —C≡C-2-furanyl |
| 1456 | 3-Cl | 7-F | —C≡C-3-furanyl |
| 1457 | 3-Cl | 7-F | —C≡C-2-thienyl |
| 1458 | 3-Cl | 7-F | —C≡C-3-thienyl |
| 1459 | 3-Cl | 7-F | —C≡C-cycPr |
| 1460 | 3-Cl | 7-F | —C≡C-Ph |
| 1461 | 3-Cl | 7-F | —C≡C-2-Pyridyl |
| 1462 | 3-Cl | 7-F | —C≡C-3-Pyridyl |
| 1463 | 3-Cl | 7-F | —C≡C-4-Pyridyl |
| 1464 | 3-Cl | 7-F | —C≡C-2-furanyl |

TABLE 6-continued

| | | | |
|---|---|---|---|
| 1465 | 3-Cl | 7-F | —C≡C-3-furanyl |
| 1466 | 3-Cl | 7-F | —C≡C-2-thienyl |
| 1467 | 3-Cl | 7-F | —C≡C-3-thienyl |
| 1468 | 3-Cl | 7-F | —CH$_2$CH$_2$-cycPr |
| 1469 | 3-Cl | 7-F | —CH$_2$CH$_2$-Ph |
| 1470 | 3-Cl | 7-F | —CH$_2$CH$_2$-2-Pyridyl |
| 1471 | 3-Cl | 7-F | —CH$_2$CH$_2$-3-Pyridyl |
| 1472 | 3-Cl | 7-F | —CH$_2$CH$_2$-4-Pyridyl |
| 1473 | 3-Cl | 7-F | —CH$_2$CH$_2$-2-furanyl |
| 1474 | 3-Cl | 7-F | —CH$_2$CH$_2$-3-furanyl |
| 1475 | 3-Cl | 7-F | —CH$_2$CH$_2$-2-thienyl |
| 1476 | 3-Cl | 7-F | —CH$_2$CH$_2$-3-thienyl |
| 1477 | 2-Me | 7-F | —OH |
| 1478 | 2-Me | 7-F | —O-methyl |
| 1479 | 2-Me | 7-F | —O-ethyl |
| 1480 | 2-Me | 7-F | —O-n-propyl |
| 1481 | 2-Me | 7-F | —O-i-propyl |
| 1482 | 2-Me | 7-F | —O-butyl |
| 1483 | 2-Me | 7-F | —O—CH$_2$-cyclopropyl |
| 1484 | 2-Me | 7-F | —O—CH$_2$-(1-methylcyclopropyl) |
| 1485 | 2-Me | 7-F | —O—CH$_2$CH$_2$-cyclopropyl |
| 1486 | 2-Me | 7-F | —O—CH$_2$-cyclobutyl |
| 1487 | 2-Me | 7-F | —O—CH$_2$CH$_2$-cyclobutyl |
| 1488 | 2-Me | 7-F | —O-benzyl |
| 1489 | 2-Me | 7-F | —O-2,2,2-trifluoroethyl |
| 1490 | 2-Me | 7-F | —O-trifluoromethyl |
| 1491 | 2-Me | 7-F | —O-3,3,3-trifluoropropyl |
| 1492 | 2-Me | 7-F | —O-allyl |
| 1493 | 2-Me | 7-F | —O-propargyl |
| 1494 | 2-Me | 7-F | —O—CH$_2$CH$_2$—N(CH$_3$)$_2$ |
| 1495 | 2-Me | 7-F | —O—CH$_2$CH$_2$—(N-morpholinyl) |
| 1496 | 2-Me | 7-F | —O—CH$_2$-3-Pyridyl |
| 1497 | 2-Me | 7-F | —O—CH$_2$-4-Pyridyl |
| 1498 | 2-Me | 7-F | —O—CH$_2$-2-furanyl |
| 1499 | 2-Me | 7-F | —O—CH$_2$-3-furanyl |
| 1500 | 2-Me | 7-F | —O—CH$_2$-2-thienyl |
| 1501 | 2-Me | 7-F | —O—CH$_2$-3-thienyl |
| 1502 | 2-Me | 7-F | —O—CH$_2$-2-oxazolyl |
| 1503 | 2-Me | 7-F | —O—CH$_2$-2-thiazolyl |
| 1504 | 2-Me | 7-F | —O—CH$_2$-4-isoxazolyl |
| 1505 | 2-Me | 7-F | —O—CH$_2$-2-imidazolyl |
| 1506 | 2-Me | 7-F | —NH-methyl |
| 1507 | 2-Me | 7-F | —NH-ethyl |
| 1508 | 2-Me | 7-F | —NH-n-propyl |
| 1509 | 2-Me | 7-F | —NH-i-propyl |
| 1510 | 2-Me | 7-F | —NH-butyl |
| 1511 | 2-Me | 7-F | —NH—CH$_2$-cyclopropyl |
| 1512 | 2-Me | 7-F | —NH—CH$_2$-(1-methylcyclopropyl) |
| 1513 | 2-Me | 7-F | —NH—CH$_2$CH$_2$-cyclopropyl |
| 1514 | 2-Me | 7-F | —NH—CH$_2$-cyclobutyl |
| 1515 | 2-Me | 7-F | —NH—CH$_2$CH$_2$-cyclobutyl |
| 1516 | 2-Me | 7-F | —NH-benzyl |
| 1517 | 2-Me | 7-F | —NH-2,2,2-trifluoroethyl |
| 1518 | 2-Me | 7-F | —NH-trifluoromethyl |
| 1519 | 2-Me | 7-F | —NH-3,3,3-trifluoropropyl |
| 1520 | 2-Me | 7-F | —NH-allyl |
| 1521 | 2-Me | 7-F | —NH-propargyl |
| 1522 | 2-Me | 7-F | —NH—CH$_2$CH$_2$—N(CH$_3$)$_2$ |
| 1523 | 2-Me | 7-F | —NH—CH$_2$CH$_2$-(N-morpholinyl) |
| 1524 | 2-Me | 7-F | —NH—CH$_2$-3-Pyridyl |
| 1525 | 2-Me | 7-F | —NH—CH$_2$-4-Pyridyl |
| 1526 | 2-Me | 7-F | —NH—CH$_2$-2-furanyl |
| 1527 | 2-Me | 7-F | —NH—CH$_2$-3-furanyl |
| 1528 | 2-Me | 7-F | —NH—CH$_2$-2-thienyl |
| 1529 | 2-Me | 7-F | —NH—CH$_2$-3-thienyl |
| 1530 | 2-Me | 7-F | —NH—CH$_2$-2-oxazolyl |
| 1531 | 2-Me | 7-F | —NH—CH$_2$-2-thiazolyl |
| 1532 | 2-Me | 7-F | —NH—CH$_2$-4-isoxazolyl |
| 1533 | 2-Me | 7-F | —NH—CH$_2$-2-imidazolyl |
| 1534 | 2-Me | 7-F | -benzyl |
| 1535 | 2-Me | 7-F | -2,2,2-trifluoroethyl |
| 1536 | 2-Me | 7-F | -trifluoromethyl |
| 1537 | 2-Me | 7-F | -methyl |
| 1538 | 2-Me | 7-F | -ethyl |
| 1539 | 2-Me | 7-F | -propyl |
| 1540 | 2-Me | 7-F | -i-propyl |
| 1541 | 2-Me | 7-F | -butyl |
| 1542 | 2-Me | 7-F | -i-butyl |
| 1543 | 2-Me | 7-F | -t-butyl |
| 1544 | 2-Me | 7-F | -pentyl |
| 1545 | 2-Me | 7-F | —CH$_2$—CH$_2$-cyclopropyl |
| 1546 | 2-Me | 7-F | —CH$_2$—CH$_2$-(1-methylcyclopropyl) |
| 1547 | 2-Me | 7-F | —CH2—CH$_2$CH$_2$-cyclopropyl |
| 1548 | 2-Me | 7-F | —CH2—CH$_2$-cyclobutyl |
| 1549 | 2-Me | 7-F | —CH2—CH$_2$CH$_2$-cyclobutyl |
| 1550 | 2-Me | 7-F | —CH2-benzyl |
| 1551 | 2-Me | 7-F | —CH2-2,2,2-trifluoroethyl |
| 1552 | 2-Me | 7-F | —CH2-trifluoromethyl |
| 1553 | 2-Me | 7-F | —CH2-3,3,3-trifluoropropyl |
| 1554 | 2-Me | 7-F | —CH2-allyl |
| 1555 | 2-Me | 7-F | —CH2-propargyl |
| 1556 | 2-Me | 7-F | —CH2—CH$_2$CH$_2$—N(CH$_3$)$_2$ |
| 1557 | 2-Me | 7-F | —CH2—CH$_2$CH$_2$—(N-morpholinyl) |
| 1558 | 2-Me | 7-F | —CH2—CH$_2$-3-Pyridyl |
| 1559 | 2-Me | 7-F | —CH2—CH$_2$-4-Pyridyl |
| 1560 | 2-Me | 7-F | —CH2—CH$_2$-2-furanyl |
| 1561 | 2-Me | 7-F | —CH2—CH$_2$-3-furanyl |
| 1562 | 2-Me | 7-F | —CH2—CH$_2$-2-thienyl |
| 1563 | 2-Me | 7-F | —CH2—CH$_2$-3-thienyl |
| 1564 | 2-Me | 7-F | —CH2—CH$_2$-2-oxazolyl |
| 1565 | 2-Me | 7-F | —CH2—CH$_2$-2-thiazolyl |
| 1566 | 2-Me | 7-F | —CH2—CH$_2$-4-isoxazolyl |
| 1567 | 2-Me | 7-F | —CH2—CH$_2$-2-imidazolyl |
| 1568 | 2-Me | 7-F | —C≡C-(2-OH)Ph |
| 1569 | 2-Me | 7-F | —C≡C-(3-OH)Ph |
| 1570 | 2-Me | 7-F | —C≡C-(4-OH)Ph |
| 1571 | 2-Me | 7-F | —C≡C-(2-OMe)Ph |
| 1572 | 2-Me | 7-F | —C≡C-(3-OMe)Ph |
| 1573 | 2-Me | 7-F | —C≡C-(4-OMe)Ph |
| 1574 | 2-Me | 7-F | —C≡C-(2-CN)Ph |
| 1575 | 2-Me | 7-F | —C≡C-(3-CN)Ph |
| 1576 | 2-Me | 7-F | —C≡C-(4-CN)Ph |
| 1577 | 2-Me | 7-F | —C≡C-(2-NO$_2$)Ph |
| 1578 | 2-Me | 7-F | —C≡C-(3-NO$_2$)Ph |
| 1579 | 2-Me | 7-F | —C≡C-(4-NO$_2$)Ph |
| 1580 | 2-Me | 7-F | —C≡C-(2-NH$_2$)Ph |
| 1581 | 2-Me | 7-F | —C≡C-(3-NH$_2$)Ph |
| 1582 | 2-Me | 7-F | —C≡C-(4-NH$_2$)Ph |
| 1583 | 2-Me | 7-F | —C≡C-(2-NMe$_2$)Ph |
| 1584 | 2-Me | 7-F | —C≡C-(3-NMe$_2$)Ph |
| 1585 | 2-Me | 7-F | —C≡C-(4-NMe$_2$)Ph |
| 1586 | 2-Me | 7-F | —C≡C-3-Pyridyl |
| 1587 | 2-Me | 7-F | —C≡C-4-Pyridyl |
| 1588 | 2-Me | 7-F | —C≡C-2-furanyl |
| 1589 | 2-Me | 7-F | —C≡C-3-furanyl |
| 1590 | 2-Me | 7-F | —C≡C-2-thienyl |
| 1591 | 2-Me | 7-F | —C≡C-3-thienyl |
| 1592 | 2-Me | 7-F | —C≡C-2-oxazolyl |
| 1593 | 2-Me | 7-F | —C≡C-2-thiazolyl |
| 1594 | 2-Me | 7-F | —C≡C-4-isoxazolyl |
| 1595 | 2-Me | 7-F | —C≡C-2-imidazolyl |
| 1596 | 2-Me | 7-F | —CH$_2$CH$_2$-cycPr |
| 1597 | 2-Me | 7-F | —CH$_2$CH$_2$CH$_2$OH |
| 1598 | 2-Me | 7-F | —CH$_2$CH$_2$—CH(OH)Me |
| 1599 | 2-Me | 7-F | —CH$_2$CH$_2$-Ph |
| 1600 | 2-Me | 7-F | —CH$_2$CH$_2$-(2-Cl)Ph |
| 1601 | 2-Me | 7-F | —CH$_2$CH$_2$-(3-Cl)Ph |
| 1602 | 2-Me | 7-F | —CH$_2$CH$_2$-(4-Cl)Ph |
| 1603 | 2-Me | 7-F | —CH$_2$CH$_2$-(2-F)Ph |
| 1604 | 2-Me | 7-F | —CH$_2$CH$_2$-(3-F)Ph |
| 1605 | 2-Me | 7-F | —CH$_2$CH$_2$-(4-F)Ph |
| 1606 | 2-Me | 7-F | —CH$_2$CH$_2$-(2-OH)Ph |
| 1607 | 2-Me | 7-F | —CH$_2$CH$_2$-(3-OH)Ph |
| 1608 | 2-Me | 7-F | —CH$_2$CH$_2$-(4-OH)Ph |
| 1609 | 2-Me | 7-F | —CH$_2$CH$_2$-(2-OMe)Ph |
| 1610 | 2-Me | 7-F | —CH$_2$CH$_2$-(3-OMe)Ph |
| 1611 | 2-Me | 7-F | —CH$_2$CH$_2$-(4-OMe)Ph |
| 1612 | 2-Me | 7-F | —CH$_2$CH$_2$-(2-CN)Ph |
| 1613 | 2-Me | 7-F | —CH$_2$CH$_2$-(3-CN)Ph |
| 1614 | 2-Me | 7-F | —CH$_2$CH$_2$-(4-CN)Ph |
| 1615 | 2-Me | 7-F | —CH$_2$CH$_2$-(2-NO$_2$)Ph |
| 1616 | 2-Me | 7-F | —CH$_2$CH$_2$-(3-NO$_2$)Ph |
| 1617 | 2-Me | 7-F | —CH$_2$CH$_2$-(4-NO$_2$)Ph |
| 1618 | 2-Me | 7-F | —CH$_2$CH$_2$-(2-NH$_2$)Ph |
| 1619 | 2-Me | 7-F | —CH$_2$CH$_2$-(3-NH$_2$)Ph |
| 1620 | 2-Me | 7-F | —CH$_2$CH$_2$-(4-NH$_2$)Ph |
| 1621 | 2-Me | 7-F | —CH$_2$CH$_2$-(2-NMe$_2$)Ph |
| 1622 | 2-Me | 7-F | —CH$_2$CH$_2$-(3-NMe$_2$)Ph |

TABLE 6-continued

| | | | |
|---|---|---|---|
| 1623 | 2-Me | 7-F | —CH$_2$CH$_2$-(4-NMe$_2$)Ph |
| 1624 | 2-Me | 7-F | —CH$_2$CH$_2$-2-Pyridyl |
| 1625 | 2-Me | 7-F | —CH$_2$CH$_2$-3-Pyridyl |
| 1626 | 2-Me | 7-F | —CH$_2$CH$_2$-4-Pyridyl |
| 1627 | 2-Me | 7-F | —CH$_2$CH$_2$-2-furanyl |
| 1628 | 2-Me | 7-F | —CH$_2$CH$_2$-3-furanyl |
| 1629 | 2-Me | 7-F | —CH$_2$CH$_2$-4-furanyl |
| 1630 | 2-Me | 7-F | —CH$_2$CH$_2$-3-thienyl |
| 1631 | 2-Me | 7-F | —CH$_2$CH$_2$-2-oxazolyl |
| 1632 | 2-Me | 7-F | —CH$_2$CH$_2$-2-thiazolyl |
| 1633 | 2-Me | 7-F | —CH$_2$CH$_2$-4-isoxazolyl |
| 1634 | 2-Me | 7-F | —CH$_2$CH$_2$-2-imidazolyl |
| 1635 | 2-Me | 7-F | —C≡C-cycPr |
| 1636 | 2-Me | 7-F | —C≡C-Ph |
| 1637 | 2-Me | 7-F | —C≡C-2-Pyridyl |
| 1638 | 2-Me | 7-F | —C≡C-3-Pyridyl |
| 1639 | 2-Me | 7-F | —C≡C-4-Pyridyl |
| 1640 | 2-Me | 7-F | —C≡C-2-furanyl |
| 1641 | 2-Me | 7-F | —C≡C-3-furanyl |
| 1642 | 2-Me | 7-F | —C≡C-2-thienyl |
| 1643 | 2-Me | 7-F | —C≡C-3-thienyl |
| 1644 | 2-Me | 7-F | —C≡C-cycPr |
| 1645 | 2-Me | 7-F | —C≡C-Ph |
| 1646 | 2-Me | 7-F | —C≡C-2-Pyridyl |
| 1647 | 2-Me | 7-F | —C≡C-3-Pyridyl |
| 1648 | 2-Me | 7-F | —C≡C-4-Pyridyl |
| 1649 | 2-Me | 7-F | —C≡C-2-furanyl |
| 1650 | 2-Me | 7-F | —C≡C-3-furanyl |
| 1651 | 2-Me | 7-F | —C≡C-2-thienyl |
| 1652 | 2-Me | 7-F | —C≡C-3-thienyl |
| 1653 | 2-Me | 7-F | —CH$_2$CH$_2$-cycPr |
| 1654 | 2-Me | 7-F | —CH$_2$CH$_2$-Ph |
| 1655 | 2-Me | 7-F | —CH$_2$CH$_2$-2-Pyridyl |
| 1656 | 2-Me | 7-F | —CH$_2$CH$_2$-3-Pyridyl |
| 1657 | 2-Me | 7-F | —CH$_2$CH$_2$-4-Pyridyl |
| 1658 | 2-Me | 7-F | —CH$_2$CH$_2$-2-furanyl |
| 1659 | 2-Me | 7-F | —CH$_2$CH$_2$-3-furanyl |
| 1660 | 2-Me | 7-F | —CH$_2$CH$_2$-2-thienyl |
| 1661 | 2-Me | 7-F | —CH$_2$CH$_2$-3-thienyl |
| 1662 | 2-Me | 7-F | —C≡C-cycPr |
| 1663 | 2-Me | 7-F | —C≡C-Ph |
| 1664 | 2-Me | 7-F | —C≡C-2-Pyridyl |
| 1665 | 2-Me | 7-F | —C≡C-3-Pyridyl |
| 1666 | 2-Me | 7-F | —C≡C-4-Pyridyl |
| 1667 | 2-Me | 7-F | —C≡C-2-furanyl |
| 1668 | 2-Me | 7-F | —C≡C-3-furanyl |
| 1669 | 2-Me | 7-F | —C≡C-2-thienyl |
| 1670 | 2-Me | 7-F | —C≡C-3-thienyl |
| 1671 | 2-Me | 7-F | —C≡C-cycPr |
| 1672 | 2-Me | 7-F | —C≡C-Ph |
| 1673 | 2-Me | 7-F | —C≡C-2-Pyridyl |
| 1674 | 2-Me | 7-F | —C≡C-3-Pyridyl |
| 1675 | 2-Me | 7-F | —C≡C-4-Pyridyl |
| 1676 | 2-Me | 7-F | —C≡C-2-furanyl |
| 1677 | 2-Me | 7-F | —C≡C-3-furanyl |
| 1678 | 2-Me | 7-F | —C≡C-2-thienyl |
| 1679 | 2-Me | 7-F | —C≡C-3-thienyl |
| 1680 | 2-Me | 7-F | —CH$_2$CH$_2$-cycPr |
| 1681 | 2-Me | 7-F | —CH$_2$CH$_2$-Ph |
| 1682 | 2-Me | 7-F | —CH$_2$CH$_2$-2-Pyridyl |
| 1683 | 2-Me | 7-F | —CH$_2$CH$_2$-3-Pyridyl |
| 1684 | 2-Me | 7-F | —CH$_2$CH$_2$-4-Pyridyl |
| 1685 | 2-Me | 7-F | —CH$_2$CH$_2$-2-furanyl |
| 1686 | 2-Me | 7-F | —CH$_2$CH$_2$-3-furanyl |
| 1687 | 2-Me | 7-F | —CH$_2$CH$_2$-2-thienyl |
| 1688 | 2-Me | 7-F | —CH$_2$CH$_2$-3-thienyl |
| 1689 | 2-OH | 7-F | —OH |
| 1690 | 2-OH | 7-F | —O-methyl |
| 1691 | 2-OH | 7-F | —O-ethyl |
| 1692 | 2-OH | 7-F | —O-n-propyl |
| 1693 | 2-OH | 7-F | —O-i-propyl |
| 1694 | 2-OH | 7-F | —O-butyl |
| 1695 | 2-OH | 7-F | —O—CH$_2$-cyclopropyl |
| 1696 | 2-OH | 7-F | —O—CH$_2$-(1-methylcyclopropyl) |
| 1697 | 2-OH | 7-F | —O—CH$_2$CH$_2$-cyclopropyl |
| 1698 | 2-OH | 7-F | —O—CH$_2$-cyclobutyl |
| 1699 | 2-OH | 7-F | —O—CH$_2$CH$_2$-cyclobutyl |
| 1700 | 2-OH | 7-F | —O-benzyl |
| 1701 | 2-OH | 7-F | —O-2,2,2-trifluoroethyl |
| 1702 | 2-OH | 7-F | —O-trifluoromethyl |
| 1703 | 2-OH | 7-F | —O-3,3,3-trifluoropropyl |
| 1704 | 2-OH | 7-F | —O-allyl |
| 1705 | 2-OH | 7-F | —O-propargyl |
| 1706 | 2-OH | 7-F | —O—CH$_2$CH$_2$—N(CH$_3$)$_2$ |
| 1707 | 2-OH | 7-F | —O—CH$_2$CH$_2$—(N-morpholinyl) |
| 1708 | 2-OH | 7-F | —O—CH$_2$-3-Pyridyl |
| 1709 | 2-OH | 7-F | —O—CH$_2$-4-Pyridyl |
| 1710 | 2-OH | 7-F | —O—CH$_2$-2-furanyl |
| 1711 | 2-OH | 7-F | —O—CH$_2$-3-furanyl |
| 1712 | 2-OH | 7-F | —O—CH$_2$-2-thienyl |
| 1713 | 2-OH | 7-F | —O—CH$_2$-3-thienyl |
| 1714 | 2-OH | 7-F | —O—CH$_2$-2-oxazolyl |
| 1715 | 2-OH | 7-F | —O—CH$_2$-2-thiazolyl |
| 1716 | 2-OH | 7-F | —O—CH$_2$-4-isoxazolyl |
| 1717 | 2-OH | 7-F | —O—CH$_2$-2-imidazolyl |
| 1718 | 2-OH | 7-F | —NH-methyl |
| 1719 | 2-OH | 7-F | —NH-ethyl |
| 1720 | 2-OH | 7-F | —NH-n-propyl |
| 1721 | 2-OH | 7-F | —NH-i-propyl |
| 1722 | 2-OH | 7-F | —NH-butyl |
| 1723 | 2-OH | 7-F | —NH—CH$_2$-cyclopropyl |
| 1724 | 2-OH | 7-F | —NH—CH$_2$-(1-methylcyclopropyl) |
| 1725 | 2-OH | 7-F | —NH—CH$_2$CH$_2$-cyclopropyl |
| 1726 | 2-OH | 7-F | —NH—CH$_2$-cyclobutyl |
| 1727 | 2-OH | 7-F | —NH—CH$_2$CH$_2$-cyclobutyl |
| 1728 | 2-OH | 7-F | —NH-benzyl |
| 1729 | 2-OH | 7-F | —NH-2,2,2-trifluoroethyl |
| 1730 | 2-OH | 7-F | —NH-trifluoromethyl |
| 1731 | 2-OH | 7-F | —NH-3,3,3-trifluoropropyl |
| 1732 | 2-OH | 7-F | —NH-allyl |
| 1733 | 2-OH | 7-F | —NH-propargyl |
| 1734 | 2-OH | 7-F | —NH—CH$_2$CH$_2$—N(CH$_3$)$_2$ |
| 1735 | 2-OH | 7-F | —NH—CH$_2$CH$_2$—(N-morpholinyl) |
| 1736 | 2-OH | 7-F | —NH—CH$_2$-3-Pyridyl |
| 1737 | 2-OH | 7-F | —NH—CH$_2$-4-Pyridyl |
| 1738 | 2-OH | 7-F | —NH—CH$_2$-2-furanyl |
| 1739 | 2-OH | 7-F | —NH—CH$_2$-3-furanyl |
| 1740 | 2-OH | 7-F | —NH—CH$_2$-2-thienyl |
| 1741 | 2-OH | 7-F | —NH—CH$_2$-3-thienyl |
| 1742 | 2-OH | 7-F | —NH—CH$_2$-2-oxazolyl |
| 1743 | 2-OH | 7-F | —NH—CH$_2$-2-thiazolyl |
| 1744 | 2-OH | 7-F | —NH—CH$_2$-4-isoxazolyl |
| 1745 | 2-OH | 7-F | —NH—CH$_2$-2-imidazolyl |
| 1746 | 2-OH | 7-F | -benzyl |
| 1747 | 2-OH | 7-F | -2,2,2-trifluoroethyl |
| 1748 | 2-OH | 7-F | -trifluoromethyl |
| 1749 | 2-OH | 7-F | -methyl |
| 1750 | 2-OH | 7-F | -ethyl |
| 1751 | 2-OH | 7-F | -propyl |
| 1752 | 2-OH | 7-F | -i-propyl |
| 1753 | 2-OH | 7-F | -butyl |
| 1754 | 2-OH | 7-F | -i-butyl |
| 1755 | 2-OH | 7-F | -t-butyl |
| 1756 | 2-OH | 7-F | -pentyl |
| 1757 | 2-OH | 7-F | —CH$_2$—CH$_2$-cyclopropyl |
| 1758 | 2-OH | 7-F | —CH$_2$—CH$_2$-(1-methylcyclopropyl) |
| 1759 | 2-OH | 7-F | —CH2—CH$_2$CH$_2$-cyclopropyl |
| 1760 | 2-OH | 7-F | —CH2—CH$_2$-cyclobutyl |
| 1761 | 2-OH | 7-F | —CH2—CH$_2$CH$_2$-cyclobutyl |
| 1762 | 2-OH | 7-F | —CH2-benzyl |
| 1763 | 2-OH | 7-F | —CH2-2,2,2-trifluoroethyl |
| 1764 | 2-OH | 7-F | —CH2-trifluoromethyl |
| 1765 | 2-OH | 7-F | —CH2-3,3,3-trifluoropropyl |
| 1766 | 2-OH | 7-F | —CH2-allyl |
| 1767 | 2-OH | 7-F | —CH2-propargyl |
| 1768 | 2-OH | 7-F | —CH2—CH$_2$CH$_2$—N(CH$_3$)$_2$ |
| 1769 | 2-OH | 7-F | —CH2—CH$_2$CH$_2$-(N-morpholinyl) |
| 1770 | 2-OH | 7-F | —CH2—CH$_2$-3-Pyridyl |
| 1771 | 2-OH | 7-F | —CH2—CH$_2$-4-Pyridyl |
| 1772 | 2-OH | 7-F | —CH2—CH$_2$-2-furanyl |
| 1773 | 2-OH | 7-F | —CH2—CH$_2$-3-furanyl |
| 1774 | 2-CH | 7-F | —CH2—CH$_2$-2-thienyl |
| 1775 | 2-OH | 7-F | —CH2—CH$_2$-3-thienyl |
| 1776 | 2-OH | 7-F | —CH2—CH$_2$-2-oxazolyl |
| 1777 | 2-OH | 7-F | —CH2—CH$_2$-2-thiazolyl |
| 1778 | 2-OH | 7-F | —CH2—CH$_2$-4-isoxazolyl |
| 1779 | 2-OH | 7-F | —CH2—CH$_2$-2-imidazolyl |
| 1780 | 2-OH | 7-F | —C≡C-(2-OH)Ph |

TABLE 6-continued

| | | | |
|---|---|---|---|
| 1781 | 2-OH | 7-F | —C=C-(3-OH)Ph |
| 1782 | 2-OH | 7-F | —C=C-(4-OH)Ph |
| 1783 | 2-OH | 7-F | —C=C-(2-OMe)Ph |
| 1784 | 2-OH | 7-F | —C=C-(3-OMe)Ph |
| 1785 | 2-OH | 7-F | —C=C-(4-OMe)Ph |
| 1786 | 2-OH | 7-F | —C=C-(2-CN)Ph |
| 1787 | 2-OH | 7-F | —C=C-(3-CN)Ph |
| 1788 | 2-OH | 7-F | —C=C-(4-CN)Ph |
| 1789 | 2-OH | 7-F | —C=C-(2-NO$_2$)Ph |
| 1790 | 2-OH | 7-F | —C=C-(3-NO$_2$)Ph |
| 1791 | 2-OH | 7-F | —C=C-(4-NO$_2$)Ph |
| 1792 | 2-OH | 7-F | —C=C-(2-NH$_2$)Ph |
| 1793 | 2-OH | 7-F | —C=C-(3-NH$_2$)Ph |
| 1794 | 2-OH | 7-F | —C=C-(4-NH$_2$)Ph |
| 1795 | 2-OH | 7-F | —C=C-(2-NMe$_2$)Ph |
| 1796 | 2-OH | 7-F | —C=C-(3-NMe$_2$)Ph |
| 1797 | 2-OH | 7-F | —C=C-(4-NMe$_2$)Ph |
| 1798 | 2-OH | 7-F | —C=C-3-Pyridyl |
| 1799 | 2-OH | 7-F | —C=C-4-Pyridyl |
| 1800 | 2-OH | 7-F | —C=C-2-furanyl |
| 1801 | 2-OH | 7-F | —C=C-3-furanyl |
| 1802 | 2-OH | 7-F | —C=C-2-thienyl |
| 1803 | 2-OH | 7-F | —C=C-3-thienyl |
| 1804 | 2-OH | 7-F | —C=C-2-oxazolyl |
| 1805 | 2-OH | 7-F | —C=C-2-thiazolyl |
| 1806 | 2-OH | 7-F | —C=C-4-isoxazolyl |
| 1807 | 2-OH | 7-F | —C=C-2-imidazolyl |
| 1808 | 2-OH | 7-F | —CH$_2$CH$_2$-cycPr |
| 1809 | 2-OH | 7-F | —CH$_2$CH$_2$CH$_2$CH$_2$OH |
| 1810 | 2-OH | 7-F | —CH$_2$CH$_2$—CH(OH)Me |
| 1811 | 2-OH | 7-F | —CH$_2$CH$_2$-Ph |
| 1812 | 2-OH | 7-F | —CH$_2$CH$_2$-(2-Cl)Ph |
| 1813 | 2-OH | 7-F | —CH$_2$CH$_2$-(3-Cl)Ph |
| 1814 | 2-OH | 7-F | —CH$_2$CH$_2$-(4-Cl)Ph |
| 1815 | 2-OH | 7-F | —CH$_2$CH$_2$-(2-F)Ph |
| 1816 | 2-OH | 7-F | —CH$_2$CH$_2$-(3-F)Ph |
| 1817 | 2-OH | 7-F | —CH$_2$CH$_2$-(4-F)Ph |
| 1818 | 2-OH | 7-F | —CH$_2$CH$_2$-(2-OH)Ph |
| 1819 | 2-OH | 7-F | —CH$_2$CH$_2$-(3-OH)Ph |
| 1820 | 2-OH | 7-F | —CH$_2$CH$_2$-(4-OH)Ph |
| 1821 | 2-OH | 7-F | —CH$_2$CH$_2$-(2-OMe)Ph |
| 1822 | 2-OH | 7-F | —CH$_2$CH$_2$-(3-OMe)Ph |
| 1823 | 2-OH | 7-F | —CH$_2$CH$_2$-(4-OMe)Ph |
| 1824 | 2-OH | 7-F | —CH$_2$CH$_2$-(2-CN)Ph |
| 1825 | 2-OH | 7-F | —CH$_2$CH$_2$-(3-CN)Ph |
| 1826 | 2-OH | 7-F | —CH$_2$CH$_2$-(4-CN)Ph |
| 1827 | 2-OH | 7-F | —CH$_2$CH$_2$-(2-NO$_2$)Ph |
| 1828 | 2-OH | 7-F | —CH$_2$CH$_2$-(3-NO$_2$)Ph |
| 1829 | 2-OH | 7-F | —CH$_2$CH$_2$-(4-NO$_2$)Ph |
| 1830 | 2-OH | 7-F | —CH$_2$CH$_2$-(2-NH$_2$)Ph |
| 1831 | 2-OH | 7-F | —CH$_2$CH$_2$-(3-NH$_2$)Ph |
| 1832 | 2-OH | 7-F | —CH$_2$CH$_2$-(4-NH$_2$)Ph |
| 1833 | 2-OH | 7-F | —CH$_2$CH$_2$-(2-NMe$_2$)Ph |
| 1834 | 2-OH | 7-F | —CH$_2$CH$_2$-(3-NMe$_2$)Ph |
| 1835 | 2-OH | 7-F | —CH$_2$CH$_2$-(4-NMe$_2$)Ph |
| 1836 | 2-OH | 7-F | —CH$_2$CH$_2$-2-Pyridyl |
| 1837 | 2-OH | 7-F | —CH$_2$CH$_2$-3-Pyridyl |
| 1838 | 2-OH | 7-F | —CH$_2$CH$_2$-4-Pyridyl |
| 1839 | 2-OH | 7-F | —CH$_2$CH$_2$-2-furanyl |
| 1840 | 2-OH | 7-F | —CH$_2$CH$_2$-3-furanyl |
| 1841 | 2-OH | 7-F | —CH$_2$CH$_2$-4-furanyl |
| 1842 | 2-OH | 7-F | —CH$_2$CH$_2$-3-thienyl |
| 1843 | 2-OH | 7-F | —CH$_2$CH$_2$-2-oxazolyl |
| 1844 | 2-OH | 7-F | —CH$_2$CH$_2$-2-thiazolyl |
| 1845 | 2-OH | 7-F | —CH$_2$CH$_2$-4-isoxazolyl |
| 1846 | 2-OH | 7-F | —CH$_2$CH$_2$-2-imidazolyl |
| 1847 | 2-OH | 7-F | —C≡C-cycPr |
| 1848 | 2-OH | 7-F | —C≡C-Ph |
| 1849 | 2-OH | 7-F | —C≡C-2-Pyridyl |
| 1850 | 2-OH | 7-F | —C≡C-3-Pyridyl |
| 1851 | 2-OH | 7-F | —C≡C-4-Pyridyl |
| 1852 | 2-OH | 7-F | —C≡C-2-furanyl |
| 1853 | 2-OH | 7-F | —C≡C-3-furanyl |
| 1854 | 2-OH | 7-F | —C≡C-2-thienyl |
| 1855 | 2-OH | 7-F | —C≡C-3-thienyl |
| 1856 | 2-OH | 7-F | —C≡C-cycPr |
| 1857 | 2-OH | 7-F | —C≡C-Ph |
| 1858 | 2-OH | 7-F | —C≡C-2-Pyridyl |
| 1859 | 2-OH | 7-F | —C≡C-3-Pyridyl |
| 1860 | 2-OH | 7-F | —C=C-4-Pyridyl |
| 1861 | 2-OH | 7-F | —C=C-2-furanyl |
| 1862 | 2-OH | 7-F | —C=C-3-furanyl |
| 1863 | 2-OH | 7-F | —C=C-2-thienyl |
| 1864 | 2-OH | 7-F | —C=C-3-thienyl |
| 1865 | 2-OH | 7-F | —CH$_2$CH$_2$-cycPr |
| 1866 | 2-OH | 7-F | —CH$_2$CH$_2$-Ph |
| 1867 | 2-OH | 7-F | —CH$_2$CH$_2$-2-Pyridyl |
| 1868 | 2-OH | 7-F | —CH$_2$CH$_2$-3-Pyridyl |
| 1869 | 2-OH | 7-F | —CH$_2$CH$_2$-4-Pyridyl |
| 1870 | 2-OH | 7-F | —CH$_2$CH$_2$-2-furanyl |
| 1871 | 2-OH | 7-F | —CH$_2$CH$_2$-3-furanyl |
| 1872 | 2-OH | 7-F | —CH$_2$CH$_2$-2-thienyl |
| 1873 | 2-OH | 7-F | —CH$_2$CH$_2$-3-thienyl |
| 1874 | 2-OH | 7-F | —C≡C-cycPr |
| 1875 | 2-OH | 7-F | —C≡C-Ph |
| 1876 | 2-OH | 7-F | —C≡C-2-Pyridyl |
| 1877 | 2-OH | 7-F | —C≡C-3-Pyridyl |
| 1878 | 2-OH | 7-F | —C≡C-4-Pyridyl |
| 1879 | 2-OH | 7-F | —C=C-2-furanyl |
| 1880 | 2-OH | 7-F | —C=C-3-furanyl |
| 1881 | 2-OH | 7-F | —C=C-2-thienyl |
| 1882 | 2-OH | 7-F | —C=C-3-thienyl |
| 1883 | 2-OH | 7-F | —C≡C-cycPr |
| 1884 | 2-OH | 7-F | —C≡C-Ph |
| 1885 | 2-OH | 7-F | —C=C-2-Pyridyl |
| 1886 | 2-OH | 7-F | —C=C-3-Pyridyl |
| 1887 | 2-OH | 7-F | —C=C-4-Pyridyl |
| 1888 | 2-OH | 7-F | —C=C-2-furanyl |
| 1889 | 2-OH | 7-F | —C=C-3-furanyl |
| 1890 | 2-OH | 7-F | —C=C-2-thienyl |
| 1891 | 2-OH | 7-F | —C=C-3-thienyl |
| 1892 | 2-OH | 7-F | —CH$_2$CH$_2$-cycPr |
| 1893 | 2-OH | 7-F | —CH$_2$CH$_2$-Ph |
| 1894 | 2-OH | 7-F | —CH$_2$CH$_2$-2-Pyridyl |
| 1895 | 2-OH | 7-F | —CH$_2$CH$_2$-3-Pyridyl |
| 1896 | 2-OH | 7-F | —CH$_2$CH$_2$-4-Pyridyl |
| 1897 | 2-OH | 7-F | —CH$_2$CH$_2$-2-furanyl |
| 1898 | 2-OH | 7-F | —CH$_2$CH$_2$-3-furanyl |
| 1899 | 2-OH | 7-F | —CH$_2$CH$_2$-2-thienyl |
| 1900 | 2-OH | 7-F | —CH$_2$CH$_2$-3-thienyl |

Utility

The compounds of this invention possess reverse transcriptase inhibitory activity and HIV inhibitory efficacy. The compounds of formula (I) possess HIV reverse transcriptase inhibitory activity and are therefore useful as antiviral agents for the treatment of HIV infection and associated diseases. The compounds of formula (I) possess HIV reverse transcriptase inhibitory activity and are effective as inhibitors of HIV growth. The ability of the compounds of the present invention to inhibit viral growth or infectivity is demonstrated in standard assay of viral growth or infectivity, for example, using the assay described below.

The compounds of formula (I) of the present invention are also useful for the inhibition of HIV in an ex vivo sample containing HIV or expected to be exposed to HIV. Thus, the compounds of the present invention may be used to inhibit HIV present in a body fluid sample (for example, a serum or semen sample) which contains or is suspected to contain or be exposed to HIV.

The compounds provided by this invention are also useful as standard or reference compounds for use in tests or assays for determining the ability of an agent to inhibit viral replication and/or HIV reverse transcriptase, for example in a pharmaceutical research program. Thus, the compounds of the present invention may be used as a control or reference compound in such assays and as a quality control standard. The compounds of the present invention may be provided in a commercial kit or container for use as such standard or reference compound.

Since the compounds of the present invention exhibit specificity for HIV reverse transcriptase, the compounds of the present invention may also be useful as diagnostic reagents in diagnostic assays for the detection of HIV reverse transcriptase. Thus, inhibition of the reverse transcriptase activity in an assay (such as the assays described herein) by a compound of the present invention would be indicative of the presence of HIV reverse transcriptase and HIV virus.

As used herein "μg" denotes microgram, "mg" denotes milligram, "g" denotes gram, "μL" denotes microliter, "mL" denotes milliliter, "μL" denotes liter, "nM" denotes nanomolar, "μM" denotes micromolar, "mM" denotes millimolar, "μM" denotes molar and "nm" denotes nanometer. "Sigma" stands for the Sigma-Aldrich Corp. of St. Louis, Mo.

Compounds tested in the assay described below are considered to be active if they exhibit a $K_i$ of $\leq 10$ μM. Preferred compounds of the present invention have $K_i$'s of $\leq 1$ μM. More preferred compounds of the present invention have $K_i$'s of $\leq 0.1$ μM. Even more preferred compounds of the present invention have $K_i$'s of $\leq 0.01$ μM. Still more preferred compounds of the present invention have $K_i$'s of $\leq 0.001$ μM.

Using the methodology described below, a number of compounds of the present invention were found to exhibit a $K_i$ of $\leq 10$ μM, thereby confirming the utility of the compounds of the present invention as effective HIV reverse transcriptase inhibitors.

HIV RNA Assay

DNA Plasmids and in vitro RNA Transcripts:

Plasmid pDAB 72 containing both gag and pol sequences of BH10 (bp 113-1816) cloned into PTZ 19R was prepared according to Erickson-Viitanen et al. *AIDS Research and Human Retroviruses* 1989, 5, 577. The plasmid was linearized with Bam HI prior to the generation of in vitro RNA transcripts using the Riboprobe Gemini system II kit (Promega) with T7 RNA polymerase. Synthesized RNA was purified by treatment with RNase free DNAse (Promega), phenol-chloroform extraction, and ethanol precipitation. RNA transcripts were dissolved in water, and stored at $-70°$ C. The concentration of RNA was determined from the $A_{260}$.

Probes:

Biotinylated capture probes were purified by HPLC after synthesis on an Applied Biosystems (Foster City, Calif.) DNA synthesizer by addition of biotin to the 5' terminal end of the oligonucleotide, using the biotin-phosphoramidite reagent of Cocuzza, *Tet. Lett.* 1989, 30, 6287. The gag biotinylated capture probe (5-biotin-CTAGCTCCCTGCTTGCCCATACTA 3') was complementary to nucleotides 889–912 of HXB2 and the pol biotinylated capture probe (5'-biotin-CCCTATC-ATTTTTGGTTTCCAT 3') was complementary to nucleotides 2374–2395 of HXB2. Alkaline phosphatase conjugated oligonucleotides used as reporter probes were prepared by Syngene (San Diego, Calif.). The pol reporter probe (5' CTGTCTTACTTTGATAAAACCTC 3') was complementary to nucleotides 2403–2425 of HXB2. The gag reporter probe (5' CCCAGTATTTGTCTACAGCCT-TCT 3') was complementary to nucleotides 950–973 of HXB2. All nucleotide positions are those of the GenBank Genetic Sequence Data Bank as accessed through the Genetics Computer Group Sequence Analysis Software Package (Devereau *Nucleic Acids Research* 1984, 12, 387). The reporter probes were prepared as 0.5 μM stocks in 2×SSC (0.3 M NaCl, 0.03 M sodium citrate), 0.05 M Tris pH 8.8, 1 mg/mL BSA. The biotinylated capture probes were prepared as 100 μM stocks in water.

Streptavidin Coated Plates:

Streptavidin coated plates were obtained from DuPont Biotechnology Systems (Boston, Mass.).

Cells and Virus Stocks:

MT-2 and MT-4 cells were maintained in RPMI 1640 supplemented with 5% fetal calf serum (FCS) for MT-2 cells or 10% FCS for MT-4 cells, 2 mM L-glutamine and 50 μg/mL gentamycin, all from Gibco. HIV-1 RF was propagated in MT-4 cells in the same medium. Virus stocks were prepared approximately 10 days after acute infection of MT-4 cells and stored as aliquots at $-70°$ C. Infectious titers of HIV-1(RF) stocks were $1-3 \times 10^7$ PFU (plaque forming units)/mL as measured by plaque assay on MT-2 cells (see below). Each aliquot of virus stock used for infection was thawed only once.

For evaluation of antiviral efficacy, cells to be infected were subcultured one day prior to infection. On the day of infection, cells were resuspended at $5 \times 10^5$ cells/mL in RPMI 1640, 5% FCS for bulk infections or at $2 \times 10^6$/mL in Dulbecco's modified Eagles medium with 5% FCS for infection in microtiter plates. Virus was added and culture continued for 3 days at 37° C.

HIV RNA Assay:

Cell lysates or purified RNA in 3 M or 5 M GED were mixed with 5 M GED and capture probe to a final guanidinium isothiocyanate concentration of 3 M and a final biotin oligonucleotide concentration of 30 nM. Hybridization was carried out in sealed U bottom 96 well tissue culture plates (Nunc or Costar) for 16–20 hours at 37° C. RNA hybridization reactions were diluted three-fold with deionized water to a final guanidinium isothiocyanate concentration of 1 M and aliquots (150 μL) were transferred to streptavidin coated microtiter plates wells. Binding of capture probe and capture probe-RNA hybrid to the immobilized streptavidin was allowed to proceed for 2 hours at room temperature, after which the plates were washed 6 times with DuPont ELISA plate wash buffer (phosphate buffered saline(PBS), 0.05% Tween 20) A second hybridization of reporter probe to the immobilized complex of capture probe and hybridized target RNA was carried out in the washed streptavidin coated well by addition of 120 μl of a hybridization cocktail containing 4×SSC, 0.66% Triton× 100, 6.66% deionized formamide, 1 mg/mL BSA and 5 nM reporter probe. After hybridization for one hour at 37° C., the plate was again washed 6 times. Immobilized alkaline phosphatase activity was detected by addition of 100 μL of 0.2 mM 4-methylumbelliferyl phosphate (MUBP, JBL Scientific) in buffer (2.5 M diethanolamine pH 8.9 (JBL Scientific), 10 mM $MgCl_2$, 5 mM zinc acetate dihydrate and 5 mM N-hydroxyethyl-ethylene-diamine-triacetic acid). The plates were incubated at 37° C. Fluorescence at 450 nM was measured using a microplate fluorometer (Dynateck) exciting at 365 nM.

Microplate Based Compound Evaluation in HIV-1 Infected MT-2 Cells:

Compounds to be evaluated were dissolved in DMSO and diluted in culture medium to twice the highest concentration to be tested and a maximum DMSO concentration of 2%. Further three-fold serial dilutions of the compound in culture medium were performed directly in U bottom microtiter plates (Nunc). After compound dilution, MT-2 cells (50 μL) were added to a final concentration of $5 \times 10^5$ per mL ($1 \times 10^5$ per well). Cells were incubated with compounds for 30 minutes at 37° C. in a $CO_2$ incubator. For evaluation of antiviral potency, an appropriate dilution of HIV-1 (RF) virus stock (50 μL) was added to culture wells containing cells and dilutions of the test compounds. The final volume in each well was 200 μL. Eight wells per plate were left uninfected with 50 μL of medium added in place of virus, while eight wells were infected in the absence of any antiviral compound. For evaluation of compound toxicity, parallel plates were cultured without virus infection.

After 3 days of culture at 37° C. in a humidified chamber inside a $CO_2$ incubator, all but 25 μL of medium/well was removed from the HIV infected plates. Thirty seven μL of 5 M GED containing biotinylated capture probe was added to the settled cells and remaining medium in each well to a final concentration of 3 M GED and 30 nM capture probe. Hybridization of the capture probe to HIV RNA in the cell lysate was carried out in the same microplate well used for virus culture by sealing the plate with a plate sealer (Costar), and incubating for 16–20 hrs in a 37° C. incubator. Distilled water was then added to each well to dilute the hybridization reaction three-fold and 150 μL of this diluted mixture was transferred to a streptavidin coated microtiter plate. HIV RNA was quantitated as described above. A standard curve, prepared by adding known amounts of pDAB 72 in vitro RNA transcript to wells containing lysed uninfected cells, was run on each microtiter plate in order to determine the amount of viral RNA made during the infection.

In order to standardize the virus inoculum used in the evaluation of compounds for antiviral activity, dilutions of virus were selected which resulted in an IC90 value (concentration of compound required to reduce the HIV RNA level by 90%) for dideoxycytidine (ddC) of 0.2 μg/mL. $IC_{90}$ values of other antiviral compounds, both more and less potent than ddC, were reproducible using several stocks of HIV-1 (RF) when this procedure was followed. This concentration of virus corresponded to ~$3\times10^5$ PFU (measured by plaque assay on MT-2 cells) per assay well and typically produced approximately 75% of the maximum viral RNA level achievable at any virus inoculum. For the HIV RNA assay, $IC_{90}$ values were determined from the percent reduction of net signal (signal from infected cell samples minus signal from uninfected cell samples) in the RNA assay relative to the net signal from infected, untreated cells on the same culture plate (average of eight wells). Valid performance of individual infection and RNA assay tests was judged according to three criteria. It was required that the virus infection should result in an RNA assay signal equal to or greater than the signal generated from 2 ng of pDAB 72 in vitro RNA transcript. The $IC_{90}$ for ddC, determined in each assay run, should be between 0.1 and 0.3 μg/mL. Finally, the plateau level of viral RNA produced by an effective reverse transcriptase inhibitor should be less than 10% of the level achieved in an uninhibited infection. A compound was considered active if its $IC_{90}$ was found to be less than 20 μM.

For antiviral potency tests, all manipulations in microtiter plates, following the initial addition of 2× concentrated compound solution to a single row of wells, were performed using a Perkin Elmer/Cetus ProPette.

Protein Binding and Mutant Resistance

In order to characterize NNRTI compounds for their clinical efficacy potential the effect of plasma proteins on antiviral potency and measurements of antiviral potency against wild type and mutant variants of HIV which carry amino acid changes in the known binding site for NNRTIs were examined. The rationale for this testing strategy is two fold:

1. Many drugs are extensively bound to plasma proteins. Although the binding affinity for most drugs for the major components of human plasma, namely, human serum albumin (HSA) or alpha-1-acid glycoprotein (AAG), is low, these major components are present in high concentration in the blood. Only free or unbound drug is available to cross the infected cell membrane for interaction with the target site (i.e., HIV-1 reverse transcriptase, HIV-1 RT). Therefore, the effect of added HSA+AAG on the antiviral potency in tissue culture more closely reflects the potency of a given compound in the clinical setting. The concentration of compound required for 90% inhibition of virus replication as measured in a sensitive viral RNA-based detection method is designated the IC90. The fold increase in apparent IC90 for test compounds in the presence or added levels of HSA and AAG that reflect in vivo concentrations (45 mg/ml HSA, 1 mg/ml AAG) was then calculated. The lower the fold increase, the more compound will be available to interact with the target site.

2. The combination of the high rate of virus replication in the infected individual and the poor fidelity of the viral RT results in the production of a quasi-species or mixtures of HIV species in the infected individual. These species will include a majority wild type species, but also mutant variants of HIV and the proportion of a given mutant will reflect its relative fitness and replication rate. Because mutant variants including mutants with changes in the amino acid sequence of the viral RT likely pre-exist in the infected individual's quasi-species, the overall potency observed in the clinical setting will reflect the ability of a drug to inhibit not only wild type HIV-1, but mutant variants as well. We thus have constructed, in a known genetic background, mutant variants of HIV-1 which carry amino acid substitutions at positions thought to be involved in NNRTI binding, and measured the ability of test compounds to inhibit replication of these mutant viruses. The concentration of compound required for 90% inhibition of virus replication as measured in a sensitive viral RNA-based detection method is designated the IC90. It is desirable to have a compound which has high activity against a variety of mutants.

Dosage and Formulation

The antiviral compounds of this invention can be administered as treatment for viral infections by any means that produces contact of the active agent with the agent's site of action, i.e., the viral reverse transcriptase, in the body of a mammal. They can be administered by any conventional means available for use in conjunction with pharmaceuticals, either as individual therapeutic agents or in a combination of therapeutic agents. They can be administered alone, but preferably are administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences*, supra, a standard reference text in this field.

Useful pharmaceutical dosage-forms for administration of the compounds of this invention can be illustrated as follows:

Capsules

A capsule formulation of the present invention can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A soft gelatin capsule formulation of the present invention can be prepared as follows. A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A tablet formulation of the present invention can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension formulation can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral formulation suitable for administration by injection can be prepared by stirring 1.5% by weight of active ingredient in 10% by volume propylene glycol and water. The solution is sterilized by commonly used techniques.

Combination Administration of Therapeutic Agents

The present invention provides a method for the treatment of HIV infection which comprises administering, in combination, to a host in need thereof a therapeutically effective amount of the following:

(a) a compound of formula (I); and (b) at least one compound selected from the group consisting of HIV reverse transcriptase inhibitors and HIV protease inhibitors, in one or more sterile containers.

Each therapeutic agent component of this combination method (i.e., component (a) and (b) set forth above) can independently be administered in any separate dosage form, such as those described above, and can be administered in various ways, as described above. In the following description component (b) is to be understood to represent one or more agents as described previously. Each individual therapeutic agent comprising component (b) may also be independently be administered in any separate dosage form, such as those described above, and can be administered in various ways, as described above.

Components (a) and any one or more of the agents comprising component (b) of the combination method of the present invention may be formulated together, in a single dosage unit (that is, combined together in one capsule, tablet, powder, or liquid, etc.) as a combination product. When component (a) and (b) are not formulated together in a single dosage unit, the component (a) may be administered at the same time as component (b) or in any order; for example component (a) of this invention may be administered first, followed by administration of component (b), or they may be administered in the revserse order. If component (b) contains more that one agent, e.g., one RT inhibitor and one protease inhibitor, these agents may be administered together or in any order. When not administered at the same time, preferably the administration of component (a) and (b) occurs less than about one hour apart. Preferably, the route of administration of component (a) and (b) is oral. The terms oral agent, oral inhibitor, oral compound, or the like, as used herein, denote compounds which may be orally administered. Although it is preferable that component (a) and component (b) both be administered by the same route (that is, for example, both orally) or dosage form, if desired, they may each be administered by different routes or dosage forms (for example, one component of the combination method may be administered orally, and another component may be administered intravenously).

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of components (a) and (b) of the combination method of this invention will be readily ascertainable by a medical practitioner skilled in the art, based upon the present disclosure. By way of general guidance, typically a daily dosage may be about 100 milligrams to about 1.5 grams of each component. If component (b) represents more than one compound, then typically a daily dosage may be about 100 milligrams to about 1.5 grams of each agent of component (b). By way of general guidance, when the compounds of component (a) and component (b) are administered in combination, the dosage amount of each component may be reduced by about 70–80% relative to the usual dosage of the component when it is administered alone as a single agent for the treatment of HIV infection, in view of the synergistic effect of the combination.

The combination products of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose or other appropriate materials as known in the art, in order to further separate the active components. The polymer coating serves to form an additional barrier to interaction with the other component. In each formulation wherein contact is prevented between components (a) and (b) via a coating or some other material, contact may also be prevented between the individual agents of component (b).

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Pharmaceutical kits useful for the treatment of HIV infection, which comprise a therapeutically effective amount of a pharmaceutical composition comprising a compound of component (a) and one or more compounds of component (b), in one or more sterile containers, are also within the ambit of the present invention. Sterilization of the container may be carried out using conventional sterilization methodology well known to those skilled in the art. Component (a) and component (b) may be in the same sterile container or in separate sterile containers. The sterile containers of materials may comprise separate containers, or one or more multi-part containers, as desired. Component (a) and component (b) may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

As will be appreciated by one of skill in the art, numerous modifications and variations of the present invention are possible in light of the above teachings. It is therefore to be understood that within the scope of the appended claims, the invention may be practiced otherwise than as specifically described herein.

What is claimed is:

1. A compound of formula (I):

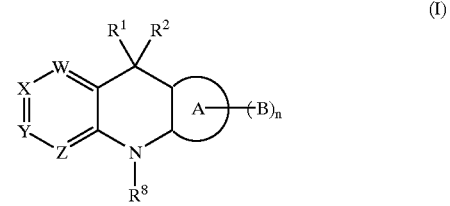

or a stereoisomeric form or mixture of stereoisomeric forms or a pharmaceutically acceptable salt form thereof, wherein:

n is selected from 0, 1, 2 and 3;

ring A is 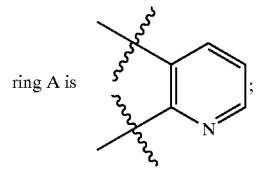;

wherein a ring nitrogen in ring A may optionally be in an N-oxide form;

said ring A being substituted with 0–3 B, said substituent B being independently selected from the group $C_{1-4}$ alkyl, —OH, $C_{1-4}$ alkoxy, —S—$C_{1-4}$alkyl, $OCF_3$, $CF_3$, F, Cl, Br, I, —$NO_2$, —CN, and $NR^5R^{5a}$;

W is $CR^3$;

X is $CR^{3a}$;

Y is $CR^{3b}$;

Z is $CR^{3c}$;

$R^1$ is selected from the group $C_{1-3}$ alkyl substituted with 1–7 halogen, and cyclopropyl substituted with 0–5 halogen;

$R^2$ is selected from the group —$R^{2c}$, —OH, —CN, —$OR^{2c}$, —$OCHR^{2a}R^{2b}$, —$OCH_2CHR^{2a}R^{2b}$, —$O(CH_2)_2CHR^{2a}R^{2b}$, —$OCHR^{2a}C(R^{2a})$=$C(R^{2b})_2$, —$OCHR^{2a}C(R^{2a})$=$C(R^{2b})_2$, $OCHR^{2a}C$≡$C$—$R^{2b}$, —$SR^{2c}$, —$SCHR^{2a}R^{2b}$, —$SCH_2CHR^{2a}R^{2b}$, —$S(CH_2)_2CHR^{2a}R^{2b}$, —$SCHR^{2a}C(R^{2a})$=$C(R^{2b})_2$, —$SCHR^{2a}C(R^{2a})$=$(R^{2b})_2$, —$SCHR^{2a}C$≡$C$—$R^{2b}$, —$NR^{2a}R^{2c}$, —$NHCHR^{2a}R^{2b}$, —$NHCH_2CHR^{2a}R^{2b}$, —NH(CH$_2$)$_2$CHR$^{2a}$R$^{2b}$, —NHCHR$^{2a}$C(R$^{2a}$)=C(R$^{2b}$)$_2$, —NHCHR$^{2a}$C(R$^{2a}$)=(R$^{2b}$)$_2$, and —NHCHR$^{2a}$C≡C—R$^{2b}$;

R$^{2a}$ is selected from the group H, CH$_3$, CH$_2$CH$_3$, CH(CH$_3$)$_2$, and CH$_2$CH$_2$CH$_3$;

R$^{2b}$ is H or R$^{2c}$;

R$^{2c}$ is selected from the group methyl substituted with 0–3 R$^{3f}$, C$_{1-6}$ alkyl substituted with 0–3 R$^4$, C$_{2-5}$ alkenyl substituted with 0–2 R$^4$, C$_{2-5}$ alkynyl substituted with 0–1 R$^4$, C$_{3-6}$ cycloalkyl substituted with 0–2 R$^{3d}$, phenyl substituted with 0–2 R$^{3d}$, and 3–6 membered heterocyclic system containing 1–3 heteroatoms selected from the group O, N, and S, substituted with 0–2 R$^{3d}$;

alternatively, in the group —NR$^{2a}$R$^{2c}$, R$^{2a}$ and R$^{2c}$ together with the N to which they are attached join together to form a 4–7 membered cyclic amine, wherein 0–1 carbon atoms are replaced by O or NR$^5$;

R$^3$ is selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, —SO$_2$NR$^5$R$^{5a}$, and a 5–6 membered heteroaromatic ring containing 1–4 heteroatoms selected from the group O, N, and S;

R$^{3a}$ is selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, —SO$_2$NR$^5$R$^{5a}$, and a 5–6 membered heteroaromatic ring containing 1–4 heteroatoms selected from the group O, N, and S;

alternatively, R$^3$ and R$^{3a}$ together form —OCH$_2$O—;

R$^{3b}$ is selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

alternatively, R$^{3a}$ and R$^{3b}$ together form —OCH$_2$O—;

R$^{3c}$ is selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

alternatively, R$^{3b}$ and R$^{3c}$ together form —OCH$_2$O—;

R$^{3d}$, at each occurrence, is independently selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^{3e}$, at each occurrence, is independently selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^{3f}$, is selected from the group group H, F, Cl, Br, I, —OH, —O—R$^{11}$, —O—C$_{3-10}$ carbocycle substituted with 0–2 R$^{3e}$, —O(CO)—R$^{13}$, —OS(O)$_2$C$_{1-4}$ alkyl, —NR$^{12}$R$^{12a}$, —C(O)R$^{13}$, —NHC(O)R$^{13}$, —NHSO$_2$R$^{10}$, and —SO$_2$NR$^{12}$R$^{12a}$;

R$^4$ is selected from the group H, F, Cl, Br, I, —OH, —O—R$^{11}$, —O—C$_{3-10}$ carbocycle substituted with 0–2 R$^{3e}$, —OS(O)$_2$C$_{1-4}$alkyl, —NR$^{12}$R$^{12a}$, C$_{1-6}$ alkyl substituted with 0–2 R$^{3e}$, C$_{3-10}$ carbocycle substituted with 0–2 R$^{3e}$, phenyl substituted with 0–5 R$^{3e}$, and a 5–10 membered heterocyclic system containing 1–3 heteroatoms selected from the group O, N, and S, substituted with 0–2 R$^{3e}$;

R$^5$ and R$^{5a}$ are independently selected from the group H and C$_{1-4}$ alkyl;

alternatively, R$^5$ and R$^{5a}$, together with the nitrogen to which they are attached, combine to form a 5–6 membered ring containing 0–1 O or N atoms;

R$^{5b}$ is selected from the group H and C$_{1-4}$ alkyl,

R$^6$ is selected from the group H, OH, C$_{1-4}$ alkyl, C$_{1-4}$ alkoxy, and NR$^5$R$^{5a}$;

R$^7$ is selected from the group H, C$_{1-3}$ alkyl and C$_{1-3}$ alkoxy;

R$^8$ is selected from the group H, (C$_{1-6}$ alkyl)carbonyl, C$_{1-6}$ alkoxyalkyl, (C$_{1-4}$ alkoxy)carbonyl, C$_{6-10}$ aryloxyalkyl, (C$_{6-10}$ aryl)oxycarbonyl, (C$_{6-10}$ aryl)methylcarbonyl, (C$_{1-4}$ alkyl)carbonyloxy(C$_{1-4}$ alkoxy)carbonyl, C$_{6-10}$ arylcarbonyloxy(C$_{1-4}$ alkoxy)carbonyl, C$_{1-6}$ alkylaminocarbonyl, phenylaminocarbonyl, phenyl(C$_{1-4}$ alkoxy)carbonyl, and (C$_{1-6}$ alkyl substiued with NR$^5$R$^{5a}$)carbonyl; and R$^{10}$ is selected from the group C$_{1-4}$ alkyl and phenyl R$^{11}$ is selected from C$_{1-6}$ alkyl, C$_{1-6}$ haloalkyl, C$_{1-6}$ alkyl substituted with C$_{3-6}$cycloalkyl, C$_{2-6}$ alkenyl, C$_{2-6}$ alkynyl, C$_{3-6}$ cycloalkyl;

R$^{12}$ and R$^{12a}$ are independently selected from H, C$_{1-6}$ alkyl, and C$_{3-6}$ cycloalkyl;

alternatively, R$^{12}$ and R$^{12a}$ can join to form 4–7 membered ring; and

R$^{13}$ is selected from the group H, C$_{1-6}$ alkyl, C$_{1-6}$ haloalkyl, C$_{1-6}$ alkoxy, C$_{2-6}$ alkenyl, C$_{2-6}$ alkynyl, —O—C$_{2-6}$ alkenyl, —O—C$_{2-6}$ alkynyl, NR$^{12}$R$^{12a}$, C$_{3-6}$carbocycle, and —O—C$_{3-6}$carbocycle.

2. A compound of claim 1 or pharmaceutically acceptable salt forms thereof, wherein:

R$^1$ is selected from the group C$_{1-3}$ alkyl substituted with 1–7 halogen, and cyclopropyl;

R$^2$ is selected from the group —R$^{2c}$, —OH, —CN, —OR$^{2c}$, —OCHR$^{2a}$R$^{2b}$, —OCH$_2$CHR$^{2a}$R$^{2b}$, —O(CH$_2$)$_2$CHR$^{2a}$R$^{2b}$, —OCHR$^{2a}$CH=CHR$^{2b}$, —OCHR$^{2a}$CH=CHR$^{2c}$, —OCHR$^{2a}$C≡CR$^{2b}$, —NR$^{2a}$R$^{2c}$, —SR$^{2c}$, —SCHR$^{2a}$R$^{2b}$, —SCH$_2$CHR$^{2a}$R$^{2b}$, —SCHR$^{2a}$CH=CHR$^{2b}$, —SCHR$^{2a}$CH=CHR$^{2c}$, and —SCHR$^{2a}$C≡CR$^{2b}$;

R$^{2a}$ is selected from the group H, CH$_3$, CH$_2$CH$_3$, CH(CH$_3$)$_2$, and CH$_2$CH$_2$CH$_3$;

R$^{2b}$ is H or R$^{2c}$;

R$^{2c}$ is selected from the group methyl substituted with 0–3 R$^{3f}$, C$_{1-5}$ alkyl substituted with 0–3 R$^4$, C$_{2-5}$ alkenyl substituted with 0–2 R$^4$, C$_{2-5}$ alkynyl substituted with 0–1 R$^4$, C$_{3-6}$ cycloalkyl substituted with 0–2 R$^{3d}$, and phenyl substituted with 0–2 R$^{3d}$;

R$^3$ and R$^{3a}$, at each occurrence, are independently selected from the group H, C$_{1-4}$ alkyl, OH, C$_{1-4}$ alkoxy, F, Cl, Br, I, NR$^5$R$^{5a}$, NO$_2$, —CN, C(O)R$^6$, NHC(O)R$^7$, NHC(O)NR$^5$R$^{5a}$, and a 5–6 membered heteroaromatic ring containing 1–4 heteroatoms selected from the group O, N, and S;

alternatively, R$^3$ and R$^{3a}$ together form —OCH$_2$O—;

R$^{3b}$ and R$^{3c}$, at each occurrence, are independently selected from the group H, C$_{1-4}$ alkyl, OH, C$_{1-4}$ alkoxy, F, Cl, Br, I, NR$_5$R$_{5a}$, NO$_2$, —CN, C(O)R$^6$, NHC(O)R$^7$, and NHC(O)NR$^5$R$^{5a}$;

alternatively, R$^{3a}$ and R$^{3b}$ together form —OCH$_2$O—;

R$^4$ is selected from the group H, Cl, F, —OH, —O—C$_{1-6}$alkyl, —O—C$_{3-5}$ carbocycle substituted with 0–2 R$^{3e}$, —OS(O)$_2$C$_{1-4}$alkyl, —NR$^{12}$R$^{12a}$, C$_{1-4}$ alkyl substituted with 0–2 R$^{3e}$, C$_{3-5}$ carbocycle substituted with 0–2 R$^{3e}$, phenyl substituted with 0–5 R$^{3e}$, and a 5–6 membered heterocyclic system containing 1–3 heteroatoms selected from the group O, N, and S, substituted with 0–2 R$^{3e}$;

R$^5$ and R$^{5a}$ are independently selected from the group H, CH$_3$ and C$_2$H$_5$;

R$^6$ is selected from the group H, OH, CH$_3$, C$_2$H$_5$, OCH$_3$, OC$_2$H$_5$, and NR$^5$R$^{5a}$; and R$^7$ is selected from the group CH$_3$, C$_2$H$_5$, CH(CH$_3$)$_2$, OCH$_3$, OC$_2$H$_5$, and OCH(CH$_3$)$_2$.

3. A compound of claim 2, wherein:
ring A is selected from

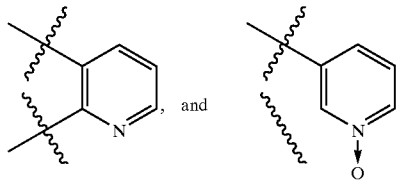
, and

R$^1$ is selected from the group CF$_3$, C$_2$F$_5$, CHF$_2$, CF$_2$CH$_3$ and cyclopropyl;

R$^2$ is selected from the group —R$^{2c}$, —OH, —CN, —OR$^{2c}$, —OCHR$^{2a}$R$^{2b}$, —OCH$_2$CHR$^{2a}$R$^{2b}$, —OCHR$^{2a}$CH═CHR$^{2b}$, —OCHR$^{2a}$CH═CHR$^{2c}$, —OCHR$^{2a}$C≡CR$^{2b}$, and —NR$^{2a}$R$^{2c}$;

R$^{2a}$ is selected from the group H, CH$_3$, CH$_2$CH$_3$, CH(CH$_3$)$_2$, and CH$_2$CH$_2$CH$_3$;

R$^{2b}$ is H or R$^{2c}$;

R$^{2c}$ is selected from the group methyl substituted with 0–3 R$^{3f}$, C$_{1-3}$ alkyl substituted with 0–3 R$^4$, C$_{2-3}$ alkenyl substituted with 0–2 R$^4$, C$_{2-3}$ alkynyl substituted with 0–1 R$^4$, and C$_{3-6}$ cycloalkyl substituted with 0–2 R$^{3d}$;

R$^3$, R$^{3a}$, R$^{3b}$, and R$^{3c}$, at each occurrence, are independently selected from the group H, C$_{1-3}$ alkyl, OH, C$_{1-3}$ alkoxy, F, Cl, Br, I, NR$^5$R$^{5a}$, NO$_2$, —CN, C(O)R$^6$, NHC(O)R$^7$, and NHC(O)NR$^5$R$^{5a}$;

alternatively, R$^3$ and R$^{3a}$ together form —OCH$_2$O—;

R$^{3e}$, at each occurrence, is independently selected from the group H, C$_{1-4}$ alkyl, —OH, C$_{1-4}$ alkoxy, OCF$_3$, F, Cl, —NR$^5$R$^{5a}$, —C(O)R$^6$, and —SO$_2$NR$^5$R$^{5a}$;

R$^{3f}$ is selected from the group group H, F, Cl, Br, —OH, —O—R$^{11}$, —O-cyclopropyl substituted with 0–2 R$^{3e}$, —O-cyclobutyl substituted with 0–2 R$^{3e}$, —O-phenyl substituted with 0–2 R$^{3e}$, —O(CO)—R$^{13}$, —OS(O)$_2$C$_{1-4}$alkyl, —NR$^{12}$R$^{12a}$, —C(O)R$^{13}$, —NHC(O)R$^{13}$, —NHSO$_2$R$^{10}$, and —SO$_2$NR$^{12}$R$^{12a}$;

R$^4$ is selected from the group H, Cl, F, —OH, —O—C$_{1-6}$alkyl, —O—C$_{3-10}$ carbocycle substituted with 0–2 R$^{3e}$, —OS(O)$_2$C$_{1-4}$alkyl, NR$^{12}$R$^{12a}$ C$_{1-4}$ alkyl substituted with 0–1 R$^{3e}$, C$_{3-5}$ carbocycle substituted with 0–2 R$^{3e}$, phenyl substituted with 0–2 R$^{3e}$, and a 5–6 membered heterocyclic system containing 1–3 heteroatoms selected from the group O, N, and S, substituted with 0–1 R$^{3e}$;

R$^5$ and R$^{5a}$ are independently selected from the group H, CH$_3$ and C$_2$H$_5$;

R$^6$ is selected from the group H, OH, CH$_3$, C$_2$H$_5$, OCH$_3$, OC$_2$H$_5$, and NR$^5$R$^{5a}$; and R$^7$ is selected from the group CH$_3$, C$_2$H$_5$, OCH$_3$, and OC$_2$H$_5$;

R$^{11}$ is selected from methyl, ethyl, propyl, i-propyl, butyl, pentyl, hexyl, CF$_3$, CH$_2$CF$_3$, CH$_2$CH$_2$CF$_3$, —CH$_2$-cyclopropyl, and cyclopropyl;

R$^{12}$ and R$^{12a}$ are independently selected from H, methyl, ethyl, propyl, i-propyl, butyl, pentyl, and cyclopropyl;

R$^{13}$ is selected from the group H, methyl, ethyl, propyl, i-propyl, butyl, pentyl, hexyl, C$_{1-6}$ haloalkyl, methoxy, ethoxy, propoxy, i-propoxy, butoxy, NR$^{12}$R$^{12a}$, cyclopropyl, cyclobutyl, cyclopropoxy, and cyclobutoxy.

4. A compound of claim 3, or a pharmaceutically acceptable salt form thereof, wherein:

R$^1$ is CF$_3$, CF$_2$CH$_3$, or CHF$_2$;

R$^2$ is selected from the group —R$^{2c}$, —OH, —CN, —OCH$_2$R$^{2b}$, —OCH$_2$CH$_2$R$^{2b}$, —OCH$_2$CH═CHR$^{2b}$, —OCH$_2$C≡CR$^{2b}$, and —NR$^{2a}$R$^{2c}$;

R$^{2b}$ is H or R$^{2c}$;

R$^{2c}$ is selected from the group methyl substituted with 0–3 R$^{3f}$, C$_{1-3}$ alkyl substituted with 0–3 R$^4$, C$_{2-3}$ alkenyl substituted with 1 R$^4$, and C$_{2-3}$ alkynyl substituted with 1 R$^4$;

R$^3$, R$^{3a}$, R$^{3b}$, and R$^{3c}$, at each occurrence, are independently selected from the group H, C$_{1-3}$ alkyl, OH, C$_{1-3}$ alkoxy, F, Cl, NR$^5$R$^{5a}$, NO$_2$, —CN, C(O)R$^6$, NHC(O)R$^7$, and NHC(O)NR$^5$R$^{5a}$;

alternatively, R$^3$ and R$^{3a}$ together form —OCH$_2$O—;

R$^{3e}$, at each occurrence, is independently selected from the group CH$_3$, —OH, OCH$_3$, OCF$_3$, F, Cl, and —NR$^5$R$^{5a}$;

R$^{3f}$, is selected from the group group H, F, Cl, —OH, —O—R$^{11}$, —O(CO)—R$^{13}$, —OS(O)$_2$C$_{1-4}$alkyl, —NR$^{12}$R$^{12a}$, and —NHC(O)NR$^{12}$R$^{12a}$;

R$^4$ is selected from the group H, Cl, F, CH$_3$, CH$_2$CH$_3$, cyclopropyl substituted with 0–1 R$^{3e}$, 1-methylcyclopropyl substituted with 0–1 R$^{3e}$, cyclobutyl substituted with 0–1 R$^{3e}$, phenyl substituted with 0–2 R$^{3e}$, and a 5–6 membered heterocyclic system containing 1–3 heteroatoms selected from the group O, N, and S, substituted with 0–1 R$^{3e}$, wherein the heterocyclic system is selected from the group 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, 2-imidazolyl, morpholinyl, piperidinyl, pyrrolidinyl, and piperazinyl;

R$^5$ and R$^{5a}$ are independently selected from the group H, CH$_3$ and C$_2$H$_5$;

R$^6$ is selected from the group H, OH, CH$_3$, C$_2$H$_5$, OCH$_3$, OC$_2$H$_5$, and NR$^5$R$^{5a}$; and R$^7$ is selected from the group CH$_3$, C$_2$H$_5$, OCH$_3$, and OC$_2$H$_5$.

5. A compound of claim 1, or a pharmaceutically acceptable salt form thereof, wherein:

n is 0 or 1;

ring A is optionally in an N-oxide form;

R$^1$ is CF$_3$, CHF$_2$, or CF$_2$CH$_3$;

R$^2$ is selected from the group —R$^{2c}$, —OR$^{2c}$, —OH, —CN, —OCH$_2$R$^{2b}$, —OCH$_2$CH$_2$R$^{2b}$, —OCH$_2$C≡C—R$^{2b}$, —OCH$_2$C≡C—R$^{2b}$, —NR$^{2a}$R$^{2c}$, —SR$^{2c}$, —SCH$_2$R$^{2b}$, —SCH$_2$CH$_2$R$^{2b}$, —SCH$_2$CH═CHR$^{2b}$, and —SCH$_2$C≡CR$^{2b}$;

R$^{2b}$ is H or R$^{2c}$;

R$^{2c}$ is selected from the group methyl substituted with 0–2 R$^{3f}$, ethyl substituted with 0–3 R$^4$, propyl substituted with 0–2 R$^4$, ethenyl substituted with 0–2 R$^4$, 1-propenyl substituted with 0–2 $R^4$, 2-propenyl substituted with 0–2 $R^4$, ethynyl substituted with 0–2 $R^4$, 1-propynyl substituted with 0–2 $R^4$, 2-propynyl substituted with 0–2 $R^4$, and cyclopropyl substituted with 0–1 $R^{3d}$;

$R^{3e}$, at each occurrence, is independently selected from the group $CH_3$, —OH, $OCH_3$, $OCF_3$, F, Cl, and —$NR^5R^{5a}$;

$R^{3f}$, is selected from the group group H, F, Cl, —OH, —O—$R^{11}$, —O(CO)—$R^{13}$, —$OS(O)_2C_{1-4}$alkyl, —$NR^{12}R^{12a}$, and —$NHC(O)NR^{12}R^{12a}$;

$R^4$ is selected from the group H, Cl, F, $CH_3$, $CH_2CH_3$, cyclopropyl substituted with 0–1 $R^{3e}$, 1-methyl-cyclopropyl substituted with 0–1 $R^{3e}$, cyclobutyl substituted with 0–1 $R^{3e}$, phenyl substituted with 0–2 $R^{3e}$, and a 5–6 membered heterocyclic system containing 1–3 heteroatoms selected from the group O, N, and S, substituted with 0–1 $R^{3e}$, wherein the heterocyclic system is selected from the group 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, 2-imidazolyl, morpholinyl, piperidinyl, pyrrolidinyl, and piperazinyl;

$R^5$ and $R^{5a}$ are independently selected from the group H, $CH_3$ and $C_2H_5$;

$R^6$ is selected from the group H, OH, $CH_3$, $C_2H_5$, $OCH_3$, $OC_2H_5$, and $NR^5R^{5a}$;

$R^7$ is selected from the group $CH_3$, $C_2H_5$, $OCH_3$, and $OC_2H_5$;

$R^8$ is H.

6. A compound of claim 4, or a pharmaceutically acceptable salt form thereof, wherein:

n is selected from 0 or 1;

A is selected from;

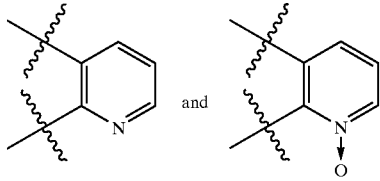

and

B is selected from methyl, ethyl, propyl, —OH, Cl, Br, —S—$CH_3$, $R^1$ is selected from $CF_3$, $CHF_2$, and $CF_2CH_3$;

$R^2$ is selected from —$R^{2c}$, —OH, —CN, —$OR^{2c}$, —$OCH_2C=C—R^{2b}$, —$OCH_2C\equiv C—R^{2b}$, and $NR^{2a}R^{2c}$;

$R^{2a}$ is H;

$R^{2b}$ is H;

$R^{2c}$ is selected from the group methyl substituted with 0–3 $R^{3f}$, ethyl substituted with 0–3 $R^4$, propyl substituted with 0–3 $R^4$, i-propyl substituted with 0–3 $R^4$, butyl substituted with 0–3 $R^4$, 1-propenyl substituted with 0–2 $R^4$, 2-propenyl substituted with 0–2 $R^4$, 1-propynyl substituted with 0–2 $R^4$, 2-propynyl substituted with 0–2 $R^4$;

$R^3$ is H;

$R^{3a}$ is H, F, Cl, or Br;

$R^{3b}$ is H;

$R^{3c}$ is H;

$R^{3e}$, at each occurrence, is independently selected from the group H, methyl, and ethyl, —OH, $C_{1-4}$ alkoxy, $OCF_3$, F, Cl, Br, I, —$NR^5R^{5a}$, —$NO_2$, —CN, —C(O)$R^6$, —$NHC(O)R^7$, —$NHC(O)NR^5R^{5a}$, —$NHSO_2R^{10}$, and —$SO_2NR^5R^{5a}$;

$R^{3f}$ is selected from H, F, Cl, OH, —$OR^{11}$, —$OSO_2$methyl, —$NR^{12}R^{12a}$, and —$NHC(O)NR^5R^{5a}$;

$R^4$ is selected from H, F, —OH, —O-i-propyl, —$OS(O)_2CH_3$, cyclopropyl substituted with 0–1 $R^{3e}$, cyclobutyl substituted with 0–1 $R^{3e}$, phenyl, N-morpholinyl, 2-pyridyl, 3-pyridyl, 4-pyridiyl, N2-methyl-N1-piperidinyl, N-piperidinyl, N-pyrrolidinyl, and N-piperazinyl;

$R^8$ is H;

$R^{11}$ is selected from H, methyl, ethyl, propyl, i-propyl, $CH_2$cyclopropyl, and cyclopropyl; and $R^{12}$ and $R^{12a}$ are independently selected from H, methyl, ethyl, propyl, i-propyl, and cyclopropyl.

7. A compound of claim 1, or a pharmaceutically acceptable salt form thereof, wherein the compound is of formula (Ic):

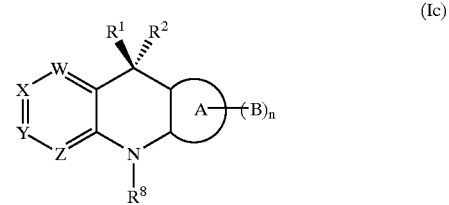

(Ic)

8. A compound of claim 1, or a pharmaceutically acceptable salt form thereof, wherein the compound is of formula (Id):

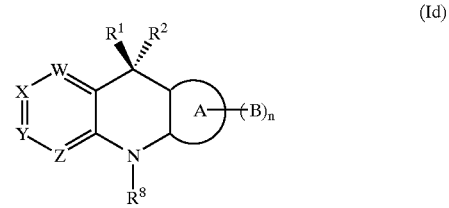

(Id)

9. A compound of claim 1, or a pharmaceutically acceptable salt form thereof or an N-oxide form thereof, wherein the compound of formula (I) is selected from:

7-Chloro-5-(cyclopropylmethoxy)-5,10-dihydro-5-(trifluoromethyl)benzo[b][1,8]naphthyridine, 7-Chloro-5-(benzyloxy)-5,10-dihydro-5-(trifluoromethyl)benzo[b][1,8]naphthyridine, 7-Chloro-5-(cyclobutylmethoxy)-5,10-dihydro-5-(trifluoromethyl)benzo[b][1,8]naphthyridine, 7-Chloro-5-(ethoxy)-5,10-dihydro-5-(trifluoromethyl)benzo[b][1,8]naphthyridine, 7-Chloro-5-(hydroxy)-5,10-dihydro-5-(trifluoromethyl)benzo[b][1,8]naphthyridine, 7-Chloro-5-(n-propoxy)-5,10-dihydro-5-(trifluoromethyl)benzo[b][1,8]naphthyridine, 7-Chloro-5-(i-propoxy)-5,10-dihydro-5-(trifluoromethyl)benzo[b][1,8]naphthyridine, 7-Chloro-5-(butyl)-5,10-dihydro-5-(trifluoromethyl)benzo[b][1,8]naphthyridine, 7-Chloro-5-(methoxy)-5,10-dihydro-5-(trifluoromethyl)benzo[b][1,8]naphthyridine, 7-Chloro-5(S)-(cyclopropylmethoxy)-5,10-dihydro-5-(trifluoromethyl)benzo[b][1,8]naphthyridine, 7-Chloro-5(R)-(cyclopropylmethoxy)-5,10-dihydro-5-(trifluoromethyl)benzo[b][1,8]naphthyridine, 7-Chloro-5-(2-cyclopropylethyl)-5,10-dihydro-5-(trifluoromethyl)benzo[b][1,8]naphthyridine, 7-Chloro-5-(2,2,2-trifluoroethoxy)-5,10-dihydro-5-(trifluoromethyl)benzo[b][1,8]naphthyridine, 7-Chloro-5-(propargoxy)-5,10-dihydro-5-(trifluoromethyl)benzo[b][1,8]naphthyridine, 7-Chloro-5-(ethyl)-5,10-dihydro-5-(trifluoromethyl)benzo[b][1,8]naphthyridine, 7-Chloro-5-(cyclopropylmethoxy)-2-methyl-5,10-dihydro-5-(trifluoromethyl)benzo[b][1,8]naphthyridine, 7-Chloro-5-(n-butyl)-2-methyl-5,10-dihydro-5-(trifluoromethyl)benzo[b][1,8]naphthyridine, 7-Chloro-5-(2-cyclopropylethyl)-2-methyl-5,10-dihydro-5-(trifluoromethyl)benzo[b][1,8]naphthyridine, 7-Chloro-5-(cyclopropylamino)-5,10-dihydro-5-(trifluoromethyl)benzo[b][1,8]naphthyridine, 7-Chloro-5-(i-propylamino)-5,10-dihydro-5-(trifluoromethyl)benzo[b][1,8]naphthyridine, 7-Chloro-5-(N,N-dimethylaminoethoxy)-5,10-dihydro-5-(trifluoromethyl)benzo[b][1,8]naphthyridine, 7-Chloro-5-(N-morpholinylethylamino)-5,10-dihydro-5-(trifluoromethyl)benzo[b][1,8]naphthyridine, 7-Chloro-5-((1-methylcyclopropyl)methoxy)-5,10-dihydro-5-(trifluoromethyl)benzo[b][1,8]naphthyridine, 7-Chloro-5-(3,3,3-trifluoroprop-1-oxy)-5,10-dihydro-5-(trifluoromethyl)benzo[b][1,8]naphthyridine, 7-Chloro-5-(cyclopropylmethylamino)-5,10-dihydro-5-(trifluoromethyl)benzo[b][1,8]naphthyridine, 7-Chloro-5-(methylamino)-5,10-dihydro-5-(trifluoromethyl)benzo[b][1,8]naphthyridine, 7-Chloro-5-(ethylamino)-5,10-dihydro-5-(trifluoromethyl)benzo[b][1,8]naphthyridine, (S)-7-Chloro-5-(cyclopropylethyl)-5,10-dihydro-5-(trifluoromethyl)benzo[b][1,8]naphthyridine, (R)-7-Chloro-5-(cyclopropylethyl)-5,10-dihydro-5-(trifluoromethyl)benzo[b][1,8]naphthyridine, 7-Fluoro-5-(cyclopropylmethoxy)-5,10-dihydro-5-(trifluoromethyl)benzo[b][1,8]naphthyridine, 7-Fluoro-5-(cyclopropylethoxy)-5,10-dihydro-5-(trifluoromethyl)benzo[b][1,8]naphthyridine, 7-Fluoro-5-(allyloxy)-5,10-dihydro-5-(trifluoromethyl)benzo[b][1,8]naphthyridine, 7-Chloro-5-(phenylamino)-5,10-dihydro-5-(trifluoromethyl)benzo[b][1,8]naphthyridine, 7-Chloro-5-(cyclopropylmethoxy)-2-methyl-5,10-dihydro-5-(trifluoromethyl)benzo[b][1,8]naphthyridine, 7-Chloro-5-(n-butyl)-2-methyl-5,10-dihydro-5-(trifluoromethyl)benzo[b][1,8]naphthyridine, 7-Chloro-5-(cyclopropylethyl)-2-methyl-5,10-dihydro-5-(trifluoromethyl)benzo[b][1,8]naphthyridine, 7-Chloro-5-cyclopropylmethoxy-5-trifluoromethyl-5,10-dihydro-benzo[b][1,8]naphthyridine 1-oxide;

5-Allyloxy-7-fluoro-5-trifluoromethyl-5,10-dihydro-benzo[b][1,8]naphthyridine;

7-Fluoro-5-trifluoromethyl-5,10-dihydro-benzo[b][1,8]naphthyridine-5-carbonitrile;

7-Fluoro-5-trifluoromethyl-5,10-dihydro-benzo[b][1,8]naphthyridin-5-ol;

5-Cyclopropylmethoxy-7-fluoro-5-trifluoromethyl-5,10-dihydro-benzo[b][1,8]naphthyridine 1-oxide;

7-Chloro-5-prop-2-ynyloxy-5-trifluoromethyl-5,10-dihydro-benzo[b][1,8]naphthyridine 1-oxide;

7-Chloro-5-(1-methyl-cyclopropylmethoxy)-5-trifluoromethyl-5,10-dihydro-benzo[b][1,8]naphthyridine 1-oxide;

7-Chloro-5-(2-cyclopropy-ethoxy)-5-trifluoromethyl-5,10-dihydro-benzo[b][1,8]naphthyridine 1-oxide;

(7-Chloro-5-trifluoromethyl-5,10-dihydro-benzo[b][1,8]naphthyridin-5-yl)-isopropyl-amine;

(7-Chloro-5-trifluoromethyl-5,10-dihydro-benzo[b][1,8]naphthyridin-5-yl)-cyclobutylmethyl-amine;

7-Chloro-5-(2-cyclopropyl-ethyl)-5-trifluoromethyl-5,10-dihydro-benzo[b][1,8]naphthyridine 1-oxide;

5-Cyclobutylmethoxy-7-fluoro-5-trifluoromethyl-5,10-dihydro-benzo[b][1,8]naphthyridine 1-oxide;

(7-Fluoro-1-oxy-5-trifluoromethyl-5,10-dihydro-benzo[b][1,8]naphthyridin-5-yl)-isopropyl-amine;

5-Cyclobutylmethoxy-7-fluoro-5-trifluoromethyl-5,10-dihydro-benzo[b][1,8]naphthyridin-2-ol;

7-Chloro-5-(pyridin-2-ylmethoxy)-5-trifluoromethyl-5,10-dihydro-benzo[b][1,8]naphthyridine;

5-Butyl-7-fluoro-5-trifluoromethyl-5,10-dihydro-benzo[b][1,8]naphthyridine;

7-Chloro-1-oxy-5-trifluoromethyl-5,10-dihydro-benzo[b][1,8]naphthyridin-5-ol;

7-Chloro-5-cyclopropylmethoxy-5-trifluoromethyl-5,10-dihydro-benzo[b][1,8]naphthyridine 1-oxide;

7-Chloro-5-pyridin-2-ylmethyl-5-trifluoromethyl-5,10-dihydro-benzo[b][1,8]naphthyridine 1-oxide;

7-Fluoro-5-pyridin-2-ylmethyl-5-trifluoromethyl-5,10-dihydro-benzo[b][1,8]naphthyridine;

5-Cyclopropylmethoxy-7-fluoro-5-trifluoromethyl-5,10-dihydro-benzo[b][1,8]naphthyridine 1-oxide;

7-Chloro-5-pyridin-2-ylmethyl-5-trifluoromethyl-5,10-dihydro-benzo[b][1,8]naphthyridine;

3,7-Dichloro-5-cyclopropylmethoxy-5-trifluoromethyl-5,10-dihydro-benzo[b][1,8]naphthyridine, 3,7-Dichloro-5-cyc(opropylmethoxy-5-trifluoromethyl-5,10-dihydro-benzo[b][1,8]naphthyridine 1-oxide;

3,7-Dichloro-5-pentyl-5-trifluoromethyl-5,10-dihydro-benzo[b][1,8]naphthyridine 1-oxide;

5-(2-Cyclopropyl-ethyl)-7-fluoro-5-trifluoromethyl-5,10-dihydro-benzo[b][1,8]naphthyridine;

5-(2-Cyclopropyl-ethyl)-7-fluoro-5-trifluoromethyl-5,10-dihydro-benzo[b][1,8]naphthyridine 1-oxide;

3,7-Dichloro-5-cyclopropylmethoxy-5-trifluoromethyl-5,10-dihydro-benzo[b][1,8]naphthyridine 1-oxide;

5-(2-Cyclopropyl-ethyl)-7-fluoro-5-trifluoromethyl-5,10-dihydro-benzo[b][1,8]naphthyridine 1-oxide;

3-Chloro-5-cyclopropylmethoxy-7-fluoro-5-trifluoromethyl-5,10-dihydro-benzo[b][1,8]naphthyridine;

3-Chloro-5-cyclopropylmethoxy-7-fluoro-5-trifluoromethyl-5,10-dihydro-benzo[b][1,8]naphthyridine 1-oxide;

7-Chloro-5-isobutoxy-5-trifluoromethyl-5,10-dihydro-benzo[b][1,8]naphthyridine 1-oxide;

5-Butyl-7-chloro-5-trifluoromethyl-5,10-dihydro-benzo[b][1,8]naphthyridine 1-oxide;

(S) 3-Chloro-5-cyclopropylmethoxy-7-fluoro-5-trifluoromethyl-5,10-dihydro-benzo[b][1,8]naphthyridine 1-oxide;

(7-Chloro-5-trifluoromethyl-5,10-dihydro-benzo[b][1,8]
naphthyridin-5-yl)-methanol;

7-Fluoro-5-isobutoxy-5-trifluoromethyl-5,10-dihydro-
benzo[b][1,8]naphthyridine 1-oxide;

7-Fluoro-5-isopropoxy-5-trifluoromethyl-5,10-dihydro-
benzo[b][1,8]naphthyridine 1-oxide;

Methanesulfonic acid 7-chloro-5-trifluoromethyl-5,10-
dihydro-benzo[b][1,8]naphthyridin-5-ylmethyl ester;

7-Chloro-5-isopropoxy-5-trifluoromethyl-5,10-dihydro-
benzo[b][1,8]naphthyridine 1-oxide;

3-Bromo-5-cyclopropylmethoxy-7-fluoro-5-
trifluoromethyl-5,10-dihydro-benzo[b][1,8]
naphthyridine 1-oxide;

5-Butyl-7-fluoro-5-trifluoromethyl-5,10-dihydro-benzo
[b][1,8]naphthyridine 1-oxide;

5-Diisopropoxymethyl-7-fluoro-5-trifluoromethyl-5,10-
dihydro-benzo[b][1,8]naphthyridine;

7-Fluoro-5-isopropoxymethyl-5-trifluoromethyl-5,10-
dihydro-benzo[b][1,8]naphthyridine 1-oxide;

7-Chloro-5-isobutyl-5-trifluoromethyl-5,10-dihydro-
benzo[b][1,8]naphthyridine 1-oxide;

7-Chloro-5-propoxy-5-trifluoromethyl-5,10-dihydro-
benzo[b][1,8]naphthyridine 1-oxide;

(S) 7-Fluoro-5-isobutoxy-5-trifluoromethyl-5,10-
dihydro-benzo[b][1,8]naphthyridine 1-oxide;

(R) 7-Fluoro-5-isobutoxy-5-trifluoromethyl-5,10-
dihydro-benzo[b][1,8]naphthyridine 1-oxide;

(7-Chloro-5-trifluoromethyl-5,10-dihydro-benzo[b][1,8]
naphthyridin-5-yl)-acetaldehyde;

7-Chloro-5-(2,2-diisopropoxy-ethyl)-5-trifluoromethyl-5,
10-dihydro-benzo[b][1,8]naphthyridine;

7-Chloro-5-(2-isopropoxy-ethyl)-5-trifluoromethyl-5,10-
dihydro-benzo[b][1,8]naphthyridine;

2-(7-Chloro-5-trifluoromethyl-5,10-dihydro-benzo[b][1,
8]naphthyridin-5-yl)-ethanol;

7-Chloro-5-(2-isopropoxy-ethyl)-5-trifluoromethyl-5,10-
dihydro-benzo[b][1,8]naphthyridine 1-oxide;

(R) 7-Fluoro-5-(2-isopropoxy-ethyl)-5-trifluoromethyl-5,
10-dihydro-benzo[b][1,8]naphthyridine 1-oxide;

(7-Fluoro-5-trifluoromethyl-5,10-dihydro-benzo[b][1,8]
naphthyridin-5-yl)-acetic acid tert-butyl ester;

(7-Fluoro-1-oxy-5-trifluoromethyl-5,10-dihydro-benzo
[b][1,8]naphthyridin-5-yl)-acetic acid tert-butyl ester;

7-Chloro-5-cyclopropylmethoxy-5-(1,1-difluoro-ethyl)-
5,10-dihydro-benzo[b][1,8]naphthyridine 1-oxide;

5-Cyclopropylmethoxy-5-(1,1-difluoro-ethyl)-7-fluoro-5,
10-dihydro-benzo[b][1,8]naphthyridine;

5-Cyclopropylmethoxy-5-(1,1-difluoro-ethyl)-7-fluoro-5,
10-dihydro-benzo[b][1,8]naphthyridine 1-oxide;

7-Chloro-5-(1,1-difluoro-ethyl)-5-isobutoxy-5,10-
dihydro-benzo[b][1,8]naphthyridine;

7-Chloro-5-(1,1-difluoro-ethyl)-5-isobutoxy-5,10-
dihydro-benzo[b][1,8]naphthyridine 1-oxide;

(R) 7-Chloro-5-cyclopropylmethoxy-5-(1,1-difluoro-
ethyl)-5,10-dihydro-benzo[b][1,8]naphthyridine
1-oxide;

(S) 7-Chloro-5-cyclopropylmethoxy-5-(1,1-difluoro-
ethyl)-5,10-dihydro-benzo[b][1,8]naphthyridine
1-oxide;

7-Chloro-5-difluoromethyl-5-isopropoxymethyl-5,10-
dihydro-benzo[b][1,8]naphthyridine;

7-Chloro-5-difluoromethyl-5-isopropoxymethyl-5,10-
dihydro-benzo[b][1,8]naphthyridine 1-oxide;

7-chloro-1,5-dihydro-5-(N-ethylaminomethyl)-5-
(trifluoromethyl)benzo[b][1,8]napthyridine;

7-chloro-5,10-dihydro-5-(N-isopropylaminomethyl)-5-
(trifluoromethyl)benzo[b][1,8]napthyridine;

7-chloro-5,10-dihydro-5-(N-isopropyl-N-
ethylaminomethyl)-5-(trifluoromethyl)benzo[b][1,8]
napthyridine;

7-chloro-5-(N, N-diethylaminomethyl)-5,10-dihydro-5-
(trifluoromethyl)benzo[b][1,8]napthyridine;

5-(acetamidomethyl)-7-chloro-5,10-dihydro-5-
(trifluoromethyl)benzo[b][1,8]napthyridine;

5,10-dihydro-7-fluoro-5-(N-methylsulfonylmethyl)-5-
(trifluoromethyl)benzo[b][1,8]napthyridine;

5,10-dihydro-7-fluoro-5-(isopropylamidomethyl)-5-
(trifluoromethyl)benzo[b][1,8]napthyridine;

5,10-dihydro-7-fluoro-5-(isopropylguanadinomethyl)-5-
(trifluormethyl)benzo[b][1,8]napthyridine;

5,10-dihydro-7-fluoro-5-(N-isopropylmethyl)-5-
(trifluoromethyl)benzo[b][1,8]napthyridine-1-(N-
oxide); 5-(N,N-diethylaminomethyl)-5,10-dihydro-7-
fluoro-5-(trifluoromethyl)benzo[b][1,8]napthyridine-
1-(N-oxide);

5,10-dihydro-5-(N,N-dimethylaminomethyl)-7-fluoro-5-
(trifluoromethyl)benzo[b][1,8]napthyridine-1-(N-
oxide);

7-chloro-5,10-dihydro-5-(N-isopropylaminomethyl)-5-
(trifluoromethyl)benzo[b][1,8]napthyridine-1-(N-
oxide);

7-chloro-5-(N,N-diethylaminomethyl)-5,10-dihydro-5-
(trifluoromethyl)benzo[b][1,8]napthyridine-1-(N-
oxide); and 7-chloro-5,10-dihydro-5-(N,N-dimethylaminomethyl)-5-
(trifluoromethyl)benzo[b][1,8]napthyridine-1-(N-
oxide.

10. A pharmaceutical composition comprising a pharmaceutically acceptable carrier and a therapeutically effective amount of a compound of claim 1 or pharmaceutically acceptable salt form thereof.

11. A method for treating HIV infection which comprises administering to a host in need of such treatment a therapeutically effective amount of a compound of claim 1 or pharmaceutically acceptable salt form thereof.

12. A pharmaceutical composition comprising a pharmaceutically acceptable carrier and a therapeutically effective amount of a compound of claim 4 or pharmaceutically acceptable salt form thereof.

13. A method for treating HIV infection which comprises administering to a host in need of such treatment a therapeutically effective amount of a compound of claim 4 or pharmaceutically acceptable salt form thereof.

14. A pharmaceutical composition comprising a pharmaceutically acceptable carrier and a therapeutically effective amount of a compound of claim 6 or pharmaceutically acceptable salt form thereof.

15. A method for treating HIV infection which comprises administering to a host in need of such treatment a therapeutically effective amount of a compound of claim 6 or pharmaceutically acceptable salt form thereof.

16. A pharmaceutical composition comprising a pharmaceutically acceptable carrier and a therapeutically effective amount of a compound of Formula (I):

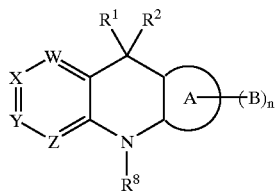

(I)

or a stereoisomeric form or mixture of stereoisomeric forms or a pharmaceutically acceptable salt form thereof, wherein:

n is selected from 0, 1, 2 and 3;

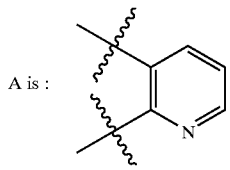

A is:

wherein a ring nitrogen in ring A may optionally be in an N-oxide form;

said ring A being substituted with 0–3 B, said substituent B being independently selected from the group $C_{1-4}$ alkyl, —OH, $C_{1-4}$ alkoxy, —S—$C_{1-4}$alkyl, $OCF_3$, $CF_3$, F, Cl, Br, I, —$NO_2$, —CN, and —$NR^5R^{5a}$;

W is $CR^3$;
X is $CR^{3a}$;
Y is $CR^{3b}$;
Z is $CR^{3c}$;

$R^1$ is selected from the group $C_{1-3}$ alkyl substituted with 0–7 halogen, and cyclopropyl substituted with 0–5 halogen;

$R^2$ is selected from the group —$R^{2c}$, —OH, —CN, —$OR^{2c}$, —$OCHR^{2a}R^{2b}$, —$OCH_2CHR^{2a}R^{2b}$, —$O(CH_2)_2CHR^{2a}R^{2b}$, —$OCHR^{2a}C(R^{2a})$=$C(R^{2b})_2$, —$OCHR^{2a}C(R^{2a})$=$C(R^{2b})_2$, $OCHR^{2a}C$≡$C—R^{2b}$, —$SR^{2c}$, —$SCHR^{2a}R^{2b}$, —$SCH_2CHR^{2a}R^{2b}$, —$S(CH_2)_2CHR^{2a}R^{2b}$, —$SCHR^{2a}C(R^{2a})$=$C(R^{2b})_2$, —$SCHR^{2a}C(R^{2a})$=$C(R^{2b})_2$, —$SCH\ R^{2a}C$≡$C—R^{2b}$, —$NR^{2a}R^{2c}$, —$NHCHR^{2a}R^{2b}$, —$NHCH_2CHR^{2a}R^{2b}$, —$NH(CH_2)_2CHR^{2a}R^{2b}$, —$NHCHR^{2a}C(R^{2a})$=$C(R^{2b})_2$, —$NHCHR^{2a}C(R^{2a})$=$C(R^{2b})_2$, and —$NHCHR^{2a}C$≡$C—R^{2b}$;

$R^{2a}$ is selected from the group H, $CH_3$, $CH_2CH_3$, $CH(CH_3)_2$, and $CH_2CH_2CH_3$;

$R^{2b}$ is H or $R^{2c}$;

$R^{2c}$ is selected from the group methyl substituted with 0–3 $R^{3f}$, $C_{1-6}$ alkyl substituted with 0–3 $R^4$, $C_{2-5}$ alkenyl substituted with 0–2 $R^4$, $C_{2-5}$ alkynyl substituted with 0–1 $R^4$, $C_{3-6}$ cycloalkyl substituted with 0–2 $R^{3d}$, phenyl substituted with 0–2 $R^{3d}$, and 3–6 membered heterocyclic system containing 1–3 heteroatoms selected from the group O, N, and S, substituted with 0–2 $R^{3d}$;

alternatively, in the group —$NR^{2a}R^{2c}$, $R^{2a}$ and $R^{2c}$ together with the N to which they are attached join together to form a 4–7 membered cyclic amine, wherein 0–1 carbon atoms are replaced by O or $NR^{5b}$;

$R^3$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, —$SO_2NR^5R^{5a}$, and a 5–6 membered heteroaromatic ring containing 1–4 heteroatoms selected from the group O, N, and S;

$R^{3a}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, —$SO_2NR^5R^{5a}$, and a 5–6 membered heteroaromatic ring containing 1–4 heteroatoms selected from the group O, N, and S;

alternatively, $R^3$ and $R^{3a}$ together form —$OCH_2O$—;

$R^{3b}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

alternatively, $R^{3a}$ and $R^{3b}$ together form —$OCH_2O$—;

$R^{3c}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

alternatively, $R^{3b}$ and $R^{3c}$ together form —$OCH_2O$—;

$R^{3d}$, at each occurrence, is independently selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

$R^{3e}$, at each occurrence, is independently selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

$R^{3f}$, is selected from the group group H, F, Cl, Br, I, —OH, —$OR^{11}$, —O—$C_{3-10}$ carbocycle substituted with 0–2 $R^{3e}$, —$O(CO)$—$R^{13}$, —$OS(O)_2C_{1-4}$alkyl, —$NR^{12}R^{12a}$, —$C(O)R^{13}$, —$NHC(O)R^{13}$, —$NHSO_2R^{10}$, and —$SO_2NR^{12}R^{12a}$;

$R^4$ is selected from the group H, F, Cl, Br, I, —OH, —O—$R^{11}$, —O—$C_{3-10}$ carbocycle substituted with 0–2 $R^{3e}$, —$OS(O)_2C_{1-4}$alkyl, —$NR^{12}R^{12a}$, $C_{1-6}$ alkyl substituted with 0–2 $R^{3e}$, $C_{3-10}$ carbocycle substituted with 0–2 $R^{3e}$, phenyl substituted with 0–5 $R^{3e}$, and a 5–10 membered heterocyclic system containing 1–3 heteroatoms selected from the group O, N, and S, substituted with 0–2 $R^{3e}$;

$R^5$ and $R^{5a}$ are independently selected from the group H and $C_{1-4}$ alkyl;

alternatively, $R^5$ and $R^{5a}$, together with the nitrogen to which they are attached, combine to form a 5–6 membered ring containing 0–10 or N atoms;

$R^{5b}$ is selected from the group H and $C_{1-4}$ alkyl;

$R^6$ is selected from the group H, OH, $C_{1-4}$ alkyl, $C_{1-4}$ alkoxy, and $NR^5R^{5a}$;

$R^7$ is selected from the group H, $C_{1-3}$ alkyl and $C_{1-3}$ alkoxy;

$R^8$ is selected from the group H, ($C_{1-6}$ alkyl)carbonyl, $C_{1-6}$ alkoxyalkyl, ($C_{1-4}$ alkoxy)carbonyl, $C_{6-10}$ aryloxyalkyl, ($C_{6-10}$ aryl)oxycarbonyl, ($C_{6-10}$ aryl)methylcarbonyl, ($C_{1-4}$ alkyl)carbonyloxy($C_{1-4}$ alkoxy)carbonyl, $C_{6-10}$ arylcarbonyloxy($C_{1-4}$ alkoxy)carbonyl, $C_{1-6}$ alkylaminocarbonyl, phenylaminocarbonyl, phenyl($C_{1-4}$ alkoxy)carbonyl, and ($C_{1-6}$ alkyl substitued with $NR^5R^{5a}$)carbonyl; and $R^{10}$ is selected from the group $C_{1-4}$ alkyl and phenyl $R^{11}$ is selected from $C_{1-6}$ alkyl, $C_{1-6}$ haloalkyl, $C_{1-6}$ alkyl substituted with $C_{3-6}$cycloalkyl, $C_{2-6}$ alkenyl, $C_{2-6}$ alkynyl, $C_{3-6}$ cycloalkyl;

$R^{12}$ and $R^{12a}$ are independently selected from H, $C_{1-6}$ alkyl, and $C_{3-6}$ cycloalkyl;

alternatively, $R^{12}$ and $R^{12a}$ can join to form 4–7 membered ring; and $R^{13}$ is selected from the group H, $C_{1-6}$ alkyl, $C_{1-6}$ haloalkyl, $C_{1-6}$ alkoxy, $C_{2-6}$ alkenyl, $C_{2-6}$ alkynyl, —O—$C_{2-6}$ alkenyl, —O—$C_{2-6}$ alkynyl, $NR^{12}R^{12a}$, $C_{3-6}$carbocycle, and —O—$C_{3-6}$carbocycle.

17. A method for treating HIV infection which comprises administering to a host in need of such treatment a therapeutically effective amount of a compound of Formula (I):

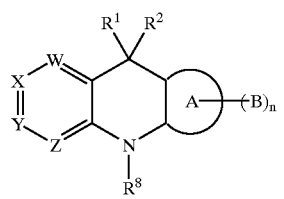

(I)

or a stereoisomeric form or mixture of stereoisomeric forms or a pharmaceutically acceptable salt form thereof, wherein:

n is selected from 0, 1, 2 and 3;

A is a ring selected from the group:

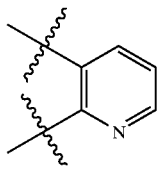

wherein a ring nitrogen in ring A may optionally be in an N-oxide form;

said ring A being substituted with 0–3 B, said substituent B being independently selected from the group $C_{1-4}$ alkyl, —OH, $C_{1-4}$ alkoxy, —S—$C_{1-4}$alkyl, $OCF_3$, $CF_3$, F, Cl, Br, I, —$NO_2$, —CN, and —$NR^5R^{5a}$;

W is $CR^3$;

X is $CR^{3a}$;

Y is $CR^{3b}$;

Z is $CR^{3c}$;

$R^1$ is selected from the group $C_{1-3}$ alkyl substituted with 0–7 halogen, and cyclopropyl substituted with 0–5 halogen;

$R^2$ is selected from the group —$R^{2c}$, —OH, —CN, —$OR^{2c}$, —$OCHR^{2a}R^{2b}$, —$OCH_2CHR^{2a}R^{2b}$, —$O(CH_2)_2CHR^{2a}R^{2b}$, —$OCHR^{2a}C(R^{2a})$=$C(R^{2b})_2$, —$OCHR^{2a}C(R^{2a})$=$C(R^{2b})_2$, —$OCHR^{2a}C$≡$C$—$R^{2b}$, —$SR^{2c}$, —$SCHR^{2a}R^{2b}$, —$SCH_2CHR^{2a}R^{2b}$, —$S(CH_2)_2CHR^{2a}R^{2b}$, —$SCHR^{2a}C(R^{2a})$=$C(R^{2b})_2$, $SCHR^{2a}C(R^{2a})$=$C(R^{2b})_2$, —$SCHR^{2a}C$≡$C$—$R^{2b}$, —$NR^{2a}R^{2c}$, —$NHCHR^{2a}R^{2b}$, —$NHCH_2CHR^{2a}R^{2b}$, —$NH(CH_2)_2CHR^{2a}R^{2b}$, —$NHCHR^{2a}C(R^{2a})$=$C(R^{2b})_2$, —$NHCHR^{2a}C(R^{2a})$=$C(R^{2b})_2$, and —$NHCHR^{2a}C$≡$C$—$R^{2b}$;

$R^{2a}$ is selected from the group H, $CH_3$, $CH_2CH_3$, $CH(CH_3)_2$, and $CH_2CH_2CH_3$;

$R^{2b}$ is H or $R^{2c}$;

$R^{2c}$ is selected from the group methyl substituted with 0–3 $R^{3f}$, $C_{1-6}$ alkyl substituted with 0–3 $R^4$, $C_{2-5}$ alkenyl substituted with 0–2 $R^4$, $C_{2-5}$ alkynyl substituted with 0–1 $R^4$, $C_{3-6}$ cycloalkyl substituted with 0–2 $R^{3d}$, phenyl substituted with 0–2 $R^{3d}$, and 3–6 membered heterocyclic system containing 1–3 heteroatoms selected from the group O, N, and S, substituted with 0–2 $R^{3d}$;

alternatively, in the group —$NR^{2a}R^{2c}$, $R^{2a}$ and $R^{2c}$ together with the N to which they are attached join together to form a 4–7 membered cyclic amine, wherein 0–1 carbon atoms are replaced by O or $NR^{5b}$;

$R^3$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, —$SO_2NR^5R^{5a}$, and a 5–6 membered heteroaromatic ring containing 1–4 heteroatoms selected from the group O, N, and S;

$R^{3a}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, —$SO_2NR^5R^{5a}$, and a 5–6 membered heteroaromatic ring containing 1–4 heteroatoms selected from the group O, N, and S;

alternatively, $R^3$ and $R^{3a}$ together form —$OCH_2O$—;

$R^{3b}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

alternatively, $R^{3a}$ and $R^{3b}$ together form —$OCH_2O$—;

$R^{3c}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

alternatively, $R^{3b}$ and $R^{3c}$ together form —$OCH_2O$—;

$R^{3d}$, at each occurrence, is independently selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

$R^{3e}$, at each occurrence, is independently selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

$R^{3f}$, is selected from the group group H, F, Cl, Br, I, —OH, —O—$R^{11}$, —O—$C_{3-10}$ carbocycle substituted with 0–2 $R^{3e}$, —$O(CO)$—$R^{13}$, —$OS(O)_2C_{1-4}$alkyl, —$NR^{12}R^{12a}$, —$C(O)R^{13}$, —$NHC(O)R^{13}$, —$NHSO_2R^{10}$, and —$SO_2NR^{12}R^{12a}$;

$R^4$ is selected from the group H, F, Cl, Br, I, —OH, —O—$R^{11}$, —O—$C_{3-10}$ carbocycle substituted with 0–2 $R^{3e}$, —$OS(O)_2C_{1-4}$alkyl, —$NR^{12}R^{12a}$, $C_{1-6}$ alkyl substituted with 0–2 $R^{3e}$, $C_{3-10}$ carbocycle substituted with 0–2 $R^{3e}$, phenyl substituted with 0–5 $R^{3e}$, and a 5–10 membered heterocyclic system containing 1–3 heteroatoms selected from the group O, N, and S, substituted with 0–2 $R^{3e}$;

$R^5$ and $R^{5a}$ are independently selected from the group H and $C_{1-4}$ alkyl;

alternatively, $R^5$ and $R^{5a}$, together with the nitrogen to which they are attached, combine to form a 5–6 membered ring containing 0–10 or N atoms;

$R^{5b}$ is selected from the group H and $C_{1-4}$ alkyl;

$R^6$ is selected from the group H, OH, $C_{1-4}$ alkyl, $C_{1-4}$ alkoxy, and $NR^5R^{5a}$;

$R^7$ is selected from the group H, $C_{1-3}$ alkyl and $C_{1-3}$ alkoxy;

$R^8$ is selected from the group H, ($C_{1-6}$ alkyl)carbonyl, $C_{1-6}$ alkoxyalkyl, ($C_{1-4}$ alkoxy)carbonyl, $C_{6-10}$ aryloxyalkyl, ($C_{6-10}$ aryl)oxycarbonyl, ($C_{6-10}$ aryl)methylcarbonyl, ($C_{1-4}$ alkyl)carbonyloxy($C_{1-4}$ alkoxy)carbonyl, $C_{6-10}$ arylcarbonyloxy($C_{1-4}$ alkoxy)carbonyl, $C_{1-6}$ alkylaminocarbonyl, phenylaminocarbonyl, phenyl($C_{1-4}$ alkoxy)carbonyl, and ($C_{1-6}$ alkyl substitued with $NR^5R^{5a}$)carbonyl; and $R^{10}$ is selected from the group $C_{1-4}$ alkyl and phenyl $R^{11}$ is selected from $C_{1-6}$ alkyl, $C_{1-6}$ haloalkyl, $C_{1-6}$ alkyl substituted with $C_{3-6}$cycloalkyl, $C_{2-6}$ alkenyl, $C_{2-6}$ alkynyl, C3-6 cycloalkyl;

$R^{12}$ and $R^{12a}$ are independently selected from H, $C_{1-6}$ alkyl, and $C_{3-6}$ cycloalkyl;

alternatively, $R^{12}$ and $R^{12a}$ can join to form 4–7 membered ring; and $R^{13}$ is selected from the group H, $C_{1-6}$ alkyl, $C_{1-6}$ haloalkyl, $C_{1-6}$ alkoxy, $C_{2-6}$ alkenyl, $C_{2-6}$ alkynyl, —O—$C_{2-6}$ alkenyl, —O—$C_{2-6}$ alkynyl, $NR^{12}R^{12a}$, $C_{3-6}$carbocycle, and —O—$C_{3-6}$carbocycle.

18. A compound of claim 1, wherein the compound of formula (I) is 7-Chloro-5-(cyclopropylmethoxy)-5,10-dihydro-5-(trifludromethyl)benzo[b][1,8]naphthyridine, or a pharmaceutically acceptable salt form thereof.

19. A compound of claim 1, wherein the compound of formula (I) is 7-Chloro-5(S)-(cyclopropylmethoxy)-5,10-dihydro-5-(trifluoromethyl)benzo[b][1,8]naphthyridine, or a pharmaceutically acceptable salt form thereof.

20. A compound of claim 1, wherein the compound of formula (I) is 7-Chloro-5(R)-(cyclopropylmethoxy)-5,10-dihydro-5-(trifluoromethyl)benzo[b][1,8]naphthyridine, or a pharmaceutically acceptable salt form thereof.

21. A compound of claim 1, wherein the compound of formula (I) is 7-Chloro-5-(2-cyclopropylethyl)-5,10-dihydro-5-(trifluoromethyl)benzo[b][1,8]naphthyridine, or a pharmaceutically acceptable salt form thereof.

22. A compound of claim 1, wherein the compound of formula (I) is (S)-7-Chloro-5-(cyclopropylethyl)-5,10-dihydro-5-(trifluoromethyl)benzo[b][1,8]naphthyridine, or a pharmaceutically acceptable salt form thereof.

23. A compound of claim 1, wherein the compound of formula (I) is (R)-7-Chloro-5-(cyclopropylethyl)-5,10-dihydro-5-(trifluoromethyl)benzo[b][1,8]naphthyridine, or a pharmaceutically acceptable salt form thereof.

24. A compound of claim 1, wherein the compound of formula (I) is 7-Fluoro-5-(cyclopropylmethoxy)-5,10-dihydro-5-(trifluoromethyl)benzo[b][1,8]naphthyridine, or a pharmaceutically acceptable salt form thereof.

25. A compound of claim 1, wherein the compound of formula (I) is 7-Chloro-5-cyclopropylmethoxy-5-trifluoromethyl-5,10-dihydro-benzo[b][1,8]naphthyridine 1-oxide; or a pharmaceutically acceptable salt form thereof.

26. A compound of claim 1, wherein the compound of formula (I) is 5-Cyclopropylmethoxy-7-fluoro-5-trifluoromethyl-5,10-dihydro-benzo[b][1,8]naphthyridine 1-oxide; or a pharmaceutically acceptable salt form thereof.

27. A compound of claim 1, wherein the compound of formula (I) is 7-Chloro-5-(2-cyclopropyl-ethyl)-5-trifluoromethyl-5,10-dihydro-benzo[b][1,8]naphthyridine 1-oxide; or a pharmaceutically acceptable salt form thereof.

28. A compound of claim 1, wherein the compound of formula (I) is 7-Chloro-5-cyclopropylmethoxy-5-trifluoromethyl-5,10-dihydro-benzo[b][1,8]naphthyridine 1-oxide; or a pharmaceutically acceptable salt form thereof.

29. A compound of claim 1, wherein the compound of formula (I) is (S) 5-Cyclopropylmethoxy-7-fluoro-5-trifluoromethyl-5,10-dihydro-benzo[b][1,8]naphthyridine 1-oxide; or a pharmaceutically acceptable salt form thereof.

30. A compound of claim 1, wherein the compound of formula (I) is 3,7-Dichloro-5-cyclopropylmethoxy-5-trifluoromethyl-5,10-dihydro-benzo[b][1,8]naphthyridine; or a pharmaceutically acceptable salt form thereof.

31. A compound of claim 1, wherein the compound of formula (I) is 3,7-Dichloro-5-cyclopropylmethoxy-5-trifluoromethyl-5,10-dihydro-benzo[b][1,8]naphthyridine 1-oxide; or a pharmaceutically acceptable salt form thereof.

32. A compound of claim 1, wherein the compound of formula (I) is 3-Chloro-5-cyclopropylmethoxy-7-fluoro-5-trifluoromethyl-5,10-dihydro-benzo[b][1,8]naphthyridine; or a pharmaceutically acceptable salt form thereof.

33. A compound of claim 1, wherein the compound of formula (I) is 3-Chloro-5-cyclopropylmethoxy-7-fluoro-5-trifluoromethyl-5,10-dihydro-benzo[b][1,8]naphthyridine 1-oxide; or a pharmaceutically acceptable salt form thereof.

34. A compound of claim 1, wherein the compound of formula (I) is (S) 3-Chloro-5-cyclopropylmethoxy-7-fluoro-5-trifluoromethyl-5,10-dihydro-benzo[b][1,8]naphthyridine 1-oxide; or a pharmaceutically acceptable salt form thereof.

35. A compound of claim 1, wherein the compound of formula (I) is (S) 7-Fluoro-5-isobutoxy-5-trifluoromethyl-5,10-dihydro-benzo[b][1,8]naphthyridine 1-oxide; or a pharmaceutically acceptable salt form thereof.

36. A compound of claim 1, wherein the compound of formula (I) is (R) 7-Fluoro-5-isobutoxy-5-trifluoromethyl-5,10-dihydro-benzo[b][1,8]naphthyridine; or a pharmaceutically acceptable salt form thereof.

37. A compound of claim 1, wherein the compound of formula (I) is (R) 7-Fluoro-5-(2-isopropoxy-ethyl)-5-trifluoromethyl-5,10-dihydro-benzo[b][1,8]naphthyridine 1-oxide; or a pharmaceutically acceptable salt form thereof.

38. A pharmaceutical composition, comprising: a pharmaceutically acceptable carrier and a therapeutically effective amount of a compound of claim 19 or a pharmaceutically acceptable salt form thereof.

39. A pharmaceutical composition, comprising: a pharmaceutically acceptable carrier and a therapeutically effective amount of a compound of claim 24 or a pharmaceutically acceptable salt form thereof.

40. A pharmaceutical composition, comprising: a pharmaceutically acceptable carrier and a therapeutically effective amount of a compound of claim 26 or a pharmaceutically acceptable salt form thereof.

41. A pharmaceutical composition, comprising: a pharmaceutically acceptable carrier and a therapeutically effective amount of a compound of claim 28 or a pharmaceutically acceptable salt form thereof.

42. A pharmaceutical composition, comprising: a pharmaceutically acceptable carrier and a therapeutically effective amount of a compound of claim 29 or a pharmaceutically acceptable salt form thereof.

43. A pharmaceutical composition, comprising: a pharmaceutically acceptable carrier and a therapeutically effective amount of a compound of claim 32 or a pharmaceutically acceptable salt form thereof.

44. A pharmaceutical composition, comprising: a pharmaceutically acceptable carrier and a therapeutically effective amount of a compound of claim 33 or a pharmaceutically acceptable salt form thereof.

45. A pharmaceutical composition, comprising: a pharmaceutically acceptable carrier and a therapeutically effective amount of a compound of claim 34 or a pharmaceutically acceptable salt form thereof.

46. A method for treating HIV infection, comprising: administering to a host in need of such treatment a therapeutically effective amount of a compound of claim 19, or a pharmaceutically acceptable salt form thereof.

47. A method for treating HIV infection, comprising: administering to a host in need of such treatment a therapeutically effective amount of a compound of claim 24, or a pharmaceutically acceptable salt form thereof.

48. A method for treating HIV infection, comprising: administering to a host in need of such treatment a therapeutically effective amount of a compound of claim 26, or a pharmaceutically acceptable salt form thereof.

49. A method for treating HIV infection, comprising: administering to a host in need of such treatment a therapeutically effective amount of a compound of claim 28, or a pharmaceutically acceptable salt form thereof.

50. A method for treating HIV infection, comprising: administering to a host in need of such treatment a therapeutically effective amount of a compound of claim 29, or a pharmaceutically acceptable salt form thereof.

51. A method for treating HIV infection, comprising: administering to a host in need of such treatment a therapeutically effective amount of a compound of claim 32, or a pharmaceutically acceptable salt form thereof.

52. A method for treating HIV infection, comprising: administering to a host in need of such treatment a therapeutically effective amount of a compound of claim 33, or a pharmaceutically acceptable salt form thereof.

53. A method for treating HIV infection, comprising: administering to a host in need of such treatment a therapeutically effective amount of a compound of claim 34, or a pharmaceutically acceptable salt form thereof.

* * * * *